(12) United States Patent
Botstein et al.

(10) Patent No.: US 6,387,657 B1
(45) Date of Patent: May 14, 2002

(54) WISP POLYPEPTIDES AND NUCLEIC ACIDS ENCODING SAME

(75) Inventors: David A. Botstein, Belmont; Robert L. Cohen, San Mateo; Audrey D. Goddard, San Francisco; Austin L. Gurney, Belmont; Kenneth J. Hillan; David A. Lawrence, both of San Francisco, all of CA (US); Arnold J. Levine, New York, NY (US); Diane Pennica, Burlingame, CA (US); Margaret Ann Roy, San Francisco, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/182,145

(22) Filed: Oct. 29, 1998

Related U.S. Application Data

(60) Provisional application No. 60/063,704, filed on Oct. 29, 1997, provisional application No. 60/073,612, filed on Feb. 4, 1998, and provisional application No. 60/081,695, filed on Apr. 14, 1998.

(51) Int. Cl.[7] .................. C12N 15/12; C12N 15/63; C12N 1/21; C12N 5/16; C12N 1/16
(52) U.S. Cl. .................. 435/69.1; 435/69.4; 435/325; 435/358; 435/243; 435/252.33; 435/255.1; 435/320.1; 536/23.1; 536/23.5; 536/23.51
(58) Field of Search .................. 435/69.1, 69.4, 435/243, 320.1, 325, 358, 252.33, 255.1; 536/23.1, 23.5, 23.51

(56) References Cited

U.S. PATENT DOCUMENTS

| 5,408,040 A | 4/1995 | Grotendorst et al. |
| 5,536,637 A | 7/1996 | Jacobs |
| 5,585,087 A | 12/1996 | Lustig et al. |
| 6,100,060 A | 8/2000 | Barnes et al. |

FOREIGN PATENT DOCUMENTS

| EP | 307247 | 3/1989 |
| WO | WO 89/06692 | 7/1989 |
| WO | WO 95/17416 | 6/1995 |
| WO | WO 98/21236 | 5/1998 |
| WO | WO 98/25956 | 6/1998 |

OTHER PUBLICATIONS

*Baculovirus Expression Vectors: A Laboratory Manual,* O'Reilley et al., Oxford, Oxford University Press, (1994).
*Current Protocols in Molecular Biology,* Ausubel et al., Green Publishing Associates and Wiley Interscience, N.Y., (1989).
"Xenopus laevis: Practical uses in Cell and Molecular Biology" in *Methods in Cell Biology,* vol. 36, Kay and Peng, Eds, New York: Academic Press, (1991).
*Molecular Cloning: A Laboratory Manual,* Sambrook et al., New York, Cold Spring Harbor Laboratory Press, (1989).
*Normal Table of Xenopus laevis: (Daudin),* Nieuwkoop and Faber, Amsterdam: North–Holland (1967).
Adams, MD et al., "Initial assesment of human gene diversity and expression of patterns based upon 83 million nucleotides of cDNA sequence", *Nature,* 377:3–17 (Sep. 28, 1995).
Alitalo K, et al., "Oncogene amplification in tumor cells", *Adv. Cancer Res.,* 47:235–281 (1986).
Altschul, S. et al., "Local alignment statistics", *Methods in Enzymology,* 266:460–80 (1996).
Attisano L, et al., "TGF–beta receptors and actions", *Biochim. Biophys. Acta,* 1222(1):71–80 (1994).
Augenlicht, LH, et al., "Low–level c–myc amplification in human colonic carcinoma cell lines and tumors: a frequent, p53–independent mutation associated with improved outcome in a randomized multi–institutional trial", *Cancer Res.,* 57(9):1769–1775. (May 1, 1997).
Babic AM, et al., "CYR61, a product of a growth factor–inducible immediate early gene, promotes angiogenesis and tumor growth", *Proc Natl Acad Sci U S A,* 95(11):6355–6360 (May 26, 1998).
Baker NE, "Embryonic and imaginal requirements for wingless, a segment–polarity gene in Drosophila", *Dev Biol,* 125(1):96–108 (Jan. 1, 1988).
Baselga J, et al., "Phase II study of weekly intravenous recombinant humanized anti–p185HER2 monoclonal antibody in patients with HER2/neu–overexpressing metastatic breast cancer", *J Clin Oncol.,* 14(3):737–744 (Mar. 1996).
Baselga J, et al., "HER2 overexpression and paclitaxel sensitivity in breast cancer: therapeutic implications", *Oncology,* 11(3 Suppl 2):43–48 (Mar. 1997).
Bennet BD, et al., "Extracellular domain–IgG fusion proteins for three human natriuretic peptide receptors. Hormone pharmacology and application to solid phase screening of synthetic peptide antisera", *J Biol Chem,* 266(34):23060–23067 (Dec. 5, 1991).
Bishop JM, "Molecular themes in oncogenesis", *Cell,* 64(2):235–248 (Jan. 25, 1991).
Bolivar F, et al., "Construction and characterization of new cloning vehicles. II. A multipurpose cloning system", *Gene,* 2(2):95–113 (1997).
Boring CC, et al., "Cancer statistics, 1993", CA *Cancer J Clin,* 43(1):7–26. (Jan.–Feb. 1993).

(List continued on next page.)

*Primary Examiner*—Christine J. Saoud
(74) *Attorney, Agent, or Firm*—Diane L. Marschang

(57) ABSTRACT

Wnt-1-Induced Secreted Proteins (WISPs) are provided, whose genes are induced at least by Wnt-1. Also provided are nucleic acid molecules encoding those polypeptides, as well as vectors and host cells comprising those nucleic acid sequences, chimeric polypeptide molecules comprising the polypeptides fused to heterologous polypeptide sequences, antibodies which bind to the polypeptides, and methods for producing the polypeptides.

24 Claims, 49 Drawing Sheets

OTHER PUBLICATIONS

Bradbury JM, et al., "Wnt–4 expression induces a pregnancy–like growth pattern in reconstituted mammary glands in virgin mice", *Dev Biol,* 170(2):553–563 (Aug. 1995).

Bradley, RS et al., "Expression of Wnt–1 in PC–12 cells results in modulation of plakoglobin and E–cadherin and increased cellular adhesion", J. Cell Biol., 123(6, Pt. 2):1857–1865 (Dec. 1993).

Bradley RS, et al., "The proto–oncogene int–1 encodes a secreted protein associated with the extracellular matrix", *EMBO J,* 9(5):1569–1575 (May 1990).

Brown AM, et al., "A retrovirus vector expressing the putative mammary oncogene int–1 causes partial transformation of a mammary epithelial cell line", *Cell,* 46(7):1001–1009 (Sep. 26, 1986).

Brown JR, et al., "Characterization of the functional gene and several processed pseudogenes in the human triosephosphate isomerase gene family", *Mol Cell Biol,* 5(7):1694–1706 (Jul. 1985).

Cadigan KM, et al., "Wnt signaling: a common theme in animal development", *Genes Dev,* 11(24):3286–32305 (Dec. 15, 1997).

Christiansen JH, et al., "Murine Wnt–11 and Wnt–12 have temporally and spatially restricted expression patterns during embryonic development", *Mech Dev.,* 51 (2–3):341–350 (Jun. 1995).

Darzynkiewicz Z, et al., "Features of apoptotic cells measured by flow cytometry", *Cytometry,* 13(8):795–808 (1992).

Diatchenko L, et al., "Suppression subtractive hybridization: a method for generating differentially regulated or tissue–specific cDNA probes and libraries", *Proc Natl Acad Sci U S A,* 93(12):6025–6030 (Jun. 11, 1996).

Dzierzak E, et al., "Mouse embryonic hematopoiesis", *Trends Genet.,* 11(9):359–366 (Sep. 1995).

Fendly BM, et al., "Characterization of murine monoclonal antibodies reactive to either the human epidermal growth factor receptor or HER2/neu gene product", *Cancer Res.,* 50(5):1550–1558 (Mar. 1, 1990).

Fracker PJ, et al., "Protein and cell membrane iodinations with a sparingly soluble choloramide, 1,3,4, 6–tetrachloro–3a,6a–diphrenylgylcoluril", *Biochem Biophys Res Commun.,* 80(4):849–857 (Feb. 28, 1978).

Gavin BJ, et al., "Expression of multiple novel Wnt–1/int–1–related genes during fetal and adult mouse development", *Genes Dev.,* 4(12B):2319–2332 (Dec. 1990).

Godowski PJ, et al., "Characterizatkon of the human growth hormone receptor gene and demonstration of a partial gene deletion in two patients with Laron–type dwarfism", *Proc Natl Acad Sci U S A,* 86(20):8083–8087 (Oct. 1989).

Hashimoto Y, et al., "Expresison of the Elm 1 gene, a novel gene of the CCN (connective tissue growth factor, Cyr61/Cef10, and neuroblastoma overexpressed gene) family, suppresses In vivo tumor growth and metastasis of K–1735 murine melanoma cells", *J Exp Med.,* 187(3):289–296 (Feb. 2, 1998).

Herman MA, et al., "The Caenorhabditis elegans gene lin–44 controls the polarity of asymmetric cell divisions", *Development,* 120(5):1035–1047 (May 1994).

Holland, P. et al., "Gene duplications and the origins of vertebrate development", *Development—Supplement,:* 125–33 (1994).

Holmes WE, et al., "Structure and functional expression of a human interleukin–8 receptor", *Science,* 253(5025):1278–1280 (Sep. 13, 1991).

Hunter T, "Cooperation between oncogenes", *Cell,* 64(2):249–270 (Jan. 25, 1991).

Hynes NE, et al., "The biology of erbB–2/neu/HER–2 and its role in cancer", *Biochim Biophys Acta,* 1198(2–3):165–184 (Dec. 30, 1994).

Jue SF, et al., "The mouse Wnt–1 gene can act via a paracrine mechanism in transformation of mammary epithelial cells", *Mol Cell Biol.,* 12(1):321–328 (Jan. 1992).

Kanatsu M, et al., "In vitro analysis of epiblast tissue potency for hematopoietic cell differentiation", *Development,* 122(3):823–830 (Mar. 1996).

Kearney JF, et al., "A new mouse myeloma cell line that has lost immunoglobulin expression but permits the construction of antibody–secreting hybrid cell lines", *J Immunol.,* 123(4):1548–1550 (Oct. 1979).

Kim HS, et al., "Identification of a family of low–affinity insulin–like growth factor binding proteins (IGFBPs): characterization of connective tissue growth factor as a member of the IGFBP superfamily", *Proc Natl Acad Sci U S A,* 94(24):12981–12986 (Nov. 25, 1997).

Klein, R.D. et al., "Selection for genes encoding secreted proteins and receptors", *Proc Natl Acad Sci U S A.,* 93(14):7108–7113 (Jul. 9, 1996).

Klingensmith J, et al., "Signaling by wingless in Drosophila", *Dev Biol.,* 166(2):396–414 (Dec. 1994).

Lee FS, et al., "Insertional mutagenesis identifies a member of the Wnt gene family as a candidate oncogene in the mammary epithelium of int–2/Fgf–3 transgenic mice", *Proc Natl Acad Sci U S A,* 92(6):2268–2272 (Mar. 14, 1995).

Lu and Gillett, "An Optimized Protocol for In Situ Hybridization Using PCR–Generated 33P–Labeled Riboprobes", *Cell Vision,* 1(2) :169–176 (1994).

Maquat LE, et al., "Human triosephosphate isomerase cDNA and protein structure. Studies of triosephosphate isomerase deficiency in man", *J Biol Chem.,* 260(6):3748–3753 (Mar. 25, 1985).

Martinerie C, et al., "Regulation of nov by WT1: a potential role for nov in nephrogenesis", *Oncogene,* 12(7):1479–1492 (Apr. 4, 1996).

Martinerie C, et al, "Physical mapping of human loci homologous to the chicken nov proto–oncogene", *Oncogene,* 7(12):2529–2534 (Dec. 1992).

Martinerie C, et al., "Structural analysis of the human nov proto–oncogene and expression in Wilms tumor", *Oncogene,* 9(9):2729–2732 (Sep. 1994).

McMahon AP, et al., "The Wnt–1 (int–1) proto–oncogene is required for development of a large region of the mouse brain", *Cell,* 62(6):1073–1085 (Sep. 21, 1990).

McMahon, A., "Wnt Family of Developmental Regulators", *Trends in Genetics,* 8(7):236–242 (1992).

Meese E, et al., "Molecular mapping of the oncogene MYB and rearrangements in malignant melanoma", *Genes Chromosomes Cancer,* 1(1):88–94 (Sep. 1989).

Morata G, et al., "The development of wingless, a homeotic mutation of Drosophila", *Dev Biol.,* 56(2):227–240 (Apr. 1977).

Nusse R, et al., "Many tumors induced by the mouse mammary tumor virus contain a provirus integrated in the same region of the host genome", *Cell,* 31(1):99–109 (Nov. 1982).

Nusse R, et al., "Wnt genes", *Cell,* 1992 Jun. 26:69(7):1073–1087 (Jun. 26, 1992).

Oemar BS, et al., "Connective tissue growth factor. Friend or foe?", *Arterioscler Thromb Vasc Biol.,* 17(8):1483–1489 (Aug. 1997).

Olson DJ, et al., "Regulated expression of Wnt family members during proliferation of C57mg mammary cells", *Cell Growth Differ.,* 5(2):197–206 (Feb. 1994).

Papkoff J, et al., "Secreted int–1 protein is associated with the cell surface.", *Mol Cell Biol.,* 10(6):2723–2730 (Jun. 1990).

Parr BA, et al., "Dorsalizing signal Wnt–7a required for normal polarity of D–V and A–P axes of mouse limb", *Nature,* 374(6520):350–353 (Mar. 23, 1995).

Pennica D, et al., "WISP genes are members of the connective tissue growth factor family that are up–regulated in wnt–1–transformed cells and aberrantly expressed in human colon tumors", Proc Natl Acad Sci U S A., 95(25):14717–22 (Dec. 8, 1998).

Picker LJ, et al., "Control of lymphocyte recirculation in man. I. Differential Regulation of the peripheral lymph node homing receptor L–selection on T cells during the virgin to memory cell transition", *J Immunol.,* 150(3):1105–121 (Feb. 1, 1993).

Possee RD, et al., "Nucleotide sequence of the Autographa californica nuclear polyhedrosis 9.4 kbp EcoRI–I and –R (polyhedrin gene) region", *Virology,* 185(1):229–241 (Nov. 1991).

Price JE, et al., "Tumorigenicity and metastasis of human breast carcinoma cell lines in nude mice", *Cancer Res.,* 50(3):717–721 (Feb. 1, 1990).

Ravdin PM, et al., "the c–erbB–2 proto–oncogene as a prognostic and predictive marker in breast cancer: a paradgm for the development of other macromolecular markers—a review", *Gene,* 159(1):19–27 (Jun. 14, 1995).

Rijsewijk F, et al., "The Drosophila homolog of the mouse mammary oncogene int–1 is identical to the segment polarity gene wingless", *Cell,* 50(4):649–657 (Aug. 14, 1987).

Ruppert S, et al., "Cloning and expression of human TAFII250: a TBP–associated factor implicated in cell–cycle regulation", *Nature,* 362(6416):175–179 (Mar. 11, 1993).

Schwab M, et al., "Amplification of cellular oncogenes: a predictor of clinical outcome in human cancer", *Genes Chromosomes Cancer,* 1(3):181–193 (Jan. 1990).

Sigel, M., "Production of Antibodies by Inoculation into Lymph Nodes" in *Methods in Enzymology,* vol. 93 (New York: Academic Press, 1983).

Slamon DJ, et al., "Human breast cancer: correlation of relapse and survival with amplification of the HER–2/neu oncogene", *Science,* 235(4758):177–182 (Jan. 9, 1987).

Slamon DJ, et al., "Studies of the HER–2/neu proto–oncogene in human breast and ovarian cancer", *Science,* 244(4905):707–712 (May 12, 1989).

Sokol S, et al., "Injection Wnt RNA induces a complete body axis in Xenopus embryos", *Cell,* 67(4):741–752 (Nov. 15, 1991).

Sompayrac, L.M. et al., "Efficient Infection of Monkey Cells with DNA of Simian Virus 40", *Proc. Natl. Acad. Sci. U.S.A.,* 78(12):7575–7578 (Dec. 1981).

Stark K, et al., "Epithelial transformation of metanephric mesenchyme in the developing kidney regulated by Wnt–4", *Nature,* 372(6507):679–683 (Dec. 15, 1994).

Suva LJ, et al., "A parthyroid hormone–related protein implicated in malignant hypercalcemia: cloning and expression", *Science,* 237(4817):893–896 (Aug. 21, 1987).

Takada S, et al., "Wnt–3 a regulates somite and tailbud formation in the mouse embryo", *Genes Dev.,* 8(2):174–189 (Jan. 1994).

Takahashi E, et al., "Mapping of the MYC gene to band 8q24.12—q24.13 by R–banding and distal to fra(8)(q24.11), FRA8E, by fluorescence in situ hybridization", *Cytogenet Cell Genet.,* 57(2–3):109–111 (1991).

Thimmappaya, B. et al., "Adenovirus VAI RNA is Required for Efficient Translation of Viral mRNAs at late Times After Infection", *Cell,* 31(3 Pt 2):543–551 (Dec. 1982).

Thomas KR, et al., "Targeted disruption of the murine int–1 proto–oncogene resulting in severe abnormalities in mid-brain and cerebellar development", *Nature,* 346(6287):847–850 (Aug. 30, 1990).

van't Veer LJ, et al., "Molecular cloning and chromosomal assignment of the human homolog of int–1, a mouse gene implicated in mammary tumorigenesis" *Mol Cell Biol.,* 4(11):2532–2534 (Nov. 1984).

Wong GT, et al., "Differential transformation of mammary eipthelial cells by Wnt genes", *Mol Cell Biol.,* 14(9):6278–6286 (Sep. 1994).

Yamanaka Y, et al., "Inhibition of insulin receptor activation by insulin–like growth factor binding proteins", *J Biol Chem.,* 272(49):30729–30734 (Dec. 5, 1997).

Zhang RD, et al., "Relative malignant potential of human breast carcinoma cell lines established from pleural effusions and a brain metastasis", *Invasion Metastasis,* 11(4):204–215 (1991).

Zhang R, et al., "Identification of rCop–1, a new member of the CCN protein family, as a negative regulator for cell transformation", *Mol Cell Biol.,* 18(10):6131–6141 (Oct. 1998).

Zheng, S et al., "The induction of ret by Wnt–1 in PC12 cells is atypically dependent on continual Wnt–1 expression", *Oncogene,* 12(3):555–562 (Feb. 1, 1996).

Zheng, S et al., "The induction of Wnt–1 in PC12 cells results in modulation of plakoglobin and E–cadherin and increased cellular adhesion", J. Cell Biol., 123(6, pt 2):1857–1865 (Dec. 1993).

Zon et al., in Gluckman and Coulombel, ed., Colloque, INSERM, 235:17–22 (1995), presented at the Joint International Workshop on Foetal and Neonatal Hematopoiesis and Mechanism of Bone Marrow Failure, Paris, France, Apr. 3–6, 1995.

```
  1 TAACAAGGCN GTCCTGCTTG GAGAGGCATC CGCATCCTCT GGGCTGAGCC GTAGCTCCTG TGACGCTGAC TTCCAGGCAT GAGGTGGCTC CTGCCCTGGA
    ATTGTTCCGN CAGGACGAAC CTCTCCGTAG GCGTAGGAGA CCCGACTCGG CATCGAGGAC ACTGCGACTG AAGGTCCGTA CTCCACCGAG GACGGGACCT
  1                                                                                   M  R  W  L    L  P  W  T

101 CGCTGGCAGC CGTGGCCAGT CTGAGGGTGG GCAACATCCT GGCCACGGCC CTCTCTCCAA CCCCCACAAC AATGACCTTC ACCCCAGCAC CACTAGAGGA
    GCGACCGTCG GCACCGGTCA GACTCCCACC CGTTGTAGGA CCGGTGCCGG GAGAGAGGTT GGGGGTGTTG TTACTGGAAG TGGGGTCGTG GTGATCTCCT
  9  L  A  A   V  A  V    L  R  V  G   N  I  L    A  T  A   L  S  P  T   P  T  T   M  T  F    T  P  A  P   L  E  E

201 AACGACTACA CGCCCCGAAT TCTGCAAGTG GCCATGTGAG TGCCCACAAT CCCCACCCTG CTGCCCACTG GGCGTCAGCC TAATCACAGA TGGCTGTGAA
    TTGCTGATGT GCGGGGCTTA AGACGTTCAC CGGTACACTC ACGGGTGTTA GGGGTGGGAC GACGGGTGAC CCGCAGTCGG ATTAGTGTCT ACCGACACTT
 42  T  T  T   R  P  E  F   C  K  W    P  C  E    C  P  Q  S    P  P  R   C  P  L    G  V  S  L   I  T  D    G  C  E

301 TGCTGTAAGA TATGTGCCCA GCAGCTTGGG GACAACTGCA CAGAGGCTGC CATCTGTGAC CCACACCGGG GCCTCTACTG CGATTACAGT GGGGATCGCC
    ACGACATTCT ATACACGGGT CGTCGAACCC CTGTTGACGT GTCTCCGACG GTAGACACTG GGTGTGGCCC CGGAGATGAC GCTAATGTCA CCCCTAGCGG
 75  C  C  K  I   C  A  Q   Q  L  G    D  N  C  T   E  A  A    I  C  D    P  H  R  G   L  Y  C    D  Y  S    G  D  R  P

401 CGAGGTACGC AATAGGAGTG TGTGCACAGG GGGCTGTGTC CTGGATGGCG TACGCTACAC CAATGGCGAG TCCTTCCAAC CCAACTGCAG
    GCTCCATGCG TTATCCTCAC ACACGTGTCC CCCGACACAG GACCTACCGC ATGCGATGTG GTTACCGCTC AGGAAGGTTG GGTTGACGTC
109  R  Y  A    I  G  V    C  A  Q  V   G  C  V    L  D  G  V   R  Y  T    N  G  E    S  F  Q  P   N  C  R

501 GTACAACTGT ACCTGCATTG ATGGCACGGT GGGCTGCACA CCGCTGTGCC TAAGCCCCAG GCCCCCACGC CTCTGTGCC GCCAGCCCCG GCACGTGAGA
    CATGTTGACA TGGACGTAAC TACCGTGCCA CCCGACGTGT GGCGACACGG ATTCGGGGTC CGGGGGTGCG GAGACCACGG CGGTCGGGGC CGTGCACTCT
142  Y  N  C   T  C  I  D   G  T  V    G  C  T    P  L  C  L    S  P  R    P  P  R   L  W  C  R    Q  P  R    H  V  R

601 GTCCCTGGCC AGTGCTGTGA GCAGTGGGTG TGTGATGATG ACGCAAGGAG ACCACGCCAG ACTGCACTGT TGGACACCAG AGCCTTTGCA GCGTCAGGCG
    CAGGGACCGG TCACGACACT CGTCACCCAC ACACTACTAC TGCGTTCCTC TGGTGCGGTC TGACGTGACA ACCTGTGGTC TCGGAAACGT CGCAGTCCGC
175  V  P  G  Q   C  C  E    Q  W  V    C  D  D  D   A  R  R    P  R  Q    T  A  L  L   D  T  R    A  F  A    A  S  G  A

701 CCGTGGAGCA ACGGTATGAG AACTGCATAG CCTACACTAG TCCCTGGAGC CCCTGCTCTA CCACCTGTGG CCTAGGTATC TCCACTCGGA TCTCTAACGT
    GGCACCTCGT TGCCATACTC TTGACGTATC GGATGTGATC AGGGACCTCG GGGACGAGAT GGTGGACACC GGATCCATAG AGGTGAGCCT AGAGATTGCA
209  V  E  Q   R  Y  E    N  C  I  A    Y  T  S    P  W  S    P  C  S  T    T  C  G    L  G  I    S  T  R  I    S  N  V

801 CAATGCCCGG TGCTGGCCAG AGCAGGAAAG TCGTCCTTTC AACCTGCGGC TTGGACGCCC AGCGGAGACG CATGTGATGT GGACATCCAA CTACACATCA AGGCAGGAA TCTCTAACGT GAAATGCCTG
    GTTACGGGCC ACGACCGGTC TCGTCCTTTC AGCAGGAAAG TTGGACGCCC AACCTGCGGC AGCGGAGACG TACACTACA CCTGTAGGTT GATGTGTAGT TCCGTCCCTT CTTTACGGAC
242  N  A  R   C  W  P  E    Q  E  S    R  L  C    N  L  R  P    C  D  V    D  I  Q    L  H  I  K    A  G  K    K  C  L
```

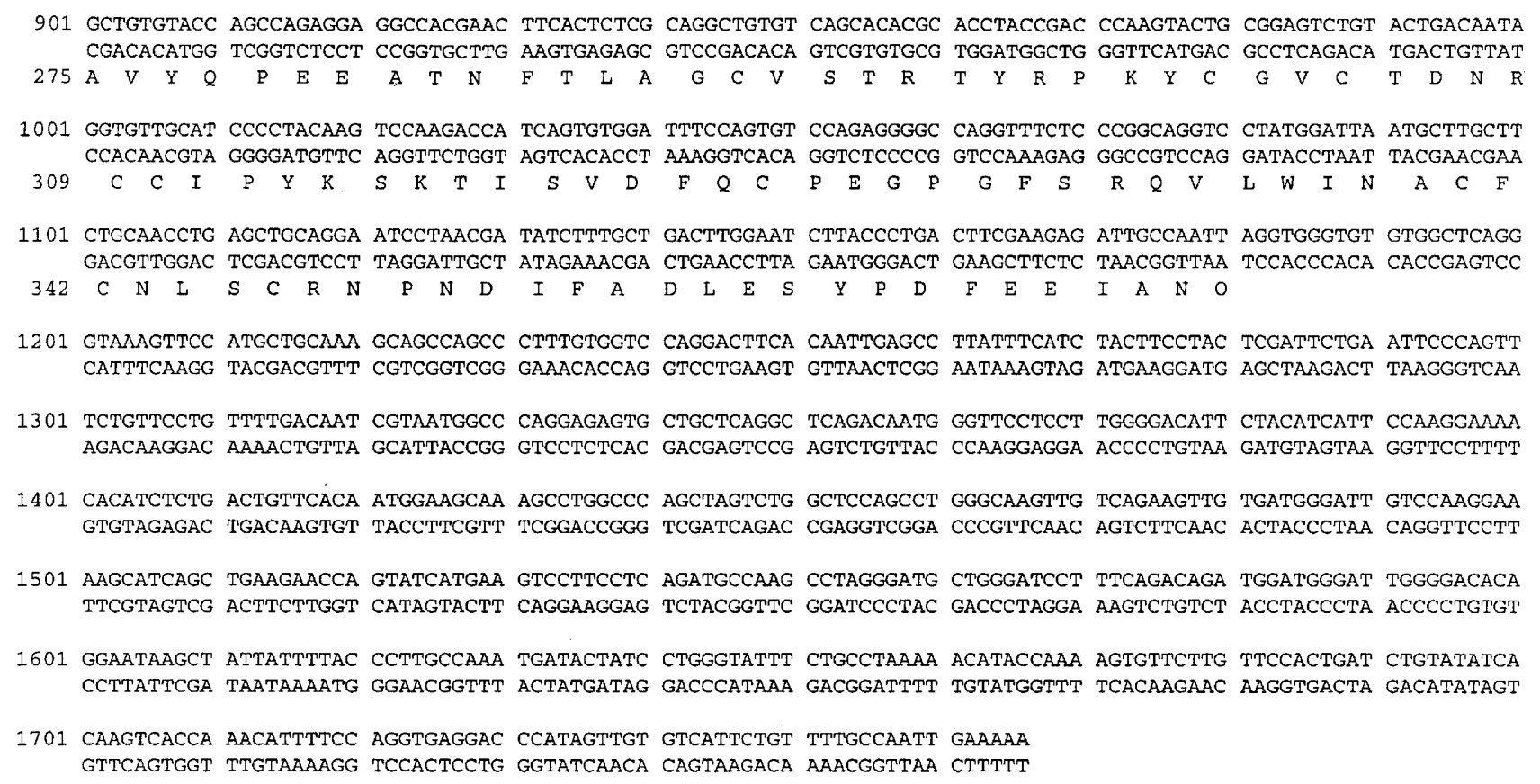

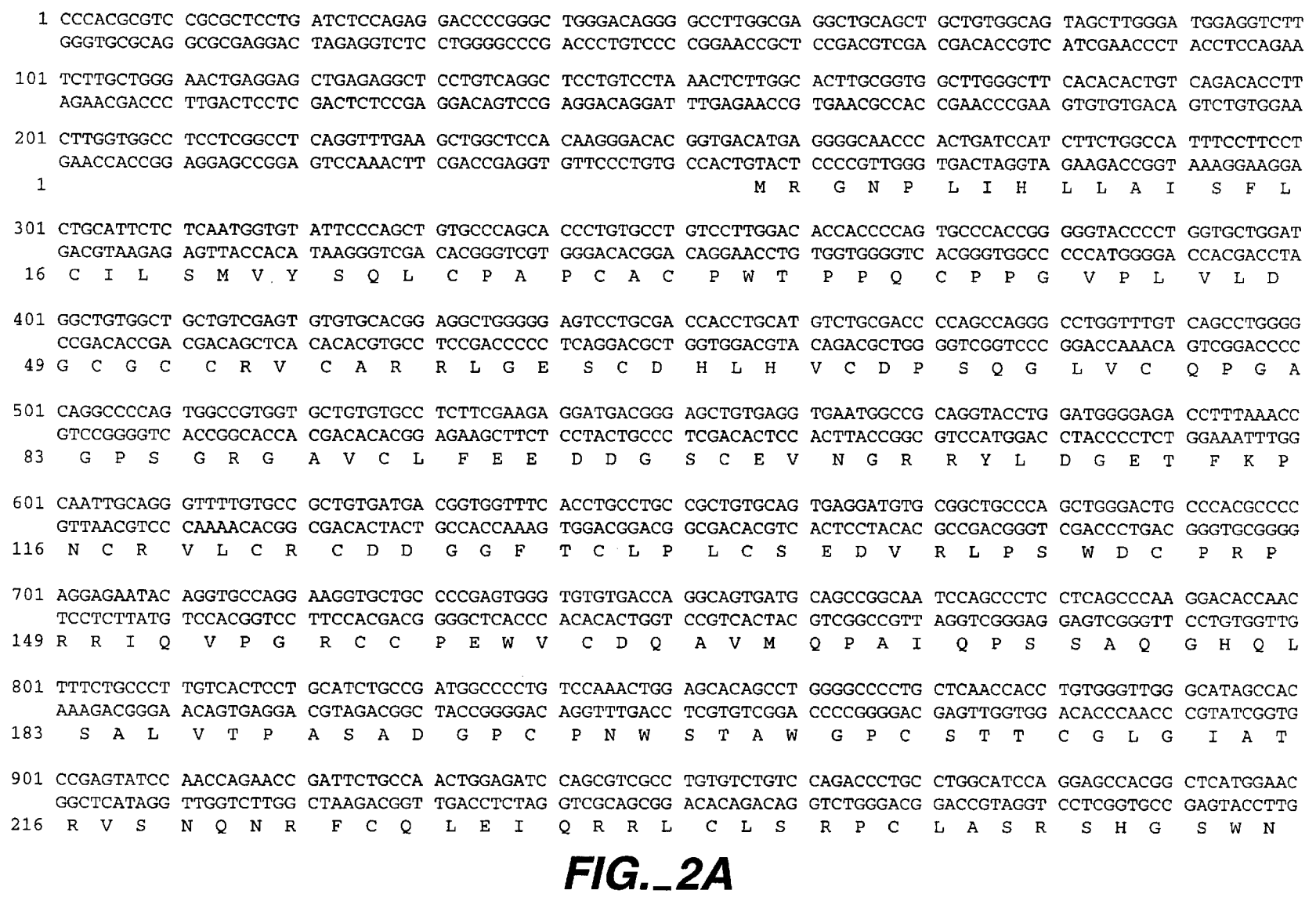

```
1001 AGTGCCTTCT AGAGCCATTG CGGGGATGTG GATACAGGGC CTGCCATTCT CAGCAAATGT CCCTAGGACC AGGCCCTGGA CTGATGGTAG ATGCCCCTCT
     TCACGGAAGA TCTCGGTAAC GCCCCTACAC CTATGTCCCG GACGGTAAGA GTCGTTTACA GGGATCCTGG TCCGGGACCT GACTACCATC TACGGGGAGA
 249  S  A  F  O

1101 CCATGCTCTT GGCTGCAGTT AACTGTCCTG GGTGGATTCA GTGTCCAGAG CCTCTGAGCG ATCCCTGCTC TGTCTGAGGT GGGGGAAGCA GGTGACCAGC
     GGTACGAGAA CCGACGTCAA TTGACAGGAC CCACCTAAGT CACAGGTCTC GGAGACTCGC TAGGGACGAG ACAGACTCCA CCCCCTTCGT CCACTGGTCG

1201 TCCATTTCTC TGGATTCTGA CCCAGGCTTC TGGGTTCTCC CTCAAAACTT CCCTGTATGA AAAGGACAAC CAAAAGGACC TTTAAAGCTA
     AGGTAAAGAG ACCTAAGACT GGGTCCGAAG ACCCAAGAGG GAGTTTTGAA GGGACATACT TTTCCTGTTG GTTTTCCTGG AAATTTCGAT

1301 AGCTGTACTG GGCAAGCCTG GCCACCATGC TGGGGATAGT GACAGTAATA GGTACCAGGC AGCAGATTGC CTGAAACATC CAGGTCCCTT CTTGGACTTC
     TCGACATGAC CCGTTCGGAC CGGTGGTACG ACCCCTATCA CTGTCATTAT CCATGGTCCG TCGTCTAACG GACTTTGTAG GTCCAGGGAA GAACCTGAAG

1401 TATGTGCTTG TCCCAAAGAT TATGGGTGAC CTTGTAAGTG TGCCTTTCCT GATCTGAGAA CACCCTGCCC GGCTGGGAAG AATTTTCTGG GAACATGAAG
     ATACACGAAC AGGGTTTCTA ATACCCACTG GAACATTCAC ACGGAAAGGA CTAGACTCTT GTGGGACGGG CCGACCCTTC TTAAAAGACC CTTGTACTTC

1501 AGATGGAATC ACACTATTCT TAAGAGCGTT TGCCAAGTCC AGGAACTTGA CCTTTGTATT TGTAAAAATA CACATCTCTT AAATGCTCAC AAAGCAAGAG
     TCTACCTTAG TGTGATAAGA ATTCTCGCAA ACGGTTCAGG TCCTTGAACT GGAAACATAA ACATTTTTAT GTGTAGAGAA TTTACGAGTG TTTCGTTCTC

1601 GCTCCACACT TCTGGCAGGC CAGGGCCTTT CTCTTCAGCA TGAGAGAGAC AAGGAACAGT AGAGTACCCT CCTCTGGAGG ACTGGCCCGG TCTGAATAA
     CGAGGTGTGA AGACCGTCCG GTCCCGGAAA GAGAAGTCGT ACTCTCTCTG TTCCTTGTCA TCTCATGGGA GGAGACCTCC TGACCGGGCC AGACCTTATT

1701 ACACCCAAAT CAAGTGTGGA AAAAAAAAAA AAAA
     TGTGGGTTTA GTTCACACCT TTTTTTTTTT TTTT
```

*FIG._2B*

```
  1 CCCACGCGTC CGCTGGGCCC AGCTCCCCCG AGAGGTGGTC GGATCCTCTG TGCCACTGAC GTCCAGGCAT GAGGTGGTTC
    GGGTGCGCAG GCGACCCGGG TCGAGGGGGC TCTCCACCAG CCTAGGAGAC ACGGTGACTG CAGGTCCGTA CTCCACCAAG
  1                                                                                M  R  W  F

101 CTGCCCTGGA CGCTGGCAGC AGTGACAGCA GCAGCCGCCA GCACCGTCCT GGCCACGGCC CTCTCTCCAG CATGGACTTT ACTCCAGCTC
    GACGGGACCT GCGACCGTCG TCACTGTCGT CGTCGGCGGT CGTGGCAGGA CCGGTGCCGG GAGAGAGGTC GTACCTGAAA TGAGGTCGAG
  5  L  P  W  T  L  A  A  V  T  A  A  A  S  T  V  L  A  T  A  L  S  P  A  M  D  F  T  P  A  P

201 CACTGGAGGA CACCTCCTCA CGCCCCCAAT TCTGCAAGTG GCCATGTGAG TGCCCGCTTG CCCCACCCCG CTGCCCGCTG TCATCACAGA
    GTGACCTCCT GTGGAGGAGT GCGGGGGTTA AGACGTTCAC CGGTACACTC ACGGGCGAAC GGGGTGGGGC GACGGGCGAC AGTAGTGTCT
 39  L  E  D  T  S  S  R  P  Q  F  C  K  W  P  C  E  C  P  P  S  P  P  R  C  P  L  G  V  S  L  I  T  D

301 TGGCTGTGAG GCAGCTTGGG GACAACTGCA CGGAGGCTGC CATCTGTGAC CTGGATGGGT GTGGCTACAA CAACGGCCAG TCCTTCCAGC
    ACGACACTC ACGACATTCT ACGACGAGT GCTCCGACG GTAGACACTG GACCTACCCA CACCGATGTT GTTGCCGGTC AGGAAGGTCG
 72  G  C  E  C  C  K  M  C  A  Q  L  G  D  N  C  T  E  A  A  I  C  D  L  D  G  C  G  Y  N  N  G  Q  S  F  Q  P

401 GGGGACCGCC CGAGTACGCC AATAGGAGTG TGTGCACAGG ACGGCTGCGTC TGGATGGGG TGGCTACACAA CCCGACGATT CCGAGTGCC CCCACCCGCG
    CCCCTGGCCG GCTCCATGCG TTATCCTCAC ACACGTGTCC TGACGACACT GACCTACCCA ACCGATGTT GTTGCCGGTC GGCTGCTGCC GGGGTGGGCGC
105  G  D  R  P  R  Y  A  I  G  V  C  A  Q  V  G  V  G  C  V  L  D  G  V  R  Y  N  G  Q  S  F  Q  P

501 CTAACTGCAA GTACAACTGC ACGTGCATCG ACGGCGCGGT GGGCGTGCACA CCACTGTGCC TCCGAGTGCG CCCCCCGCGT GGGGGCGCG GGGTGGGCGC
    GATTGACGTT CATGTTGACG TGCACGTAGC TGCCGCGCCA CCCGACGTGT GGTGACACGG AGGCTCACGC GGGGGCGCA CCCGCCGCG CCACCCGCG
139  N  C  K  Y  N  C  T  C  I  D  G  A  V  G  C  T  P  L  C  L  R  V  R  P  P  R  L  W  C  P  H  P  R

601 GCGCGTGAGC ACTGCTGTGA GCAGTGGGTA TGTGAGGACG ACACTCCTGC ACGCCAAGAG GCCACGCAAG ACCGCACCC GTGACACAGG AGCCTTCGAT
    CGCGCACTCG TGACGACACT CGTCACCCAT ACACTCCTGC TGTGAGGACG TGCGGTTCTC TGCGGTTGCC TGGCGTGTCC CACTGTGTCC TCGGAAGCTA
172  R  V  S  I  P  G  H  C  C  E  Q  W  V  C  E  D  D  A  K  R  P  R  K  T  A  P  R  D  T  G  A  F  D

701 GCTGTGGGGTG AGGTGGAGGC ATGGCACAGG AACTGCATAG CCTACACAAG CCCCTGGAGC CCTTGCTCA CCAGCTGCGG CCTGGGGGTG TCCACTCGGA
    CGACACCCAC TCCACCCTCG TACCGTGTCC TTGACGTATC GGATGTGTTC GGGGACCTCG GGAACGAGCT GGTCGACGCC GGACCCCCAC AGGTGAGCCT
205  A  V  G  E  V  E  A  W  H  R  N  C  I  A  Y  T  S  P  W  S  P  C  S  T  S  C  G  L  G  V  S  T  R  I

801 TCTCCAATGT TAACGCCCAA TGCTGGCCTG AGCAAGAGAG CCGCCTCTGC AACTTGCGGC CATGCGATGT GGACATCCAT ACACTCATTA AGGCAGGGAA
    AGAGGTTACA ATTGCGGGTC ACGACCGGAC TCGTTCTCTC GGCGGAGACG TTGAACGCCG GTACGCTACA CCTGTAGGTA TGTGAGTAAT TCCGTCCCTT
239  S  N  V  N  A  Q  C  W  P  E  Q  E  S  R  L  C  N  L  R  P  C  D  V  D  I  H  T  L  I  K  A  G  K
```

*FIG._3A*

```
 901 GAAGTGTCTG GCTGTGTACC AGCCAGAGGC ATCCATGAAC TTCACACTTG CGGGCTGCAT CAGCACACGC TCCTATCAAC CCAAGTACTG TGGAGTTTGC
     CTTCACAGAC CGACACATGG TCGGTCTCCG TAGGTACTTG AAGTGTGAAC GCCCGACGTA GTCGTGTGCG AGGATAGTTG GGTTCATGAC ACCTCAAACG
 272   K  C  L    A  V  Y  Q    P  E  A    S  M  N    F  T  L  A    G  C  I    S  T  R    S  Y  Q  P    K  Y  C    G  V  C

1001 ATGGACAATA GGTGCTGCAT CCCCTACAAG TCTAAGACTA TCGACGTGTC CTTCCAGTGT CCTGATGGGC TTGGCTTCTC CCGCCAGGTC CTATGGATTA
     TACCTGTTAT CCACGACGTA GGGGATGTTC AGATTCTGAT AGCTGCACAG GAAGGTCACA GGACTACCCG AACCGAAGAG GGCGGTCCAG GATACCTAAT
 305   M  D  N  R    C  C  I    P  Y  K    S  K  T  I    D  V  S    F  Q  C    P  D  G  L    G  F  S    R  Q  V    L  W  I  N

1101 ATGCCTGCTT CTGTAACCTG AGCTGTAGGA CATCTTTGCT GACTTGGAAT CCTACCCTGA CTTCTCAGAA ATTGCCAACT AGGCAGGCAC
     TACGGACGAA GACATTGGAC TCGACATCCT GTAGAAACGA CTGAACCTTA GGATGGGACT GAAGAGTCTT TAACGGTTGA TCCGTCCGTG
 339   A  C  F    C  N  L    S  C  R  N    P  N  D    I  F  A    D  L  E  S    Y  P  D    F  S  E    I  A  N  Q

1201 AAATCTTGGG TCTTGGGGAC TAACCCAATG CCTGTGAAGC AGTCAGCCCT TATGGCCAAT AACTTTCAC CAATGAGCCT TAGTTACCCT GATCTGGACC
     TTTAGAACCC AGAACCCCTG ATTGGGTTAC GGACACTTCG TCAGTCGGGA ATACCGGTTA TTGAAAAGTG GTTACTCGGA ATCAATGGGA CTAGACCTGG
                                                                        F  S  E    I  A  N  Q

1301 CTTGGCCTCC ATTTCTGTCT CTAACCATTC AAATGACGCC TGATGGTGCT GCTCAGGCCC ATGCTATGAG TTTTCTCCTT GATATCATTC AGCATCTACT
     GAACCGGAGG TAAAGACAGA GATTGGTAAG TTTACTGCGG ACTACCACGA CGAGTCCGGG TACGATACTC AAAAGAGAA CTATAGTAAG TCGTAGATGA

1401 CTAAAGAAAA ATGCCTGTCT CTAGCTGTTC TGGACTACAC CCAAGCCTTT TTCTTTAGAT CCAGCCTTGA ATGCTATGAG AAGACTCACT CCTAAATCCC
     GATTCTTTT TACGGACAGA GATCGACAAG ACCTGATGTG GGTTCGGAAA AAGAAATCTA GGTCGGAACT TACGATACTC TTCTGAGAAA GGATTTAGGG

1501 AAGAAATGGA ATCAGGTAGA ATATTCTATT ATTTGGAGCC CTTTAATAAT CACTAATTTC TTCTTTAGAT GCCAAAACCAC AAGACTCTTT GGGTCCATTC AGATGAATAG ATGGAATTTG
     TTCTTTACCT TAGTCCATCT TATTAGATAA TAAACCTCGG GAAATTATTA GTGATTAAAG AAGAAATCTA CGGTTTGGTG TTCTGAGAAA CCCAGGTAAG TCTACTTATC TACCTAAAC

1601 GAACAATAGA ATCAGGTAGA ATATTCTATT ATTTGGAGCC TGCCAAGAGG TACTGTAATG TACTGTAATG GGTAATTCTG ACGTCAGCGC ACCAAAACTA TCCTGATTCC AAATATGTAT
     CTTGTTATCT TAGTCCATCT TATTAGATAA TAAACCTCGG ACGGTTCTCC ATGACATTAC CCATTAAGAC TGCAGTGCG TGGTTTTGAT AGGACTAAGG TTTATACATA

1701 GCACCTCAAG GTCATCAAAC ATTTGCCAAG TGAGTTGAAT AGTTGCTTAA TAGGTTTGTC CCAGTCAGAA ATAAAATTTG ATAAACATTC CTGTTGATGG ATTGTTGAGG
     CGTGGAGTTC CAGTAGTTTG TAAACGGTTC ACTCAACTTA TCAACGAATT TCAAGACTCT TGGTCAGTCT TATTTTAAAC TATTTGTAAG GACAACTGG TAACAACTCC

1801 TTAAGTTTCT CTTCACCCCT ACACTGTGAA GGGTACAGAT TAGGTTTGTC ATCCAAACAG ATAAAATTTG ATAAACATTC CTGTTGATGG GAAAAGCCCC
     AATTCAAAGA GAAGTGGGGA TGTGACACTT CCCATGTCTA ATCCAAACAG GGTCAGTCTT TATTTTAAAC TATTTGTAAG GACAACTACC CTTTTCGGGG

1901 CAGTTAATAC TCCAGAGACA GGGAAAGGTC AGCCCATTTC AGAAGGACCA ATTGACTCTC ACACTGAATC AGCTGCTGAC TGGCAGGGCT TTGGGCAGTT
     GTCAATTATG AGGTCTCTGT CCCTTTCCAG TCGGGTAAAG TCTTCCTGGT TAACTGAGAG TGTGACTTAG TCGACGACTG ACCGTCCCGA AACCCGTCAA
```

FIG._3B

```
2001 GGCCAGGCTC TTCCTTGAAT CTTCTCCCTT GTCCTGCTTG GGTTCATAGG AATTGGTAAG GCCTCTGGAC TGGCCTGTCT GGCCCCTGAG AGTGGTGCCC
     CCGGTCCGAG AAGGAACTTA GAAGAGGGAA CAGGACGAAC CCAAGTATCC TTAACCATTC CGGAGACCTG ACCGGACACA CCGGGGACTC TCACCACGGG

2101 TGGAACACTC CTCTACTCTT ACAGAGCCTT GAGAGACCCA ATGCCAGACC CACTGAAATG ACCAAGACAG GTTCAGGTAG GGGTGTGGGT
     ACCTTGTGAG GAGATGAGAA TGTCTCGGAA CTCTCTGGGT TACGGTCTGG GTGACTTTAC TGGTTCTGTC CAAGTCCATC CCCACACCCA

2201 CAAACCAAGA AGTGGGTGCC CTTGGTAGCA GCCTGGGGTG ACCTCTAGAG CTGGAGGCTG TGGGACTCCA GGGGCCCCCG TGTTCAGGAC ACATCTATTG
     GTTTGGTTCT TCACCCACGG GAACCATCGT CGGACCCCAC TGGAGATCTC GACCTCCGAC ACCCTGAGGT CCCCGGGGGC ACAAGTCCTG TGTAGATAAC

2301 CAGAGACTCA TTTCACAGCC CTGACCAAAT GGCCAGTTTT CTGGTAGGAA GATGGAGGTT TACCAGTTGT TTAGAAACAG AAATAGACTT
     GTCTCTGAGT AAAGTGTCGG AAAGCAAGAC GACTGGTTTA CCGGTCAAAA GACCATCCTT CTACCTCCAA ATGGTCAACA AATCTTTGTC TTTATCTGAA

2401 AATAAAGGTT TAAAGCTGAA GAGGTTGAAG CTAAAAGGAA AAGGTGTTG TTAATGAATA ATTTATTGTA TTAGGAAAAT ATAATATTTA
     TTATTTCCAA ATTTCGACTT CTCCAACTTC GATTTTCCTT TTCCAACACA AATTACTTAT TAAATAACAT AATCCTTTTA TATTATAAAT

2501 CTGTTAGAAT TCTTTTATTT AGGGCCTTTT CTGTGCCAGA CATTGCTCTC AGTGCTTTGC TCACTGAATC TTCACGACAA TGTTGAGAAG
     GACAATCTTA AGAAAATAAA TCCCGGAAAA GACACGGTCT GTAACGAGAG TCACGAAACG AGTGACTTAG AAGTGCTGTT ACAACTCTTC

2601 TTCCCATTAT TATTTCTGTT CTTACAAATG TGAAACGGAA GCTCATAGAG GTGAGAAAAC TCAACCAGAG TCACCCAGTT GGTGACTGGG AAAGTTAGGA
     AAGGTAATA ATAAAGACAA GAATGTTTAC ACTTTGCCTT CGAGTATCTC CACTCTTTTG AGTTGGTCTC AGTGGGTCAA CCACTGACCC TTTCAATCCT

2701 TTTCAGATCGA AATTGGACTG TCTTTATAAC CCCCTGTTTT TAGAGCTTCC AAATGTGTCA GAATAGGAAA ACATTGCAAT AAATGGCTTG
     AAGTCTAGCT TTAACCTGAC AGAAATATTG GGGACAAAA ATCTCGAAGG TTTACACAGT CTTATCCTTT TGTAACGTTA TTTACCGAAC

2801 ATTTTTTAAA AAAAAAAAA AAAAAAAAAA
     TAAAAAATTT TTTTTTTTTT TTTTTTTTTT
```

FIG._3C

```
  1 CCCACGCGTC CGGCTGGGGA CATGAGAGGC ACACCGAAGA CCCACCTCCT GGCCTTCTCC TCCTCTCAAA GGTGCGTACC CAGCTGTGCC
    GGGTGCGCAG GCCGACCCCT GTACTCTCCG TGTGGCTTCT GGGTGGAGGA CCGGAAGAGG AGGAGACGG AGGAGAGTT CCACGCATGG GTCGACACGG
  1                                              M  R  G    T  P  K  T    H  L  L    A  F  S    L  L  C  L    L  S  K    V  R  T    Q  L  C  P

101 CGACACCATG TACCTGCCCC TGGCCACCTC CCCGATGCCC GCTGGGAGTA CCCCTGGTGC TGGATGGCTG TGGCTGCTGC CGGGTATGTG CACGGCGGCT
    GCTGTGGTAC ATGGACGGGG ACCGGTGGAG GGGCTACGGG CGACCCTCAT GGGGACCACG ACCTACCGAC ACCGACGACG GCCCATACAC GTGCCGCCGA
 28  T  P  C    T  C  P    W  P  P  P    R  C  P    L  G  V    P  L  V  L    D  G  C    G  C  C    R  V  C  A    R  R  L

201 GGGGGAGCCC TGCGACCAAC TCCACGTCTG CGACGCCAGC CAGGGCCTGG TCTGCCAGCC CGGGGCCAGGA CCCGGTGGCC GGGGGGCCCT GTGCCTCTTG
    CCCCCTCGGG ACGCTGGTTG AGGTGCAGAC GCTGCGGTCG GTCCCGGACC AGACGGTCGG GCCCCGGTCCT GGGCCACCGG CCCCCGGGA CACGGAGAAC
 61  G  E  P    C  D  Q  L    H  V  C    D  A  S    Q  G  L  V    C  Q  P    G  A  G    P  G  G  R    G  A  L    C  L  L

301 GCAGAGGACG ACAGCAGCTG TGAGGTGAAC GGCCGCCTGT ATCGGGAAGG GGAGACCTTC CAGCCCCACT GCAGCATCCG CTGCCGCTGC GAGGACGGCG
    CGTCTCCTGC TGTCGTCGAC ACTCCACTTG CCGGCGGACA TAGCCCTTCC CCTCTGGAAG GTCGGGGTGA CGTCGTAGGC GACGGCGACG CTCCTGCCGC
 94  A  E  D  D    S  S  C    E  V  N    G  R  L  Y    R  E  G    E  T  F    Q  P  H  C    S  I  R    C  R  C    E  D  G  G

401 GCTTCACCTG CGTGCCGCTG TGCAGCGAGG ATGTGCGGCT GCCCAGCTGG GACTGCCCCC ACCCCAGGAG GGTCGAGGTC CTGGGCAAGT GCTGCCCTGA
    CGAAGTGGAC GCACGGCGAC ACGTCGCTCC TACACGCCGA CGGGTCGACC CTGACGGGGG TGGGGTCCTC CCAGCTCCAG GACCCGTTCA CGACGGGACT
128  F  T  C    V  P  L    C  S  E  D    V  R  L    P  S  W    D  C  P  H    P  R  R    V  E  V    L  G  K  C    C  P  E

501 GTGGGTGTGC GGCCAAGGAG GGGGACTGGG GACCCAGCCC CTTCCAGCCC AAGGACCCCA GTTTTCTGGC CCCTGCCCCC TGGTGTCCCC
    CACCCACACG CCGGTTCCTC CCCCTGACCC CTGGGTCGGG GAAGGTCGGG TTCCTGGGGT CAAAAGACCG GGGACGGGGG ACCACAGGGG
161  W  V  C    G  Q  G  G    G  L  G    D  P  S    L  P  A  Q    G  P  Q    F  S  G    L  V  S  S    L  P  P    G  V  P

601 TGCCCAGAAT GGAGCACGGC CTGGGGACCC TGCTCGACCA CCTGTGGGCT GGGCATGGCC ACCCGGGGTGT CCAACCAGAA GGTTGGTCTT CCGCTTCTCGC CGACTGGAGA
    ACGGGTCTTA CCTCGTGCCG GACCCCTGGG ACGACGTGGT GGACACCCGA CCCGTACCGG TGGGCCACA AGTTGGTCTT CCAACCAGAA CCGGAAGACG GCTGACTCT
194  C  P  E  W    S  T  A    W  G  P    C  S  T  T    C  G  L    G  M  A    T  R  V  S    N  Q  N    R  F  C    R  L  E  T

701 CCCAGCGCCG CCTGTGCCTG TCCAGGCCCT CAGGGGTCGG AGTCCAGGGC GTCCCCAGCC CAGGGGTCGG AGTCCACAAA ACAGTGCCTT CTAGAGCCGG GCTGGGAATG GGGACACGGT
    GGGTCGCGGC GGACACGGAC AGGTCCGGGA GTCCCCAGCC CAGGGGTCGG CAGGGGTCGC ACACCCGGA TGTCACGGAA GATCTCGGCC CGACCCTTAC CCCTGTGCCA
228  Q  R  R    L  C  L    S  R  P  C    P  P  S    R  G  R    S  P  Q  N    S  A  F    O

801 GTCCACCATC CCCAGCTGGT GGCCCTGTGC CTGGGCCTG CTGGGCCTGT GGCTGATGGA AGATGGTCCG TGCCCAGGCC CTTGGCTGCA GGCAACACTT TAGCTTGGGT
    CAGGTGGTAG GGGTCGACCA CCGGGACACG GACCGGGAC GACCCGGGAC CCGACTACCT TCTACCAGGC ACGGGTCCGG GAACCGACGT CCGTTGTGAA ATCGAACCCA
```

FIG._4A

```
 901  CCACCATGCA GAACACCAAT ATTAACACGC TGCCTGGTCT CGAGGTATGG CAGAGGTGCA AGACCTAGTC CCCTTTCCTC TAACTCACTG
      GGTGGTACGT CTTGTGGTTA TAATTGTGCG ACGGACCAGA CAGACCTAGG GCTCCATACC GTCTCCACGT TCTGGATCAG GGGAAAGGAG ATTGAGTGAC
1001  CCTAGGAGGC TGGCCAAGGT GTCCAGGGTC CTCTAGCCCA CTCCCTGCCT ACACACACAG CCTATATCAA ACATGCACAC GGGCGAGCTT TCTCTCCGAC
      GGATCCTCCG ACCGGTTCCA CAGGTCCCAG GAGATCGGGT GAGGGACGGA TGTGTGTGTC GGATATAGTT TGTACGTGTG CCCGCTCGAA AGAGAGGCTG
1101  TTCCCCTGGG CAAGAGATGG GACAAGCAGT CCCTTAATAT TGAGGCTGCA GCAGGTGCTG GGCTGGACTG GCCATTTTTC TGGGGGTAGG ATGAAGAGAA
      AAGGGGACCC GTTCTCGTCA CTGTTCGTCA GGGAATTATA ACTCCGACGT CGTCCACGAC CCGACCTGAC CGGTAAAAAG ACCCCATCC TACTTCTCTT
1201  GGCACACAGA GATTCTGGAT CTCCCTGCTGC GTTTGTAAAA TTGTTCCTGA ATACAAGCCT ATGCGTGAAA AAAAAAAAAA AAA
      CCGTGTGTCT CTAAGACCTA GAGGACGACG GAAAAGACCT CAAACATTTT AACAAGGACT TATGTTCGGA TACGCACTTT TTTTTTTTTT TTT
```

FIG._4B

```
1    5'-CTGCAGGGGACATGAGAGGCACACCGAAGACCCACCTCCTGGCCTTCTC
51      CCTCCTCTGCCTCCTCTCAAAGGTGCGTACCCAGCTGTGCCCGACACCAT
101     GTACCTGCCCCTGGCCACCTCCCCGATGCCCGCTGGGAGTACCCCTGGTG
151     GTGGATGGCTGTGGCTGCTGCCGGGTATGTGCACGGCGGCTGGGGAGCC
201     CTGCGACCAACTCCACGTCTGCGACGCCAGCCAGGGCCTGGTCTGCCAGC
251     CCGGGGCAGGACCCGGTGGCCGGGGGCCCTGTGCCTCTTGGCAGAGGAC
301     GACAGCAGCTGTGAGGTGAACGGCCGCCTGTATCGGGAAGGGGAGACCTT
351     CCAGCCCCACTGCAGCATCCGCTGCCGCTGCGAGGACGGCGGCTTCACCT
401     GCGTGCCGCTGTGCAGCGAGGATGTGCGGCTGCCCAGCTGGGACTGCCCC
451     CACCCCAGGAGGGTCGAGGTCCTGGGCAAGTGCTGCCCTGAGTGGGTGTG
501     CGGCCAAGGAGGGGGACTGGGGACCAGCCCTTCCAGCCCAAGGACCCC
551     AGTTTTCTGGCCTTGTCTCTTCCCTGCCCCTGGTGTCCCTGCCCAGAA
601     TGGAGCACGGCCTGGGGACCCTGCTCGACCACCTGTGGGCTGGGCATGGC
651     CACCCGGGTGTCCAACCAGAACCGCTTCTGCCGACTGGAGACCCAGCGCC
701     GCCTGTGCCTGTCCAGGCCCTGCCCACCCTCCAGGGGTCGCAGTCCACAA
751     AACAGTGCCTTCTAGAGCCGGGCTGGGAATGGGGACACGGTGTCCACCAT
801     CCCCAGCTGGTGGCCCTGTGCCTGGGCCCTGGGCTGATGGAAGA
```

FIG._5

```
  1  GTGGGGTTTGCAGAGAGAGACAGGGGGAGCTTTGTGTACCCGGAGCAATGAACAAGCGGCGACTTCTCTACC
     CACCCCAAACGTCTCTCTGTCCCCTGAAACACATGGGCCTCGTTACTTGTTCGCCGCTGAAGAGATGG
  1                                             M  N  K  R  R  L  L  Y  P

71  CCTCAGGGTGGCTCCACGGTCCAGCGACA
     GGAGTCCCACCGAGGTGCCAGGGTCGCTGT
 10   S  G  W  L  H  G  P  S  D  M

101  TGCAGGGGCTCCTCTTCTCCACTCTTCTGCTTGCTGGCCTGGCACAGTTCTGCTGCAGGTACAGGGCAC
     ACGTCCCCGAGGAGAAGAGAGGTGAGAAGACGAACGACCGGACCGTGTCAAGACGACGTCCATGTCCCGTG
 20   Q  G  L  L  F  S  T  L  L  L  A  G  L  A  Q  F  C  C  R  V  Q  G  T

171  TGGACCATTAGATACAACACCTGAAGGAAG
     ACCTGGTAATCTATGTTGTGGACTTCCTTC
 43   G  P  L  D  T  T  P  E  G  R

201  GCCTGGAGAAGTGTCAGATGCCACCTCAGCGTAAACACGTTTTGTCACTGGCCCTGCAAATGCCCTCAGCAG
     CGGACCTCTTCACAGTCTACGTGGAGTCGCATTTGTCAAAACAGTGACCGGGACGTTTACGGGAGTCGTC
 53   P  G  E  V  S  D  A  P  Q  R  K  Q  F  C  H  W  P  C  K  C  P  Q  Q

271  AAGCCCCGTGCCCTCCTGGAGTGAGCCTG
     TTCGGGGCAACGGGAGACCTCACTCGGAC
 76   K  P  R  C  P  P  G  V  S  L

301  GTGAGAGATGGCTGTGGATGCTGTAAAATCTGTGCCAAGCAACCAGGGAGAAATCTGCAATGAAGCTGACC
     CACTCTCTACCGACACTACGACATTTAGACACGGTTCGTTGGTCCCCTTTAGACGTTACTTCGACTGG
 86   V  R  D  G  C  G  C  C  K  I  C  A  K  Q  P  G  E  I  C  N  E  A  D  L

371  TCTGTGACCCACCACAAAGGCTGTATTGTG
     AGACACTGGGTGTGTTTCCGACATAACAC
110   C  D  P  H  K  G  L  Y  C  D

401  ACTACTCAGTAGACAGGCCTAGGTACGAGACTGGAGTGTGTGCATACCTTTGTAGCTGTTGGGTGCGAGTT
     TGATGAGTCATCTGTCCGGATCCATGCTCTGACCTCACACGTATGGAACATCGACATCGACAACCCACGCTCAA
120   Y  S  V  D  R  P  R  Y  E  T  G  V  C  A  Y  L  V  A  V  G  C  E  F

471  CAACCAGGTACATTATCATAATGGCCAAGT
     GTTGGTCCATGTAATAGTATTACCGGTTCA
143   N  Q  V  H  Y  H  N  G  Q  V
```

FIG._6A

```
501  GTTTCAGCCCAACCCCTTGTTCAGCTGCCTCTGTGTTGAGTGGGGCCATTGGATGCACACCTCTGTTCATA
     CAAAGTCGGGTTGGGGAACAAGTCGACGGAGACACACTCACCCGTAACCTACGTGTGGAGACAAGTAT
153  F  Q  P  N  P  L  F  S  C  L  C  V  S  G  A  I  G  C  T  P  L  F  I

571  CCAAAGCTGGCTGCGACCGACCGTCAGTGACGAGACCT
     GGTTTCGACCGACGCTGGCAGTCACTGCTCTGA
176  P  K  L  A  G  S  H  C  S  G

601  GCTAAAGGTGGAAAGAAGTCTGATCAGTCAGACTAGTCAGTTTGACATCGGACCTTGGTAATGATGTCGTCGAAAGTTGTT
     CGATTTCCACCTTTCTTCAGACTAGTCAGTTTGACATCGGACCTTGGTAATGATGTCGTCGAAAGTTGTT
186  A  K  G  G  K  K  S  D  Q  S  N  C  S  L  E  P  L  L  Q  Q  L  S  T  S

671  GCTACAAAACAATGCCAGCTTATAGAGATC
     CGATGTTTTGTTACGGTCGAATATCTCTAG
210  Y  K  T  M  P  A  Y  R  D  L

701  TCCCACTTATTTGGAAAAAAAATGTCTTGTGCAAGCAACAAAATGGACTCCCTGCTCCAGAACATGTGG
     AGGGTGAATAAACCTTTTTTTTACAGAACACGTTCGTTGTTTACCTGAGGGACGAGGTCTTGTACACC
220  P  L  I  W  K  K  C  L  V  Q  A  T  K  W  T  P  C  S  R  T  C  G

771  GATGGGAATATCTAACAGGGTGACCAATGA
     CTACCCTTATAGATTGTCCCACTGGTTACT
243  M  G  I  S  N  R  V  T  N  E

801  AAACAGCAACTGTGAAATGAGAAGAGAAAAGACTGTGTTACATTCAGCCTTGCGACAGCAATATATTA
     TTTGTCGTTGACACTTTACTCTTCTTTTCTGACACAATGTAAGTCGGAACGCTGTCGTTATATAAT
253  N  S  N  C  E  M  R  K  E  K  R  L  C  Y  I  Q  P  C  D  S  N  I  L

871  AAGACAATAAAGATTCCCAAAGGAAAAACA
     TTCTGTTATTTCTAAGGGTTTCCTTTTTGT
276  K  T  I  K  I  P  P  K  G  K  T

901  TGCCAACCTACTTTCCAACTCTCCAAAGCTGAAAAATTTGTCTTTTTCTGGATGCTCAAGTACTCAGAGTT
     ACGGTTGGATGAAAGGTTGAGAGTTTCGACTTTTTAAACAGAAAAGACCTACGAGTTCATGAGTCTCAA
286  C  Q  P  T  F  Q  L  S  K  A  E  K  F  V  F  S  G  C  S  S  T  Q  S  Y

971  ACAAACCCACTTTTTGGGTGAAATATGCTTGG
     TGTTTGGGTGAAAAACACCTTATACGAACC
310  K  P  T  F  C  G  I  C  L  D
```

FIG._6B

```
1001  ATAAGAGATGCTGTATCCCTAATAAGTCTAAAATGATTACTATTCAATTTGATTGCCCAAATGAGGGGTC
      TATTCTCTACGACATAGGGATTATTCAGATTTTACTAATGATAAGTTAACTAACGGGTTACTCCCCAG
 320   K  R  C  C  I  P  N  K  S  K  M  I  T  I  Q  F  D  C  P  N  E  G  S

1071  ATTTAAATGGAAGATGCTGTGGATTACATC
      TAAATTTACCTTCTACGACACCTAATGTAG
 343   F  K  W  K  M  L  W  I  T  S

1101  TTGTGTGTGTCAGAGAAACTGCAGAGAACCTGGAGATATATTTCTGAGCTCAAGATTCTGTAAAACCAA
      AACACACACAGTCTCTTTGACGTCTCTTGGACCTCTATATAAAGACTCGAGTTCTAAGACATTTGGTT
 353   C  V  C  Q  R  N  C  R  E  P  G  D  I  F  S  E  L  K  I  L  Q

1171  GCAAATGGGGGAAAAGTTAGTCAATCCTGT
      CGTTTACCCCCTTTTCAATCAGTTAGGACA

1201  CATANAATAAAAAATTAGTGAGTATAAAATGGTGGCAAATCTACTTTGTTTAAAACAGTATGAATGCCT
      GTATNTTATTTTTTTAATCACTCATATTTACCACCGTTTAGATGAAACAAATTTGTCATACTTACGGA

1271  ATTCTCAGATCACTACACATTTAAGGCATTAG
      TAAGAGTCTAGTGATGTAAATTCCGTAATC

1301  AAACTTTAAAAGTTANCTTAAAAATATACATAA
      TTTGAAAATTTTCAATNGAATTTTATATGTATT
```

```
  1 CACGGTCCAGCGACATGCAGGGGCTCCTCTTCTCCACTCTTCTGCTCTGGCCTGGCACAGTTCTGCT
    GTGCCAGGGTCGCTGTACGTCCCCGAGGAGAAGAGAGGTGAGAAGCGAACGGACCGTGTCAAGACGA
  1                 M  Q  G  L  L  F  S  T  L  L  L  A  G  L  A  Q  F  C

71 GCAGGGTACAGGGCACTGGACCATTAGATA
    CGTCCCATGTCCCGTGACCTGGTAATCTAT
 20  R  V  Q  G  T  G  P  L  D  T

101 CAACACCTGAAGGAAGGCCTGGAGACTCTTCCGGACCTCTTCAGATGCACCTCAGCGTAAACAGTTTTGTCACTGGCCCTG
    GTTGTGGACTTCCTTCCGGACCTCTGAGAAGGCCTGGAGAAGGCCTGGAGTCGCATTTGTCAAAACAGTGACCGGGAC
 30  T  P  E  G  R  P  G  E  V  S  D  A  P  Q  R  K  Q  F  C  H  W  P  C

171 CAAATGCCCTCAGCAGAAGCCCGTTGCCC
    GTTTACGGGAGTCGTCTTCGGGGCAACGGG
 53  K  C  P  Q  Q  K  P  R  C  P

201 TCCTGGAGTGAGCCTGGTGAGAGATGGCTGTGAGGATGCTGTAAAATCTGTGCCAAGCAACCAGGGAAATC
    AGGACCTCACTCGGACCACTCTCTACCGACACTGCTACGACATTTTAGACACGGTTCGTTGGTCCCCTTTAG
 63  P  G  V  S  L  V  R  D  G  C  C  C  K  I  C  A  K  Q  P  G  E  I

271 TGCAATGAAGCTGACCTCTGTGACCACAC
    ACGTTACTTCGACTGGAGACACTGGGTGTG
 86  C  N  E  A  D  L  C  D  D  P  H

301 AAAGGGCTGTATTGTGACTACTCAGTAGACAGGCCTAGGTACGAGACTGGAGTGTGTGCATACCTTGTAG
    TTTCCCGACATAACACTGATGAGTCATCTGTCCGGATCCATGCTCTGACCTCACACGTATGAACATC
 96  K  G  L  Y  C  D  Y  S  V  D  R  P  R  Y  E  T  G  V  C  A  Y  L  V  A

371 CTGTTGGGTGCGAGTTCAACCAGGTACATT
    GACAACCCACGCTCAAGTTGGTCCATGTAA
120  V  G  C  E  F  N  Q  V  H  Y

401 ATCATAATGCCAAGTGTTTCAGCCCAACCCCTTGTTCAGCCTGCCTCTGTTCAGTGGGCCATTGGATG
    TAGTATTACGGTTCACAAAGTCGGGTTGGGAACAAGTCGACGGAGACACACTCACCCGGTAACCTAC
130  H  N  G  Q  V  F  Q  P  N  P  L  F  S  C  L  C  V  S  G  A  I  G  C

471 CACACCTCTGTTCATACCAAAGCTGGCTGG
    GTGTGGAGACAAGTATGGTTTCGACCGACC
153  T  P  L  F  I  P  K  L  A  G
```

```
501  CAGTCACTGCTCTGGAGCTAAAGGTGGAAAGAAGTCTGATCAGTCAAACTGTAGCCTGGAACCATTACTA
     GTCAGTGACGAGACCTCGATTTCCACCTTTCTTCAGACTAGTCAGTTTGACATCGGACCTTGGTAATGAT
163  S  H  C  S  G  A  K  G  G  K  K  S  D  Q  S  N  C  S  L  E  P  L  L

571  CAGCAGCTTTCAACAAGCTACAAAACAATG
     GTCGTCGAAAGTTGTTCGATGTTTTGTTAC
186  Q  Q  L  S  T  S  Y  K  T  M

601  CCAGCTTATAGAAATCTCCCACTTATTTGGAAAAAAAAATGTCTTGTGCAAGCAACAAAAATGGACTCCCT
     GGTCGAATATCTTTAGAGGGTGAATAAACCTTTTTTTTTTACAGAACACGTTCGTTGTTTTACCTGAGGA
196  P  A  Y  R  N  L  P  L  I  W  K  K  K  C  L  V  Q  A  T  K  W  T  P  C

671  GCTCCAGAACATGTGGGATGGGAATATCTA
     CGAGGTCTTGTACACCCTACCCTTATAGAT
220  S  R  T  C  G  M  G  I  S  N

701  ACAGGGTGACCAATAGCAGCAACTGTGAAATGAAGAAAAGAGAAAAGACTGTGTTACATTCAGCCTTG
     TGTCCCACTGGTACTTTGTCGTTGACACTTTACTCTTTTCTCTTTTCTGACACAATGTAAGTCGGAAC
230  R  V  T  N  E  N  S  N  C  E  M  R  K  E  K  R  L  C  Y  I  Q  P  C

771  CGACAGCAATATATTAAAGACAATAAAGAT
     GCTGTCGTTATATAATTTCTGTTATTTCTA
253  D  S  N  I  L  K  T  I  K  I

801  TCCCAAAGGAAAAACATGCCAACTCTTCCAACTCTCCAAAGCTGAAAAATTTGTCTTTTCTGGATGC
     AGGGTTCCTTTTTGTACGGTTGAGAGGTTCGAAGGTTGAGAGGTTTCGACTTTTTAAACAGAAAGACCTACG
263  P  K  G  K  T  C  Q  P  T  F  Q  L  S  K  A  E  K  F  V  F  S  G  C

871  TCAAGTACTCAGAGTTACAAACCCACTTTT
     AGTTCATGAGTCTCAATGTTTGGGTGAAAA
286  S  S  T  Q  S  Y  K  P  T  F
```

FIG._7B

```
 901 TGTGGAATATGCTTGGATAAGAGAGATGCTGTATCCCTAATAAGTCTAAAAATGATTACTATTCAATTTGATT
     ACACCTTATACGAACCTATTCTCTACGACATAGGGATTATTCAGATTTTACTAATGATAAGTTAAACTAA
 296 C G I C L D K R C C I P N K S K M I T I Q F D C

971 GCCCAAATGAGGGGTCATTTAAATGGAAGA
     CGGGTTTACTCCCCAGTAAATTTACCTTCT
 320 P N E G S F K W K M

1001 TGCTGTGGATTACATCTTGTGTGTCAGAGAAACTGCAGAGAACCTGGAGATATATTTCTGAGCTCAA
     ACGACACCTAATGTAGAACACAGTCTCTTTGACGTCTCTTGGACCTCTATATAAAGACTCGAGTT
 330 L W I T S C V C Q R N C R E P G D I F S E L K

1071 GATTCTGTAAAACCAAGCAAATGGGGAAA
     CTAAGACATTTGGTTCGTTTACCCCCTTT
 353 I L O

1101 AGTTAGTCAATCCTGTCATATATAAAAAAATTAGTGAGTAAAAAAAAAAAAAAAAAAAAAAAAA
     TCAATCAGTTAGGACAGTATATTATTTTTAATCACTCATTTTTTTTTTTTTTTTTTTTTTTTT

1171 AAAAAAAAAAAAAAAAAAAAAAAAAAGAAAAA
     TTTTTTTTTTTTTTTTTTTTTTTCTTTTTTT

1201 AAAAAAAAAA
     TTTTTTTTTT
```

FIG._7C

```
mouse.wisp-1    1  M R W L L P W T L A A V A V L R V G N I L A T A L S P T P T T M T F T P A P L E E T T R P E F C K
human.wisp-1    1  M R W F L P W T L A A V T A A A A S T V L A T A L S P A P T T M D F T P A P L E D T S S R P Q F C K mouse.wisp-1   51  W P C E C P Q S P P R C P L G V S L I T D G C E C C K I C A Q Q L G D N C T E A A I C D P H R G L Y
human.wisp-1   51  W P C E C P P S P P R C P L G V S L I T D G C E C C K M C A Q Q L G D N C T E A A I C D P H R G L Y mouse.wisp-1  101  C D Y S G D R P R Y A I G V C A Q V V G V G C V L D G V R Y T N G E S F Q P N C R Y N C T C I D G T
human.wisp-1  101  C D Y S G D R P R Y A I G V C A Q V V G V G C V L D G V R Y N N G Q S F Q P N C K Y N C T C I D G A mouse.wisp-1  151  V G C T P L C L S P R P P R L W C R Q P R H V R V P G Q C C E Q W V C D D D A R R P R Q T A L L D T
human.wisp-1  151  V G C T P L C L R V R P P R L W C P H P R R V S I P G H C C E Q W V C E D D A K R P R K T A P R D T mouse.wisp-1  201  R A F A A S G A V E Q R Y E N C I A Y T S P W S P C S T T C G L G I S T R I S N V N A R C W P E Q E
human.wisp-1  201  G A F D A V G E V E A W H R N C I A Y T S P W S P C S T S C G L G V S T R I S N V N A Q C W P E Q E mouse.wisp-1  251  S R L C N L R P C D V D I Q L H I K A G K K C L A V Y Q P E E A T N F T L A G C V S T R T Y R P K Y
human.wisp-1  251  S R L C N L R P C D V D I H T L I K A G K K C L A V Y Q P E A S M N F T L A G C I S T R S Y Q P K Y mouse.wisp-1  301  C G V C T D N R C C I P Y K S K T I S V D F Q C P E G P P G F S R Q V L W I N A C F C N L S C R N P N
human.wisp-1  301  C G V C M D N R C C I P Y K S K T I D V S F Q C P D G L P G F S R Q V L W I N A C F C N L S C R N P N mouse.wisp-1  351  D I F A D L E S Y P D F E E I A N
human.wisp-1  351  D I F A D L E S Y P D F S E I A N
```

FIG._8

```
mouse.wisp-2    1  M R G N P L I H L L A I S F L C I L S M V Y S Q L C P A P C A C P W T P P Q C P P P G V P L V L D G C
human.wisp-2    1  M R G T P K T H L L A F S L L C L L S K V R T Q L C P T P C T C P W P P P R C P L G V P L V L D G C mouse.wisp-2   51  G C C R V C A R R L G E S C D H L H V C D P S Q G L V C Q P G A G P S G R G A V C L F E E D D G S C
human.wisp-2   51  G C C R V C A R R L G E P C D Q L H V C D A S Q G L V C Q P G A G P G G R G A L C L L A E D D S S C mouse.wisp-2  101  E V N G R R Y L D G E T F K P N C R V L C R C D D G G F T C L P L C S E D V R L P S W D C P R P R R
human.wisp-2  101  E V N G R L Y R E G E T F Q P H C S I R C R C E D G G F T C V P L C S E D V R L P S W D C P H P R R mouse.wisp-2  151  I Q V P G R C C P E W V C D Q A V M Q P A I Q P S S A Q G H Q L S A L V T P A S A D G P C P N W S T
human.wisp-2  151  V E V L G K C C P E W V C G Q G G - G L G T Q P L P A Q G P Q F S G L V S S L P P G V P C P E W S T mouse.wisp-2  201  A W G P C S T T C G L G I A T R V S N Q N R F C Q L E I Q R R L C L S R P C L A S R S H G S W N S A
human.wisp-2  200  A W G P C S T T C G L G M A T R V S N Q N R F C R L E T Q R R L C L S R P C P P S R G R S P Q N S A mouse.wisp-2  251  F
human.wisp-2  250  F
```

FIG._9

```
                              10        20        30        40        50
hWISP-3.DNA56350   MNKRRLLYPSGWLHGPSDMQGLLFSTLLLAGLAQFCCRVQGTGPLDTTPE
                                     **********************************
hWISP-3.DNA58800                     MQGLLFSTLLLAGLAQFCCRVQGTGPLDTTPE
                                              10        20        30

60        70        80        90       100
hWISP-3.DNA56350   GRPGEVSDAPQRKQFCHWPCKCPQQKPRCPPGVSLVRDGCGCCKICAKQP
                   **************************************************
hWISP-3.DNA58800   GRPGEVSDAPQRKQFCHWPCKCPQQKPRCPPGVSLVRDGCGCCKICAKQP
                            40        50        60        70        80

110       120       130       140       150
hWISP-3.DNA56350   GEICNEADLCDPHKGLYCDYSVDRPRYETGVCAYLVAVGCEFNQVHYHNG
                   **************************************************
hWISP-3.DNA58800   GEICNEADLCDPHKGLYCDYSVDRPRYETGVCAYLVAVGCEFNQVHYHNG
                            90       100       110       120       130

160       170       180       190       200
hWISP-3.DNA56350   QVFQPNPLFSCLCVSGAIGCTPLFIPKLAGSHCSGAKGGKKSDQSNCSLE
                   **************************************************
hWISP-3.DNA58800   QVFQPNPLFSCLCVSGAIGCTPLFIPKLAGSHCSGAKGGKKSDQSNCSLE
                           140       150       160       170       180

210       220       230       240       250
hWISP-3.DNA56350   PLLQQLSTSYKTMPAYRDLPLIWKKKCLVQATKWTPCSRTCGMGISNRVT
                   ****************.*********************************
hWISP-3.DNA58800   PLLQQLSTSYKTMPAYRNLPLIWKKKCLVQATKWTPCSRTCGMGISNRVT
                           190       200       210       220       230

260       270       280       290       300
hWISP-3.DNA56350   NENSNCEMRKEKRLCYIQPCDSNILKTIKIPKGKTCQPTFQLSKAEKFVF
                   **************************************************
hWISP-3.DNA58800   NENSNCEMRKEKRLCYIQPCDSNILKTIKIPKGKTCQPTFQLSKAEKFVF
                           240       250       260       270       280

310       320       330       340       350
hWISP-3.DNA56350   SGCSSTQSYKPTFCGICLDKRCCIPNKSKMITIQFDCPNEGSFKWKMLWI
                   **************************************************
hWISP-3.DNA58800   SGCSSTQSYKPTFCGICLDKRCCIPNKSKMITIQFDCPNEGSFKWKMLWI
                           290       300       310       320       330

360       370
hWISP-3.DNA56350   TSCVCQRNCREPGDIFSELKIL
                   **********************
hWISP-3.DNA58800   TSCVCQRNCREPGDIFSELKIL
                           340       350
```

FIG._10

```
hWISP-3.DNA56350    GTGGGGTTTGCAGAGGAGACAGGGGAGCTTTGTGTACCCGGAGCAATGAA
                            10        20        30        40        50 huWISP-1                                                                             A
                                                                                     *
hWISP-3.DNA56350    CAAGCGGCGACTTCTCTACCCCTCAGGGTGGCTCCACGGTCCCAGCGACA
                            60        70        80        90       100

10        20        30        40
huWISP-1            TGAGGTGGTTCCTGCCCTGGAC---GCTGGCAGCAGTGACAGCAGCAGCC
                    **  * ** ****   ** **   ***  ** *   ***  ***      *
hWISP-3.DNA56350    TGCAGGGGCTCCTCTTCTCCACTCTTCTGCTTGCTGGCCTGGCACAGTTC
                           110       120       130       140       150

50        60        70        80        90
huWISP-1            GCCAGCACCGTCCTGGCCACGGCCCTCTCTCCAGCCCCTACGACCATGGA
                     * ***   ** * ** *** *        ***     *** **    **
hWISP-3.DNA56350    TGCTGCAGGGTACAGGGCACTG------GACCATTAGATACAACACCTGA
                           160       170             180       190

100       110       120       130       140
huWISP-1            CTTTACTCCAGCTCCACTGGAGGACACCTCCTCACGCCCCCAATTCTGCA
                       *  ** *     * **  **  *  *     **   ** ** ** **
hWISP-3.DNA56350    AGGAAGGCCTGGAGAAGTGTCAGATGCACCTCAGCGTAAACAGTTTTGTC
                           200       210       220       230       240

150       160       170       180       190
huWISP-1            AGTGGCCATGTGAGTGCCCGCCATCCCCACCCCGCTGCCCGCTGGGGGTC
                    * ***** ** * ***** *         *****  *****  *  ** **
hWISP-3.DNA56350    ACTGGCCCTGCAAATGCCCTCAGCAGAAGCCCCGTTGCCCTCCTGGAGTG
                           250       260       270       280       290

200       210       220       230       240
huWISP-1            AGCCTCATCACAGATGGCTGTGAGTGCTGTAAGATGTGCGCTCAGCAGCT
                    *****  *  * ********** ******** **  ** **     **** *
hWISP-3.DNA56350    AGCCTGGTGAGAGATGGCTGTGGATGCTGTAAAATCTGTGCCAAGCAACC
                           300       310       320       330       340

250       260       270       280       290
huWISP-1            TGGGGACAACTGCACGGAGGCTGCCATCTGTGACCCCCACCGGGGCCTCT
                    *****   * ***** ** **** *  ********** ***   **  ** *
hWISP-3.DNA56350    AGGGGAAATCTGCAATGAAGCTGACCTCTGTGACCCACACAAAGGGCTGT
                           350       360       370       380       390

300       310       320       330       340
huWISP-1            ACTGTGACTACAGCGGGGACCGCCCGAGGTACGCAATAGGAGTGTGTGCA
                    * ********    *  *** * **  *******   *   **********
hWISP-3.DNA56350    ATTGTGACTACTCAGTAGACAGGCCTAGGTACGAGACTGGAGTGTGTGCA
                           400       410       420       430       440

350       360       370       380       390
huWISP-1            CAGGTGGTCGGTGTGGGCTGCGTCCTGGATGGGGTGCGCTACAACAACGG
                     *  ** * *** ** ****     *  *   ***   ** * ** **   **
hWISP-3.DNA56350    TACCTTGTAGCTGTTGGGTGCGAGTTCAACCAGGTACATTATCATAATGG
                           450       460       470       480       490
```

FIG._11A

```
                    400        410        420        430        440
huWISP-1        CCAGTCCTTCCAGCCTAACTGCAAGTACAACTGCACGTGCATCGACGGCG
                 ***   ** ***** ***  *  ** ** ****  **  *    ** *
hWISP-3.DNA56350 CCAAGTGTTTCAGCCCAACCCCTTGTTCAGCTGCCTCTGTGTGAGTGGGG
                    500        510        520        530        540

450        460        470        480        490
huWISP-1        CGGTGGGCTGCACACCACTGTGCCTCCGAGTGCGCCCCCCGCGTCTCTGG
                 *  *  ** ******** ****  *  *  **            *  ****
hWISP-3.DNA56350 CCATTGGATGCACACCTCTGTTCATACCAAAGC----------TGGCTGG
                    550        560        570                   580

500        510        520        530        540
huWISP-1        TGCCCCCACCCGCGGCGCGTGAGC-ATACCTGGCCACTGCTGTGAGCAGT
                  **  *  ** *  ****  *  *   ***   *   *  *  *** ****
hWISP-3.DNA56350 ------CAGTCACTGCTCTGGAGCTAAAGGTGGAAAGAAGTCTGATCAGT
                          590        600        610        620

550        560        570        580        590
huWISP-1        GGGTATGTGAGGACGACGCCAAGAGGCCACGCAAGACCGCACCCCGTGAC
                  ***  **    *    ***  *  * **     **  *    *   **
hWISP-3.DNA56350 CAAACTGT-AGCCTGGAACCATTA--CTACAGCAGCTTTCAACAAGCTAC
                 630        640        650         660        670

600        610        620        630        640
huWISP-1        ACAGGAGCCTTCGATGCTGTGGGTGAGGTGGAGGCATGGCACAGGAACTG
                 *  *     * *  *  *   * *          *** * *  ** **
hWISP-3.DNA56350 AAAACAATGCCAGCTTATAGAGATCTCCCACTTATTTGGAAAAAAAAATG
                    680        690        700        710        720

650        660        670        680        690
huWISP-1        CATAGCCTACACAAGCCCCTGGAGCCCTTGCTCCACCAGCTGCGGCCTGG
                  *  *   *    ***   **** ** *******  *  ** **   ***
hWISP-3.DNA56350 TCTTGTGCAAGCAACAAAATGGACTCCCTGCTCCAGAACATGTGGGATGG
                    730        740        750        760        770

700        710        720        730        740
huWISP-1        GGGTCTCCACTCGGATCTCCAATGTTAACGCCCAGTGCTGGCCTGAGCAA
                 *   * ** *   ** *  ******  *** * * **             **
hWISP-3.DNA56350 GAATATCTAACAGGGTGACCAATGAAAACAGCAACTGTGAAATGAGAAAA
                    780        790        800        810        820

750        760        770        780        790
huWISP-1        GAGAGCCGCCTCTGCAACTTGCGGCCATGCGATGTGGACATCCATACACT
                 ****   *  ** **   ** * * ***  *****    *  **    *
hWISP-3.DNA56350 GAGAAAGACTGTGTTACATTCAGCCTTGCGACAGCAATATATTAAAGAC
                    830        840        850        860        870

800        810        820        830        840
huWISP-1        CATTAAG------GCAGGGAAGAAGTGTCTGGCTGTGTACCAGCCAGAGG
                 ** ***      *** ** * ** **  **  **  * *** *
hWISP-3.DNA56350 AATAAAGATTCCCAAAGGAAAAACATGCCAACCTACTTTCCAACTCTCCA
                    880        890        900        910        920

850        860        870        880        890
huWISP-1        CATCCATGAACTTCACACTTGCGGGCTGCATCAGCACACGCTCCTATCAA
                 * *  ** **  ** *** *** ** ** ***  ** **   *     **
hWISP-3.DNA56350 AAGCTGAAAAATTTGTCTTTTCTGGATGCTCAAGTACTCAGAGTTACAAA
                    930        940        950        960        970
```

*FIG._11B*

```
                   900       910       920       930       940
huWISP-1       CCCAAGTACTGTGGAGTTTGCATGGACAATAGGTGCTGCATCCCCTACAA
               ****  * ****** * *** **** ** ** ***** *****  * **
hWISP-3.DNA56350 CCCACTTTTTGTGGAATATGCTTGGATAAGAGATGCTGTATCCCTAATAA
                   980       990      1000      1010      1020

950       960       970       980       990
huWISP-1       GTCTAAGACTATCGACGTGTCCTTCCAGTGTCCTGATGGGCTTGGCTTCT
               ****** * **   *  ** * ** **  *** *            **
hWISP-3.DNA56350 GTCTAAAATGATTACTATTCAATTTGATTGCCCAAATGAGGGGTCATTTA
                  1030      1040      1050      1060      1070

1000      1010      1020      1030      1040
huWISP-1       CCCGCCAGGTCCTATGGATTAATGCCTGCTTCTGTAACCTGAGCTGTAGG
                 * ** * ** *******    *  **  * ***  *  *  *** **
hWISP-3.DNA56350 AATGGAAGATGCTGTGGATTACATCTTGTGTGTGTCAGAGAAACTGCAGA
                  1080      1090      1100      1110      1120

1050      1060      1070      1080      1090
huWISP-1       AATCCCAATGACATCTTTGCTGACTTGGAATCCTACCCTGACTTCTCAGA
               * **   ** ** *** ****   *  *              **  ** *
hWISP-3.DNA56350 GAACCTGGAGATATATTTTCTGAGCTCAAGATTCTGTAAAACCAAGCAAA
                  1130      1140      1150      1160      1170

1100
huWISP-1       AATTGCCAAC
                * **
hWISP-3.DNA56350 TGGGGGAAAAGTTAGTCAATCCTGTCATANAATAAAAAAATTAGTGAGTA
                  1180      1190      1200      1210      1220 hWISP-3.DNA56350 TAAAATGGTGGCAAATCTACTTTGTTTAAAACAGTATGAATGCCTATTCT
                  1230      1240      1250      1260      1270 hWISP-3.DNA56350 CAGATCACTACATTTAAGGCATTAGAAACTTTTAAAAAGTTANCTTAAAA
                  1280      1290      1300      1310      1320 hWISP-3.DNA56350 ATATACATAA
                  1330
```

FIG._11C

```
                             10        20        30        40
hWISP-3.DNA56350    MNKRRLLYPSGWLHGPSDMQGLLFSTL-LLAGLAQFCCRVQGTGPLDTTP
                       *. .*  **  ...   *           ..*  **
huWISP-1                       MRWFLPWTLAAVTAAAASTVLATALSPAPTTM
                                  10        20        30

50        60        70        80        90
hWISP-3.DNA56350    EGRPGEVSDAPQRKQFCHWPCKCPQQKPRCPPGVSLVRDGCGCCKICAKQ
                    .  *. . *.. * *** *** **    **** ****. *** ***.**.*
huWISP-1            DFTPAPLEDTSSRPQFCKWPCECPPSPPRCPLGVSLITDGCECCKMCAQQ
                         40        50        60        70        80

100       110       120       130       140
hWISP-3.DNA56350    PGEICNEADLCDPHKGLYCDYSVDRPRYETGVCAYLVAVGCEFNQVHYHN
                    *.  *  ** .****.******* *****  ****  .*.***  .. *.*.*
huWISP-1            LGDNCTEAAICDPHRGLYCDYSGDRPRYAIGVCAQVVGVGCVLDGVRYNN
                          90       100       110       120       130

150       160       170       180       190
hWISP-3.DNA56350    GQVFQPNPLFSCLCVSGAIGCTPL-FIPKLAGSHCSGAK----GGKKSDQ
                    ** **** ..* *. **.*****  .  .   *  ...    *    * .*
huWISP-1            GQSFQPNCKYNCTCIDGAVGCTPLCLRVRPPRLWCPHPRRVSIPGHCCEQ
                         140       150       160       170       180

200       210       220       230       240
hWISP-3.DNA56350    SNCSLEPLLQQLSTSYKTMPAYRDLPLI--WKKKCLVQATKWTPCSRTCG
                    *   ..  . ... .    *.  .   *  ..*.  .. *.*** .**
huWISP-1            WVCEDDAKRPRKTAP-RDTGAFDAVGEVEAWHRNCIAYTSPWSPCSTSCG
                         190       200       210       220       230

250       260       270       280       290
hWISP-3.DNA56350    MGISNRVTNENSNCEMRKEKRLCYIQPCDSNILKTIKIPKGKTCQPTFQL
                    .*.* *...*  *...*     .* ***  .***  .*    **  ** * . .*
huWISP-1            LGVSTRISNVNAQCWPEQESRLCNLRPCDVDIHTLIK--AGKKCLAVYQP
                         240       250       260       270

300       310       320       330       340
hWISP-3.DNA56350    SKAEKFVFSGCSSTQSYKPTFCGICLDKRCCIPNKSKMITIQFDCPNEGS
                    . .*  ..** **.**.* .**.*.*.***** *** * . *.**.  .
huWISP-1            EASMNFTLAGCISTRSYQPKYCGVCMDNRCCIPYKSKTIDVSFQCPDGLG
                   280       290       300       310       320

350       360       370
hWISP-3.DNA56350    FKWKMLWITSCVCQRNCREPGDIFSELKIL
                    *  ...*** .*  *. .**.*  ***..*
huWISP-1            FSRQVLWINACFCNLSCRNPNDIFADLESYPDFSEIAN
                         330       340       350       360
```

FIG._12

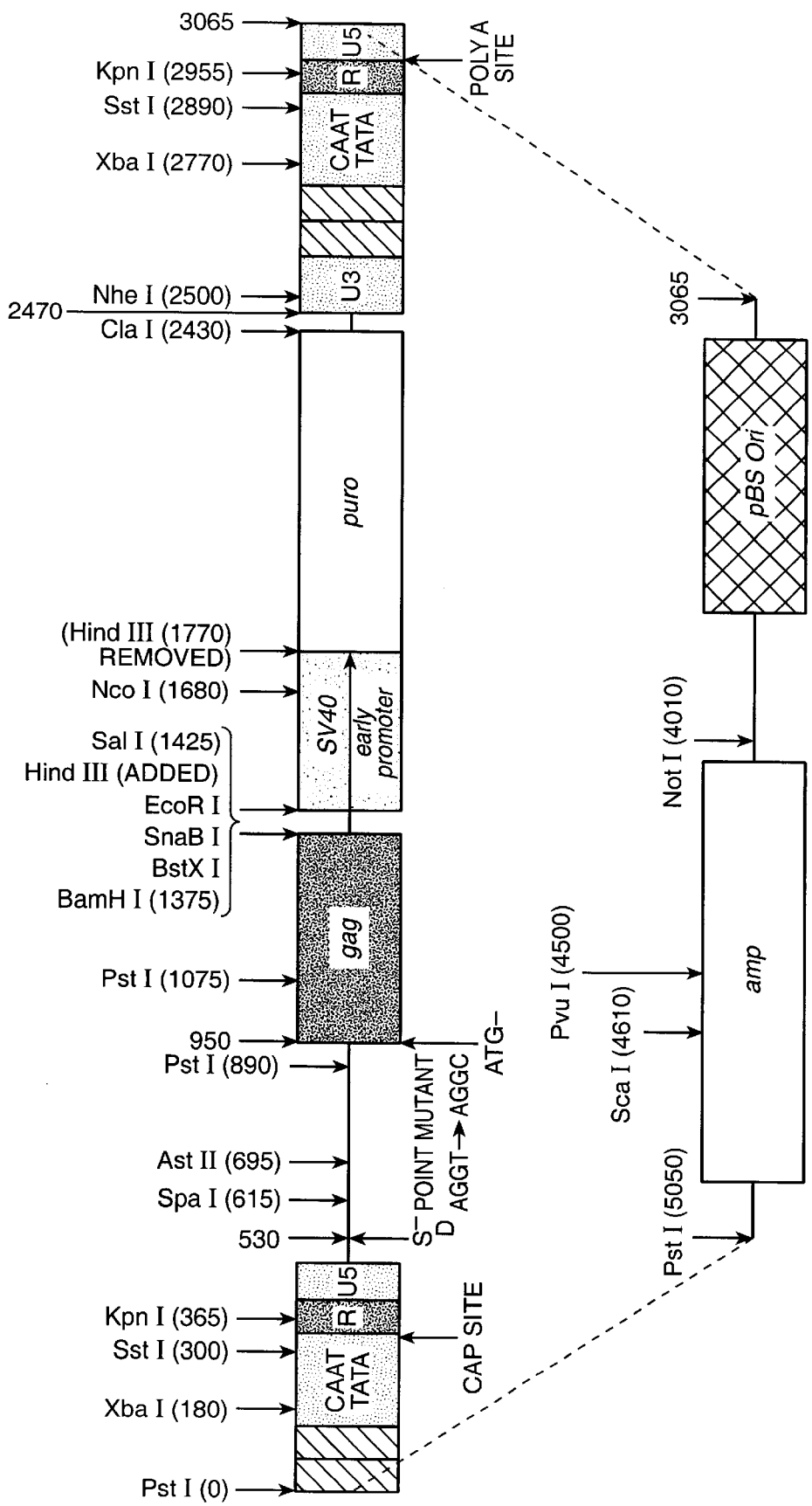
FIG._13

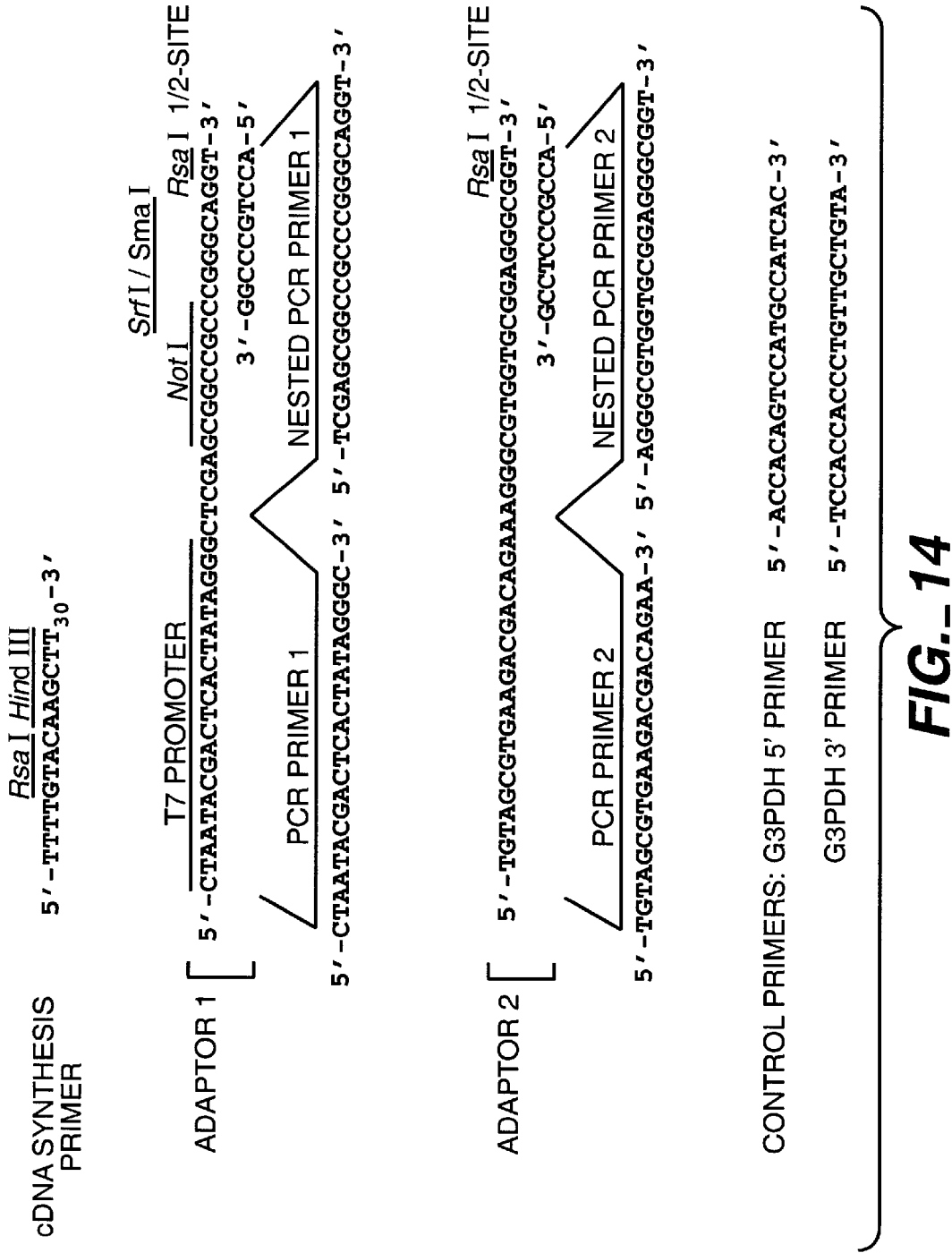
FIG._14

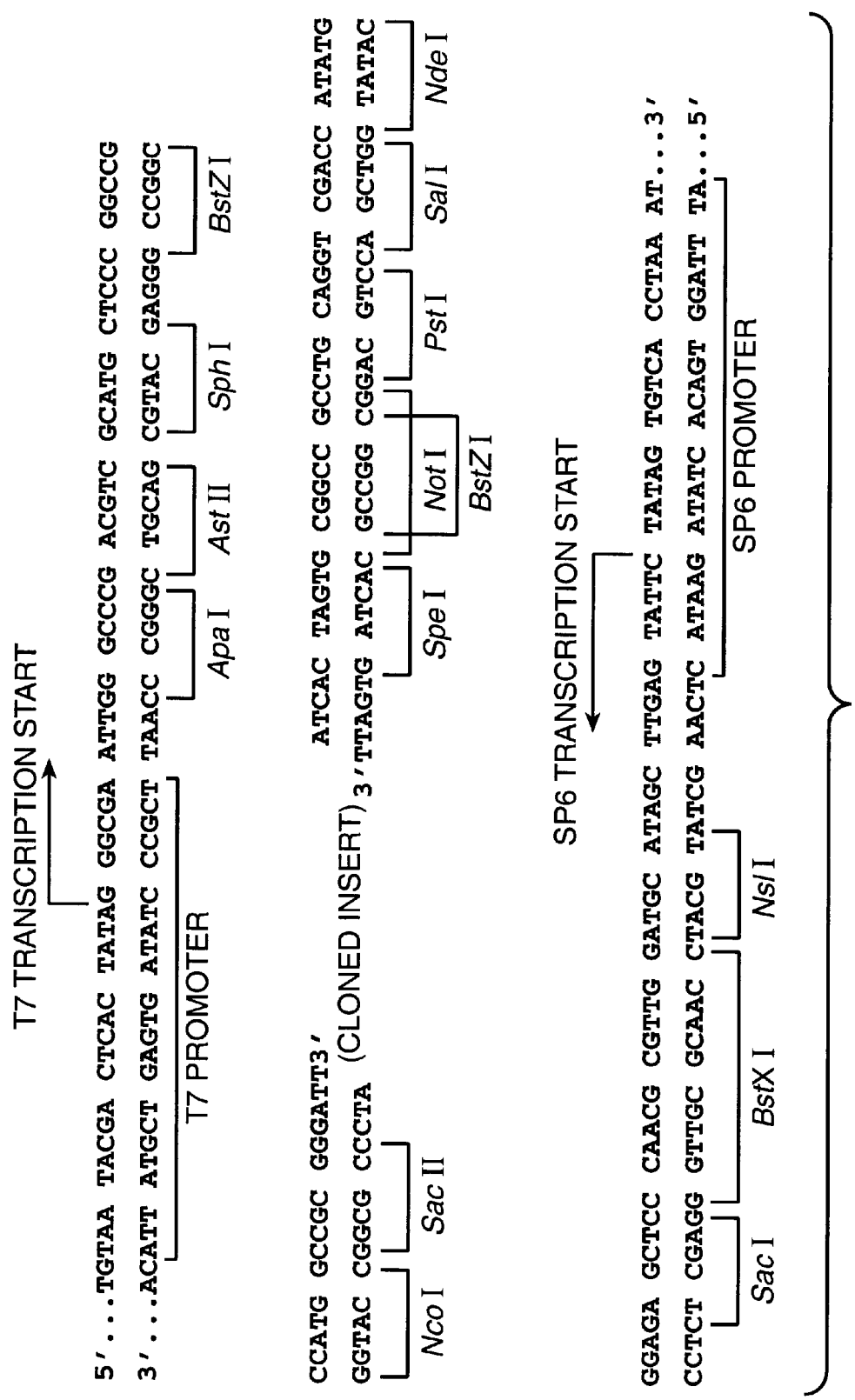
FIG._15

```
TTCGAGCTCGCCCGACATTGATTATTGACTAGAGTCGATCACCGGTTATTAATAGTAATC
AATTACGGGGTCATAGTTCATAGCCCATATATGGAGTTCCGCGTTACATAACTTACGGTA
AATGGCCCGCCTGGCTGACCGCCCAACGACCCCCGCCCATTGACGTCAATAATGACGTAT
GTTCCCATAGTAACGCCAATAGGGACTTTCCATTGACGTCAATGGGTGGAGTATTTACGG
TAAACTGCCCACTTGGCAGTACATCAAGTGTATCATATGCCAAGTACGCCCCCTATTGAC
GTCAATGACGGTAAATGGCCCGCCTGGCATTATGCCCAGTACATGACCTTATGGGACTTT
CCTACTTGGCAGTACATCTACGTATTAGTCATCGCTATTACCATGGTGATGCGGTTTTGG
CAGTACATCAATGGGCGTGGATAGCGGTTTGACTCACGGGGATTTCCAAGTCTCCACCCC
ATTGACGTCAATGGGAGTTTGTTTTGGCACCAAAATCAACGGGACTTTCCAAAATGTCGT
AACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGAC
CTGGGCCCGGCCGAGGCCGCCTCGGCCTCTGAGCTATTCCAGAAGTAGTGAGGAGGCTTT
TTTGGAGGCCTAGGCTTTTGCAAAAAGCTAGCTTATCCGGCCGGGAACGGTGCATTGGAA
CGCGGATTCCCCGTGCCAAGAGT
><splice donor>
GACGTAAGTACCGCCTATAGAGCGACTAGTCCACC
><PUR>
ATGACCGAGTACAAGCCCACGGTGCGCCTCGCCACCCGCGACGACGTCCCGCGGGCCGTA
CGCACCCTCGCCGCCGCGTTCGCCGACTACCCCGCCACGCGCCACACCGTAGACCCGGAC
CGCCACATCGAGCGGGTCACCGAGCTGCAAGAACTCTTCCTCACGCGCGTCGGGCTCGAC
ATCGGCAAGGTGTGGGTCGCGGACGACGGCGCCGCGGTGGCGGTCTGGACCACGCCGGAG
AGCGTCGAAGCGGGGGCGGTGTTCGCCGAGATCGGCCCGCGCATGGCCGAGTTGAGCGGT
TCCCGGCTGGCCGCGCAGCAACAGATGGAAGGCCTCCTGGCGCCGCACCGGCCCAAGGAG
CCCGCGTGGTTCCTGGCCACCGTCGGCGTCTCGCCCGACCACCAGGGCAAGGGTCTGGGC
AGCGCCGTCGTGCTCCCCGGAGTGGAGGCGGCCGAGCGCGCCGGGGTGCCCGCCTTCCTG
GAGACCTCCGCGCCCCGCAACCTCCCCTTCTACGAGCGGCTCGGCTTCACCGTCACCGCC
GACGTCGAGTGCCCGAAGGACCGCGCGACCTGGTGCATGACCCGCAAGCCCGGTGCCAAC
><DHFR ATG>
ATGGTTCGACCATTGAACTGCATCGTCGCCGTGTCCCAAAATATGGGGATTGGCAAGAAC
GGAGACCTACCCTGCCCTCCGCTCAGGAACGCGTTCAAGTACTTCCAAAGAATGACCACA
ACCTCTTCAGTGGAAGGTAAACAGAATCTGGTGATTATGGGTAGGAAAACCTGGTTCTCC
ATTCCTGAGAAGAATCGACCTTTAAAGGACAGAATTAATATAGTTCTCAGTAGAGAACTC
AAAGAACCACCACGAGGAGCTCATTTTCTTGCCAAAAGTTTGGATGATGCCTTAAGACTT
ATTGAACAACCGGAATTGGCAAGTAAAGTAGACATGGTTTGGATAGTCGGAGGCAGTTCT
GTTTACCAGGAAGCCATGAATCAACCAGGCCACCTTAGACTCTTTGTGACAAGGATCATG
CAGGAATTTGAAAGTGACACGTTTTTCCCAGAAATTGATTTGGGGAAATATAAACCTCTC
CCAGAATACCCAGGCGTCCTCTCTGAGGTCCAGGAGGAAAAAGGCATCAAGTATAAGTTT
GAAGTCTACGAGAAGAAAGACTAA
><End DHFR>
CGTTAACTGCTCCCCTCCTAAAGCTATGCATTTTTATAAGACCATGGGACTTTTGCTGGC
TTTAGATCCCCTTGGCTTCGTTAGAACGCAGCTACAATTAATACATAACCTTATGTATCA
TACACATACGATTTAGGTGACACTATAGATAACATCCACTTTGCCTTTCTCTCCACAGGT
GTCCACTCCCAGGTCCAACTGCACCTCGGTTCTATCGATTGAATTCCCCGGGGATCCTCT
AGAGTCGACCTGCAGAAGCTTCGATGGCCGCCATGGCCCAACTTGTTTATTGCAGCTTAT
AATGGTTACAAATAAAGCAATAGCATCACAAATTTCACAAATAAAGCATTTTTTTCACTG
CATTCTAGTTGTGGTTTGTCCAAACTCATCAATGTATCTTATCATGTCTGGATCGATCGG
<sv40 origin>
GAATTAATTCGGCGCAGCACCATGGCCTGAAATAACCTCTGAAAGAGGAACTTGGTTA
<Kpn-SAR-Kpn insert here>
GGTACCGACTAGTCGCGTTACATAACTTACGGTAAATGGCCCGCCTGGCTGACCGCCCAA
```

FIG._16A

```
CGACCCCCGCCCATTGACGTCAATAATGACGTATGTTCCCATAGTAACGCCAATAGGGAC
TTTCCATTGACGTCAATGGGTGGAGTATTTACGGTAAACTGCCCACTTGGCAGTACATCA
AGTGTATCATATGCCAAGTACGCCCCCTATTGACGTCAATGACGGTAAATGGCCCGCCTG
GCATTATGCCCAGTACATGACCTTATGGGACTTTCCTACTTGGCAGTACATCTACGTATT
AGTCATCGCTATTACCATGGTGATGCGGTTTTGGCAGTACATCAATGGGCGTGGATAGCG
GTTTGACTCACGGGATTTCCAAGTCTCCACCCCATTGACGTCAATGGGAGTTTGTTTTG
ACTAGTAGCAAGGTCGCCACGCACAAGATCAATATTAACAATCAGTCATCTCTCTTTAGC
AATAAAAGGTGAAAATTACATTTTAAAAATGACACCATAGACGATGTATGAAAATAAT
CTACTTGGAAATAAATCTAGGCAAAGAAGTGCAAGACTGTTACCCAGAAAACTTACAAAT
TGTAAATGAGAGGTTAGTGAAGATTTAAATGAATGAAGATCTAAATAAACTTATAAATTG
TGAGAGAAATTAATGAATGTCTAAGTTAATGCAGAAACGGAGAGACATACTATATTCATG
AACTAAAAGACTTAATATTGTGAAGGTATACTTTCTTTTCACATAAATTTGTAGTCAATA
TGTTCACCCCAAAAAAGCTGTTTGTTAACTTGTCAACCTCATTTCAAAATGTATATAGAA
AGCCCAAAGACAATAACAAAAATATTCTTGTAGAACAAAATGGGAAGAATGTTCCACTA
AATATCAAGATTTAGAGCAAAGCATGAGATGTGTGGGGATAGACAGTGAGGCTGATAAAA
TAGAGTAGAGCTCAGAAACAGACCCATTGATATATGTAAGTGACCTATGAAAAAATATG
GCATTTTACAATGGGAAAATGATGATCTTTTCTTTTTAGAAAACAGGGAAATATATT
TATATGTAAAAAATAAAAGGGAACCCATATGTCATACCATACACAAAAAAATTCCAGT
GAATTATAAGTCTAAATGGAGAAGGCAAAACTTTAAATCTTTTAGAAAATAATATAGAAG
CATGCCATCATGACTTCAGTGTAGAGAAAAATTTCTTATGACTCAAAGTCCTAACCACAA
AGAAAAGATTGTTAATTAGATTGCATGAATATTAAGACTTATTTTTAAAATTAAAAAACC
ATTAAGAAAAGTCAGGCCATAGAATGACAGAAAATATTTGCAACACCCCAGTAAAGAGAA
TTGTAATATGCAGATTATAAAAGAAGTCTTACAAATCAGTAAAAAATAAAACTAGACAA
AAATTTGAACAGATGAAAGAGAAACTCTAAATAATCATTACACATGAGAAACTCAATCTC
AGAAATCAGAGAACTATCATTGCATATACACTAAATTAGAGAAATATTAAAAGGCTAAGT
AACATCTGTGGCAATATTGATGGTATATAACCTTGATATGATGTGATGAGAACAGTACTT
TACCCCATGGCTTCCTCCCCAAACCCTTACCCCAGTATAAATCATGACAAATATACTTT
AAAAACCATTACCCTATATCTAACCAGTACTCCTCAAAACTGTCAAGGTCATCAAAAATA
AGAAAAGTCTGAGGAACTGTCAAAACTAAGAGGAACCCAAGGAGACATGAGAATTATATG
TAATGTGGCATTCTGAATGAGATCCCAGAACAGAAAAGAACAGTAGCTAAAAAACTAAT
GAAATATAAATAAAGTTTGAACTTTAGTTTTTTTTAAAAAAGAGTAGCATTAACACGGCA
AAGTCATTTTCATATTTTTCTTGAACATTAAGTACAAGTCTATAATTAAAAATTTTTTAA
ATGTAGTCTGGAACATTGCCAGAAACAGAAGTACAGCAGCTATCTGTGCTGTCGCCTAAC
TATCCATAGCTGATTGGTCTAAAATGAGATACATCAACGCTCCTCCATGTTTTTTGTTTT
CTTTTTAAATGAAAACTTTATTTTTTAAGAGGAGTTTCAGGTTCATAGCAAAATTGAGA
GGAAGGTACATTCAAGCTGAGGAAGTTTTCCTCTATTCCTAGTTTACTGAGAGATTGCAT
CATGAATGGGTGTTAAATTTTGTCAAATGCTTTTTCTGTGTCTATCAATATGACCATGTG
ATTTTCTTCTTTAACCTGTTGATGGGACAAATTACGTTAATTGATTTCAAACGTTGAAC
CACCCTTACATATCTGGAATAAATTCTACTTGGTTGTGGTGTATATTTTTGATACATTC
TTGGATTCTTTTTGCTAATATTTGTTGAAATGTTTGTATCTTTGTTCATGAGAGATAT
TGGTCTGTTGTTTCTTTTCTTGTAATGTCATTTTCTAGTTCCGGTATTAAGGTAATGCT
GGCCTAGTTGAATGATTTAGGAAGTATTCCCTCTGCTTCTGTCTTCTGAGGTACCGCGGC
CGCCCGTCGTTTTAC
```

FIG._16B

<start pUC118>
<linearization linker inserted into HpaI site>
AACGTCGTGACTGGGAAAACCCTGGCGTTACCCAACTTAATCGCCTTGCAGCACATCCCC
CTTTCGCCAGCTGGCGTAATAGCGAAGAGGCCCGCACCGATCGCCCTTCCCAACAGTTGC
GCAGCCTGAATGGCGAATGGC
<start M13>
GCCTGATGCGGTATTTTCTCCTTACGCATCTGTGCGGTATTTCACACCGCATACGTCAAA
GCAACCATAGTACGCGCCCTGTAGCGGCGCATTAAGCGCGGCGGGTGTGGTGGTTACGCG
CAGCGTGACCGCTACACTTGCCAGCGCCCTAGCGCCCGCTCCTTTCGCTTTCTTCCCTTC
CTTTCTCGCCACGTTCGCCGGCTTTCCCCGTCAAGCTCTAAATCGGGGGCTCCCTTTAGG
GTTCCGATTTAGTGCTTTACGGCACCTCGACCCCAAAAAACTTGATTTGGGTGATGGTTC
ACGTAGTGGGCCATCGCCCTGATAGACGGTTTTTCGCCCTTTGACGTTGGAGTCCACGTT
CTTTAATAGTGGACTCTTGTTCCAAACTGGAACAACACTCAACCCTATCTCGGGCTATTC
TTTTGATTTATAAGGGATTTTGCCGATTTCGGCCTATTGGTTAAAAAATGAGCTGATTTA
ACAAAAATTTAACGCGAATTTTAACAAAATATTAACGTTTACAATTTTATGGTGCACTCT
CAGTACAATCTGCTCTGATGCCGCATAGTTAAGCCAGCCCCGACACCCGCCAACACCCGC
TGACGCGCCCTGACGGGCTTGTCTGCTCCCGGCATCCGCTTACAGACAAGCTGTGACCGT
CTCCGGGAGCTGCATGTGTCAGAGGTTTTCACCGTCATCACCGAAACGCGCGAG
<                 HincII (2271) to GTCATC>
<                 PstI (1973) to CTGCTG>
<                 AccI (183) delete 6 bp>
<Arbitrarily change EcoRI (1) to GAATAC>
<pUCx 83.11.25 sequence not fully known>
ACGAAAGGGCCTCGTGATACGCCTATTTTTATAGGTTAATGTCATGATAATAATGGTTTC
TTAGACGTCAGGTGGCACTTTTCGGGGAAATGTGCGCGGAACCCCTATTTGTTTATTTTT
CTAAATACATTCAAATATGTATCCGCTCATGAGACAATAACCCTGATAAATGCTTCAATA
ATATTGAAAAAGGAAGAGTATGAGTATTCAACATTTCCGTGTCGCCCTTATTCCCTTTTT
TGCGGCATTTTGCCTTCCTGTTTTTGCTCACCCAGAAACGCTGGTGAAAGTAAAAGATGC
TGAAGATCAGTTGGGTGCACGAGTGGGTTACATCGAACTGGATCTCAACAGCGGTAAGAT
CCTTGAGAGTTTTCGCCCCGAAGAACGTTTTCCAATGATGAGCACTTTTAAAGTTCTGCT
ATGTGGCGCGGTATTATCCCGTATTGACGCCGGGCAAGAGCAACTCGGTCGCCGCATACA
CTATTCTCAGAATGACTTGGTTGAGTACTCACCAGTCACAGAAAAGCATCTTACGGATGG
CATGACAGTAAGAGAATTATGCAGTGCTGCCATAACCATGAGTGATAACACTGCGGCCAA
CTTACTTCTGACAACGATCGGAGGACCGAAGGAGCTAACCGCTTTTTGCACAACATGGG
GGATCATGTAACTCGCCTTGATCGTTGGGAACCGGAGCTGAATGAAGCCATACCAAACGA
CGAGCGTGACACCACGATGCCTGTAGCAATGGCAACAACGTTGCGCAAACTATTAACTGG
CGAACTACTTACTCTAGCTTCCCGGCAACAATTAATAGACTGGATGGAGGCGGATAAAGT
TGCAGGACCACTTCTGCGCTCGGCCCTTCCGGCTGGCTGGTTTATTGCTGATAAATCTGG
AGCCGGTGAGCGTGGGTCTCGCGGTATCATTGCAGCACTGGGGCCAGATGGTAAGCCCTC
CCGTATCGTAGTTATCTACACGACGGGGAGTCAGGCAACTATGGATGAACGAAATAGACA
GATCGCTGAGATAGGTGCCTCACTGATTAAGCATTGGTAACTGTCAGACCAAGTTTACTC
ATATATACTTTAGATTGATTTAAAACTTCATTTTAATTTAAAAGGATCTAGGTGAAGAT
CCTTTTTGATAATCTCATGACCAAAATCCCTTAACGTGAGTTTTCGTTCCACTGAGCGTC
AGACCCCGTAGAAAAGATCAAAGGATCTTCTTGAGATCCTTTTTTTCTGCGCGTAATCTG
CTGCTTGCAAACAAAAAAACCACCGCTACCAGCGGTGGTTTGTTTGCCGGATCAAGAGCT
ACCAACTCTTTTTCCGAAGGTAACTGGCTTCAGCAGAGCGCAGATACCAAATACTGTCCT
TCTAGTGTAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTCTTACCGG
GTTGGACTCAAGACGATAGTTACCGGATAAGGCGCAGCGGTCGGGCTGAACGGGGGGTTC

FIG._16C

GTGCACACAGCCCAGCTTGGAGCGAACGACCTACACCGAACTGAGATACCTACAGCGTGA
GCTATGAGAAAGCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCCTGGTATCTTTA
TAGTCCTGTCGGGTTTCGCCACCTCTGACTTGAGCGTCGATTTTTGTGATGCTCGTCAGG
GGGGCGGAGCCTATGGAAAAACGCCAGCAACGCGGCCTTTTTACGGTTCCTGGCCTTTTG
CTGGCCTTTTGCTCACATGTTCTTTCCTGCGTTATCCCCTGATTCTGTGGATAACCGTAT
TACCGCCTTTGAGTGAGCTGATACCGCTCGCCGCAGCCGAACGACCGAGCGCAGCGAGTC
AGTGAGCGAGGAAGCG
<Sap-SAR-Sap insert here>
GAAGAGCCCGCGGGCAAGGTCGCCACGCACAAGATCAATATTAACAATCAGTCATCTCTC
TTTAGCAATAAAAAGGTGAAAAATTACATTTTAAAAATGACACCATAGACGATGTATGAA
AATAATCTACTTGGAAATAAATCTAGGCAAAGAAGTGCAAGACTGTTACCCAGAAAACTT
ACAAATTGTAAATGAGAGGTTAGTGAAGATTTAAATGAATGAAGATCTAAATAAACTTAT
AAATTGTGAGAGAAATTAATGAATGTCTAAGTTAATGCAGAAACGGAGAGACATACTATA
TTCATGAACTAAAAGACTTAATATTGTGAAGGTATACTTTCTTTTCACATAAATTTGTAG
TCAATATGTTCACCCCAAAAAAGCTGTTTGTTAACTTGTCAACCTCATTTCAAAATGTAT
ATAGAAAGCCCAAAGACAATAACAAAAATATTCTTGTAGAACAAAATGGGAAAGAATGTT
CCACTAAATATCAAGATTTAGAGCAAAGCATGAGATGTGTGGGGATAGACAGTGAGGCTG
ATAAAATAGAGTAGAGCTCAGAAACAGACCCATTGATATATGTAAGTGACCTATGAAAAA
AATATGGCATTTTACAATGGGAAAATGATGATCTTTTTCTTTTTTAGAAAAACAGGGAAA
TATATTTATATGTAAAAAATAAAAGGGAACCCATATGTCATACCATACACACAAAAAAAT
TCCAGTGAATTATAAGTCTAAATGGAGAAGGCAAAACTTTAAATCTTTTAGAAAATAATA
TAGAAGCATGCCATCATGACTTCAGTGTAGAGAAAAATTTCTTATGACTCAAAGTCCTAA
CCACAAAGAAAAGATTGTTAATTAGATTGCATGAATATTAAGACTTATTTTTAAAATTAA
AAAACCATTAAGAAAAGTCAGGCCATAGAATGACAGAAAATATTTGCAACACCCCAGTAA
AGAGAATTGTAATATGCAGATTATAAAAAGAAGTCTTACAAATCAGTAAAAAATAAAACT
AGACAAAAATTTGAACAGATGAAAGAGAAACTCTAAATAATCATTACACATGAGAAACTC
AATCTCAGAAATCAGAGAACTATCATTGCATATACACTAAATTAGAGAAATATTAAAAGG
CTAAGTAACATCTGTGGCAATATTGATGGTATATAACCTTGATATGATGTGATGAGAACA
GTACTTTACCCCATGGGCTTCCTCCCCAAACCCTTACCCCAGTATAAATCATGACAAATA
TACTTTAAAAACCATTACCCTATATCTAACCAGTACTCCTCAAAACTGTCAAGGTCATCA
AAAATAAGAAAAGTCTGAGGAACTGTCAAAACTAAGAGGAACCCAAGGAGACATGAGAAT
TATATGTAATGTGGCATTCTGAATGAGATCCCAGAACAGAAAAAGAACAGTAGCTAAAAA
ACTAATGAAATATAAATAAAGTTTGAACTTTAGTTTTTTTAAAAAAGAGTAGCATTAAC
ACGGCAAAGTCATTTTCATATTTTTCTTGAACATTAAGTACAAGTCTATAATTAAAAATT
TTTTAAATGTAGTCTGGAACATTGCCAGAAACAGAAGTACAGCAGCTATCTGTGCTGTCG
CCTAACTATCCATAGCTGATTGGTCTAAAATGAGATACATCAACGCTCCTCCATGTTTTT
TGTTTTCTTTTTAAATGAAAAACTTTATTTTTTAAGAGGAGTTTCAGGTTCATAGCAAAA
TTGAGAGGAAGGTACATTCAAGCTGAGGAAGTTTTCCTCTATTCCTAGTTTACTGAGAGA
TTGCATCATGAATGGGTGTTAAATTTTGTCAAATGCTTTTTCTGTGTCTATCAATATGAC
CATGTGATTTTCTTCTTTAACCTGTTGATGGGACAAATTACGTTAATTGATTTTCAAACG
TTGAACCACCCTTACATATCTGGAATAAATTCTACTTGGTTGTGGTGTATATTTTTTGAT
ACATTCTTGGATTCTTTTTGCTAATATTTTGTTGAAAATGTTTGTATCTTTGTTCATGAG
AGATATTGGTCTGTTGTTTTCTTTTCTTGTAATGTCATTTTCTAGTTCCGGTATTAAGGT
AATGCTGGCCTAGTTGAATGATTTAGGAAGTATTCCCTCTGCTTCTGTCTTCTGAAGCGG
AAGAGC
<end M13>
GCCCAATACGCAAACCGCCTCTCCCCGCGCGTTGGCCGATTCATTAATGCAGCTGGCACG
ACAGGTTTCCCGACTGGAAAGCGGGCAGTGAGCGCAACGCAATTAATGTGAGTTAGCTCA
CTCATTAGGCACCCCAGGCTTTACACTTTATGCTTCCGGCTCGTATGTTGTGTGGAATTG
TGAGCGGATAACAATTTCACACAGGAAACAGCTATGACATGATTACGAATTAA

FIG._16D

AAGCTTTACTCGTAAAGCGAGTTGAAGGATCATATTTAGTTGCGTTTATGAGATAAGATT
GAAAGCACGTGTAAA
><start ORF504 (PTP)>
ATGTTTCCCGCGCGTTGGCACAACTATTTACAATGCGGCCAAGTTATAAAAGATTCTAAT
CTGATATGTTTTAAAACACCTTTGCGGCCCGAGTTGTTTGCGTACGTGACTAGCGAAGAA
GATGTGTGGACCGCAGAACAGATAGTAAAACAAAACCCTAGTATTGGAGCAATAATCGAT
TTAACCAACACGTCTAAATATTATGATGGTGTGCATTTTTTGCGGGCGGGCCTGTTATAC
AAAAAAATTCAAGTACCTGGCCAGACTTTGCCGCCTGAAAGCATAGTTCAAGAATTTATT
GACACGGTAAAAGAATTTACAGAAAAGTGTCCCGGCATGTTGGTGGGCGTGCACTGCACA
CACGGTATTAATCGCACCGGTTACATGGTGTGCAGATATTTAATGCACACCCTGGGTATT
GCGCCGCAGGAAGCCATAGATAGATTCGAAAAAGCCAGAGGTCACAAAATTGAAAGACAA
AATTACGTTCAAGATTTATTAATTTAATTAATATTATTTGCATTCTTTAACAAATACTTT
ATCCTATTTTCAAATTGTTGCGCTTCTTCCAGCGAACCAAAACTATGCTTCGCTTGCTCC
GTTTAGCTTGTAGCCGATCAGTGGCGTTGTTCCAATCGACGGTAGGATTAGGCCGGATAT
TCTCCACCACAATGTTGGCAACGTTGATGTTACGTTTATGCTTTTGGTTTTCCACGTACG
TCTTTTGGCCGGTAATAGCCGTAAACGTAGTGCCGTCGCGCGTCACGCACAACACCGGAT
GTTTGCGCTTGTCCGCGGGTATTGAACCGCGCGATCCGACAAATCCACCACTTTGGCAA
CTAAATCGGTGACCTGCGCGTCTTTTTCTGCATTATTTCGTCTTTCTTTTGCATGGTTT
CCTGGAAGCCGGTGTACATGCGGTTTAGATCAGTCATGACGCGCGTGACCTGCAAATCTT
TGGCCTCGATCTGCTTGTCCTTGATGGCAACGATGCGTTCAATAAACTCTTGTTTTTAA
CAAGTTCCTCGGTTTTTGCGCCACCACCGCTTGCAGCGCGTTTGTGTGCTCGGTGAATG
TCGCAATCAGCTTAGTCACCAACTGTTTGCTCTCCTCCTCCCGTTGTTTGATCGCGGGAT
CGTACTTGCCGGTGCAGAGCACTTGAGGAATTACTTCTTCTAAAAGCCATTCTTGTAATT
CTATGGCGTAAGGCAATTTGGACTTCATAATCAGCTGAATCACGCCGGATTTAGTAATGA
GCACTGTATGCGGCTGCAAATACAGCGGGTCGCCCCTTTTCACGACGCTGTTAGAGGTAG
GGCCCCCATTTTGGATGGTCTGCTCAAATAACGATTTGTATTTATTGTCTACATGAACAC
GTATAGCTTTATCACAAACTGTATATTTTAAACTGTTAGCGACGTCCTTGGCCACGAACC
GGACCTGTTGGTCGCGCTCTAGCACGTACCGCAGGTTGAACGTATCTTCTCCAAATTTAA
ATTCTCCAATTTTAACGCGAGCCA
><start ORF984 (ORF2)>
TTTTGATACACGTGTGTCGATTTTGCAACAACTATTGTTTTTTAACGCAAACTAAACTTA
TTGTGGTAAGCAATAATTAAATATGGGGGAACATGCGCCGCTACAACACTCGTCGTTATG
AACGCAGACGGCGCCGGTCTCGGCGCAAGCGGCTAAAACGTGTTGCGCGTTCAACGCGGC
AAACATCGCAAAAGCCAATAGTACAGTTTTGATTTGCA
><start conotoxin>
TATTAACGGCGATTTTTTAAATTATCTTATTTAATAAATAGTTATGACGCCTACAACTCC
CCGCCCGCGTTGACTCGCTGCACCTCGAGCAGTTCGTTGACGCCTTCCTCCGTGTGGCCG
AACACGTCGAGCGGGTGGTCGATGACCAGCGGCGTGCCGCACGCGACGCACAAGTATCTG
TACACCGAATGATCGTCGGGCGAAGGCACGTCGGCCTCCAAGTGGCAATATTGGCAAATT
CGAAAATATATACAGTTGGGTTGTTTGCGCATATCTATCGTGGCGTTGGGCATGTACGTC
CGAACGTTGATTTGCATGCAAGCCGAAATTAAATCATTGCGATTAGTGCGATTAAAACGT
TGTACATCCTCGCTTTTAATCATGCCGTCGATTAAATCGCGCAATCGAGTCAAGTGATCA
AAGTGTGGAATAATGTTTTCTTTGTATTCCCGAGTCAAGCGCAGCGCGTATTTTAACAAA
CTAGCCATCTTGTAAGTTAGTTTCA
><start ORF453>

TTTAATGCAACTTTATCCAATAATATATT
><start ORF327>
ATGTATCGCACGTCAAGAATTAACAATGCGCCCGTTGTCGCATCTCAACACGACTATGAT
AGAGATCAAATAAAGCGCGAATTAAATAGCTTGCGACGCAACGTGCACGATCTGTGCACG
CGTTCCGGCACGAGCTTTGATTGTAATAAGTTTTTACGAAGCGATGACATGACCCCCGTA
GTGACAACGATCACGCCCAAAAGAACTGCCGACTACAAAATTACCGAGTATGTCGGTGAC
GTTAAAACTATTAAGCCATCCAATCGACCGTTAGTCGAATCAGGACCGCTGGTGCGAGAA
GCCGCGAAGT
><start ORF630>

FIG._17A

ATGGCGAATGCATCGTATAACGTGTGGAGTCCGCTCATTAGAGCGTCATGTTTAGACAAG
AAAGCTACATATTTAATTGATCCGATGATTTTATTGATAAATTGACCCTAACTCCATAC
ACGGTATTCTACAATGGCGGGGTTTTGGTCAAAATTTCCGGACTGCGATTGTACATGCTG
TTAACGGCTCCGCCCACTATTAATGAAATTAAAAATTCCAATTTTAAAAAACGCAGCAAG
AGAAACATTTGTATGAAAGAATGCGTAGAAGGAAAGAAAAATGTCGTCGACATGCTGAAC
AACAAGATTAATATGCCTCCGTGTATAAAAAAAATATTGAACGATTTGAAAGAAAACAAT
GTACCGCGCGGCGGTATGTACAGGAAGAGGTTTATACTAAACTGTTACATTGCAAACGTG
GTTTCGTGTGCCAAGTGTGAAAACCGATGTTTAATCAAGGCTCTGACGCATTTCTACAAC
CACGACTCCAAGTGTGTGGGTGAAGTCATGCATCTTTTAATCAAATCCCAAGATGTGTAT
AAACCACCAAACTGCCAAAAAATGAAAACTGTCGACAAGCTCTGTCCGTTGCTGGCAAC
TGCAAGGGTCTCAATCCTATTTGTAATTATTGAATAATAAAACAATTATAAATGCTAAAT
TTGTTTTTTATTAACGATACAAACCAAACGCAACAAGAACATTTGTAGTATTATCTATAA
TTGAAAACGCGTAGTTATAATCGCTGAGGTAATATTTAAAATCATTTTCAAATGATTCAC
AGTTAATTTGCGACAATATAATTTTATTTTCACATAAACTAGACGCCTTGTCGTCTTCTT
CTTCGTATTCCTTCTCTTTTTCATTTTTCTCCTCATAAAAATTAACATAGTTATTATCGT
ATCCATATATGTATCTATCGTATAGAGTAAATTTTTTGTTGTCATAAATATATATGTCTT
TTTTAATGGGGTGTATAGTACCGCTGCGCATAGTTTTTCTGTAATTTACAACAGTGCTAT
TTTCTGGTAGTTCTTCGGAGTGTGTTGCTTTAATTATTAAATTTATATAATCAATGAATT
TGGGATCGTCGGTTTTGTACAATATGTTGCCGGCATAGTACGCAGCTTCTTCTAGTTCAA
TTACACCATTTTTTAGCAGCACCGGATTAACATAACTTTCCAAAATGTTGTACGAACCGT
TAAACAAAAACAGTTCACCTCCCTTTTCTATACTATTGTCTGCGAGCAGTTGTTTGTTGT
TAAAAATAACAGCCA
><start ORF603>
TTGTAATGAGACGCACAAACTAATATCACAAACTGGAAATGTCTATCAATATATAGTTGC
TGATATCATGGAGATAATTAAAATGATAACCATCTCGCAAATAAA
><start of polh transcription>
TAAGTATTTTACTGTTTTCGTAACAGTTTTGTAATAAAAAAACCTATAAAT
><mutated polh start codon>
ATTCCGGATTATTCATACCGTCCCACCATCGGGCGC
><start polylinker >
GGATCCGCGGCCGCGAATTCTAAACCACCATGGCTAGCAGGCCT
><start of IgG>
GACAAAACTCACACATGCCCACCGTGCCCAGCACCTGAACTCCTGGGGGGACCGTCAGTC
TTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGAC
GGCGTGGAGGTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAAGAGATGACCAAG
AACCAGGTCAGCCTGACCTGCCTGGTCAAAGGCTTCTATCCCAGCGACATCGCCGTGGAG
TGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGG
AACGTCTTCTCATGCTCCGTGATGCATGAGGCTCTGCACAACCACTACACGCAGAAGAGC
CTCTCCCTGTCTCCGGGTAAA
><end of IgG>
TGACATAGGG
><untranslated His tag>
CATCATCATCATCATCATCATCATTAATTCTAGACTAGTCTGCAGATC
><end polylinker>
T

FIG._17B

><polh coding sequences>
GATCCTTTCCTGGGACCCGGCAAGAACCAAAAACTCACTCTCTTCAAGGAAATCCGTAAT
GTTAAACCCGACACGATGAAGCTTGTCGTTGGATGGAAAGGAAAAGAGTTCTACAGGGAA
ACTTGGACCCGCTTCATGGAAGACAGCTTCCCCATTGTTAACGACCAAGAAGTGATGGAT
GTTTTCCTTGTTGTCAACATGCGTCCCACTAGACCCAACCGTTGTTACAAATTCCTGGCC
CAACACGCTCTGCGTTGCGACCCCGACTATGTACCTCATGACGTGATTAGGATCGTCGAG
CCTTCATGGGTGGGCAGCAACAACGAGTACCGCATCAGCCTGGCTAAGAAGGGCGGCGGC
TGCCCAATAATGAACCTTCACTCTGAGTACACCAACTCGTTCGAACAGTTCATCGATCGT
GTCATCTGGGAGAACTTCTACAAGCCCATCGTTTACATCGGTACCGACTCTGCTGAAGAG
GAGGAAATTCTCCTTGAAGTTTCCCTGGTGTTCAAAGTAAAGGAGTTTGCACCAGACGCA
CCTCTGTTCACTGGTCCGGCGTATTAAAACACGATACATTGTTATTAGTACATTTATTAA
GCGCTAGATTCTGTGCGTTGTTGATTTACAGACAATTGTTGTACGTATTTTAATAATTCA
TTAAATTTATAATCTTTAGGGTGGTATGTTAGAGCGAAAATCAAATGATTTTCAGCGTCT
TTATATCTGAATTTAAATATTAAATCCTCAATAGATTTGTAAAATAGGTTTCGATTAGTT
TCAAACAAGGGTTGTTTTTCCGAACCGATGGCTGGACTATCTAATGGATTTTCGCTCAAC
GCCACAAAACTTGCCAAATCTTGTAGCAGCAATCTAGCTTTGTCGATATTCGTTTGTGTT
TTGTTTTGTAATAAAGGTTCGACGTCGTTCAAAATATTATGCGCTTTTGTATTTCTTTCA
TCACTGTCGTTAGTGTACAATTGACTCGACGTAAACACGTTAAATAAAGCTTGGACATAT
TTAACATCGGGCGTGTTAGCTTTATTAGGCCGATTATCGTCGTCGTCCCAACCCTCGTCG
TTAGAAGTTGCTTCCGAAGACGATTTTGCCATAGCCACACGACGCCTATTAATTGTGTCG
GCTAACACGTCCGCGATCAAATTTGTAGTTGAGCTTTTTGGAATTATTTCTGATTGCGGG
CGTTTTTGGGCGGGTTTCAATCTAACTGTGCCCGATTTTAATTCAGACAACACGTTAGAA
AGCGATGGTGCAGGCGGTGGTAACATTTCAGACGGCAAATCTACTAATGGCGGCGGTGGT
GGAGCTGATGATAAATCTACCATCGGTGGAGGCGCAGGCGGGGCTGGCGGCGGAGGCGGA
GGCGGAGGTGGTGGCGGTGATGCAGACGGCGGTTTAGGCTCAAATGTCTCTTTAGGCAAC
ACAGTCGGCACCTCAACTATTGTACTGGTTTCGGGCGCCGTTTTTGGTTTGACCGGTCTG
AGACGAGTGCGATTTTTTCGTTTCTAATAGCTTCCAACAATTGTTGTCTGTCGTCTAAA
GGTGCAGCGGGTTGAGGTTCCGTCGGCATTGGTGGAGCGGGCGGCAATTCAGACATCGAT
GGTGGTGGTGGTGGTGGAGGCGCTGGAATGTTAGGCACGGGAGAAGGTGGTGGCGGCGGT
GCCGCCGGTATAATTTGTTCTGGTTTAGTTTGTTCGCGCACGATTGTGGGCACCGGCGCA
GGCGCCGCTGGCTGCACAACGGAAGGTCGTCTGCTTCGAGGCAGCGCTTGGGGTGGTGGC
AATTCAATATTATAATTGGAATACAAATCGTAAAAATCTGCTATAAGCATTGTAATTTCG
CTATCGTTTACCGTGCCGATATTTAACAACCGCTCAATGTAAGCAATTGTATTGTAAAGA
GATTGTCTCAAGCTCCGCACGCCGATAACAAGCCTTTTCATTTTTACTACAGCATTGTAG
TGGCGAGACACTTCGCTGTCGTCGACGTACATGTATGCTTTGTTGTCAAAAACGTCGTTG
GCAAGCTTTAAAATATTTAAAAGAACATCTCTGTTCAGCACCACTGTGTTGTCGTAAATG
TTGTTTTTGATAATTTGCGCTTCCGCAGTATCGACACGTTCAAAAAATTGATGCGCATCA
ATTTTGTTGTTCCTATTATTGAATAAATAAGATTGTACAGATTCATATCTACGATTCGTC
><start ORF588>
A
><start ORF1629>
TGGCCACCACAAATGCTACGCTGCAAACGCTGGTACAATTTTACGAAAACTGCAAAAACG
TCAAAACTCGGTATAAAATAATCAACGGGCGCTTTGGCAAAATATCTATTTTATCGCACA
AGCCCACTAGCAAATTGTATTTGCAGAAAACAATTTCGGCGCACAATTTTAACGCTGACG
AAATAAAAGTTCACCAGTTAATGAGCGACCACCCAAATTTTATAAAAATCTATTTTAATC
ACGGTTCCATCAACAACCAAGTGATCGTGATGGACTACATTGACTGTCCCGATTTATTTG
AAACACTACAAATTAAAGGCGAGCTTTCGTACCAACTTGTTAGCAATATTATTAGACAGC
TGTGTGAAGCGCTAACGATTTGCACAAGCACAATTTCATACACAACGACATAAAACTCG
AAAATGTCTTATATTTCGAAGCACTTGATCGCGTGTATGTTTGCGATTACGGATTGTGCA
AACACGAAAACTCACTTAGCGTGCACGACGGCACGTTGGAGTATTTTAGTCCGGAAAAAA
TTCGACACACAACTATGCACGTTTCGTTTGACTGGTACGCGGCGTGTTAACATACAAGTT
GCTAACCGGCGG

FIG._17C

><end of polh locus fragment>
TTCGTAATCATGGTCATAGCTGTTTCCTGTGTGAAATTGTTATCCGCTCACAATTCCACA
CAACATACGAGCCGGAAGCATAAAGTGTAAAGCCTGGGGTGCCTAATGAGTGAGCTAACT
CACATTAATTGCGTTGCGCTCACTGCCCGCTTTCCAGTCGGGAAACCTGTCGTGCCAGCT
GCATTAATGAATCGGCCAACGCGCGGGGAGAGGCGGTTTGCGTATTG
><border ColE1 origin>
GGCGCTCTTCCGCTTCCTCGCTCACTGACTCGCTGCGCTCGGTCGTTCGGCTGCGGCGAG
CGGTATCAGCTCACTCAAAGGCGGTAATACGGTTATCCACAGAATCAGGGGATAACGCAG
GAAAGAACATGTGAGCAAAAGGCCAGCAAAAGGCCAGGAACCGTAAAAAGGCCGCGTTGC
TGGCGTTTTTCCATAGGCTCCGCCCCCCTGACGAGCATCACAAAAATCGACGCTCAAGTC
AGAGGTGGCGAAACCCGACAGGACTATAAAGATACCAGGCGTTTCCCCCTGGAAGCTCCC
TCGTGCGCTCTCCTGTTCCGACCCTGCCGCTTACCGGATACCTGTCCGCCTTTCTCCCTT
CGGGAAGCGTGGCGCTTTCTCATAGCTCACGCTGTAGGTATCTCAGTTCGGTGTAGGTCG
TTCGCTCCAAGCTGGGCTGTGTGCACGAACCCCCCGTTCAGCCCGACCGCTGCGCCTTAT
CCGGTAACTATCGTCTTGAGTCCAACCCGGTAAGACACGACTTATCGCCACTGGCAGCAG
CCACTGGTAACAGGATTAGCAGAGCGAGGTATGTAGGCGGTGCTACAGAGTTCTTGAAGT
GGTGGCCTAACTACGGCTACACTAGAAGGACAGTATTTGGTATCTGCGCTCTGCTGAAGC
CAGTTACCTTCGGAAAAAGAGTTGGTAGCTCTTGATCCGGCAAACAAACCACCGCTGGTA
GCGGTGGTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGGA
TTTTGGTCATGAGATTATCAAAAAGGATCTTCACCTAGATCCTTTT ><border ColE1 origin>
AAATTAAAAATGAAGTTTTAAATCAATCTAAAGTATATATGAGTAAACTTGGTCTGACAG
TTACCAATGCTTAATCAGTGAGGCACCTATCTCAGCGATCTGTCTATTTCGTTCATCCAT
AGTTGCCTGACTCCCCGTCGTGTAGATAACTACGATACGGGAGGGCTTACCATCTGGCCC
CAGTGCTGCAATGATACCGCGAGACCCACGCTCACCGGCTCCAGATTTATCAGCAATAAA
CCAGCCAGCCGGAAGGGCCGAGCGCAGAAGTGGTCCTGCAACTTTATCCGCCTCCATCCA
GTCTATTAATTGTTGCCGGGAAGCTAGAGTAAGTAGTTCGCCAGTTAATAGTTTGCGCAA
CGTTGTTGCCATTGCTACAGGCATCGTGGTGTCACGCTCGTCGTTTGGTATGGCTTCATT
CAGCTCCGGTTCCCAACGATCAAGGCGAGTTACATGATCCCCCATGTTGTGCAAAAAAGC
GGTTAGCTCCTTCGGTCCTCCGATCGTTGTCAGAAGTAAGTTGGCCGCAGTGTTATCACT
CATGGTTATGGCAGCACTGCATAATTCTCTTACTGTCATGCCATCCGTAAGATGCTTTTC
TGTGACTGGTGAGTACTCAACCAAGTCATTCTGAGAATAGTGTATGCGGCGACCGAGTTG
CTCTTGCCCGGCGTCAATACGGGATAATACCGCGCCACATAGCAGAACTTTAAAAGTGCT
CATCATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACCAG
CGTTTCTGGGTGAGCAAAAACAGGAAGGCAAAATGCCGCAAAAAAGGGAATAAGGGCGAC
ACGGAAATGTTGAATACTCA
><Start Amp>
TACTCTTCCTTTTTCAATATTATTGAAGCATTTATCAGGGTTATTGTCTCATGAGCGGAT
ACATATTTGAATGTATTTAGAAAAATAAACAAATAGGGGTTCCGCGCACATTTCCCCGAA
AAGTGCCACCTGACGTCTAAGAAACCATTATTATCATGACATTAACCTATAAAAATAGGC
GTATCACGAGGCCCTTTCGTCTCGCGCGTTTCGGTGATGACGGTGAAAACCTCTGACACA
TGCAGCTCCCGGAGACGGTCACAGCTTGTCTGTAAGCGGATGCCGGGAGCAGACAAGCCC
GTCAGGGCGCGTCAGCGGGTGTTGGCGGGTGTCGGGCTGGCTTAACTATGCGGCATCAG
AGCAGATTGTACTGAGAGTGCACCATATATGCGGTGTGAAATACCGCACAGATGCGTAAG
GAGAAAATACCGCATCAGGCGCCATTCGCCATTCAGGCTGCGCAACTGTTGGGAAGGGCG
ATCGGTGCGGGCCTCTTCGCTATTACGCCAGCTGGCGAAAGGGGGATGTGCTGCAAGGCG
ATTAAGTTGGGTAACGCCAGGGTTTTCCCAGTCACGACGTTGTAAAACGACGGCCAGTGC
C

FIG._17D

AAGCTTTACTCGTAAAGCGAGTTGAAGGATCATATTTAGTTGCGTTTATGAGATAAGATT
GAAAGCACGTGTAAA
><start ORF504 (PTP)>
ATGTTTCCCGCGCGTTGGCACAACTATTTACAATGCGGCCAAGTTATAAAAGATTCTAAT
CTGATATGTTTTAAAACACCTTTGCGGCCCGAGTTGTTTGCGTACGTGACTAGCGAAGAA
GATGTGTGGACCGCAGAACAGATAGTAAAACAAAACCCTAGTATTGGAGCAATAATCGAT
TTAACCAACACGTCTAAATATTATGATGGTGTGCATTTTTTGCGGGCGGGCCTGTTATAC
AAAAAAATTCAAGTACCTGGCCAGACTTTGCCGCCTGAAAGCATAGTTCAAGAATTTATT
GACACGGTAAAAGAATTTACAGAAAAGTGTCCCGGCATGTTGGTGGGCGTGCACTGCACA
CACGGTATTAATCGCACCGGTTACATGGTGTGCAGATATTTAATGCACACCCTGGGTATT
GCGCCGCAGGAAGCCATAGATAGATTCGAAAAAGCCAGAGGTCACAAAATTGAAAGACAA
AATTACGTTCAAGATTTATTAATTTAATTAATATTATTTGCATTCTTTAACAAATACTTT
ATCCTATTTTCAAATTGTTGCGCTTCTTCCAGCGAACCAAAACTATGCTTCGCTTGCTCC
GTTTAGCTTGTAGCCGATCAGTGGCGTTGTTCCAATCGACGGTAGGATTAGGCCGGATAT
TCTCCACCACAATGTTGGCAACGTTGATGTTACGTTTATGCTTTTGGTTTTCCACGTACG
TCTTTTGGCCGGTAATAGCCGTAAACGTAGTGCCGTCGCGCGTCACGCACAACACCGGAT
GTTTGCGCTTGTCCGCGGGGTATTGAACCGCGCGATCCGACAAATCCACCACTTTGGCAA
CTAAATCGGTGACCTGCGCGTCTTTTTTCTGCATTATTTCGTCTTTCTTTTGCATGGTTT
CCTGGAAGCCGGTGTACATGCGGTTTAGATCAGTCATGACGCGCGTGACCTGCAAATCTT
TGGCCTCGATCTGCTTGTCCTTGATGGCAACGATGCGTTCAATAAACTCTTGTTTTTTAA
CAAGTTCCTCGGTTTTTTGCGCCACCACCGCTTGCAGCGCGTTTGTGTGCTCGGTGAATG
TCGCAATCAGCTTAGTCACCAACTGTTTGCTCTCCTCCTCCCGTTGTTTGATCGCGGGAT
CGTACTTGCCGGTGCAGAGCACTTGAGGAATTACTTCTTCTAAAAGCCATTCTTGTAATT CTATGGCGTAAGGCAATTTGGACTTCATAATCAGCTGAATCACGCCGGATTTAGTAATGA
GCACTGTATGCGGCTGCAAATACAGCGGGTCGCCCCTTTTCACGACGCTGTTAGAGGTAG
GGCCCCCATTTTGGATGGTCTGCTCAAATAACGATTTGTATTTATTGTCTACATGAACAC
GTATAGCTTTATCACAAACTGTATATTTTAAACTGTTAGCGACGTCCTTGGCCACGAACC
GGACCTGTTGGTCGCGCTCTAGCACGTACCGCAGGTTGAACGTATCTTCTCCAAATTTAA
ATTCTCCAATTTTAACGCGAGCCA
><start ORF984 (ORF2)>
TTTTGATACACGTGTGTCGATTTTGCAACAACTATTGTTTTTTAACGCAAACTAAACTTA
TTGTGGTAAGCAATAATTAAATATGGGGAACATGCGCCGCTACAACACTCGTCGTTATG
AACGCAGACGGCGCCGGTCTCGGCGCAAGCGGCTAAAACGTGTTGCGCGTTCAACGCGGC
AAACATCGCAAAAGCCAATAGTACAGTTTTGATTTGCA
><start conotoxin>
TATTAACGGCGATTTTTTAAATTATCTTATTTAATAAATAGTTATGACGCCTACAACTCC
CCGCCCGCGTTGACTCGCTGCACCTCGAGCAGTTCGTTGACGCCTTCCTCCGTGTGGCCG
AACACGTCGAGCGGGTGGTCGATGACCAGCGGCGTGCCGCACGCGACGCACAAGTATCTG
TACACCGAATGATCGTCGGGCGAAGGCACGTCGGCCTCCAAGTGGCAATATTGGCAAATT
CGAAAATATATACAGTTGGGTTGTTTGCGCATATCTATCGTGGCGTTGGGCATGTACGTC
CGAACGTTGATTTGCATGCAAGCCGAAATTAAATCATTGCGATTAGTGCGATTAAAACGT
TGTACATCCTCGCTTTTAATCATGCCGTCGATTAAATCGCGCAATCGAGTCAAGTGATCA
AAGTGTGGAATAATGTTTTCTTTGTATTCCCGAGTCAAGCGCAGCGCGTATTTTAACAAA
CTAGCCATCTTGTAAGTTAGTTTCA

FIG._18A

```
><start ORF453>
TTTAATGCAACTTTATCCAATAATATATT
><start ORF327>
ATGTATCGCACGTCAAGAATTAACAATGCGCCCGTTGTCGCATCTCAACACGACTATGAT
AGAGATCAAATAAAGCGCGAATTAAATAGCTTGCGACGCAACGTGCACGATCTGTGCACG
CGTTCCGGCACGAGCTTTGATTGTAATAAGTTTTTACGAAGCGATGACATGACCCCCGTA
GTGACAACGATCACGCCCAAAAGAACTGCCGACTACAAAATTACCGAGTATGTCGGTGAC
GTTAAAACTATTAAGCCATCCAATCGACCGTTAGTCGAATCAGGACCGCTGGTGCGAGAA
GCCGCGAAGT
><start ORF630>
ATGGCGAATGCATCGTATAACGTGTGGAGTCCGCTCATTAGAGCGTCATGTTTAGACAAG
AAAGCTACATATTTAATTGATCCCGATGATTTTATTGATAAATTGACCCTAACTCCATAC
ACGGTATTCTACAATGGCGGGGTTTTGGTCAAAATTTCCGGACTGCGATTGTACATGCTG
TTAACGGCTCCGCCCACTATTAATGAAATTAAAAATTCCAATTTTAAAAAACGCAGCAAG
AGAAACATTTGTATGAAAGAATGCGTAGAAGGAAAGAAAAATGTCGTCGACATGCTGAAC
AACAAGATTAATATGCCTCCGTGTATAAAAAAATATTGAACGATTTGAAAGAAAACAAT
GTACCGCGCGGCGGTATGTACAGGAAGAGGTTTATACTAAACTGTTACATTGCAAACGTG
GTTTCGTGTGCCAAGTGTGAAAACCGATGTTTAATCAAGGCTCTGACGCATTTCTACAAC
CACGACTCCAAGTGTGTGGGTGAAGTCATGCATCTTTTAATCAAATCCCAAGATGTGTAT
AAACCACCAAACTGCCAAAAAATGAAAACTGTCGACAAGCTCTGTCCGTTTGCTGGCAAC
TGCAAGGGTCTCAATCCTATTTGTAATTATTGAATAATAAAACAATTATAAATGCTAAAT
TTGTTTTTTATTAACGATACAAACCAAACGCAACAAGAACATTTGTAGTATTATCTATAA
TTGAAAACGCGTAGTTATAATCGCTGAGGTAATATTTAAAATCATTTTCAAATGATTCAC
AGTTAATTTGCGACAATATAATTTTATTTTCACATAAACTAGACGCCTTGTCGTCTTCTT
CTTCGTATTCCTTCTCTTTTTCATTTTTCTCCTCATAAAAATTAACATAGTTATTATCGT
ATCCATATATGTATCTATCGTATAGAGTAAATTTTTTGTTGTCATAAATATATATGTCTT
TTTTAATGGGGTGTATAGTACCGCTGCGCATAGTTTTTCTGTAATTTACAACAGTGCTAT
TTTCTGGTAGTTCTTCGGAGTGTGTTGCTTTAATTATTAAATTTATATAATCAATGAATT
TGGGATCGTCGGTTTTGTACAATATGTTGCCGGCATAGTACGCAGCTTCTTCTAGTTCAA
TTACACCATTTTTTAGCAGCACCGGATTAACATAACTTTCCAAAATGTTGTACGAACCGT
TAAACAAAAACAGTTCACCTCCCTTTTCTATACTATTGTCTGCGAGCAGTTGTTTGTTGT
TAAAAATAACAGCCA
><start ORF603>
TTGTAATGAGACGCACAAACTAATATCACAAACTGGAAATGTCTATCAATATATAGTTGC
TGATATCATGGAGATAATTAAAATGATAACCATCTCGCAAATAAA
><start of polh transcription>
TAAGTATTTTACTGTTTTCGTAACAGTTTTGTAATAAAAAAACCTATAAAT
><mutated polh start codon>
ATTCCGGATTATTCATACCGTCCCACCATCGGGCGC
><start polylinker >
GGATCCGCGGCCGCGAATTCTAAACCACCATGGGCAGCTGCCCGGG
><His tag>
CATCATCATCATCATCATCATCATTAATTCTAGACTAGTCTGCAGATC
><end polylinker>
T
```

FIG._18B

><polh coding sequences>
GATCCTTTCCTGGGACCCGGCAAGAACCAAAAACTCACTCTCTTCAAGGAAATCCGTAAT
GTTAAACCCGACACGATGAAGCTTGTCGTTGGATGGAAAGGAAAAGAGTTCTACAGGGAA
ACTTGGACCCGCTTCATGGAAGACAGCTTCCCCATTGTTAACGACCAAGAAGTGATGGAT
GTTTTCCTTGTTGTCAACATGCGTCCCACTAGACCCAACCGTTGTTACAAATTCCTGGCC
CAACACGCTCTGCGTTGCGACCCCGACTATGTACCTCATGACGTGATTAGGATCGTCGAG
CCTTCATGGGTGGGCAGCAACAACGAGTACCGCATCAGCCTGGCTAAGAAGGGCGGCGGC
TGCCCAATAATGAACCTTCACTCTGAGTACACCAACTCGTTCGAACAGTTCATCGATCGT
GTCATCTGGGAGAACTTCTACAAGCCCATCGTTTACATCGGTACCGACTCTGCTGAAGAG
GAGGAAATTCTCCTTGAAGTTTCCCTGGTGTTCAAAGTAAAGGAGTTTGCACCAGACGCA
CCTCTGTTCACTGGTCCGGCGTATTAAAACACGATACATTGTTATTAGTACATTTATTAA
GCGCTAGATTCTGTGCGTTGTTGATTTACAGACAATTGTTGTACGTATTTTAATAATTCA
TTAAATTTATAATCTTTAGGGTGGTATGTTAGAGCGAAAATCAAATGATTTTCAGCGTCT
TTATATCTGAATTTAAATATTAAATCCTCAATAGATTTGTAAAATAGGTTTCGATTAGTT
TCAAACAAGGGTTGTTTTCCGAACCGATGGCTGGACTATCTAATGGATTTTCGCTCAAC
GCCACAAAACTTGCCAAATCTTGTAGCAGCAATCTAGCTTTGTCGATATTCGTTTGTGTT
TTGTTTTGTAATAAAGGTTCGACGTCGTTCAAAATATTATGCGCTTTTGTATTTCTTTCA
TCACTGTCGTTAGTGTACAATTGACTCGACGTAAACACGTTAAATAAAGCTTGGACATAT
TTAACATCGGGCGTGTTAGCTTTATTAGGCCGATTATCGTCGTCGTCCCAACCCTCGTCG
TTAGAAGTTGCTTCCGAAGACGATTTTGCCATAGCCACACGACGCCTATTAATTGTGTCG
GCTAACACGTCCGCGATCAAATTTGTAGTTGAGCTTTTTGGAATTATTTCTGATTGCGGG
CGTTTTTGGGCGGGTTTCAATCTAACTGTGCCCGATTTTAATTCAGACAACACGTTAGAA
AGCGATGGTGCAGGCGGTGGTAACATTTCAGACGGCAAATCTACTAATGGCGGCGGTGGT
GGAGCTGATGATAAATCTACCATCGGTGGAGGCGCAGGCGGGGCTGGCGGCGGAGGCGGA
GGCGGAGGTGGTGGCGGTGATGCAGACGGCGGTTTAGGCTCAAATGTCTCTTTAGGCAAC
ACAGTCGGCACCTCAACTATTGTACTGGTTTCGGGCGCCGTTTTGGTTTGACCGGTCTG
AGACGAGTGCGATTTTTTTCGTTTCTAATAGCTTCCAACAATTGTTGTCTGTCGTCTAAA
GGTGCAGCGGGTTGAGGTTCCGTCGGCATTGGTGGAGCGGGCGGCAATTCAGACATCGAT
GGTGGTGGTGGTGGAGGCGCTGGAATGTTAGGCACGGGAGAAGGTGGTGGCGGCGGT
GCCGCCGGTATAATTTGTTCTGGTTTAGTTTGTTCGCGCACGATTGTGGGCACCGGCGCA
GGCGCCGCTGGCTGCACAACGGAAGGTCGTCTGCTTCGAGGCAGCGCTTGGGGTGGTGGC
AATTCAATATTATAATTGGAATACAAATCGTAAAAATCTGCTATAAGCATTGTAATTTCG
CTATCGTTTACCGTGCCGATATTTAACAACCGCTCAATGTAAGCAATTGTATTGTAAAGA
GATTGTCTCAAGCTCCGCACGCCGATAACAAGCCTTTTCATTTTTACTACAGCATTGTAG
TGGCGAGACACTTCGCTGTCGTCGACGTACATGTATGCTTTGTTGTCAAAAACGTCGTTG
GCAAGCTTTAAAATATTTAAAAGAACATCTCTGTTCAGCACCACTGTGTTGTCGTAAATG
TTGTTTTTGATAATTTGCGCTTCCGCAGTATCGACACGTTCAAAAAATTGATGCGCATCA
ATTTGTTGTTCCTATTATTGAATAAATAAGATTGTACAGATTCATATCTACGATTCGTC
><start ORF588>
A
><start ORF1629>
TGGCCACCACAAATGCTACGCTGCAAACGCTGGTACAATTTTACGAAAACTGCAAAAACG
TCAAAACTCGGTATAAAATAATCAACGGGCGCTTTGGCAAAATATCTATTTTATCGCACA
AGCCCACTAGCAAATTGTATTTGCAGAAAACAATTTCGGCGCACAATTTTAACGCTGACG
AAATAAAAGTTCACCAGTTAATGAGCGACCACCCAAATTTTATAAAAATCTATTTTAATC
ACGGTTCCATCAACAACCAAGTGATCGTGATGGACTACATTGACTGTCCCGATTTATTTG
AAACACTACAAATTAAAGGCGAGCTTTCGTACCAACTTGTTAGCAATATTATTAGACAGC
TGTGTGAAGCGCTCAACGATTTGCACAAGCACAATTTCATACACAACGACATAAAACTCG
AAAATGTCTTATATTTCGAAGCACTTGATCGCGTGTATGTTTGCGATTACGGATTGTGCA

FIG._18C

AACACGAAAACTCACTTAGCGTGCACGACGGCACGTTGGAGTATTTTAGTCCGGAAAAAA
TTCGACACACAACTATGCACGTTTCGTTTGACTGGTACGCGGCGTGTTAACATACAAGTT
GCTAACCGGCGG
><end of polh locus fragment>
TTCGTAATCATGGTCATAGCTGTTTCCTGTGTGAAATTGTTATCCGCTCACAATTCCACA
CAACATACGAGCCGGAAGCATAAAGTGTAAAGCCTGGGGTGCCTAATGAGTGAGCTAACT
CACATTAATTGCGTTGCGCTCACTGCCCGCTTTCCAGTCGGGAAACCTGTCGTGCCAGCT
GCATTAATGAATCGGCCAACGCGCGGGGAGAGGCGGTTTGCGTATTG
><border ColE1 origin>
GGCGCTCTTCCGCTTCCTCGCTCACTGACTCGCTGCGCTCGGTCGTTCGGCTGCGGCGAG
CGGTATCAGCTCACTCAAAGGCGGTAATACGGTTATCCACAGAATCAGGGGATAACGCAG
GAAAGAACATGTGAGCAAAAGGCCAGCAAAAGGCCAGGAACCGTAAAAAGGCCGCGTTGC
TGGCGTTTTTCCATAGGCTCCGCCCCCCTGACGAGCATCACAAAAATCGACGCTCAAGTC
AGAGGTGGCGAAACCCGACAGGACTATAAAGATACCAGGCGTTTCCCCCTGGAAGCTCCC
TCGTGCGCTCTCCTGTTCCGACCCTGCCGCTTACCGGATACCTGTCCGCCTTTCTCCCTT
CGGGAAGCGTGGCGCTTTCTCATAGCTCACGCTGTAGGTATCTCAGTTCGGTGTAGGTCG
TTCGCTCCAAGCTGGGCTGTGTGCACGAACCCCCCGTTCAGCCCGACCGCTGCGCCTTAT
CCGGTAACTATCGTCTTGAGTCCAACCCGGTAAGACACGACTTATCGCCACTGGCAGCAG
CCACTGGTAACAGGATTAGCAGAGCGAGGTATGTAGGCGGTGCTACAGAGTTCTTGAAGT
GGTGGCCTAACTACGGCTACACTAGAAGGACAGTATTTGGTATCTGCGCTCTGCTGAAGC
CAGTTACCTTCGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGGA
TTTTGGTCATGAGATTATCAAAAGGATCTTCACCTAGATCCTTTT
><border ColE1 origin>
AAATTAAAAATGAAGTTTTAAATCAATCTAAAGTATATATGAGTAAACTTGGTCTGACAG
TTACCAATGCTTAATCAGTGAGGCACCTATCTCAGCGATCTGTCTATTTCGTTCATCCAT
AGTTGCCTGACTCCCCGTCGTGTAGATAACTACGATACGGGAGGGCTTACCATCTGGCCC
CAGTGCTGCAATGATACCGCGAGACCCACGCTCACCGGCTCCAGATTTATCAGCAATAAA
CCAGCCAGCCGGAAGGGCCGAGCGCAGAAGTGGTCCTGCAACTTTATCCGCCTCCATCCA
GTCTATTAATTGTTGCCGGGAAGCTAGAGTAAGTAGTTCGCCAGTTAATAGTTTGCGCAA
CGTTGTTGCCATTGCTACAGGCATCGTGGTGTCACGCTCGTCGTTTGGTATGGCTTCATT
CAGCTCCGGTTCCCAACGATCAAGGCGAGTTACATGATCCCCCATGTTGTGCAAAAAAGC
GGTTAGCTCCTTCGGTCCTCCGATCGTTGTCAGAAGTAAGTTGGCCGCAGTGTTATCACT
CATGGTTATGGCAGCACTGCATAATTCTCTTACTGTCATGCCATCCGTAAGATGCTTTTC
TGTGACTGGTGAGTACTCAACCAAGTCATTCTGAGAATAGTGTATGCGGCGACCGAGTTG
CTCTTGCCCGGCGTCAATACGGGATAATACCGCGCCACATAGCAGAACTTTAAAAGTGCT
CATCATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACCAG
CGTTTCTGGGTGAGCAAAAACAGGAAGGCAAAATGCCGCAAAAAAGGGAATAAGGGCGAC
ACGGAAATGTTGAATACTCA
><Start Amp>
TACTCTTCCTTTTTCAATATTATTGAAGCATTTATCAGGGTTATTGTCTCATGAGCGGAT
ACATATTTGAATGTATTTAGAAAAATAAACAAATAGGGGTTCCGCGCACATTTCCCCGAA
AAGTGCCACCTGACGTCTAAGAAACCATTATTATCATGACATTAACCTATAAAAATAGGC
GTATCACGAGGCCCTTTCGTCTCGCGCGTTTCGGTGATGACGGTGAAAACCTCTGACACA
TGCAGCTCCCGGAGACGGTCACAGCTTGTCTGTAAGCGGATGCCGGGAGCAGACAAGCCC
GTCAGGGCGCGTCAGCGGGTGTTGGCGGGTGTCGGGCTGGCTTAACTATGCGGCATCAG
AGCAGATTGTACTGAGAGTGCACCATATATGCGGTGTGAAATACCGCACAGATGCGTAAG
GAGAAAATACCGCATCAGGCGCCATTCGCCATTCAGGCTGCGCAACTGTTGGGAAGGGCG
ATCGGTGCGGGCCTCTTCGCTATTACGCCAGCTGGCGAAAGGGGGATGTGCTGCAAGGCG
ATTAAGTTGGGTAACGCCAGGGTTTTCCCAGTCACGACGTTGTAAAACGACGGCCAGTGC
C

FIG._18D

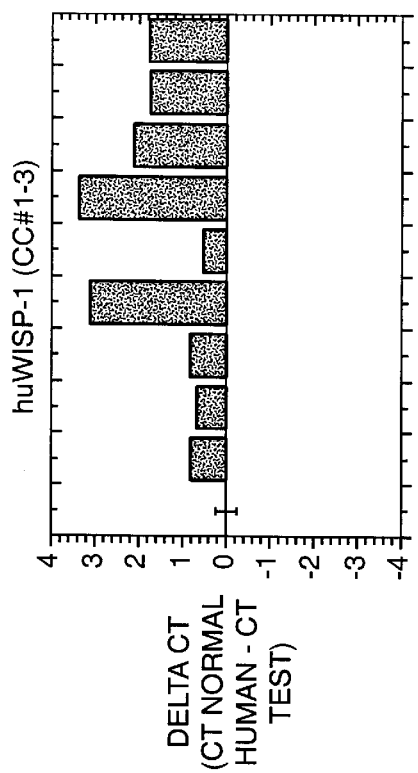
FIG._19B
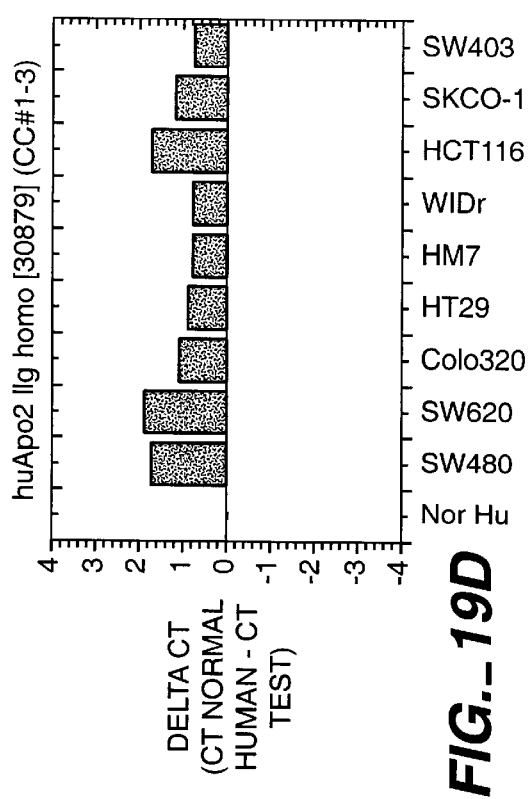
FIG._19D
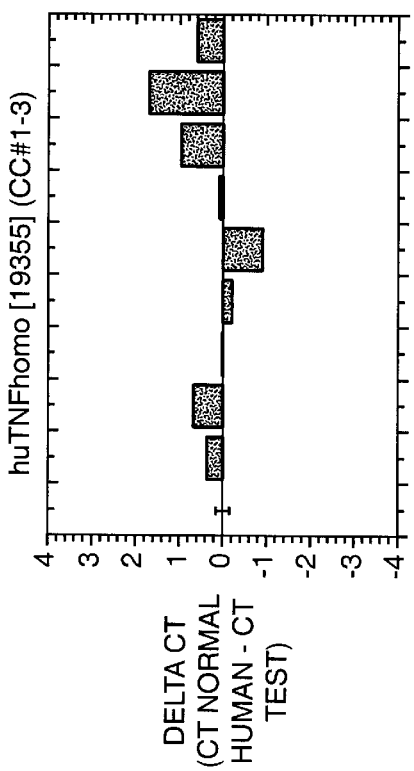
FIG._19A
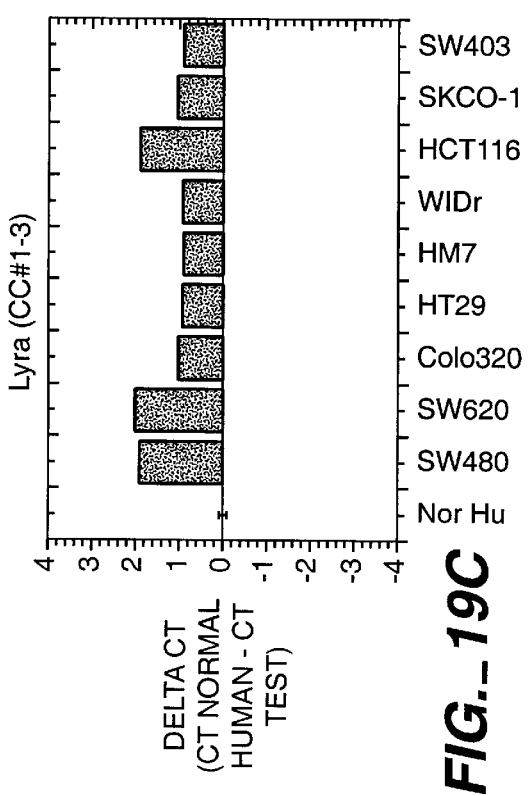
FIG._19C

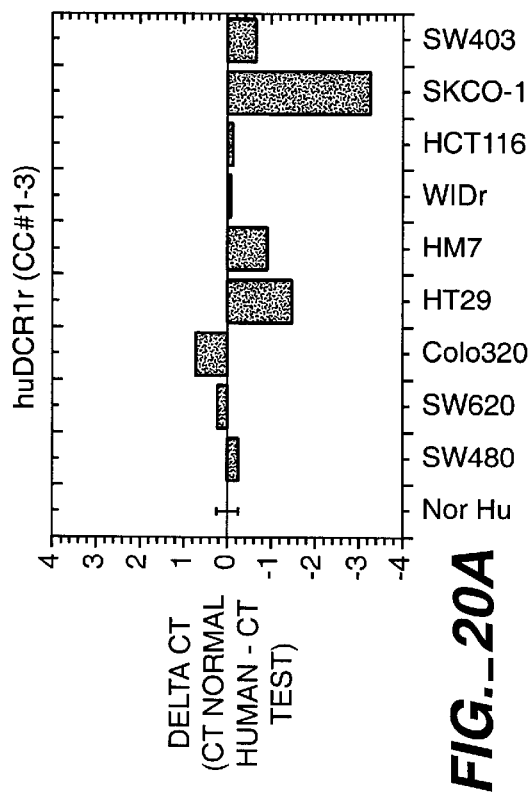
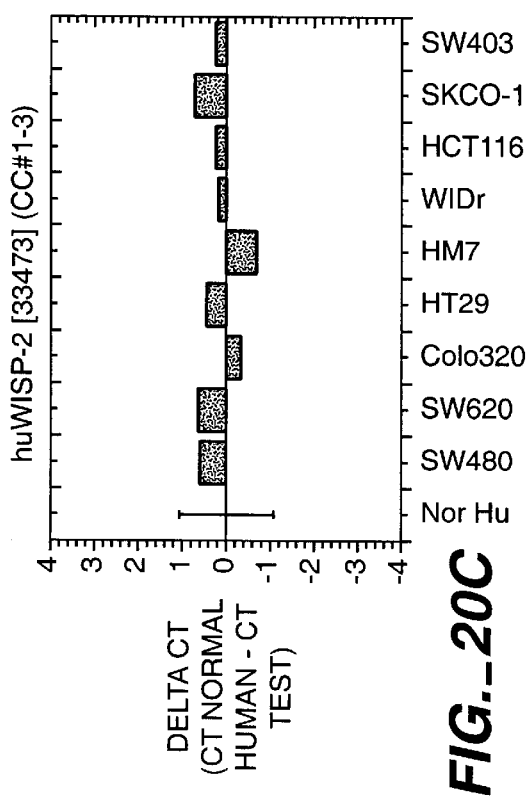
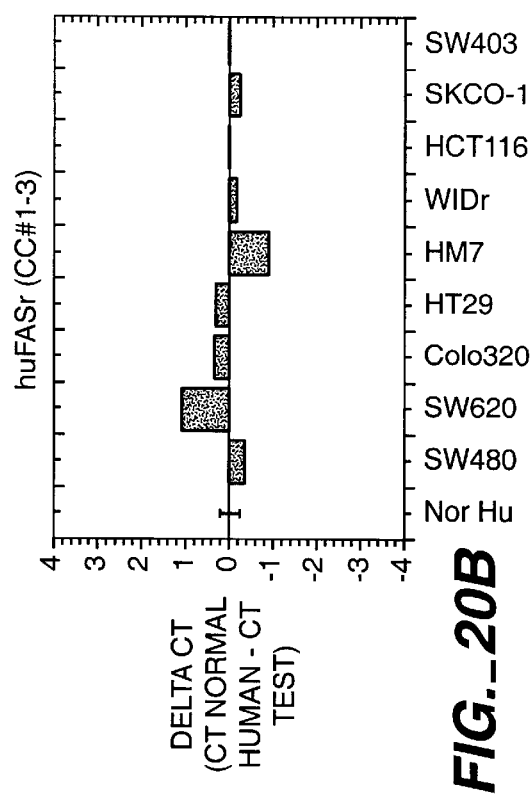
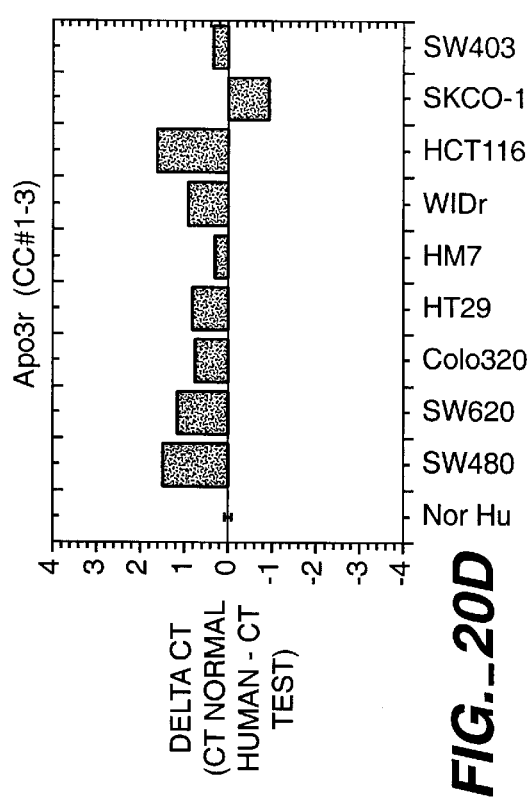
FIG._20A  FIG._20B  FIG._20C  FIG._20D

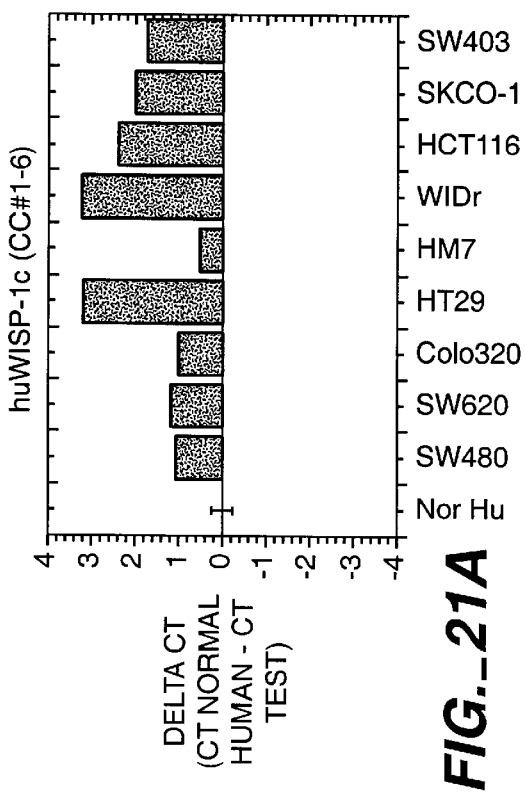
FIG._21A
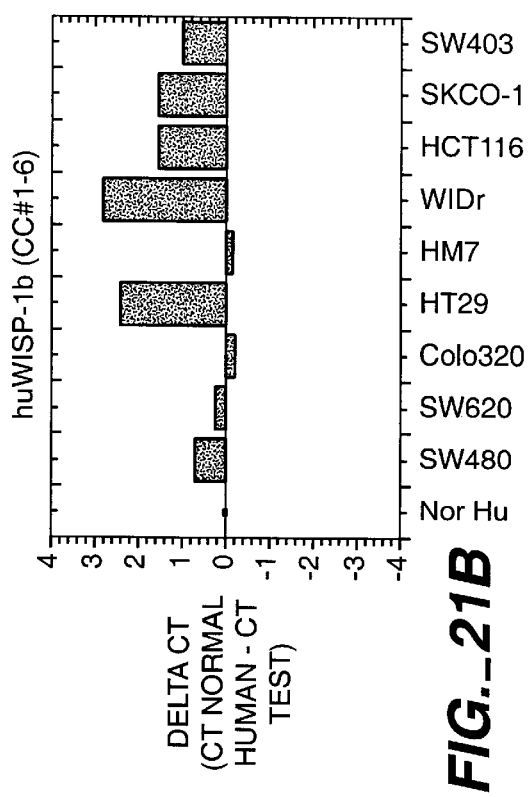
FIG._21B
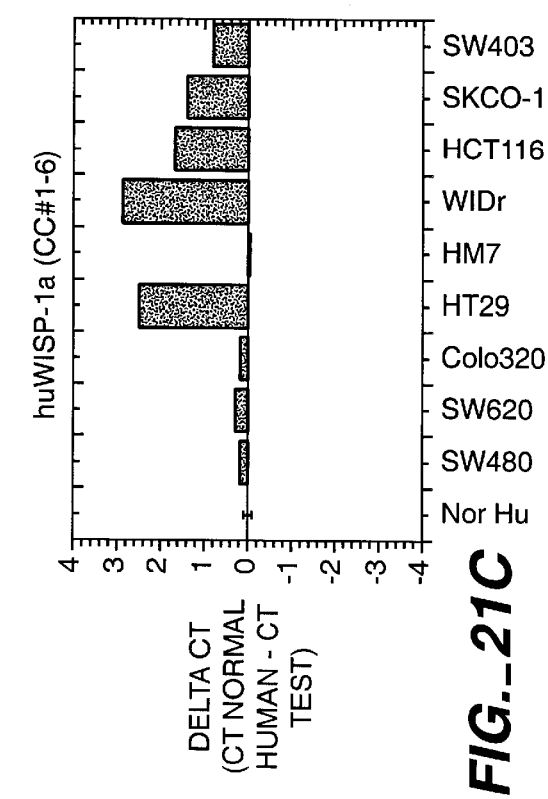
FIG._21C
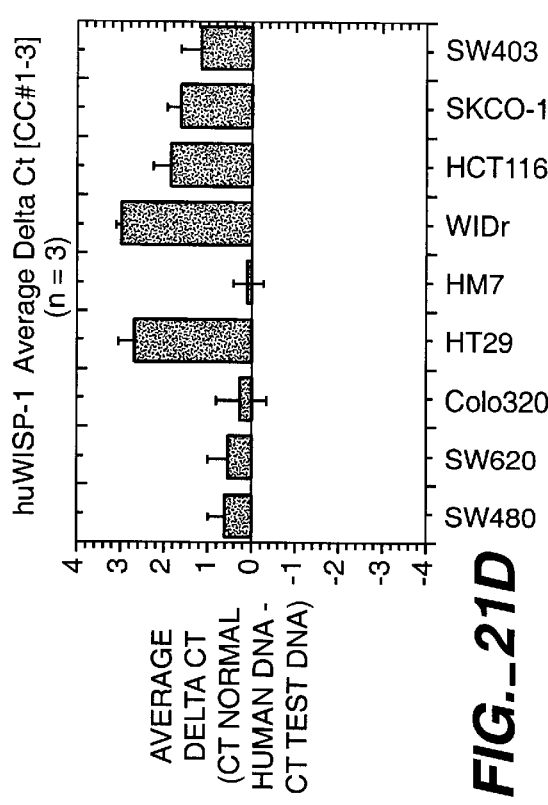
FIG._21D

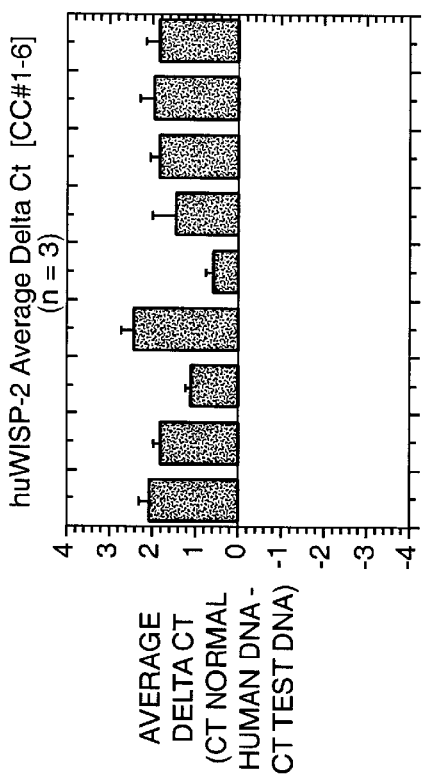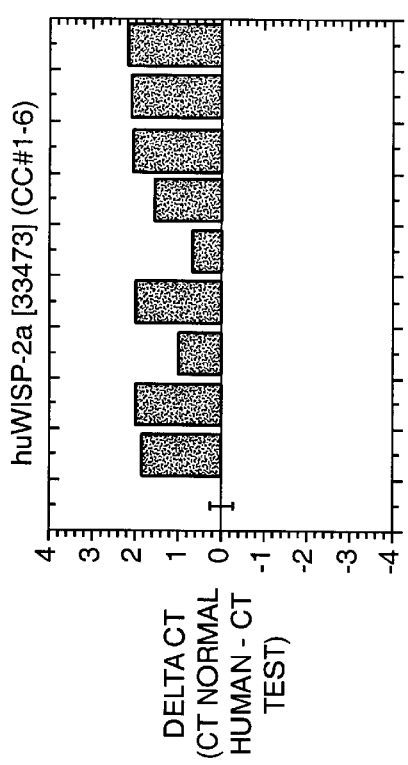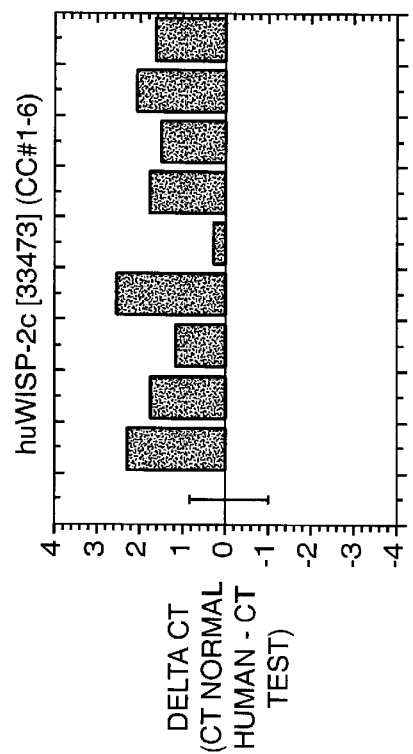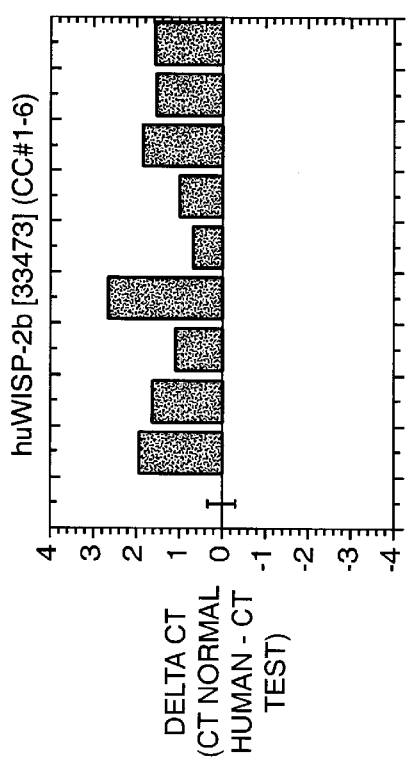
FIG._22A  FIG._22B  FIG._22C  FIG._22D

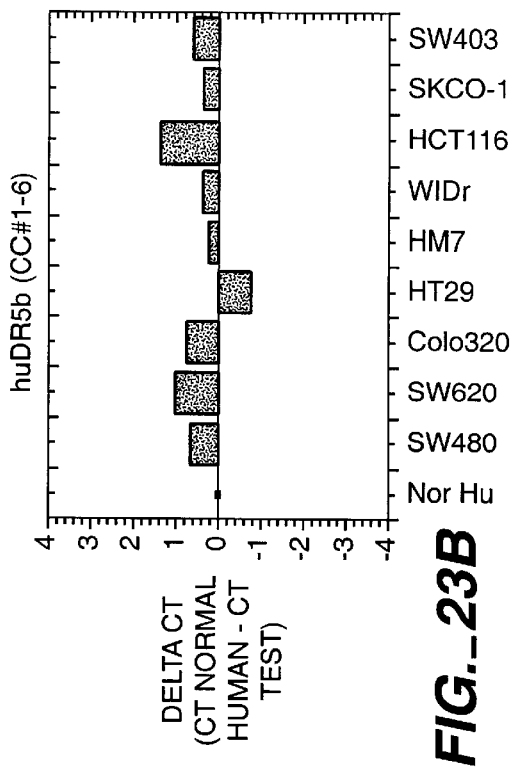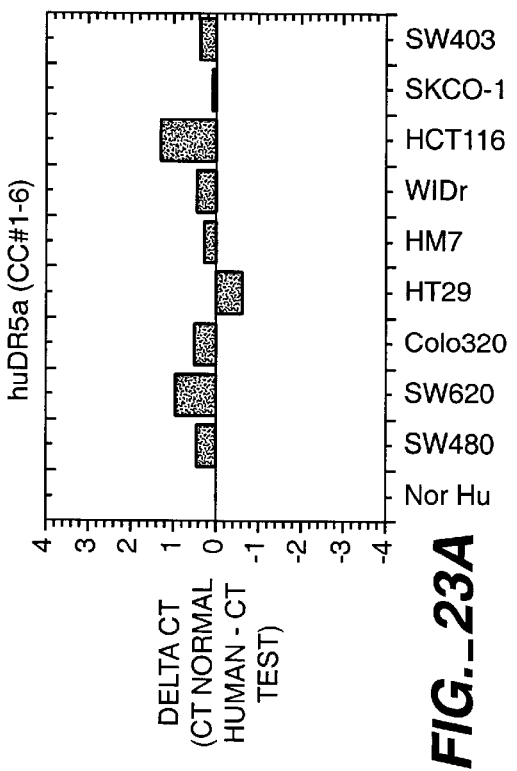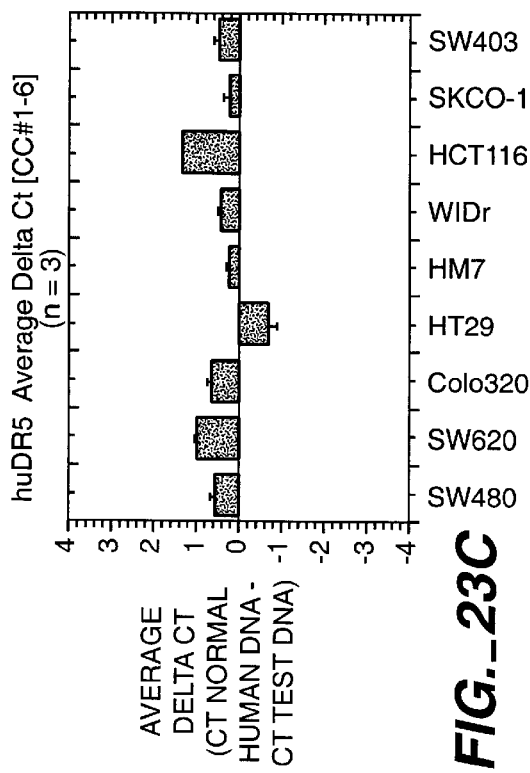
FIG._23B
FIG._23A
FIG._23C

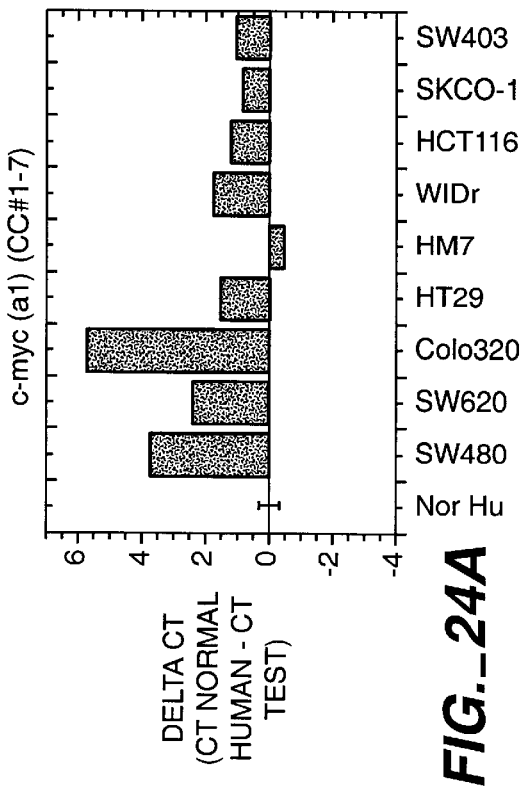
FIG._24A
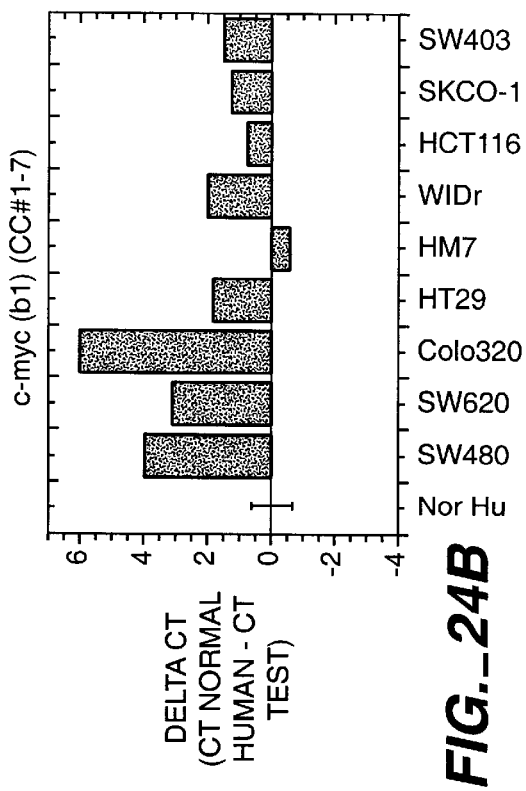
FIG._24B
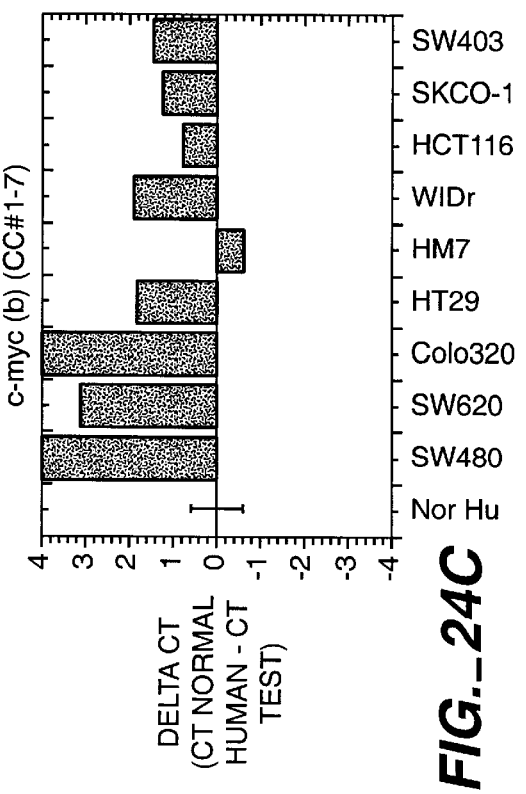
FIG._24C
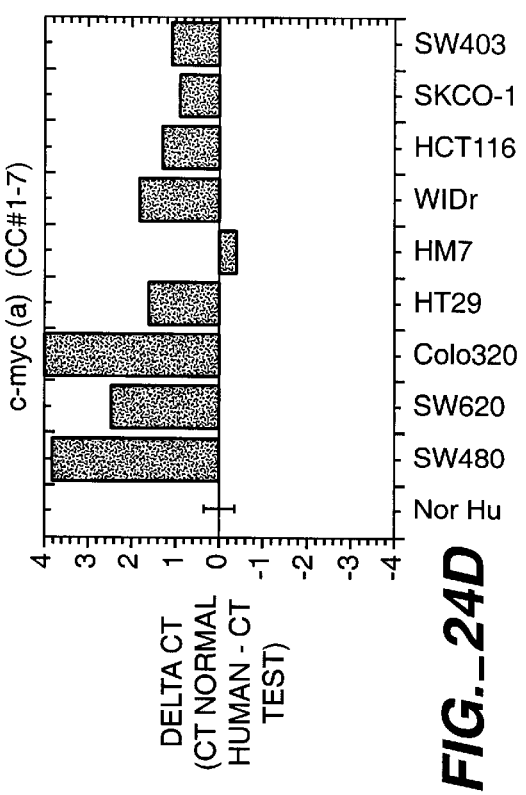
FIG._24D

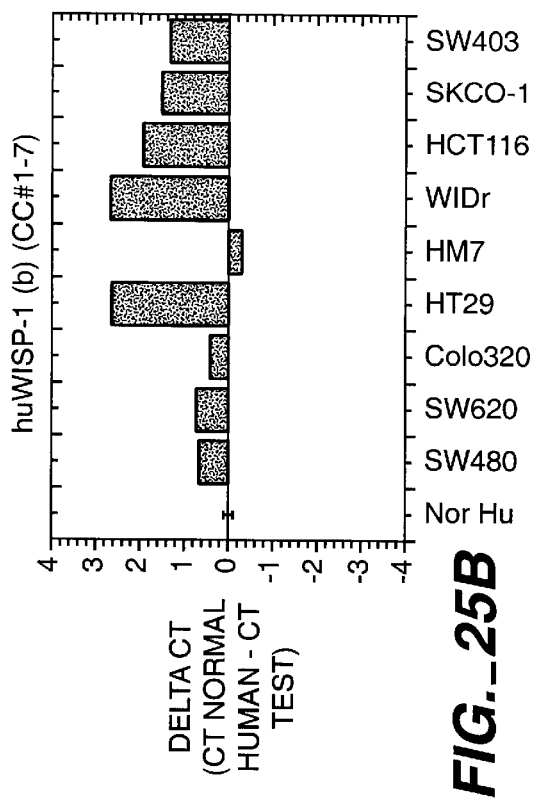
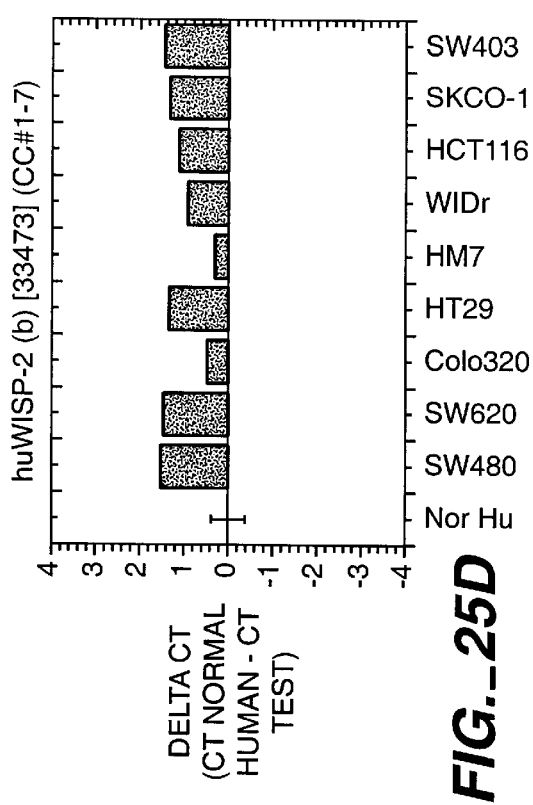
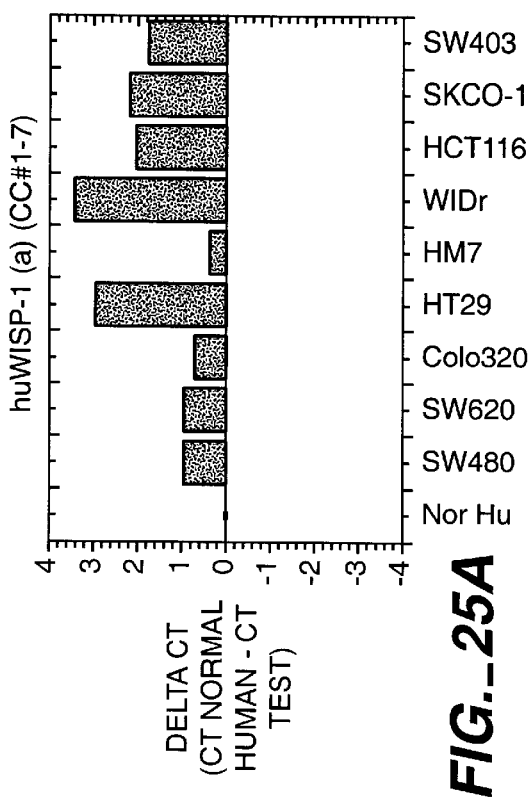
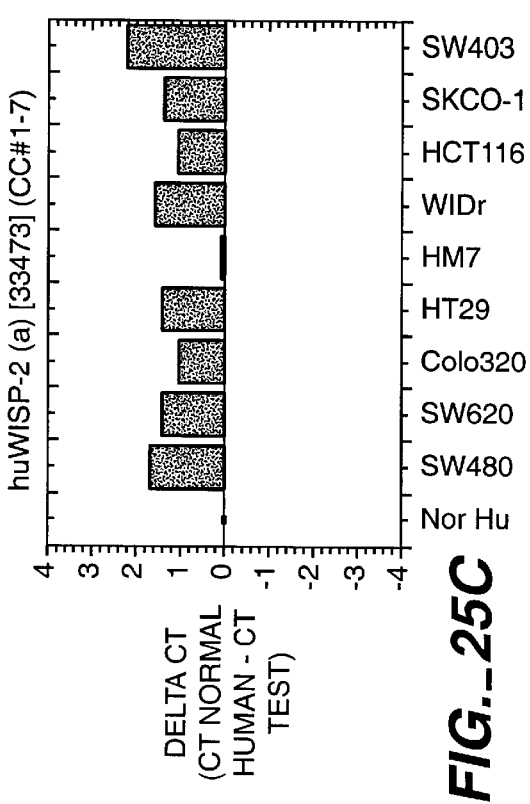
FIG._25A  FIG._25B  FIG._25C  FIG._25D 5'-GCCAGTCTGGGCCCAGCTCCCCCGAGAGGTGGTCGGATCCTCTGGGCTGCTCGGTCGATG
CCTGTGCCACTGACGTCCAGGCATGAGGTGGTTCCTGCCCTGGACGCTGGCAGCAGTGAC
AGCAGCAGCCGCCAGCACCGTCCTGGCCACGGCCCTCTCTCCAGCCCCTACGACCATGGA
CTTTACCCCAGCTCCACTGGAGGACACCTCCTCACGCCCCCAATTCTGCAAGTGGCCATG
TGAGTGCCCGCCATCCCCACCCCGCTGCCCGCTGGGGGTCAGCCTCATCACAGATGGCTG
TGAGTGCTGTAAGATGTGCGCTCAGCAGCTTGGGGACAACTGCACGGAGGCTGCCATCTG
TGACCCCACCGGGGCCTCTACTGTGACTACAGCGGGGACCGCCCGAGAGGTGGTCGGTG
TGGGCTGCGTCCTGGATGGGGTGCGCTACAACAACGGCCAGTCCTTCCAGCCTAACTGCA
AGTACAACTGCACGTGCATCGACGGCGCGGTGGGCTGCACACCACTGTGCCTCCGAGTGC
GCCCCCCGCGTCTCTGGTGCCCCCACCCGCGGCGCGTGAGCATACCTGGCCACTGCTGTG
AGCAGTGGGTATGTGAGGACGACGCCAAGAGGCCACGCAAGACCGCACCCGTGACACAG
GAGCCTTCGATGCTGTGGGTGAGGTGGAGGCATGGCACAGGAACTGCATAGCCTACACAA
GCCCCTGGAGCCCTTGCTCCACCAGCTGCGGCCTGGGGGTCTCCACTCGGATCTCCAATG
TTAACGCCCAGTGCTGGCCTGAGCAAGAGAGCCGCCTCTGCAACTTGCGGCCATGCGATG
TGGACATCCATACACTCATTAAGGCAGGGAAGAAGTGTCTGGCTGTGTACCAGCCAGAGG
CATCCATGAACTTCACACTTGCGGGCTGCATCAGCACACGCTCCTATCAACCCAAGTACT
GTGGAGTTTGCATGGACAATAGGTGCTGCATCCCCTACAAGTCTAAGACTATCGACGTGT
CCTTCCAGTGTCCTGATGGGCTTGGCTTCTCCCGCCAGGTCCTATGGATTAATGCCTGCT
TCTGTAACCTGAGCTGTAGGAATCCCAATGACATCTTTGCTGACTTGGAATCCTACCCTG
ACTTCTCAGAAATTGCCAACTAGGCAGGCACAAATCTTGGGTCTTGGGGACTAACCCAAT
GCCTGTGAAGCAGTCAGCCCTTATGGCCAATAACTTTTCACCAATGAGCCTTAGTTACCC
TGATCTGGACCCTTGGCCTCCATTTCTGTCTCTAACCATTCAAATGACGCCTGATGGTGC
TGCTCAGGCCCATGCTATGAGTTTTCTCCTTGATATCATTCAGCATCTACTCTAAAGAAA
AATGCCTGTCTCTAGCTGTTCTG

FIG._26

5'-TTTAATTAAACCCCCAAGGGCTGCGGAAGGAGCATATCTGGTGCTCCTGATGGGCCGGCC
AGTCTGGGCCCAGCTCCCCCGAGAGGTGGTCGGATCCTCTGGGCTGCTCGGTCGATGCCT
GTGCCACTGACGTCCAGGCATGAGGTGGTTCCTGCCCTGGACGCTGGCAGCAGTGACAGC
AGCAGCCGCCAGCACCGTCCTGGCCACGGCCCTCTCTCCAGCCCCTACGACCATGGACTT
TACCCCAGCTCCACTGGAGGACACCTCCTCACGCCCCCAATTCTGCAAGTGGCCATGTGA
GTGCCCGCCATCCCCACCCCGCTGCCCGCTGGGGGTCAGCCTCATCACAGATGGCTGTGA
GTGCTGTAAGATGTGCGCTCAGCAGCTTGGGGACAACTGCACGGAGGCTGCCATCTGTGA
CCCCACCGGGGCCTCTACTGTGACTACAGCGGGGACCGCCCGAGGTACGCAATAGGAGT
GTGTGCACGCAGGGAAGAAGTGTCTGGCTGTGTACCAGCCAGAGGCATCCATGAACTTCA
CACTTGCGGGCTGCATCAGCACACGCTCCTATCAACCCAAGTACTGTGGAGTTTGCATGG
ACAACAGGTGCTGCATCCCCTACAAGTCTAAGACTATCGACGTGTCCTTCCAGTGTCCTG
ATGGGCTTGGCTTCTCCCGCCAGGTCCTATGGA

FIG._27

5'-CAGAATTTGAACTGGGATCCACCTGTCTCTAAAGATGGGTTTCCTCCCATGCTTCCACAC
TGCCTCTCTTGATCAGAAACATACAAGGAGCTGAGAACATGTCCTCCACTCCCTGGGTAC
CTTTGCTGGTTAGAAGCCAACTTGCTGTCCTGTGGGGAGGTACAGCCAATTTCTGTGTTC
CTCTGAGTTCTGGGGACCGCAGACCTTAGTGTGGTGAAAGTGAGCGTTGGGGGCTGGTGG
GAGCTGTAGATTCATGCAGATTCTGTTCCCCACACACAGATGCTGTGGGTGAGGTGGAGG
CATGGCACAGGAACTGCATAGCCTACACAAGCCCTGGAGCCCTTGCTCCACCAGCTGCG
GCCTGGGGGTCTCCACTCGGATCTCCAATGTTAACGCCCAGTGCTGGCCTGAGCAAGAGA
GCCGCCTCTGCAACTTGCGGCCATGCGATGTGGACATCCATACACTCATTAAGGCAGGGA
AGAAGTGTCTGGCTGTGTACCAGCCAGAGGCATCCATGAACTTCACACTTGCGGGCTGCA
TCAGCACACGCTCCTATCAACCCAAGTACTGTGGAGTTTGCATGGACAATAGGTGCTGCA
TCCCCTACAAGTCTAAGACTATCGACGTGTCCTTCCAGTGTCCTGATGGGCTTGGCTTCT
CCCGCCAGGTCGTATGGATTAAT

FIG._28

5'-GTCTGGGCCCAGCTCCCCCGAGAGGTGGTCGGATCCTCTGGGCTGCTCGGTCGATGCCTG
TGCCACTGACGTCCAGGCATGAGGTGGTTCCTGCCCTGGACGCTGGCAGCAGTGACAGCA
GCAGCCGCCAGCACCGTCCTGGCCACGGCCCTCTCTCCAGCCCCTACGACCATGGACTTT
ACCCCAGCTCCACTGGAGGACACCTCCTCACGCCCCCAATTCTGCAAGTGGCCATGTGAG
TGCCCGCCATCCCCACCCCGCTGCCCGCTGGGGGTCAGCCTCATCACAGATGGCTGTGAG
TGCTGTAAGATGTGCGCTCAGCAGCTTGGGGACAACTGCACGGAGGCTGCCATCTGTGAC
CCCCACCGGGGCCTCTACTGTGACTACAGCGGGGACCGCCCGAGGTACGCAATAGGAGTG
TGTGCACGCAGGGAAGAAGTGTCTGGCTGTGTACCAGCCAGAGGCATCCATGAACTTCAC
ACTTGCGGGCTGCATCAGCACACGCTCCTATCAACCCAAGTACTGTGGAGTTTGCATGGA
CAACAGGTGCTGCATCCCCTACAAGTCTAAGACTATCGACGTGTCCTTCCAGTGTCCTGA
TGGGCTTGGCTTCTCCCGCCAGGTCCTATGGATTAATGCCTGCTTCTGTAACCTGAGCTG
TAGGAATCCCAATGACATCTTTGCTGACTTGGAATCCTACCCTGACTTCTCAGAAATTGC
CAACTAGGCAGGCACAAATCTTGGGTCTTGGGGACTAACCCAATGCCTGTGAAGCAGTCA
GCCCTTATGGCCAATAACTTTTCACCAATGAGCCTTAGTTACCCTGATCTGGACCCTTGG
CCTCCATTTCTGTCTCTAACCATTCAAATGACGCCTGATGGTGCTGCTCAGGCCCATGCT
ATGAGTTTTCTCCTTGATATCATTCAGCATCTACTCTAAAGAAAAATGCCTGTCTCTAGC
TGTTCTGGACTACACCCAAGCCTGATCCAGCCTTTCCAAGTCACTAGAAGTCCTGCTGGA
TCTTGCCTAAATCCCAAGAAATGGAATCAGGTAGACTTTTAATATCACTAATTTCTTCTT
TAGATGCCAAACCACAAGACTCTTTGGGTCCATTCAGATGAATAGATGGAATTTGGAACA
ATAGAATAATCTATTATTTGGAGCCTGCCAAGAGGTACTGTAATGGGTAATTCTGACGTC
AG

FIG._29

5'-CAGAACAGCTAGAGACAGGCATTTTTCTTTAGAGTAGATGCTGAATGATATCAAGGAGAA
AACTCATAGCATGGGCCTGAGCAGCACCATCAGGCGTCATTTGAATGGTTAGAGACAGAA
ATGGAGGCCAAGGGTCCAGATCAGGGTAACTAAGGCTCATTGGTGAAAAGTTATTGGCCA
TAAGGGCTGACTGCTTCACAGGCATTGGGTTAGTCCCCAAGACCCAAGATTTGTGCCTGC
CTAGTTGGCAATTTCTGAGAAGTCAGGGTAGGATTCCAAGTCAGCAAAGATGTCATTGGG
ATTCCTACAGCTCAGGTTACAGAAGCAGGCATTAATCCATAGGACCTGGCGGGAGAAGCC
AAGCCCATCAGGACACTGGAAGGACACGTCGATAGTCTTAGACTTGTAGGGGATGCAGCA
CCTATTGTCCATGCAAACTCCACAGTACTTGGGTTGATAGGAGCGTGTGCTGATGCAGCC
CGCAAGTGTGAAGTTCATGGATGCCTCTGGCTGGTACACAGCCAGACACTTCTTCCCTGC
CTTAATGAGTGTATGGATGTCCACATCGCATGGCCGCAAGTTGCAGAGGCGGCTCTCTTG
CTCAGGCCAGCACTGGGCGTTAACATTGGAGATCCGAGTGGAGACCCCCAGGCCGCAGCT
GGTGGAGCAAGGGCTCCAGGGGCTTGTGTAGGCTATGCAGTTCCTGTGCCATGCCTCCAC
CTCACCCACAGCATCTGTGTGTGGGAACAGAATCTGCATGAATCTACAGCTCCCACCAG
CCCCCAACGCTCACTTTCACCACACTAAGGTCTGCGGTCCCCAGAACTCAGAGGAACACA
GAAATTGGCTGTACCTCCCCACAGGACAGCAAGTTGGCTTCTAACCAGCAAAGGTACCCA
GGGAGTGGAGGACATGTTCTCAGCTCCTTGTATGTTTCTGATCAAGAGAGGCAGTGTGGA
AGCATGGGAGGAAACCCATCTTTAGAGACAGGTGGATCCCAGTTCAAATTCTGCTCTACC
ACCTACAAGCTGTGTGATCTTAGATAACCCACCCTGGGCCTGTCTCCCCATTAGAACAAT
AACACCTGCCTGTGCGGCTGGCAACACAATAATAAGGGCCTAGATTTTTACTGAGTATGC
ATCAATCATCCTTGCTAAGTGCTGGGAATGGGACTTTTTTTTT

FIG._30

5'-CCTGATCTGGACCCTTGGCCTCCAATTCTGTCTGTAACCATTCAAATGACGCCTGGTGGT
GCTGCTCAGGCCCATAGCAAGGTTCAGCCTGGTTAAGTCCAAGCTGAATTAGCGGCCGCG
TCGACAGTAGGAGTGTGTGCACATGCTGTGGGTGAGGTGGAGGCATGGCACAGGAACTGC
ATAGCCTACACAAGCCCCTGGAGCCCTTGCTCCACCAGCTGCGGCCTGGGGGTCTCCACT
CGGATCTCCAATGTTAACGCCCAGTGCTGGCCTGAGCAAGAGAGCCGCCTCTGCAACTTG
CGGCCATGCGATGTGGACATCCATACACTCATTAAGGCAGGGAAGAAGTGTCTGGCTGTG
TACCAGCCAGAGGCATCCATGAACTTCACACTTGCGGGCTGCATCAGCACACGCTCCTAT
CAACCCAAGTACTGTGGAGTTTGCATGGACAATAGGTGCTGCATCCCCTACAAGTCTAAG
ACTATCGACGTGTCCTTCCAGTGTCCTGATGGGCTTGGCTTCTCCCGCCAGGTCCTATGG
ATTAAT

FIG._31

5'-GGCCCAGCTCCCCCGAGAGGTGGTCGGATCCTCTGGGCTGCTCGGTCGATGCCTGTGCCA
CTGACGTCCAGGCATGAGGTGGTTCCTGCCCTGGACGCTGGCAGCAGTGACAGCAGCAGC
CGCCAGCACCGTCCTGGCCACGGCCCTCTCTCCAGCCCCTACGACCATGGACTTTACCCC
AGCTCCACTGGAGGACACCTCCTCACGCCCCAATTCTGCAAGTGGCCATGTGAGTGCCC
GCCATCCCCACCCCGCTGCCCGCTGGGGGTCAGCCTCATCACAGATGGCTGTGAGTGCTG
TAAGATGTGCGCTCAGCAGCTTGGGGACAACTGCACGGAGGCTGCCATCTGTGACCCCCA
CCGGGGCCTCTACTGTGACTACAGCGGGGACCGCCCGAGAGGTGGTCGGTGTGGGCTGCG
TCCTGGATGGGGTGCGCTACAACAACGGCCAGTCCTTCCAGCCTAACTGCAAGTACAACT
GCACGTGCATCGACGGCGCGGTGGGCTGCACACCACTGTGCCTCCGAGTGCGCCCCCGC
GTCTCTGGTGCCCCACCCGCGGCGCGTGAGCATACCTGGCCACTGCTGTGAGCAGTGGA
TATGTGAGGACGACGCCAAGAGGCCACGCAAGACCGCACCCCGTGACACAGGAGCCTTCG
ATGCCAGAAGCGCCCGCTCCCTCAGAGATGTGACAACCAAAATCATCTCCAGACCTTTCC
AAATACACCCTAGGAGACAAAATTGCTCGGTGGAGAAGCAGTCCTGTGAGGACAGGAGGA
GGCGTGGAGGAAAGCTTTGTCCCCAGCAGCCCCAGGGAAGCAAGGCAGCTCTCCCACCAC
CACCTCCCCAGGAGGGCCACACGAGGGTCACGGGGGGAGCAGGGAGGCGGAAGCTGTCTG
CCATTGTGTCTGGCCCAGTGACCCTGTTCTGACCGAGCACAAGCGGAGCCCCTGCCTAGC
CGAGATGCTGTGGGTGAGGTGGAGGCATGGCACAGGAACTGCATAGCCTACACAAGCCCC
TGGAGCCCTTGCTCCACCAGCTGCGGCCTGGGGGTCTCCACTCGGATCTCCAATGTTAAC
GCCCAGTGCTGGCCTGAGCAA

FIG._32

SEQUENCE LISTING

```
<160> NUMBER OF SEQ ID NOS: 156

<210> SEQ ID NO 1
<211> LENGTH: 2830
<212> TYPE: DNA
<213> ORGANISM: Homo sapiens

<400> SEQUENCE: 1
cccacgcgtc cgctgggccc agctcccccg agaggtggtc ggatcctctg         50
ggctgctcgg tcgatgcctg tgccactgac gtccaggcat gaggtggttc        100
ctgccctgga cgctggcagc agtgacagca gcagccgcca gcaccgtcct        150
ggccacggcc ctctctccag ccctacgac catggacttt actccagctc         200
```

-continued

```
cactggagga cacctcctca cgcccccaat tctgcaagtg gccatgtgag         250
tgcccgccat ccccaccccg ctgcccgctg ggggtcagcc tcatcacaga         300
tggctgtgag tgctgtaaga tgtgcgctca gcagcttggg gacaactgca         350
cggaggctgc catctgtgac ccccaccggg gcctctactg tgactacagc         400
ggggaccgcc cgaggtacgc aataggagtg tgtgcacagg tggtcggtgt         450
gggctgcgtc ctggatgggg tgcgctacaa caacggccag tccttccagc         500
ctaactgcaa gtacaactgc acgtgcatcg acggcgcggt gggctgcaca         550
ccactgtgcc tccgagtgcg cccccgcgt ctctggtgcc cccacccgcg          600
gcgcgtgagc atacctggcc actgctgtga gcagtgggta tgtgaggacg         650
acgccaagag gccacgcaag accgcacccc gtgacacagg agccttcgat         700
gctgtgggtg aggtggaggc atggcacagg aactgcatag cctacacaag         750
cccctggagc ccttgctcca ccagctgcgg cctgggggtc tccactcgga         800
tctccaatgt taacgcccag tgctggcctg agcaagagag ccgcctctgc         850
aacttgcggc catgcgatgt ggacatccat acactcatta aggcagggaa         900
gaagtgtctg gctgtgtacc agccagaggc atccatgaac ttcacacttg         950
cgggctgcat cagcacacgc tcctatcaac caagtactg tggagtttgc         1000 atggacaata ggtgctgcat cccctacaag tctaagacta cgacgtgtc          1050 cttccagtgt cctgatgggc ttggcttctc ccgccaggtc ctatggatta         1100
atgcctgctt ctgtaacctg agctgtagga atcccaatga catctttgct         1150
gacttggaat cctaccctga cttctcagaa attgccaact aggcaggcac         1200
aaatcttggg tcttggggac taccccaatg cctgtgaagc agtcagccct         1250
tatggccaat aacttttcac caatgagcct tagttaccct gatctggacc         1300
cttggcctcc atttctgtct ctaaccattc aaatgacgcc tgatggtgct         1350
gctcaggccc atgctatgag ttttctcctt gatatcattc agcatctact         1400
ctaaagaaaa atgcctgtct ctagctgttc tggactacac ccaagcctga         1450
tccagccttt ccaagtcact agaagtcctg ctggatcttg cctaaatccc         1500
aagaaatgga atcaggtaga cttttaatat cactaatttc ttcttttagat        1550 gccaaaccac aagactcttt gggtccattc agatgaatag atggaatttg         1600
gaacaataga ataatctatt atttggagcc tgccaagagg tactgtaatg         1650
ggtaattctg acgtcagcgc accaaaacta tcctgattcc aaatatgtat         1700
gcacctcaag gtcatcaaac atttgccaag tgagttgaat agttgcttaa         1750
ttttgatttt taatggaaag ttgtatccat taacctgggc attgttgagg         1800 ttaagttttct cttcacccct acactgtgaa gggtacagat taggtttgtc        1850
ccagtcagaa ataaaatttg ataaacattc ctgttgatgg gaaaagcccc         1900
cagttaatac tccagagaca gggaaaggtc agcccatttc agaaggacca         1950
attgactctc acactgaatc agctgctgac tgcagggct ttgggcagtt          2000 ggccaggctc ttccttgaat cttctcccctt gtcctgcttg ggttcatagg        2050
aattggtaag gcctctggac tggcctgtct ggccctgag agtggtgccc          2100 tggaacactc ctctactctt acagagcctt gagagaccca gctgcagacc         2150
```

-continued

| | |
|---|---|
| atgccagacc cactgaaatg accaagacag gttcaggtag gggtgtgggt | 2200 |
| caaaccaaga agtgggtgcc cttggtagca gcctggggtg acctctagag | 2250 |
| ctggaggctg tgggactcca ggggcccccg tgttcaggac acatctattg | 2300 |
| cagagactca tttcacagcc tttcgttctg ctgaccaaat ggccagtttt | 2350 |
| ctggtaggaa gatggaggtt taccagttgt ttagaaacag aaatagactt | 2400 |
| aataaaggtt taaagctgaa gaggttgaag ctaaaaggaa aaggttgttg | 2450 |
| ttaatgaata tcaggctatt atttattgta ttaggaaaat ataatattta | 2500 |
| ctgttagaat tcttttattt agggcctttt ctgtgccaga cattgctctc | 2550 |
| agtgctttgc atgtattagc tcactgaatc ttcacgacaa tgttgagaag | 2600 |
| ttcccattat tatttctgtt cttacaaatg tgaaacggaa gctcatagag | 2650 |
| gtgagaaaac tcaaccagag tcacccagtt ggtgactggg aaagttagga | 2700 |
| ttcagatcga aattggactg tctttataac ccatattttc ccctgtttt | 2750 |
| tagagcttcc aaatgtgtca gaataggaaa acattgcaat aaatggcttg | 2800 |
| attttttaaa aaaaaaaaa aaaaaaaaa | 2830 |

<210> SEQ ID NO 2
<211> LENGTH: 2830
<212> TYPE: DNA
<213> ORGANISM: Homo sapiens

<400> SEQUENCE: 2

| | |
|---|---|
| tttttttttt tttttttttt tttaaaaaat caagccattt attgcaatgt | 50 |
| tttcctattc tgacacattt ggaagctcta aaaacagggg gaaaatatgg | 100 |
| gttataaaga cagtccaatt tcgatctgaa tcctaacttt cccagtcacc | 150 |
| aactgggtga ctctggttga gttttctcac ctctatgagc ttccgtttca | 200 |
| catttgtaag aacagaaata ataatgggaa cttctcaaca ttgtcgtgaa | 250 |
| gattcagtga gctaatacat gcaaagcact gagagcaatg tctggcacag | 300 |
| aaaaggccct aaataaaaga attctaacag taaatattat attttcctaa | 350 |
| tacaataaat aatagcctga tattcattaa caacaaccct ttccttttag | 400 |
| cttcaacctc ttcagcttta aacctttatt aagtctattt ctgtttctaa | 450 |
| acaactggta aacctccatc ttcctaccag aaaactggcc atttggtcag | 500 |
| cagaacgaaa ggctgtgaaa tgagtctctg caatagatgt gtcctgaaca | 550 |
| cggggggccc tggagtccca cagcctccag ctctagaggt cacccaggc | 600 |
| tgctaccaag ggcacccact tcttggtttg acccacaccc ctacctgaac | 650 |
| ctgtcttggt catttcagtg ggtctggcat ggtctgcagc tgggtctctc | 700 |
| aaggctctgt aagagtagag gagtgttcca gggcaccact ctcaggggcc | 750 |
| agacaggcca gtccagaggc cttaccaatt cctatgaacc caagcaggac | 800 |
| aagggagaag attcaaggaa gagcctggcc aactgcccaa agccctgcca | 850 |
| gtcagcagct gattcagtgt gagagtcaat tggtccttct gaaatgggct | 900 |
| gacctttccc tgtctctgga gtattaactg ggggcttttc ccatcaacag | 950 |
| gaatgtttat caaattttat ttctgactgg gacaaaccta atctgtaccc | 1000 |
| ttcacagtgt agggggtgaag agaaacttaa cctcaacaat gcccaggtta | 1050 |
| atggatacaa ctttccatta aaaatcaaaa ttaagcaact attcaactca | 1100 |

-continued

```
cttggcaaat gtttgatgac cttgaggtgc atacatattt ggaatcagga        1150
tagttttggt gcgctgacgt cagaattacc cattacagta cctcttggca        1200
ggctccaaat aatagattat tctattgttc caaattccat ctattcatct        1250
gaatggaccc aaagagtctt gtggtttggc atctaaagaa gaaattagtg        1300
atattaaaag tctacctgat tccatttctt gggatttagg caagatccag        1350
caggacttct agtgacttgg aaaggctgga tcaggcttgg gtgtagtcca        1400
gaacagctag agacaggcat ttttctttag agtagatgct gaatgatatc        1450
aaggagaaaa ctcatagcat gggcctgagc agcaccatca ggcgtcattt        1500
gaatggttag agacagaaat ggaggccaag ggtccagatc agggtaacta        1550
aggctcattg gtgaaaagtt attggccata agggctgact gcttcacagg        1600
cattgggtta gtccccaaga cccaagattt gtgcctgcct agttggcaat        1650
ttctgagaag tcagggtagg attccaagtc agcaaagatg tcattgggat        1700
tcctacagct caggttacag aagcaggcat taatccatag gacctggcgg        1750
gagaagccaa gcccatcagg acactggaag gacacgtcga tagtcttaga        1800
cttgtagggg atgcagcacc tattgtccat gcaaactcca cagtacttgg        1850
gttgatagga gcgtgtgctg atgcagcccg caagtgtgaa gttcatggat        1900
gcctctggct ggtacacagc cagacacttc ttccctgcct taatgagtgt        1950
atggatgtcc acatcgcatg gccgcaagtt gcagaggcgg ctctcttgct        2000
caggccagca ctgggcgtta acattggaga tccgagtgga gaccccagg        2050 ccgcagctgg tggagcaagg gctccagggg cttgtgtagg ctatgcagtt        2100
cctgtgccat gcctccacct cacccacagc atcgaaggct cctgtgtcac        2150
ggggtgcggt cttgcgtggc ctcttggcgt cgtcctcaca tacccactgc        2200
tcacagcagt ggccaggtat gctcacgcgc gcgggtggg ggcaccagag        2250 acgcgggggg cgcactcgga ggcacagtgg tgtgcagccc accgcgccgt        2300
cgatgcacgt gcagttgtac ttgcagttag gctggaagga ctggccgttg        2350
ttgtagcgca ccccatccag gacgcagccc acaccgacca cctgtgcaca        2400
cactcctatt gcgtacctcg ggcggtcccc gctgtagtca cagtagaggc        2450
cccggtgggg gtcacagatg gcagcctccg tgcagttgtc cccaagctgc        2500
tgagcgcaca tcttacagca ctcacagcca tctgtgatga ggctgacccc        2550
cagcgggcag cggggtgggg atggcgggca ctcacatggc cacttgcaga        2600 attggggcg tgaggaggtg tcctccagtg gagctggagt aaagtccatg        2650
gtcgtagggg ctggagagag ggccgtggcc aggacgtgtc tggcggctgc        2700
tgctgtcact gctgccagcg tccagggcag gaaccacctc atgcctggac        2750
gtcagtggca caggcatcga ccgagcagcc cagaggatcc gaccacctct        2800
cgggggagct gggcccagcg gacgcgtggg                              2830
```

<210> SEQ ID NO 3
<211> LENGTH: 345
<212> TYPE: PRT
<213> ORGANISM: Homo sapiens

<400> SEQUENCE: 3

```
Thr Ala Leu Ser Pro Ala Pro Thr Thr Met Asp Phe Thr Pro Ala
 1               5                  10                  15

Pro Leu Glu Asp Thr Ser Ser Arg Pro Gln Phe Cys Lys Trp Pro
             20                  25                  30

Cys Glu Cys Pro Pro Ser Pro Pro Arg Cys Pro Leu Gly Val Ser
             35                  40                  45

Leu Ile Thr Asp Gly Cys Glu Cys Cys Lys Met Cys Ala Gln Gln
             50                  55                  60

Leu Gly Asp Asn Cys Thr Glu Ala Ala Ile Cys Asp Pro His Arg
             65                  70                  75

Gly Leu Tyr Cys Asp Tyr Ser Gly Asp Arg Pro Arg Tyr Ala Ile
             80                  85                  90

Gly Val Cys Ala Gln Val Val Gly Val Gly Cys Val Leu Asp Gly
             95                  100                 105

Val Arg Tyr Asn Asn Gly Gln Ser Phe Gln Pro Asn Cys Lys Tyr
             110                 115                 120

Asn Cys Thr Cys Ile Asp Gly Ala Val Gly Cys Thr Pro Leu Cys
             125                 130                 135

Leu Arg Val Arg Pro Pro Arg Leu Trp Cys Pro His Pro Arg Arg
             140                 145                 150

Val Ser Ile Pro Gly His Cys Cys Glu Gln Trp Val Cys Glu Asp
             155                 160                 165

Asp Ala Lys Arg Pro Arg Lys Thr Ala Pro Arg Asp Thr Gly Ala
             170                 175                 180

Phe Asp Ala Val Gly Glu Val Glu Ala Trp His Arg Asn Cys Ile
             185                 190                 195

Ala Tyr Thr Ser Pro Trp Ser Pro Cys Ser Thr Ser Cys Gly Leu
             200                 205                 210

Gly Val Ser Thr Arg Ile Ser Asn Val Asn Ala Gln Cys Trp Pro
             215                 220                 225

Glu Gln Glu Ser Arg Leu Cys Asn Leu Arg Pro Cys Asp Val Asp
             230                 235                 240

Ile His Thr Leu Ile Lys Ala Gly Lys Lys Cys Leu Ala Val Tyr
             245                 250                 255

Gln Pro Glu Ala Ser Met Asn Phe Thr Leu Ala Gly Cys Ile Ser
             260                 265                 270

Thr Arg Ser Tyr Gln Pro Lys Tyr Cys Gly Val Cys Met Asp Asn
             275                 280                 285

Arg Cys Cys Ile Pro Tyr Lys Ser Lys Thr Ile Asp Val Ser Phe
             290                 295                 300

Gln Cys Pro Asp Gly Leu Gly Phe Ser Arg Gln Val Leu Trp Ile
             305                 310                 315

Asn Ala Cys Phe Cys Asn Leu Ser Cys Arg Asn Pro Asn Asp Ile
             320                 325                 330

Phe Ala Asp Leu Glu Ser Tyr Pro Asp Phe Ser Glu Ile Ala Asn
             335                 340                 345

<210> SEQ ID NO 4
<211> LENGTH: 367
<212> TYPE: PRT
<213> ORGANISM: Homo sapiens

<400> SEQUENCE: 4

Met Arg Trp Phe Leu Pro Trp Thr Leu Ala Ala Val Thr Ala Ala
 1               5                  10                  15
```

Ala Ala Ser Thr Val Leu Ala Thr Ala Leu Ser Pro Ala Pro Thr
            20                  25                  30

Thr Met Asp Phe Thr Pro Ala Pro Leu Glu Asp Thr Ser Ser Arg
            35                  40                  45

Pro Gln Phe Cys Lys Trp Pro Cys Glu Cys Pro Pro Ser Pro Pro
            50                  55                  60

Arg Cys Pro Leu Gly Val Ser Leu Ile Thr Asp Gly Cys Glu Cys
            65                  70                  75

Cys Lys Met Cys Ala Gln Gln Leu Gly Asp Asn Cys Thr Glu Ala
            80                  85                  90

Ala Ile Cys Asp Pro His Arg Gly Leu Tyr Cys Asp Tyr Ser Gly
            95                  100                 105

Asp Arg Pro Arg Tyr Ala Ile Gly Val Cys Ala Gln Val Val Gly
            110                 115                 120

Val Gly Cys Val Leu Asp Gly Val Arg Tyr Asn Asn Gly Gln Ser
            125                 130                 135

Phe Gln Pro Asn Cys Lys Tyr Asn Cys Thr Cys Ile Asp Gly Ala
            140                 145                 150

Val Gly Cys Thr Pro Leu Cys Leu Arg Val Arg Pro Pro Arg Leu
            155                 160                 165

Trp Cys Pro His Pro Arg Arg Val Ser Ile Pro Gly His Cys Cys
            170                 175                 180

Glu Gln Trp Val Cys Glu Asp Asp Ala Lys Arg Pro Arg Lys Thr
            185                 190                 195

Ala Pro Arg Asp Thr Gly Ala Phe Asp Ala Val Gly Glu Val Glu
            200                 205                 210

Ala Trp His Arg Asn Cys Ile Ala Tyr Thr Ser Pro Trp Ser Pro
            215                 220                 225

Cys Ser Thr Ser Cys Gly Leu Gly Val Ser Thr Arg Ile Ser Asn
            230                 235                 240

Val Asn Ala Gln Cys Trp Pro Glu Gln Glu Ser Arg Leu Cys Asn
            245                 250                 255

Leu Arg Pro Cys Asp Val Asp Ile His Thr Leu Ile Lys Ala Gly
            260                 265                 270

Lys Lys Cys Leu Ala Val Tyr Gln Pro Glu Ala Ser Met Asn Phe
            275                 280                 285

Thr Leu Ala Gly Cys Ile Ser Thr Arg Ser Tyr Gln Pro Lys Tyr
            290                 295                 300

Cys Gly Val Cys Met Asp Asn Arg Cys Cys Ile Pro Tyr Lys Ser
            305                 310                 315

Lys Thr Ile Asp Val Ser Phe Gln Cys Pro Asp Gly Leu Gly Phe
            320                 325                 330

Ser Arg Gln Val Leu Trp Ile Asn Ala Cys Phe Cys Asn Leu Ser
            335                 340                 345

Cys Arg Asn Pro Asn Asp Ile Phe Ala Asp Leu Glu Ser Tyr Pro
            350                 355                 360

Asp Phe Ser Glu Ile Ala Asn
            365     367

<210> SEQ ID NO 5
<211> LENGTH: 345
<212> TYPE: PRT
<213> ORGANISM: Homo sapiens

<400> SEQUENCE: 5

Thr Ala Leu Ser Pro Ala Pro Thr Thr Met Asp Phe Thr Pro Ala
 1               5                  10                  15

Pro Leu Glu Asp Thr Ser Ser Arg Pro Gln Phe Cys Lys Trp Pro
                20                  25                  30

Cys Glu Cys Pro Pro Ser Pro Pro Arg Cys Pro Leu Gly Val Ser
                35                  40                  45

Leu Ile Thr Asp Gly Cys Glu Cys Cys Lys Met Cys Ala Gln Gln
                50                  55                  60

Leu Gly Asp Asn Cys Thr Glu Ala Ala Ile Cys Asp Pro His Arg
                65                  70                  75

Gly Leu Tyr Cys Asp Tyr Ser Gly Asp Arg Pro Arg Tyr Ala Ile
                80                  85                  90

Gly Val Cys Ala Gln Val Val Gly Val Gly Cys Val Leu Asp Gly
                95                  100                 105

Val Arg Tyr Asn Asn Gly Gln Ser Phe Gln Pro Asn Cys Lys Tyr
                110                 115                 120

Asn Cys Thr Cys Ile Asp Gly Ala Val Gly Cys Thr Pro Leu Cys
                125                 130                 135

Leu Arg Val Arg Pro Pro Arg Leu Trp Cys Pro His Pro Arg Arg
                140                 145                 150

Val Ser Ile Pro Gly His Cys Cys Glu Gln Trp Ile Cys Glu Asp
                155                 160                 165

Asp Ala Lys Arg Pro Arg Lys Thr Ala Pro Arg Asp Thr Gly Ala
                170                 175                 180

Phe Asp Ala Val Gly Glu Val Glu Ala Trp His Arg Asn Cys Ile
                185                 190                 195

Ala Tyr Thr Ser Pro Trp Ser Pro Cys Ser Thr Ser Cys Gly Leu
                200                 205                 210

Gly Val Ser Thr Arg Ile Ser Asn Val Asn Ala Gln Cys Trp Pro
                215                 220                 225

Glu Gln Glu Ser Arg Leu Cys Asn Leu Arg Pro Cys Asp Val Asp
                230                 235                 240

Ile His Thr Leu Ile Lys Ala Gly Lys Lys Cys Leu Ala Val Tyr
                245                 250                 255

Gln Pro Glu Ala Ser Met Asn Phe Thr Leu Ala Gly Cys Ile Ser
                260                 265                 270

Thr Arg Ser Tyr Gln Pro Lys Tyr Cys Gly Val Cys Met Asp Asn
                275                 280                 285

Arg Cys Cys Ile Pro Tyr Lys Ser Lys Thr Ile Asp Val Ser Phe
                290                 295                 300

Gln Cys Pro Asp Gly Leu Gly Phe Ser Arg Gln Val Leu Trp Ile
                305                 310                 315

Asn Ala Cys Phe Cys Asn Leu Ser Cys Arg Asn Pro Asn Asp Ile
                320                 325                 330

Phe Ala Asp Leu Glu Ser Tyr Pro Asp Phe Ser Glu Ile Ala Asn
                335                 340                 345

<210> SEQ ID NO 6
<211> LENGTH: 345
<212> TYPE: PRT
<213> ORGANISM: Homo sapiens

<400> SEQUENCE: 6

-continued

```
Thr Ala Leu Ser Pro Ala Pro Thr Thr Met Asp Phe Thr Pro Ala
 1               5                  10                  15

Pro Leu Glu Asp Thr Ser Arg Pro Gln Phe Cys Lys Trp Pro
             20                  25                  30

Cys Glu Cys Pro Pro Ser Pro Pro Arg Cys Pro Leu Gly Val Ser
             35                  40                  45

Leu Ile Thr Asp Gly Cys Glu Cys Cys Lys Met Cys Ala Gln Gln
             50                  55                  60

Leu Gly Asp Asn Cys Thr Glu Ala Ala Ile Cys Asp Pro His Arg
             65                  70                  75

Gly Leu Tyr Cys Asp Tyr Ser Gly Asp Arg Pro Arg Tyr Ala Ile
             80                  85                  90

Gly Val Cys Ala Gln Val Val Gly Val Gly Cys Val Leu Asp Gly
             95                 100                 105

Val Arg Tyr Asn Asn Gly Gln Ser Phe Gln Pro Asn Cys Lys Tyr
            110                 115                 120

Asn Cys Thr Cys Ile Asp Gly Ala Val Gly Cys Thr Pro Leu Cys
            125                 130                 135

Leu Arg Val Arg Pro Pro Arg Leu Trp Cys Pro His Pro Arg Arg
            140                 145                 150

Val Ser Ile Pro Gly His Cys Cys Glu Gln Trp Val Cys Glu Asp
            155                 160                 165

Asp Ala Lys Arg Pro Arg Lys Thr Ala Pro Arg Asp Thr Gly Ser
            170                 175                 180

Phe Asp Ala Val Gly Glu Val Glu Ala Trp His Arg Asn Cys Ile
            185                 190                 195

Ala Tyr Thr Ser Pro Trp Ser Pro Cys Ser Thr Ser Cys Gly Leu
            200                 205                 210

Gly Val Ser Thr Arg Ile Ser Asn Val Asn Ala Gln Cys Trp Pro
            215                 220                 225

Glu Gln Glu Ser Arg Leu Cys Asn Leu Arg Pro Cys Asp Val Asp
            230                 235                 240

Ile His Thr Leu Ile Lys Ala Gly Lys Lys Cys Leu Ala Val Tyr
            245                 250                 255

Gln Pro Glu Ala Ser Met Asn Phe Thr Leu Ala Gly Cys Ile Ser
            260                 265                 270

Thr Arg Ser Tyr Gln Pro Lys Tyr Cys Gly Val Cys Met Asp Asn
            275                 280                 285

Arg Cys Cys Ile Pro Tyr Lys Ser Lys Thr Ile Asp Val Ser Phe
            290                 295                 300

Gln Cys Pro Asp Gly Leu Gly Phe Ser Arg Gln Val Leu Trp Ile
            305                 310                 315

Asn Ala Cys Phe Cys Asn Leu Ser Cys Arg Asn Pro Asn Asp Ile
            320                 325                 330

Phe Ala Asp Leu Glu Ser Tyr Pro Asp Phe Ser Glu Ile Ala Asn
            335                 340                 345
```

<210> SEQ ID NO 7
<211> LENGTH: 367
<212> TYPE: PRT
<213> ORGANISM: Homo sapiens

<400> SEQUENCE: 7

```
Met Arg Trp Phe Leu Pro Trp Thr Leu Ala Ala Val Thr Ala Ala
 1               5                  10                  15
```

```
Ala Ala Ser Thr Val Leu Ala Thr Ala Leu Ser Pro Ala Pro Thr
                 20                  25                  30

Thr Met Asp Phe Thr Pro Ala Pro Leu Glu Asp Thr Ser Ser Arg
         35                  40                  45

Pro Gln Phe Cys Lys Trp Pro Cys Glu Cys Pro Pro Ser Pro Pro
             50                  55                  60

Arg Cys Pro Leu Gly Val Ser Leu Ile Thr Asp Gly Cys Glu Cys
                 65                  70                  75

Cys Lys Met Cys Ala Gln Gln Leu Gly Asp Asn Cys Thr Glu Ala
             80                  85                  90

Ala Ile Cys Asp Pro His Arg Gly Leu Tyr Cys Asp Tyr Ser Gly
                 95                 100                 105

Asp Arg Pro Arg Tyr Ala Ile Gly Val Cys Ala Gln Val Val Gly
                110                 115                 120

Val Gly Cys Val Leu Asp Gly Val Arg Tyr Asn Asn Gly Gln Ser
                125                 130                 135

Phe Gln Pro Asn Cys Lys Tyr Asn Cys Thr Cys Ile Asp Gly Ala
                140                 145                 150

Val Gly Cys Thr Pro Leu Cys Leu Arg Val Arg Pro Pro Arg Leu
                155                 160                 165

Trp Cys Pro His Pro Arg Arg Val Ser Ile Pro Gly His Cys Cys
                170                 175                 180

Glu Gln Trp Ile Cys Glu Asp Asp Ala Lys Arg Pro Arg Lys Thr
                185                 190                 195

Ala Pro Arg Asp Thr Gly Ala Phe Asp Ala Val Gly Glu Val Glu
                200                 205                 210

Ala Trp His Arg Asn Cys Ile Ala Tyr Thr Ser Pro Trp Ser Pro
                215                 220                 225

Cys Ser Thr Ser Cys Gly Leu Gly Val Ser Thr Arg Ile Ser Asn
                230                 235                 240

Val Asn Ala Gln Cys Trp Pro Glu Gln Glu Ser Arg Leu Cys Asn
                245                 250                 255

Leu Arg Pro Cys Asp Val Asp Ile His Thr Leu Ile Lys Ala Gly
                260                 265                 270

Lys Lys Cys Leu Ala Val Tyr Gln Pro Glu Ala Ser Met Asn Phe
                275                 280                 285

Thr Leu Ala Gly Cys Ile Ser Thr Arg Ser Tyr Gln Pro Lys Tyr
                290                 295                 300

Cys Gly Val Cys Met Asp Asn Arg Cys Cys Ile Pro Tyr Lys Ser
                305                 310                 315

Lys Thr Ile Asp Val Ser Phe Gln Cys Pro Asp Gly Leu Gly Phe
                320                 325                 330

Ser Arg Gln Val Leu Trp Ile Asn Ala Cys Phe Cys Asn Leu Ser
                335                 340                 345

Cys Arg Asn Pro Asn Asp Ile Phe Ala Asp Leu Glu Ser Tyr Pro
                350                 355                 360

Asp Phe Ser Glu Ile Ala Asn
                365     367

<210> SEQ ID NO 8
<211> LENGTH: 367
<212> TYPE: PRT
<213> ORGANISM: Homo sapiens
```

-continued

```
<400> SEQUENCE: 8

Met Arg Trp Phe Leu Pro Trp Thr Leu Ala Ala Val Thr Ala Ala
 1               5                  10                  15

Ala Ala Ser Thr Val Leu Ala Thr Ala Leu Ser Pro Ala Pro Thr
                20                  25                  30

Thr Met Asp Phe Thr Pro Ala Pro Leu Glu Asp Thr Ser Ser Arg
                35                  40                  45

Pro Gln Phe Cys Lys Trp Pro Cys Glu Cys Pro Pro Ser Pro Pro
                50                  55                  60

Arg Cys Pro Leu Gly Val Ser Leu Ile Thr Asp Gly Cys Glu Cys
                65                  70                  75

Cys Lys Met Cys Ala Gln Gln Leu Gly Asp Asn Cys Thr Glu Ala
                80                  85                  90

Ala Ile Cys Asp Pro His Arg Gly Leu Tyr Cys Asp Tyr Ser Gly
                95                 100                 105

Asp Arg Pro Arg Tyr Ala Ile Gly Val Cys Ala Gln Val Val Gly
               110                 115                 120

Val Gly Cys Val Leu Asp Gly Val Arg Tyr Asn Asn Gly Gln Ser
               125                 130                 135

Phe Gln Pro Asn Cys Lys Tyr Asn Cys Thr Cys Ile Asp Gly Ala
               140                 145                 150

Val Gly Cys Thr Pro Leu Cys Leu Arg Val Arg Pro Pro Arg Leu
               155                 160                 165

Trp Cys Pro His Pro Arg Arg Val Ser Ile Pro Gly His Cys Cys
               170                 175                 180

Glu Gln Trp Val Cys Glu Asp Ala Lys Arg Pro Arg Lys Thr
               185                 190                 195

Ala Pro Arg Asp Thr Gly Ser Phe Asp Ala Val Gly Glu Val Glu
               200                 205                 210

Ala Trp His Arg Asn Cys Ile Ala Tyr Thr Ser Pro Trp Ser Pro
               215                 220                 225

Cys Ser Thr Ser Cys Gly Leu Gly Val Ser Thr Arg Ile Ser Asn
               230                 235                 240

Val Asn Ala Gln Cys Trp Pro Glu Gln Glu Ser Arg Leu Cys Asn
               245                 250                 255

Leu Arg Pro Cys Asp Val Asp Ile His Thr Leu Ile Lys Ala Gly
               260                 265                 270

Lys Lys Cys Leu Ala Val Tyr Gln Pro Glu Ala Ser Met Asn Phe
               275                 280                 285

Thr Leu Ala Gly Cys Ile Ser Thr Arg Ser Tyr Gln Pro Lys Tyr
               290                 295                 300

Cys Gly Val Cys Met Asp Asn Arg Cys Cys Ile Pro Tyr Lys Ser
               305                 310                 315

Lys Thr Ile Asp Val Ser Phe Gln Cys Pro Asp Gly Leu Gly Phe
               320                 325                 330

Ser Arg Gln Val Leu Trp Ile Asn Ala Cys Phe Cys Asn Leu Ser
               335                 340                 345

Cys Arg Asn Pro Asn Asp Ile Phe Ala Asp Leu Glu Ser Tyr Pro
               350                 355                 360

Asp Phe Ser Glu Ile Ala Asn
               365     367

<210> SEQ ID NO 9
```

```
<211> LENGTH: 1766
<212> TYPE: DNA
<213> ORGANISM: Mus musculus
<220> FEATURE:
<221> NAME/KEY: Unsure
<222> LOCATION: 10
<223> OTHER INFORMATION: Unknown base

<400> SEQUENCE: 9
```

| | | | | |
|---|---|---|---|---|
| taacaaggcn | gtcctgcttg | gagaggcatc | cgcatcctct | gggctgagcc | 50 |
| gtagctcctg | tgacgctgac | ttccaggcat | gaggtggctc | ctgccctgga | 100 |
| cgctggcagc | cgtggcagtc | ctgagggtgg | gcaacatcct | ggccacggcc | 150 |
| ctctctccaa | cccccacaac | aatgaccttc | accccagcac | cactagagga | 200 |
| aacgactaca | cgccccgaat | tctgcaagtg | gccatgtgag | tgcccacaat | 250 |
| ccccacctcg | ctgcccactg | ggcgtcagcc | taatcacaga | tggctgtgaa | 300 |
| tgctgtaaga | tatgtgccca | gcagcttggg | gacaactgca | cagaggctgc | 350 |
| catctgtgac | ccacaccggg | gcctctactg | cgattacagt | ggggatcgcc | 400 |
| cgaggtacgc | aataggagtg | tgtgcacagg | tggtcggtgt | gggctgtgtc | 450 |
| ctggatggcg | tacgctacac | caatggcgag | tccttccaac | ccaactgcag | 500 |
| gtacaactgt | acctgcattg | atggcacggt | gggctgcaca | ccgctgtgcc | 550 |
| taagccccag | gccccacgc | ctctggtgcc | gccagcccg | gcacgtgaga | 600 |
| gtccctggcc | agtgctgtga | gcagtgggtg | tgtgatgatg | acgcaaggag | 650 |
| accacgccag | actgcactgt | tggacaccag | agcctttgca | gcgtcaggcg | 700 |
| ccgtggagca | acggtatgag | aactgcatag | cctacactag | tccctggagc | 750 |
| ccctgctcta | ccacctgtgg | cctaggtatc | tccactcgga | tctctaacgt | 800 |
| caatgcccgt | gctggccag | agcaggaaag | tcgcctctgc | aacctgcggc | 850 |
| catgtgatgt | ggacatccaa | ctacacatca | aggcagggaa | gaaatgcctg | 900 |
| gctgtgtacc | agccagagga | ggccacgaac | ttcactctcg | caggctgtgt | 950 |
| cagcacacgc | acctaccgac | ccaagtactg | cggagtctgt | actgacaata | 1000 |
| ggtgttgcat | ccctacaag | tccaagacca | tcagtgtgga | tttccagtgt | 1050 |
| ccagagggc | caggtttctc | ccggcaggtc | ctatggatta | atgcttgctt | 1100 |
| ctgcaacctg | agctgcagga | atcctaacga | tatctttgct | gacttggaat | 1150 |
| cttaccctga | cttcgaagag | attgccaatt | aggtgggtgt | gtggctcagg | 1200 |
| gtaaagttcc | atgctgcaaa | gcagccagcc | ctttgtggtc | caggacttca | 1250 |
| caattgagcc | ttatttcatc | tacttcctac | tcgattctga | attcccagtt | 1300 |
| tctgttcctg | ttttgacaat | cgtaatggcc | caggagagtg | ctgctcaggc | 1350 |
| tcagacaatg | ggttcctcct | tggggacatt | ctacatcatt | ccaaggaaaa | 1400 |
| cacatctctg | actgttcaca | atggaagcaa | agcctggccc | agctagtctg | 1450 |
| gctccagcct | gggcaagttg | tcagaagttg | tgatgggatt | gtccaaggaa | 1500 |
| aagcatcagc | tgaagaacca | gtatcatgaa | gtccttcctc | agatgccaag | 1550 |
| cctagggatg | ctgggatcct | ttcagacaga | tggatgggat | tggggacaca | 1600 |
| ggaataagct | attattttac | ccttgccaaa | tgatactatc | ctgggtattt | 1650 |
| ctgcctaaaa | acataccaaa | agtgttcttg | ttccactgat | ctgtatatca | 1700 |
| caagtcacca | aacatttcc | aggtgaggac | ccatagttgt | gtcattctgt | 1750 |

| | |
|---|---|
| tttgccaatt gaaaaa | 1766 |

<210> SEQ ID NO 10
<211> LENGTH: 1766
<212> TYPE: DNA
<213> ORGANISM: Mus musculus
<220> FEATURE:
<221> NAME/KEY: Unsure
<222> LOCATION: 1757
<223> OTHER INFORMATION: Unknown base.

<400> SEQUENCE: 10

| | |
|---|---|
| tttttcaatt ggcaaaacag aatgacacaa ctatgggtcc tcacctggaa | 50 |
| aatgtttggt gacttgtgat atacagatca gtggaacaag aacacttttg | 100 |
| gtatgttttt aggcagaaat acccaggata gtatcatttg gcaagggtaa | 150 |
| aataatagct tattcctgtg tccccaatcc catccatctg tctgaaagga | 200 |
| tcccagcatc cctaggcttg gcatctgagg aaggacttca tgatactggt | 250 |
| tcttcagctg atgcttttcc ttggacaatc ccatcacaac ttctgacaac | 300 |
| ttgcccaggc tggagccaga ctagctgggc caggctttgc ttccattgtg | 350 |
| aacagtcaga gatgtgtttt ccttggaatg atgtagaatg tccccaagga | 400 |
| ggaacccatt gtctgagcct gagcagcact ctcctgggcc attacgattg | 450 |
| tcaaaacagg aacagaaact gggaattcag aatcgagtag gaagtagatg | 500 |
| aaataaggct caattgtgaa gtcctggacc acaaagggct ggctgctttg | 550 |
| cagcatggaa ctttaccctg agccacacac ccacctaatt ggcaatctct | 600 |
| tcgaagtcag ggtaagattc caagtcagca agatatcgt taggattcct | 650 |
| gcagctcagg ttgcagaagc aagcattaat ccataggacc tgccgggaga | 700 |
| aacctggccc ctctggacac tggaaatcca cactgatggt cttggacttg | 750 |
| tagggggatgc aacacctatt gtcagtacag actccgcagt acttgggtcg | 800 |
| gtaggtgcgt gtgctgacac agcctgcgag agtgaagttc gtggcctcct | 850 |
| ctggctggta cacagccagg catttcttcc ctgccttgat gtgtagttgg | 900 |
| atgtccacat cacatggccg caggttgcag aggcgacttt cctgctctgg | 950 |
| ccagcaccgg gcattgacgt tagagatccg agtggagata cctaggccac | 1000 |
| aggtggtaga gcaggggctc cagggactag tgtaggctat gcagttctca | 1050 |
| taccgttgct ccacggcgcc tgacgctgca aaggctctgg tgtccaacag | 1100 |
| tgcagtctgg cgtggtctcc ttgcgtcatc atcacacacc cactgctcac | 1150 |
| agcactggcc agggactctc acgtgccggg gctggcggca ccagaggcgt | 1200 |
| gggggcctgg ggcttaggca cagcggtgtg cagcccaccg tgccatcaat | 1250 |
| gcaggtacag ttgtacctgc agttgggttg gaaggactcg ccattggtgt | 1300 |
| agcgtacgcc atccaggaca cagcccacac cgaccacctg tgcacacact | 1350 |
| cctattgcgt acctcgggcg atccccactg taatcgcagt agaggccccg | 1400 |
| gtgtgggtca cagatggcag cctctgtgca gttgtcccca agctgctggg | 1450 |
| cacatatctt acagcattca cagccatctg tgattaggct gacgcccagt | 1500 |
| gggcagcgag gtgggattg tgggcactca catggccact tgcagaattc | 1550 |
| ggggcgtgta gtcgtttcct ctagtggtgc tggggtgaag gtcattgttg | 1600 |

```
tgggggttgg agagagggcc gtggccagga tgttgcccac cctcaggact        1650
gccacggctg ccagcgtcca gggcaggagc cacctcatgc ctggaagtca        1700
gcgtcacagg agctacggct cagcccagag gatgcggatg cctctccaag       1750
caggacngcc ttgtta                                             1766
```

<210> SEQ ID NO 11
<211> LENGTH: 345
<212> TYPE: PRT
<213> ORGANISM: Mus musculus

<400> SEQUENCE: 11

```
Thr Ala Leu Ser Pro Thr Pro Thr Thr Met T hr Phe Thr Pro Ala
  1               5                  10                  15

Pro Leu Glu Glu Thr Thr Thr Arg Pro Glu P he Cys Lys Trp Pro
                 20                  25                  30

Cys Glu Cys Pro Gln Ser Pro Pro Arg Cys P ro Leu Gly Val Ser
             35                  40                  45

Leu Ile Thr Asp Gly Cys Glu Cys Cys Lys I le Cys Ala Gln Gln
         50                  55                  60

Leu Gly Asp Asn Cys Thr Glu Ala Ala Ile C ys Asp Pro His Arg
     65                  70                  75

Gly Leu Tyr Cys Asp Tyr Ser Gly Asp Arg P ro Arg Tyr Ala Ile
 80                  85                  90

Gly Val Cys Ala Gln Val Val Gly Val Gly C ys Val Leu Asp Gly
             95                 100                 105

Val Arg Tyr Thr Asn Gly Glu Ser Phe Gln P ro Asn Cys Arg Tyr
            110                 115                 120

Asn Cys Thr Cys Ile Asp Gly Thr Val Gly C ys Thr Pro Leu Cys
            125                 130                 135

Leu Ser Pro Arg Pro Pro Arg Leu Trp Cys A rg Gln Pro Arg His
            140                 145                 150

Val Arg Val Pro Gly Gln Cys Cys Glu Gln T rp Val Cys Asp Asp
            155                 160                 165

Asp Ala Arg Arg Pro Arg Gln Thr Ala Leu L eu Asp Thr Arg Ala
            170                 175                 180

Phe Ala Ala Ser Gly Ala Val Glu Gln Arg T yr Glu Asn Cys Ile
            185                 190                 195

Ala Tyr Thr Ser Pro Trp Ser Pro Cys Ser T hr Thr Cys Gly Leu
            200                 205                 210

Gly Ile Ser Thr Arg Ile Ser Asn Val Asn A la Arg Cys Trp Pro
            215                 220                 225

Glu Gln Glu Ser Arg Leu Cys Asn Leu Arg P ro Cys Asp Val Asp
            230                 235                 240

Ile Gln Leu His Ile Lys Ala Gly Lys Lys C ys Leu Ala Val Tyr
            245                 250                 255

Gln Pro Glu Glu Ala Thr Asn Phe Thr Leu A la Gly Cys Val Ser
            260                 265                 270

Thr Arg Thr Tyr Arg Pro Lys Tyr Cys Gly V al Cys Thr Asp Asn
            275                 280                 285

Arg Cys Cys Ile Pro Tyr Lys Ser Lys Thr I le Ser Val Asp Phe
            290                 295                 300

Gln Cys Pro Glu Gly Pro Gly Phe Ser Arg G ln Val Leu Trp Ile
            305                 310                 315
```

-continued

Asn Ala Cys Phe Cys Asn Leu Ser Cys Arg Asn Pro Asn Asp Ile
                320                 325                 330

Phe Ala Asp Leu Glu Ser Tyr Pro Asp Phe Glu Glu Ile Ala Asn
                335                 340                 345

<210> SEQ ID NO 12
<211> LENGTH: 367
<212> TYPE: PRT
<213> ORGANISM: Mus musculus

<400> SEQUENCE: 12

Met Arg Trp Leu Leu Pro Trp Thr Leu Ala Ala Val Ala Val Leu
 1               5                  10                  15

Arg Val Gly Asn Ile Leu Ala Thr Ala Leu Ser er Pro Thr Pro Thr
                 20                  25                  30

Thr Met Thr Phe Thr Pro Ala Pro Leu Glu Glu Thr Thr Thr Arg
                 35                  40                  45

Pro Glu Phe Cys Lys Trp Pro Cys Glu Cys Pro Gln Ser Pro Pro
                 50                  55                  60

Arg Cys Pro Leu Gly Val Ser Leu Ile Thr Asp Gly Cys Glu Cys
                 65                  70                  75

Cys Lys Ile Cys Ala Gln Gln Leu Gly Asp Asn Cys Thr Glu Ala
                 80                  85                  90

Ala Ile Cys Asp Pro His Arg Gly Leu Tyr Cys Asp Tyr Ser Gly
                 95                 100                 105

Asp Arg Pro Arg Tyr Ala Ile Gly Val Cys Ala Gln Val Val Gly
                110                 115                 120

Val Gly Cys Val Leu Asp Gly Val Arg Tyr Thr Asn Gly Glu Ser
                125                 130                 135

Phe Gln Pro Asn Cys Arg Tyr Asn Cys Thr Cys Ile Asp Gly Thr
                140                 145                 150

Val Gly Cys Thr Pro Leu Cys Leu Ser Pro Arg Pro Pro Arg Leu
                155                 160                 165

Trp Cys Arg Gln Pro Arg His Val Arg Val Pro Gly Gln Cys Cys
                170                 175                 180

Glu Gln Trp Val Cys Asp Asp Ala Arg Arg Pro Arg Gln Thr
                185                 190                 195

Ala Leu Leu Asp Thr Arg Ala Phe Ala Ala Ser Gly Ala Val Glu
                200                 205                 210

Gln Arg Tyr Glu Asn Cys Ile Ala Tyr Thr Ser Pro Trp Ser Pro
                215                 220                 225

Cys Ser Thr Thr Cys Gly Leu Gly Ile Ser Thr Arg Ile Ser Asn
                230                 235                 240

Val Asn Ala Arg Cys Trp Pro Glu Gln Glu Ser Arg Leu Cys Asn
                245                 250                 255

Leu Arg Pro Cys Asp Val Asp Ile Gln Leu His Ile Lys Ala Gly
                260                 265                 270

Lys Lys Cys Leu Ala Val Tyr Gln Pro Glu Glu Ala Thr Asn Phe
                275                 280                 285

Thr Leu Ala Gly Cys Val Ser Thr Arg Thr Tyr Arg Pro Lys Tyr
                290                 295                 300

Cys Gly Val Cys Thr Asp Asn Arg Cys Cys Ile Pro Tyr Lys Ser
                305                 310                 315

Lys Thr Ile Ser Val Asp Phe Gln Cys Pro Glu Gly Pro Gly Phe
                320                 325                 330

Ser Arg Gln Val Leu Trp Ile Asn Ala Cys Phe Cys Asn Leu Ser
                335                 340                 345

Cys Arg Asn Pro Asn Asp Ile Phe Ala Asp Leu Glu Ser Tyr Pro
                350                 355                 360

Asp Phe Glu Glu Ile Ala Asn
                365     367

<210> SEQ ID NO 13
<211> LENGTH: 1293
<212> TYPE: DNA
<213> ORGANISM: Homo sapiens

<400> SEQUENCE: 13

| | | |
|---|---|---|
| cccacgcgtc cggctgggga catgagaggc acaccgaaga cccacctcct | 50 |
| ggccttctcc ctcctctgcc tcctctcaaa ggtgcgtacc cagctgtgcc | 100 |
| cgacaccatg tacctgcccc tggccacctc cccgatgccc gctgggagta | 150 |
| cccctggtgc tggatggctg tggctgctgc cgggtatgtg cacggcggct | 200 |
| gggggagccc tgcgaccaac tccacgtctg cgacgccagc cagggcctgg | 250 |
| tctgccagcc cggggcagga cccggtggcc ggggggccct gtgcctcttg | 300 |
| gcagaggacg acagcagctg tgaggtgaac ggccgcctgt atcgggaagg | 350 |
| ggagaccttc cagccccact gcagcatccg ctgccgctgc gaggacggcg | 400 |
| gcttcacctg cgtgccgctg tgcagcgagg atgtgcggct gcccagctgg | 450 |
| gactgccccc accccaggag ggtcgaggtc ctgggcaagt gctgccctga | 500 |
| gtgggtgtgc ggccaaggag ggggactggg gacccagccc cttccagccc | 550 |
| aaggacccca gttttctggc cttgtctctt ccctgccccc tggtgtcccc | 600 |
| tgcccagaat ggagcacggc ctggggaccc tgctcgacca cctgtgggct | 650 |
| gggcatggcc acccgggtgt ccaaccagaa ccgcttctgc cgactggaga | 700 |
| cccagcgccg cctgtgcctg tccaggccct gcccaccctc cagggtcgc | 750 |
| agtccacaaa acagtgcctt ctagagccgg gctgggaatg gggacacggt | 800 |
| gtccaccatc cccagctggt ggccctgtgc ctgggcctg gctgatgga | 850 |
| agatggtccg tgcccaggcc cttggctgca ggcaacactt tagcttgggt | 900 |
| ccaccatgca gaacaccaat attaacacgc tgcctggtct gtctggatcc | 950 |
| cgaggtatgg cagaggtgca agacctagtc ccctttcctc taactcactg | 1000 |
| cctaggaggc tggccaaggt gtccagggtc tctagccca ctccctgcct | 1050 |
| acacacacag cctatatcaa acatgcacac gggcgagctt tctctccgac | 1100 |
| ttccctggg caagagatgg gacaagcagt cccttaatat tgaggctgca | 1150 |
| gcaggtgctg ggctggactg gccattttc tgggggtagg atgaagagaa | 1200 |
| ggcacacaga gattctggat ctcctgctgc cttttctgga gtttgtaaaa | 1250 |
| ttgttcctga atacaagcct atgcgtgaaa aaaaaaaaa aaa | 1293 |

<210> SEQ ID NO 14
<211> LENGTH: 1293
<212> TYPE: DNA
<213> ORGANISM: Homo sapiens

<400> SEQUENCE: 14

| | |
|---|---|
| ttttttttt tttttcacg cataggcttg tattcaggaa caatttaca | 50 |

```
aactccagaa aaggcagcag gagatccaga atctctgtgt gccttctctt        100
catcctaccc ccagaaaaat ggccagtcca gcccagcacc tgctgcagcc        150
tcaatattaa gggactgctt gtcccatctc ttgcccaggg gaagtcggag        200
agaaagctcg cccgtgtgca tgtttgatat aggctgtgtg tgtaggcagg        250
gagtgggcta gaggaccctg gacaccttgg ccagcctcct aggcagtgag        300
ttagaggaaa ggggactagg tcttgcacct ctgccatacc tcgggatcca        350
gacagaccag gcagcgtgtt aatattggtg ttctgcatgg tggacccaag        400
ctaaagtgtt gcctgcagcc aagggcctgg gcacggacca tcttccatca        450
gcccagggcc caggcacagg gccaccagct ggggatggtg gacaccgtgt        500
ccccattccc agcccggctc tagaaggcac tgttttgtgg actgcgaccc        550
ctggagggtg ggcagggcct ggacaggcac aggcggcgct gggtctccag        600
tcggcagaag cggttctggt tggacacccg ggtggccatg cccagcccac        650
aggtggtcga gcagggtccc caggccgtgc tccattctgg cagggggaca        700
ccagggggca gggaagagac aaggccagaa aactggggtc cttgggctgg        750
aaggggctgg gtccccagtc cccctccttg gccgcacacc cactcagggc        800
agcacttgcc caggacctcg accctcctgg ggtgggggca gtcccagctg        850
ggcagccgca catcctcgct gcacagcggc acgcaggtga agccgccgtc        900
ctcgcagcgg cagcggatgc tgcagtgggg ctggaaggtc tcccttccc         950
gatacaggcg gccgttcacc tcacagctgc tgtcgtcctc tgccaagagg       1000
cacagggccc cccggccacc gggtcctgcc ccgggctggc agaccaggcc       1050
ctggctggcg tcgcagacgt ggagttggtc cagggctcc cccagccgcc        1100
gtgcacatac ccggcagcag ccacagccat ccagcaccag gggtactccc       1150
agcgggcatc ggggaggtgg ccaggggcag gtacatggtg tcgggcacag       1200
ctgggtacgc acctttgaga ggaggcagag gagggagaag gccaggaggt       1250
gggtcttcgg tgtgcctctc atgtccccag ccggacgcgt ggg              1293
```

<210> SEQ ID NO 15
<211> LENGTH: 227
<212> TYPE: PRT
<213> ORGANISM: Homo sapiens

<400> SEQUENCE: 15

```
Gln Leu Cys Pro Thr Pro Cys Thr Cys Pro Trp Pro Pro Pro Arg
  1               5                  10                  15

Cys Pro Leu Gly Val Pro Leu Val Leu Asp Gly Cys Gly Cys Cys
                 20                  25                  30

Arg Val Cys Ala Arg Arg Leu Gly Glu Pro Cys Asp Gln Leu His
                 35                  40                  45

Val Cys Asp Ala Ser Gln Gly Leu Val Cys Gln Pro Gly Ala Gly
                 50                  55                  60

Pro Gly Gly Arg Gly Ala Leu Cys Leu Leu Ala Glu Asp Asp Ser
                 65                  70                  75

Ser Cys Glu Val Asn Gly Arg Leu Tyr Arg Glu Gly Glu Thr Phe
                 80                  85                  90

Gln Pro His Cys Ser Ile Arg Cys Arg Cys Glu Asp Gly Gly Phe
                 95                 100                 105
```

```
Thr Cys Val Pro Leu Cys Ser Glu Asp Val A rg Leu Pro Ser Trp
                110                 115                 120

Asp Cys Pro His Pro Arg Arg Val Glu Val L eu Gly Lys Cys Cys
                125                 130                 135

Pro Glu Trp Val Cys Gly Gln Gly Gly L eu Gly Thr Gln Pro
                140                 145                 150

Leu Pro Ala Gln Gly Pro Gln Phe Ser Gly L eu Val Ser Ser Leu
                155                 160                 165

Pro Pro Gly Val Pro Cys Pro Glu Trp Ser T hr Ala Trp Gly Pro
                170                 175                 180

Cys Ser Thr Thr Cys Gly Leu Gly Met Ala T hr Arg Val Ser Asn
                185                 190                 195

Gln Asn Arg Phe Cys Arg Leu Glu Thr Gln A rg Arg Leu Cys Leu
                200                 205                 210

Ser Arg Pro Cys Pro Pro Ser Arg Gly Arg S er Pro Gln Asn Ser
                215                 220                 225

Ala Phe
    227

<210> SEQ ID NO 16
<211> LENGTH: 250
<212> TYPE: PRT
<213> ORGANISM: Homo sapiens

<400> SEQUENCE: 16

Met Arg Gly Thr Pro Lys Thr His Leu Leu A la Phe Ser Leu Leu
  1               5                  10                  15

Cys Leu Leu Ser Lys Val Arg Thr Gln Leu C ys Pro Thr Pro Cys
                 20                  25                  30

Thr Cys Pro Trp Pro Pro Pro Arg Cys Pro L eu Gly Val Pro Leu
                 35                  40                  45

Val Leu Asp Gly Cys Gly Cys Cys Arg Val C ys Ala Arg Arg Leu
                 50                  55                  60

Gly Glu Pro Cys Asp Gln Leu His Val Cys A sp Ala Ser Gln Gly
                 65                  70                  75

Leu Val Cys Gln Pro Gly Ala Gly Pro Gly G ly Arg Gly Ala Leu
                 80                  85                  90

Cys Leu Leu Ala Glu Asp Asp Ser Ser Cys G lu Val Asn Gly Arg
                 95                 100                 105

Leu Tyr Arg Glu Gly Glu Thr Phe Gln Pro H is Cys Ser Ile Arg
                110                 115                 120

Cys Arg Cys Glu Asp Gly Gly Phe Thr Cys V al Pro Leu Cys Ser
                125                 130                 135

Glu Asp Val Arg Leu Pro Ser Trp Asp Cys P ro His Pro Arg Arg
                140                 145                 150

Val Glu Val Leu Gly Lys Cys Cys Pro Glu T rp Val Cys Gly Gln
                155                 160                 165

Gly Gly Gly Leu Gly Thr Gln Pro Leu Pro A la Gln Gly Pro Gln
                170                 175                 180

Phe Ser Gly Leu Val Ser Ser Leu Pro Pro G ly Val Pro Cys Pro
                185                 190                 195

Glu Trp Ser Thr Ala Trp Gly Pro Cys Ser T hr Thr Cys Gly Leu
                200                 205                 210

Gly Met Ala Thr Arg Val Ser Asn Gln Asn A rg Phe Cys Arg Leu
```

```
                  215                 220                 225
        Glu Thr Gln Arg Arg Leu Cys Leu Ser Arg Pro Cys Pro Pro Ser
                      230                 235                 240
        Arg Gly Arg Ser Pro Gln Asn Ser Ala Phe
                      245                 250

<210> SEQ ID NO 17
<211> LENGTH: 1734
<212> TYPE: DNA
<213> ORGANISM: Mus musculus

<400> SEQUENCE: 17
cccacgcgtc cgcgctcctg atctccagag gaccccgggc tgggacaggg              50
gccttggcga ggctgcagct gctgtggcag tagcttggga tggaggtctt             100
tcttgctggg aactgaggag ctgagaggct cctgtcaggc tcctgtccta             150
aactcttggc acttgcggtg gcttgggctt cacacactgt cagacacctt             200
cttggtggcc tcctcggcct caggtttgaa gctggctcca caagggacac             250
ggtgacatga ggggcaaccc actgatccat cttctggcca tttccttcct             300
ctgcattctc tcaatggtgt attcccagct gtgcccagca ccctgtgcct             350
gtccttggac accaccccag tgcccaccgg ggtaccccct ggtgctggat             400
ggctgtggct gctgtcgagt gtgtgcacgg aggctggggg agtcctgcga             450
ccacctgcat gtctgcgacc ccagccaggg cctggtttgt cagcctgggg             500
caggccccag tggccgtggt gctgtgtgcc tcttcgaaga ggatgacggg             550
agctgtgagt tgaatggccg caggtacctg gatggggaga cctttaaacc             600
caattgcagg gttttgtgcc gctgtgatga cggtggtttc acctgcctgc             650
cgctgtgcag tgaggatgtg cggctgccca gctgggactg ccacgcccc              700 aggagaatac aggtgccagg aaggtgctgc cccgagtggg tgtgtgacca             750
ggcagtgatg cagccggcaa tccagccctc ctcagcccaa ggacaccaac             800
tttctgccct tgtcactcct gcatctgccg atggcccctg tccaaactgg             850
agcacagcct gggcccctg ctcaaccacc tgtgggttgg catagccac               900 ccgagtatcc aaccagaacc gattctgcca actggagatc cagcgtcgcc             950
tgtgtctgtc cagaccctgc ctggcatcca ggagccacgg ctcatggaac            1000
agtgccttct agagccattg cggggatgtg gatacagggc ctgccattct            1050
cagcaaatgt ccctaggacc aggccctgga ctgatggtag atgccctct             1100 ccatgctctt ggctgcagtt aactgtcctg ggtggattca gtgtccagag            1150
cctctgagcg atccctgctc tgtctgaggt gggggaagca ggtgaccagc            1200
tccatttctc tggattctga cccaggcttc tgggttctcc tggctagttc            1250
ctcaaaactt ccctgtatga aaggacaac caaaaggacc tttaaagcta             1300
agctgtactg ggcaagcctg gccaccatgc tgggatagt gacagtaata             1350 ggtaccaggc agcagattgc ctgaaacatc caggtcccct cttggacttc            1400
tatgtgcttg tcccaaagat tatgggtgac cttgtaagtg tgcctttcct            1450
gatctgagaa caccctgccc ggctgggaag aatttctgg gaacatgaag             1500 agatggaatc acactattct taagagcgtt tgccaagtcc aggaacttga            1550
cctttgtatt tgtaaaaata cacatctctt aaatgctcac aaagcaagag            1600
```

```
gctccacact tctggcaggc cagggccttt ctcttcagca tgagagagac      1650
aaggaacagt agagtaccct cctctggagg actgcccgg tctggaataa       1700 acacccaaat caagtgtgga aaaaaaaaaa aaaa                       1734
```

<210> SEQ ID NO 18
<211> LENGTH: 1734
<212> TYPE: DNA
<213> ORGANISM: Mus musculus

<400> SEQUENCE: 18

```
tttttttttt ttttccaca cttgatttgg gtgtttattc cagaccgggc       50
cagtcctcca gaggagggta ctctactgtt ccttgtctct ctcatgctga      100
agagaaaggc cctggcctgc cagaagtgtg gagcctcttg ctttgtgagc      150
atttaagaga tgtgtatttt tacaaataca aggtcaagt tcctggactt       200 ggcaaacgct cttaagaata gtgtgattcc atctcttcat gttcccagaa      250
aattcttccc agccgggcag ggtgttctca gatcaggaaa gcacactta       300 caaggtcacc cataatcttt gggacaagca catagaagtc caagaaggga     350
cctggatgtt tcaggcaatc tgctgcctgg tacctattac tgtcactatc     400
cccagcatgg tggccaggct tgcccagtac agcttagctt taaaggtcct     450
tttggttgtc cttttcatac agggaagttt tgaggaacta gccaggagaa     500
cccagaagcc tgggtcagaa tccagagaaa tggagctggt cacctgcttc     550
ccccacctca gacagagcag ggatcgctca gaggctctgg acactgaatc     600
cacccaggac agttaactgc agccaagagc atggagaggg gcatctacca     650
tcagtccagg gcctggtcct agggacattt gctgagaatg gcaggccctg     700
tatccacatc cccgcaatgg ctctagaagg cactgttcca tgagccgtgg     750
ctcctggatg ccaggcaggg tctggacaga cacaggcgac gctggatctc     800
cagttggcag aatcggttct ggttggatac tcgggtggct atgcccaacc     850
cacaggtggt tgagcagggg ccccaggctg tgctccagtt tggacagggg     900
ccatcggcag atgcaggagt gacaagggca gaaagttggt gtccttgggc     950
tgaggagggc tggattgccg gctgcatcac tgcctggtca cacacccact    1000
cggggcagca ccttcctggc acctgtattc tcctggggcg tgggcagtcc    1050
cagctgggca gccgcacatc ctcactgcac agcggcaggc aggtgaaacc    1100
accgtcatca cagcggcaca aaaccctgca attgggttta aaggtctccc    1150
catccaggta cctgcggcca ttcacctcac agctcccgtc atcctcttcg    1200
aagaggcaca cagcaccacg gccactgggg cctgccccag gctgacaaac    1250
caggccctgg ctgggtcgc agacatgcag gtggtcgcag gactccccca    1300
gcctccgtgc acacactcga cagcagccac agccatccag caccagggt    1350 accccggtg ggcactgggg tggtgtccaa ggacaggcac agggtgctgg    1400
gcacagctgg gaatacacca ttgagagaat gcagaggaag gaaatggcca    1450
gaagatggat cagtgggttg cccctcatgt caccgtgtcc cttgtggagc    1500
cagcttcaaa cctgaggccg aggaggccac caagaaggtg tctgacagtg    1550
tgtgaagccc aagccaccgc aagtgccaag agtttaggac aggagcctga    1600
```

-continued

```
caggagcctc tcagctcctc agttcccagc aagaaagacc tccatcccaa         1650
gctactgcca cagcagctgc agcctcgcca aggcccctgt cccagcccgg         1700
ggtcctctgg agatcaggag cgcggacgcg tggg                          1734
```

<210> SEQ ID NO 19
<211> LENGTH: 228
<212> TYPE: PRT
<213> ORGANISM: Mus musculus

<400> SEQUENCE: 19

```
Gln Leu Cys Pro Ala Pro Cys Ala Cys Pro Trp Thr Pro Pro Gln
 1               5                  10                  15

Cys Pro Pro Gly Val Pro Leu Val Leu Asp Gly Cys Gly Cys Cys
                20                  25                  30

Arg Val Cys Ala Arg Arg Leu Gly Glu Ser Cys Asp His Leu His
                35                  40                  45

Val Cys Asp Pro Ser Gln Gly Leu Val Cys Gln Pro Gly Ala Gly
                50                  55                  60

Pro Ser Gly Arg Gly Ala Val Cys Leu Phe Glu Glu Asp Asp Gly
                65                  70                  75

Ser Cys Glu Val Asn Gly Arg Arg Tyr Leu Asp Gly Glu Thr Phe
                80                  85                  90

Lys Pro Asn Cys Arg Val Leu Cys Arg Cys Asp Asp Gly Gly Phe
                95                 100                 105

Thr Cys Leu Pro Leu Cys Ser Glu Asp Val Arg Leu Pro Ser Trp
               110                 115                 120

Asp Cys Pro Arg Pro Arg Arg Ile Gln Val Pro Gly Arg Cys Cys
               125                 130                 135

Pro Glu Trp Val Cys Asp Gln Ala Val Met Gln Pro Ala Ile Gln
               140                 145                 150

Pro Ser Ser Ala Gln Gly His Gln Leu Ser Ala Leu Val Thr Pro
               155                 160                 165

Ala Ser Ala Asp Gly Pro Cys Pro Asn Trp Ser Thr Ala Trp Gly
               170                 175                 180

Pro Cys Ser Thr Thr Cys Gly Leu Gly Ile Ala Thr Arg Val Ser
               185                 190                 195

Asn Gln Asn Arg Phe Cys Gln Leu Glu Ile Gln Arg Arg Leu Cys
               200                 205                 210

Leu Ser Arg Pro Cys Leu Ala Ser Arg Ser His Gly Ser Trp Asn
               215                 220                 225

Ser Ala Phe
        228
```

<210> SEQ ID NO 20
<211> LENGTH: 251
<212> TYPE: PRT
<213> ORGANISM: Mus musculus

<400> SEQUENCE: 20

```
Met Arg Gly Asn Pro Leu Ile His Leu Leu Ala Ile Ser Phe Leu
 1               5                  10                  15

Cys Ile Leu Ser Met Val Tyr Ser Gln Leu Cys Pro Ala Pro Cys
                20                  25                  30

Ala Cys Pro Trp Thr Pro Pro Gln Cys Pro Pro Gly Val Pro Leu
                35                  40                  45
```

```
Val Leu Asp Gly Cys Gly Cys Cys Arg Val Cys Ala Arg Arg Leu
                50                  55                  60

Gly Glu Ser Cys Asp His Leu His Val Cys Asp Pro Ser Gln Gly
                65                  70                  75

Leu Val Cys Gln Pro Gly Ala Gly Pro Ser Gly Arg Gly Ala Val
                80                  85                  90

Cys Leu Phe Glu Glu Asp Asp Gly Ser Cys Glu Val Asn Gly Arg
                95                 100                 105

Arg Tyr Leu Asp Gly Glu Thr Phe Lys Pro Asn Cys Arg Val Leu
               110                 115                 120

Cys Arg Cys Asp Asp Gly Gly Phe Thr Cys Leu Pro Leu Cys Ser
               125                 130                 135

Glu Asp Val Arg Leu Pro Ser Trp Asp Cys Pro Arg Pro Arg Arg
               140                 145                 150

Ile Gln Val Pro Gly Arg Cys Cys Pro Glu Trp Val Cys Asp Gln
               155                 160                 165

Ala Val Met Gln Pro Ala Ile Gln Pro Ser Ser Ala Gln Gly His
               170                 175                 180

Gln Leu Ser Ala Leu Val Thr Pro Ala Ser Ala Asp Gly Pro Cys
               185                 190                 195

Pro Asn Trp Ser Thr Ala Trp Gly Pro Cys Ser Thr Thr Cys Gly
               200                 205                 210

Leu Gly Ile Ala Thr Arg Val Ser Asn Gln Asn Arg Phe Cys Gln
               215                 220                 225

Leu Glu Ile Gln Arg Arg Leu Cys Leu Ser Arg Pro Cys Leu Ala
               230                 235                 240

Ser Arg Ser His Gly Ser Trp Asn Ser Ala Phe
               245                 250 251

<210> SEQ ID NO 21
<211> LENGTH: 345
<212> TYPE: PRT
<213> ORGANISM: Homo sapiens

<400> SEQUENCE: 21

Thr Ala Leu Ser Pro Ala Pro Thr Thr Met Asp Phe Thr Pro Ala
  1               5                  10                  15

Pro Leu Glu Asp Thr Ser Ser Arg Pro Gln Phe Cys Lys Trp Pro
                20                  25                  30

Cys Glu Cys Pro Pro Ser Pro Arg Cys Pro Leu Gly Val Ser
                35                  40                  45

Leu Ile Thr Asp Gly Cys Glu Cys Cys Lys Met Cys Ala Gln Gln
                50                  55                  60

Leu Gly Asp Asn Cys Thr Glu Ala Ala Ile Cys Asp Pro His Arg
                65                  70                  75

Gly Leu Tyr Cys Asp Tyr Ser Gly Asp Arg Pro Arg Tyr Ala Ile
                80                  85                  90

Gly Val Cys Ala Gln Val Val Gly Val Cys Val Leu Asp Gly
                95                 100                 105

Val Arg Tyr Asn Asn Gly Gln Ser Phe Gln Pro Asn Cys Lys Tyr
               110                 115                 120

Asn Cys Thr Cys Ile Asp Gly Ala Val Gly Cys Thr Pro Leu Cys
               125                 130                 135

Leu Arg Val Arg Pro Pro Arg Leu Trp Cys Pro His Pro Arg Arg
               140                 145                 150
```

-continued

```
Val Ser Ile Pro Gly His Cys Cys Glu Gln Trp Ile Cys Glu Asp
            155                 160                 165

Asp Ala Lys Arg Pro Arg Lys Thr Ala Pro Arg Asp Thr Gly Ser
            170                 175                 180

Phe Asp Ala Val Gly Glu Val Glu Ala Trp His Arg Asn Cys Ile
            185                 190                 195

Ala Tyr Thr Ser Pro Trp Ser Pro Cys Ser Thr Ser Cys Gly Leu
            200                 205                 210

Gly Val Ser Thr Arg Ile Ser Asn Val Asn Ala Gln Cys Trp Pro
            215                 220                 225

Glu Gln Glu Ser Arg Leu Cys Asn Leu Arg Pro Cys Asp Val Asp
            230                 235                 240

Ile His Thr Leu Ile Lys Ala Gly Lys Lys Cys Leu Ala Val Tyr
            245                 250                 255

Gln Pro Glu Ala Ser Met Asn Phe Thr Leu Ala Gly Cys Ile Ser
            260                 265                 270

Thr Arg Ser Tyr Gln Pro Lys Tyr Cys Gly Val Cys Met Asp Asn
            275                 280                 285

Arg Cys Cys Ile Pro Tyr Lys Ser Lys Thr Ile Asp Val Ser Phe
            290                 295                 300

Gln Cys Pro Asp Gly Leu Gly Phe Ser Arg Gln Val Leu Trp Ile
            305                 310                 315

Asn Ala Cys Phe Cys Asn Leu Ser Cys Arg Asn Pro Asn Asp Ile
            320                 325                 330

Phe Ala Asp Leu Glu Ser Tyr Pro Asp Phe Ser Glu Ile Ala Asn
            335                 340                 345

<210> SEQ ID NO 22
<211> LENGTH: 367
<212> TYPE: PRT
<213> ORGANISM: Homo sapiens

<400> SEQUENCE: 22

Met Arg Trp Phe Leu Pro Trp Thr Leu Ala Ala Val Thr Ala Ala
 1               5                  10                  15

Ala Ala Ser Thr Val Leu Ala Thr Ala Leu Ser Pro Ala Pro Thr
                20                  25                  30

Thr Met Asp Phe Thr Pro Ala Pro Leu Glu Asp Thr Ser Ser Arg
                35                  40                  45

Pro Gln Phe Cys Lys Trp Pro Cys Glu Cys Pro Pro Ser Pro Pro
                50                  55                  60

Arg Cys Pro Leu Gly Val Ser Leu Ile Thr Asp Gly Cys Glu Cys
                65                  70                  75

Cys Lys Met Cys Ala Gln Gln Leu Gly Asp Asn Cys Thr Glu Ala
                80                  85                  90

Ala Ile Cys Asp Pro His Arg Gly Leu Tyr Cys Asp Tyr Ser Gly
                95                 100                 105

Asp Arg Pro Arg Tyr Ala Ile Gly Val Cys Ala Gln Val Val Gly
               110                 115                 120

Val Gly Cys Val Leu Asp Gly Val Arg Tyr Asn Asn Gly Gln Ser
               125                 130                 135

Phe Gln Pro Asn Cys Lys Tyr Asn Cys Thr Cys Ile Asp Gly Ala
               140                 145                 150

Val Gly Cys Thr Pro Leu Cys Leu Arg Val Arg Pro Pro Arg Leu
```

```
                    155                 160                 165
Trp Cys Pro His Pro Arg Arg Val Ser Ile P ro Gly His Cys Cys
            170                 175                 180
Glu Gln Trp Ile Cys Glu Asp Asp Ala Lys A rg Pro Arg Lys Thr
        185                 190                 195
Ala Pro Arg Asp Thr Gly Ser Phe Asp Ala V al Gly Glu Val Glu
    200                 205                 210
Ala Trp His Arg Asn Cys Ile Ala Tyr Thr S er Pro Trp Ser Pro
            215                 220                 225
Cys Ser Thr Ser Cys Gly Leu Gly Val Ser T hr Arg Ile Ser Asn
            230                 235                 240
Val Asn Ala Gln Cys Trp Pro Glu Gln Glu S er Arg Leu Cys Asn
            245                 250                 255
Leu Arg Pro Cys Asp Val Asp Ile His Thr L eu Ile Lys Ala Gly
            260                 265                 270
Lys Lys Cys Leu Ala Val Tyr Gln Pro Glu A la Ser Met Asn Phe
            275                 280                 285
Thr Leu Ala Gly Cys Ile Ser Thr Arg Ser T yr Gln Pro Lys Tyr
            290                 295                 300
Cys Gly Val Cys Met Asp Asn Arg Cys Cys I le Pro Tyr Lys Ser
            305                 310                 315
Lys Thr Ile Asp Val Ser Phe Gln Cys Pro A sp Gly Leu Gly Phe
            320                 325                 330
Ser Arg Gln Val Leu Trp Ile Asn Ala Cys P he Cys Asn Leu Ser
            335                 340                 345
Cys Arg Asn Pro Asn Asp Ile Phe Ala Asp L eu Glu Ser Tyr Pro
            350                 355                 360
Asp Phe Ser Glu Ile Ala Asn
            365     367

<210> SEQ ID NO 23
<211> LENGTH: 1403
<212> TYPE: DNA
<213> ORGANISM: Homo sapiens

<400> SEQUENCE: 23
gccagtctgg gcccagctcc ccgagaggt ggtcggatcc tctgggctgc         50
tcggtcgatg cctgtgccac tgacgtccag gcatgaggtg gttcctgccc        100
tggacgctgg cagcagtgac agcagcagcc gccagcaccg tcctggccac        150
ggccctctct ccagccccta cgaccatgga ctttacccca gctccactgg        200
aggacacctc ctcacgcccc caattctgca gtggccatg tgagtgcccg         250 ccatccccac cccgctgccc gctgggggtc agcctcatca cagatggctg        300
tgagtgctgt aagatgtgcg ctcagcagct tggggacaac tgcacggagg        350
ctgccatctg tgaccccac cggggcctct actgtgacta cagcggggac         400
cgcccgagag gtggtcggtg tgggctgcgt cctggatggg gtgcgctaca        450
acaacggcca gtccttccag cctaactgca gtacaactg cacgtgcatc         500 gacggcgcgg tgggctgcac accactgtgc ctccgagtgc gcccccgcg         550 tctctggtgc ccccacccgc ggcgcgtgag catacctggc cactgctgtg        600
agcagtgggt atgtgaggac gacgccaaga ggccacgcaa gaccgcaccc        650
cgtgacacag gagccttcga tgctgtgggt gaggtggagg catggcacag        700
```

```
gaactgcata gcctacacaa gccctggag cccttgctcc accagctgcg        750 gcctggggt ctccactcgg atctccaatg ttaacgccca gtgctggcct        800
gagcaagaga gccgcctctg caacttgcgg ccatgcgatg tggacatcca       850
tacactcatt aaggcaggga agaagtgtct ggctgtgtac cagccagagg       900
catccatgaa cttcacactt gcgggctgca tcagcacacg ctcctatcaa       950
cccaagtact gtggagtttg catggacaat aggtgctgca tcccctacaa      1000
gtctaagact atcgacgtgt ccttccagtg tcctgatggg cttggcttct      1050
cccgccaggt cctatggatt aatgcctgct tctgtaacct gagctgtagg      1100
aatcccaatg acatctttgc tgacttggaa tcctaccctg acttctcaga      1150
aattgccaac taggcaggca caaatcttgg gtcttgggga ctaacccaat      1200
gcctgtgaag cagtcagccc ttatggccaa taacttttca ccaatgagcc      1250
ttagttaccc tgatctggac ccttggcctc catttctgtc tctaaccatt      1300
caaatgacgc ctgatggtgc tgctcaggcc catgctatga gttttctcct      1350
tgatatcatt cagcatctac tctaaagaaa aatgcctgtc tctagctgtt      1400
ctg                                                        1403

<210> SEQ ID NO 24
<211> LENGTH: 693
<212> TYPE: DNA
<213> ORGANISM: Homo sapiens

<400> SEQUENCE: 24
tttaattaaa cccccaaggg ctgcggaagg agcatatctg gtgctcctga        50
tgggccggcc agtctgggcc cagctccccc gagaggtggt cggatcctct       100
gggctgctcg gtcgatgcct gtgccactga cgtccaggca tgaggtggtt      150
cctgccctgg acgctggcag cagtgacagc agcagccgcc agcaccgtcc       200
tggccacggc cctctctcca gcccctacga ccatggactt taccccagct       250
ccactggagg acacctcctc acgccccaa ttctgcaagt ggccatgtga       300
gtgcccgcca tccccacccc gctgcccgct gggggtcagc ctcatcacag      350
atggctgtga gtgctgtaag atgtgcgctc agcagcttgg ggacaactgc      400
acggaggctg ccatctgtga ccccaccgg ggcctctact gtgactacag       450
cggggaccgc ccgaggtacg caataggagt gtgtgcacgc agggaagaag       500
tgtctggctg tgtaccagcc agaggcatcc atgaacttca cacttgcggg      550
ctgcatcagc acacgctcct atcaacccaa gtactgtgga gtttgcatgg      600
acaacaggtg ctgcatcccc tacaagtcta agactatcga cgtgtccttc      650
cagtgtcctg atgggcttgg cttctcccgc caggtcctat gga            693

<210> SEQ ID NO 25
<211> LENGTH: 683
<212> TYPE: DNA
<213> ORGANISM: Homo sapiens

<400> SEQUENCE: 25
cagaatttga actgggatcc acctgtctct aaagatgggt ttcctcccat        50
gcttccacac tgcctctctt gatcagaaac atacaaggag ctgagaacat      100
```

| | |
|---|---|
| gtcctccact ccctgggtac ctttgctggt tagaagccaa cttgctgtcc | 150 |
| tgtggggagg tacagccaat ttctgtgttc ctctgagttc tggggaccgc | 200 |
| agaccttagt gtggtgaaag tgagcgttgg gggctggtgg gagctgtaga | 250 |
| ttcatgcaga ttctgttccc cacacacaga tgctgtgggt gaggtggagg | 300 |
| catggcacag gaactgcata gcctacacaa gcccctggag cccttgctcc | 350 |
| accagctgcg gcctgggggt ctccactcgg atctccaatg ttaacgccca | 400 |
| gtgctggcct gagcaagaga gccgcctctg caacttgcgg ccatgcgatg | 450 |
| tggacatcca tacactcatt aaggcaggga agaagtgtct ggctgtgtac | 500 |
| cagccagagg catccatgaa cttcacactt gcgggctgca tcagcacacg | 550 |
| ctcctatcaa cccaagtact gtggagtttg catggacaat aggtgctgca | 600 |
| tcccctacaa gtctaagact atcgacgtgt ccttccagtg tcctgatggg | 650 |
| cttggcttct cccgccaggt cgtatggatt aat | 683 |

<210> SEQ ID NO 26
<211> LENGTH: 1202
<212> TYPE: DNA
<213> ORGANISM: Homo sapiens

<400> SEQUENCE: 26

| | |
|---|---|
| gtctgggccc agctcccccg agaggtggtc ggatcctctg ggctgctcgg | 50 |
| tcgatgcctg tgccactgac gtccaggcat gaggtggttc ctgccctgga | 100 |
| cgctggcagc agtgacagca gcagccgcca gcaccgtcct ggccacggcc | 150 |
| ctctctccag cccctacgac catggacttt accccagctc cactggagga | 200 |
| cacctcctca cgcccccaat tctgcaagtg gccatgtgag tgcccgccat | 250 |
| ccccaccccg ctgcccgctg ggggtcagcc tcatcacaga tggctgtgag | 300 |
| tgctgtaaga tgtgcgctca gcagcttggg gacaactgca cggaggctgc | 350 |
| catctgtgac ccccaccggg gcctctactg tgactacagc ggggaccgcc | 400 |
| cgaggtacgc aataggagtg tgtgcacgca gggaagaagt gtctggctgt | 450 |
| gtaccagcca gaggcatcca tgaacttcac acttgcgggc tgcatcagca | 500 |
| cacgctccta tcaacccaag tactgtggag tttgcatgga caacaggtgc | 550 |
| tgcatcccct acaagtctaa gactatcgac gtgtccttcc agtgtcctga | 600 |
| tgggcttggc ttctcccgcc aggtcctatg gattaatgcc tgcttctgta | 650 |
| acctgagctg taggaatccc aatgacatct ttgctgactt ggaatcctac | 700 |
| cctgacttct cagaaattgc aactaggca ggcacaaatc ttgggtcttg | 750 |
| gggactaacc caatgcctgt gaagcagtca gcccttatgg ccaataactt | 800 |
| ttaccaatg agccttagtt accctgatct ggacccttgg cctccatttc | 850 |
| tgtctctaac cattcaaatg acgcctgatg tgctgctca ggcccatgct | 900 |
| atgagttttc tccttgatat cattcagcat ctactctaaa gaaaaatgcc | 950 |
| tgtctctagc tgttctggac tacacccaag cctgatccag cctttccaag | 1000 |
| tcactagaag tcctgctgga tcttgcctaa atcccaagaa atggaatcag | 1050 |
| gtagactttt aatatcacta atttcttctt tagatgccaa accacaagac | 1100 |
| tctttgggtc cattcagatg aatagatgga atttggaaca atagaataat | 1150 |
| ctattatttg gagcctgcca agaggtactg taatgggtaa ttctgacgtc | 1200 | ag                                                                          1202

<210> SEQ ID NO 27
<211> LENGTH: 1183
<212> TYPE: DNA
<213> ORGANISM: Homo sapiens

<400> SEQUENCE: 27
cagaacagct agagacaggc attttctttt agagtagatg ctgaatgata          50
tcaaggagaa aactcatagc atgggcctga gcagcaccat caggcgtcat         100
ttgaatggtt agagacagaa atggaggcca agggtccaga tcagggtaac         150
taaggctcat tggtgaaaag ttattggcca taagggctga ctgcttcaca         200
ggcattgggt tagtccccaa gacccaagat ttgtgcctgc ctagttggca         250
atttctgaga agtcaggqta ggattccaag tcagcaaaga tgtcattggg         300
attcctacag ctcaggttac agaagcaggc attaatccat aggacctggc         350
gggagaagcc aagcccatca ggacactgga aggacacgtc gatagtctta         400
gacttgtagg ggatgcagca cctattgtcc atgcaaactc cacagtactt         450
gggttgatag gagcgtgtgc tgatgcagcc cgcaagtgtg aagttcatgg         500
atgcctctgg ctggtacaca gccagacact tcttccctgc cttaatgagt         550
gtatggatgt ccacatcgca tggccgcaag ttgcagaggc ggctctcttg         600
ctcaggccag cactgggcgt taacattgga gatccgagtg gagaccccca         650
ggccgcagct ggtggagcaa gggctccagg ggcttgtgta ggctatgcag         700
ttcctgtgcc atgcctccac ctcacccaca gcatctgtgt gtgggaaca          750
gaatctgcat gaatctacag ctcccaccag cccccaacgc tcactttcac         800
cacactaagg tctgcggtcc ccagaactca gaggaacaca gaaattggct         850
gtacctcccc acaggacagc aagttggctt ctaaccagca aagtaccca          900
gggagtggag gacatgttct cagctccttg tatgtttctg atcaagagag         950
gcagtgtgga agcatgggag gaaacccatc tttagagaca ggtggatccc        1000
agttcaaatt ctgctctacc acctacaagc tgtgtgatct tagataaccc        1050
accctgggcc tgtctcccca ttagaacaat aacacctgcc tgtgcggctg        1100
gcaacacaat aataagggcc tagattttta ctgagtatgc atcaatcatc        1150
cttgctaagt gctgggaatg ggactttttt ttt                         1183

<210> SEQ ID NO 28
<211> LENGTH: 546
<212> TYPE: DNA
<213> ORGANISM: Homo sapiens

<400> SEQUENCE: 28
cctgatctgg acccttggcc tccaattctg tctgtaacca ttcaaatgac          50
gcctggtggt gctgctcagg cccatagcaa ggttcagcct ggttaagtcc         100
aagctgaatt agcggccgcg tcgacagtag gagtgtgtgc acatgctgtg         150
ggtgaggtgg aggcatggca caggaactgc atagcctaca caagcccctg         200
gagcccttgc tccaccagct gcggcctggg ggtctccact cggatctcca         250
atgttaacgc ccagtgctgg cctgagcaag agagccgcct ctgcaacttg         300

| | |
|---|---|
| cggccatgcg atgtggacat ccatacactc attaaggcag ggaagaagtg | 350 |
| tctggctgtg taccagccag aggcatccat gaacttcaca cttgcgggct | 400 |
| gcatcagcac acgctcctat caacccaagt actgtggagt ttgcatggac | 450 |
| aataggtgct gcatcccca caagtctaag actatcgacg tgtccttcca | 500 |
| gtgtcctgat gggcttggct ctcccgcca ggtcctatgg attaat | 546 |

<210> SEQ ID NO 29
<211> LENGTH: 1101
<212> TYPE: DNA
<213> ORGANISM: Homo sapiens

<400> SEQUENCE: 29

| | |
|---|---|
| ggcccagctc ccccgagagg tggtcggatc tctgggctg ctcggtcgat | 50 |
| gcctgtgcca ctgacgtcca ggcatgaggt ggttcctgcc ctggacgctg | 100 |
| gcagcagtga cagcagcagc cgccagcacc gtcctggcca cggccctctc | 150 |
| tccagcccct acgaccatgg actttacccc agctccactg gaggacacct | 200 |
| cctcacgccc ccaattctgc aagtggccat gtgagtgccc gccatcccca | 250 |
| ccccgctgcc cgctgggggt cagcctcatc acagatggct gtgagtgctg | 300 |
| taagatgtgc gctcagcagc ttggggacaa ctgcacggag gctgccatct | 350 |
| gtgacccca ccggggcctc tactgtgact acagcgggga ccgcccgaga | 400 |
| ggtggtcggt gtgggctgcg tcctggatgg ggtgcgctac aacaacggcc | 450 |
| agtccttcca gcctaactgc aagtacaact gcacgtgcat cgacggcgcg | 500 |
| gtgggctgca caccactgtg cctccgagtg cgcccccgc gtctctggtg | 550 |
| ccccaccg cggcgcgtga gcatacctgg ccactgctgt gagcagtgga | 600 |
| tatgtgagga cgacgccaag aggccacgca agaccgcacc ccgtgacaca | 650 |
| ggagccttcg atgccagaag cgcccgctcc ctcagagatg tgacaaccaa | 700 |
| aatcatctcc agacctttcc aaatacaccc taggagacaa aattgctcgg | 750 |
| tggagaagca gtcctgtgag gacaggagga ggcgtggagg aaagctttgt | 800 |
| ccccagcagc cccagggaag caaggcagct ctcccaccac cacctcccca | 850 |
| ggagggccac acgagggtca cgggggagc agggaggcgg aagctgtctg | 900 |
| ccattgtgtc tggcccagtg accctgttct gaccgagcac aagcggagcc | 950 |
| cctgcctagc cgagatgctg tgggtgaggt ggaggcatgg cacaggaact | 1000 |
| gcatagccta cacaagcccc tggagcccctt gctccaccag ctgcggcctg | 1050 |
| ggggtctcca ctcggatctc caatgttaac gcccagtgct ggcctgagca | 1100 |
| a | 1101 |

<210> SEQ ID NO 30
<211> LENGTH: 1335
<212> TYPE: DNA
<213> ORGANISM: Homo sapiens
<220> FEATURE:
<221> NAME/KEY: Unsure
<222> LOCATION: 1205, 1318
<223> OTHER INFORMATION: Unknown base.

<400> SEQUENCE: 30

| | |
|---|---|
| gtggggtttg cagaggagac aggggagctt tgtgtacccg gagcaatgaa | 50 |
| caagcggcga cttctctacc cctcagggtg gctccacggt cccagcgaca | 100 |

```
tgcagggct cctcttctcc actcttctgc ttgctggcct ggcacagttc      150
tgctgcaggg tacagggcac tggaccatta gatacaacac ctgaaggaag      200
gcctggagaa gtgtcagatg cacctcagcg taaacagttt tgtcactggc      250
cctgcaaatg ccctcagcag aagccccgtt gccctcctgg agtgagcctg      300
gtgagagatg gctgtggatg ctgtaaaatc tgtgccaagc aaccagggga      350
aatctgcaat gaagctgacc tctgtgaccc acacaaaggg ctgtattgtg      400
actactcagt agacaggcct aggtacgaga ctggagtgtg tgcataccctt     450 gtagctgttg ggtgcgagtt caaccaggta cattatcata atggccaagt      500
gtttcagccc aacccctttgt tcagctgcct ctgtgtgagt ggggccattg     550
gatgcacacc tctgttcata ccaaagctgg ctggcagtca ctgctctgga      600
gctaaaggtg gaaagaagtc tgatcagtca aactgtagcc tggaaccatt      650
actacagcag ctttcaacaa gctacaaaac aatgccagct tatagagatc      700
tcccacttat ttggaaaaaa aaatgtcttg tgcaagcaac aaaatggact      750
ccctgctcca gaacatgtgg gatgggaata tctaacaggg tgaccaatga      800
aaacagcaac tgtgaaatga gaaaagagaa aagactgtgt tacattcagc      850
cttgcgacag caatatatta aagacaataa agattcccaa aggaaaaaca      900
tgccaaccta ctttccaact ctccaaagct gaaaaatttg tcttttctgg      950
atgctcaagt actcagagtt acaaacccac tttttgtgga atatgcttgg     1000
ataagagatg ctgtatcct aataagtcta aatgattac tattcaattt       1050 gattgcccaa atgagggggtc atttaaatgg aagatgctgt ggattacatc    1100
ttgtgtgtgt cagagaaact gcagagaacc tggagatata ttttctgagc     1150
tcaagattct gtaaaccaa gcaaatgggg gaaaagttag tcaatcctgt      1200
catanaataa aaaaattagt gagtataaaa tggtggcaaa tctactttgt     1250
ttaaaacagt atgaatgcct attctcagat cactacattt aaggcattag     1300
aaacttttaa aaagttanct taaaaatata cataa                     1335
```

<210> SEQ ID NO 31
<211> LENGTH: 1335
<212> TYPE: DNA
<213> ORGANISM: Homo sapiens
<220> FEATURE:
<221> NAME/KEY: Unsure
<222> LOCATION: 18, 131
<223> OTHER INFORMATION: Unknown base.

<400> SEQUENCE: 31

```
ttatgtatat ttttaagnta actttttaaa agtttctaat gccttaaatg      50
tagtgatctg agaataggca ttcatactgt tttaaacaaa gtagatttgc      100 caccattta tactcactaa ttttttttatt ntatgacagg attgactaac      150 ttttcccca tttgcttggt tttacagaat cttgagctca gaaaatatat      200
ctccaggttc tctgcagttt ctctgacaca cacaagatga aatccacagc     250
atcttccatt taaatgaccc ctcatttggg caatcaaatt gaatagtaat     300
cattttagac ttattaggga tacagcatct cttatccaag catattccac     350
aaaaagtggg tttgtaactc tgagtacttg agcatccaga aaagacaaat    400
```

-continued

| | |
|---|---|
| ttttcagctt tggagagttg gaaagtaggt tggcatgttt ttcctttggg | 450 |
| aatctttatt gtctttaata tattgctgtc gcaaggctga atgtaacaca | 500 |
| gtcttttctc ttttctcatt tcacagttgc tgttttcatt ggtcaccctg | 550 |
| ttagatattc ccatcccaca tgttctggag cagggagtcc attttgttgc | 600 |
| ttgcacaaga catttttttt tccaaataag tgggagatct ctataagctg | 650 |
| gcattgtttt gtagcttgtt gaaagctgct gtagtaatgg ttccaggcta | 700 |
| cagtttgact gatcagactt cttttccacct ttagctccag agcagtgact | 750 |
| gccagccagc tttggtatga acagaggtgt gcatccaatg gccccactca | 800 |
| cacagaggca gctgaacaag gggttgggct gaaacacttg ccattatga | 850 |
| taatgtacct ggttgaactc gcacccaaca gctacaaggt atgcacacac | 900 |
| tccagtctcg tacctaggcc tgtctactga gtagtcacaa tacagccctt | 950 |
| tgtgtgggtc acagaggtca gcttcattgc agatttcccc tggttgcttg | 1000 |
| gcacagattt tacagcatcc acagccatct ctcaccaggc tcactccagg | 1050 |
| agggcaacgg ggcttctgct gagggcattt gcagggccag tgacaaaact | 1100 |
| gtttacgctg aggtgcatct gacacttctc caggccttcc ttcaggtgtt | 1150 |
| gtatctaatg gtccagtgcc ctgtaccctg cagcagaact gtgccaggcc | 1200 |
| agcaagcaga agagtggaga agaggagccc ctgcatgtcg ctgggaccgt | 1250 |
| ggagccaccc tgagggtag agaagtcgcc gcttgttcat tgctccgggt | 1300 |
| acacaaagct ccctgtctc ctctgcaaac cccac | 1335 |

<210> SEQ ID NO 32
<211> LENGTH: 339
<212> TYPE: PRT
<213> ORGANISM: Homo sapiens

<400> SEQUENCE: 32

```
Gln Phe Cys Cys Arg Val Gln Gly Thr Gly Pro Leu Asp Thr Thr
  1               5                  10                  15

Pro Glu Gly Arg Pro Gly Glu Val Ser Asp Ala Pro Gln Arg Lys
                 20                  25                  30

Gln Phe Cys His Trp Pro Cys Lys Cys Pro Gln Gln Lys Pro Arg
                 35                  40                  45

Cys Pro Pro Gly Val Ser Leu Val Arg Asp Gly Cys Gly Cys Cys
                 50                  55                  60

Lys Ile Cys Ala Lys Gln Pro Gly Glu Ile Cys Asn Glu Ala Asp
                 65                  70                  75

Leu Cys Asp Pro His Lys Gly Leu Tyr Cys Asp Tyr Ser Val Asp
                 80                  85                  90

Arg Pro Arg Tyr Glu Thr Gly Val Cys Ala Tyr Leu Val Ala Val
                 95                 100                 105

Gly Cys Glu Phe Asn Gln Val His Tyr His Asn Gly Gln Val Phe
                110                 115                 120

Gln Pro Asn Pro Leu Phe Ser Cys Leu Cys Val Ser Gly Ala Ile
                125                 130                 135

Gly Cys Thr Pro Leu Phe Ile Pro Lys Leu Ala Gly Ser His Cys
                140                 145                 150

Ser Gly Ala Lys Gly Gly Lys Lys Ser Asp Gln Ser Asn Cys Ser
                155                 160                 165
```

-continued

```
Leu Glu Pro Leu Leu Gln Gln Leu Ser Thr Ser Tyr Lys Thr Met
                170                 175                 180

Pro Ala Tyr Arg Asp Leu Pro Leu Ile Trp Lys Lys Lys Cys Leu
                185                 190                 195

Val Gln Ala Thr Lys Trp Thr Pro Cys Ser Arg Thr Cys Gly Met
                200                 205                 210

Gly Ile Ser Asn Arg Val Thr Asn Glu Asn Ser Asn Cys Glu Met
                215                 220                 225

Arg Lys Glu Lys Arg Leu Cys Tyr Ile Gln Pro Cys Asp Ser Asn
                230                 235                 240

Ile Leu Lys Thr Ile Lys Ile Pro Lys Gly Lys Thr Cys Gln Pro
                245                 250                 255

Thr Phe Gln Leu Ser Lys Ala Glu Lys Phe Val Phe Ser Gly Cys
                260                 265                 270

Ser Ser Thr Gln Ser Tyr Lys Pro Thr Phe Cys Gly Ile Cys Leu
                275                 280                 285

Asp Lys Arg Cys Cys Ile Pro Asn Lys Ser Lys Met Ile Thr Ile
                290                 295                 300

Gln Phe Asp Cys Pro Asn Glu Gly Ser Phe Lys Trp Lys Met Leu
                305                 310                 315

Trp Ile Thr Ser Cys Val Cys Gln Arg Asn Cys Arg Glu Pro Gly
                320                 325                 330

Asp Ile Phe Ser Glu Leu Lys Ile Leu
                335                 339

<210> SEQ ID NO 33
<211> LENGTH: 372
<212> TYPE: PRT
<213> ORGANISM: Homo sapiens

<400> SEQUENCE: 33

Met Asn Lys Arg Arg Leu Leu Tyr Pro Ser Gly Trp Leu His Gly
  1               5                  10                  15

Pro Ser Asp Met Gln Gly Leu Leu Phe Ser Thr Leu Leu Leu Ala
                 20                  25                  30

Gly Leu Ala Gln Phe Cys Cys Arg Val Gln Gly Thr Gly Pro Leu
                 35                  40                  45

Asp Thr Thr Pro Glu Gly Arg Pro Gly Glu Val Ser Asp Ala Pro
                 50                  55                  60

Gln Arg Lys Gln Phe Cys His Trp Pro Cys Lys Cys Pro Gln Gln
                 65                  70                  75

Lys Pro Arg Cys Pro Pro Gly Val Ser Leu Val Arg Asp Gly Cys
                 80                  85                  90

Gly Cys Cys Lys Ile Cys Ala Lys Gln Pro Gly Glu Ile Cys Asn
                 95                 100                 105

Glu Ala Asp Leu Cys Asp Pro His Lys Gly Leu Tyr Cys Asp Tyr
                110                 115                 120

Ser Val Asp Arg Pro Arg Tyr Glu Thr Gly Val Cys Ala Tyr Leu
                125                 130                 135

Val Ala Val Gly Cys Glu Phe Asn Gln Val His Tyr His Asn Gly
                140                 145                 150

Gln Val Phe Gln Pro Asn Pro Leu Phe Ser Cys Leu Cys Val Ser
                155                 160                 165

Gly Ala Ile Gly Cys Thr Pro Leu Phe Ile Pro Lys Leu Ala Gly
                170                 175                 180
```

```
                Ser His Cys Ser Gly Ala Lys Gly Gly Lys L ys Ser Asp Gln Ser
                                185                 190                 195

Asn Cys Ser Leu Glu Pro Leu Leu Gln Gln L eu Ser Thr Ser Tyr
                                200                 205                 210

Lys Thr Met Pro Ala Tyr Arg Asp Leu Pro L eu Ile Trp Lys Lys
                                215                 220                 225

Lys Cys Leu Val Gln Ala Thr Lys Trp Thr P ro Cys Ser Arg Thr
                                230                 235                 240

Cys Gly Met Gly Ile Ser Asn Arg Val Thr A sn Glu Asn Ser Asn
                                245                 250                 255

Cys Glu Met Arg Lys Glu Lys Arg Leu Cys T yr Ile Gln Pro Cys
                                260                 265                 270

Asp Ser Asn Ile Leu Lys Thr Ile Lys Ile P ro Lys Gly Lys Thr
                                275                 280                 285

Cys Gln Pro Thr Phe Gln Leu Ser Lys Ala G lu Lys Phe Val Phe
                                290                 295                 300

Ser Gly Cys Ser Ser Thr Gln Ser Tyr Lys P ro Thr Phe Cys Gly
                                305                 310                 315

Ile Cys Leu Asp Lys Arg Cys Cys Ile Pro A sn Lys Ser Lys Met
                                320                 325                 330

Ile Thr Ile Gln Phe Asp Cys Pro Asn Glu G ly Ser Phe Lys Trp
                                335                 340                 345

Lys Met Leu Trp Ile Thr Ser Cys Val Cys G ln Arg Asn Cys Arg
                                350                 355                 360

Glu Pro Gly Asp Ile Phe Ser Glu Leu Lys I le Leu
                                365                 370  372

<210> SEQ ID NO 34
<211> LENGTH: 1212
<212> TYPE: DNA
<213> ORGANISM: Homo sapiens

<400> SEQUENCE: 34
cacggtccca gcgacatgca ggggctcctc ttctccactc ttctgcttgc           50
tggcctggca cagttctgct gcagggtaca gggcactgga ccattagata          100
caacacctga aggaaggcct ggagaagtgt cagatgcacc tcagcgtaaa          150
cagttttgtc actggccctg caaatgccct cagcagaagc ccgttgccc           200 tcctggagtg agcctggtga gagatggctg tggatgctgt aaaatctgtg          250
ccaagcaacc agggaaatc tgcaatgaag ctgacctctg tgacccacac           300
aaagggctgt attgtgacta ctcagtagac aggcctaggt acgagactgg          350
agtgtgtgca taccttgtag ctgttgggtg cgagttcaac caggtacatt          400
atcataatgg ccaagtgttt cagcccaacc ccttgttcag ctgcctctgt          450
gtgagtgggg ccattggatg cacacctctg ttcataccaa agctggctgg          500
cagtcactgc tctggagcta aggtggaaa gaagtctgat cagtcaaact            550
gtagcctgga accattacta cagcagcttt caacaagcta caaaacaatg          600
ccagcttata gaaatctccc acttatttgg aaaaaaaat gtcttgtgca            650 agcaacaaaa tggactccct gctccagaac atgtgggatg gaatatcta           700 acagggtgac caatgaaaac agcaactgtg aaatgagaaa agagaaaaga          750
ctgtgttaca ttcagccttg cgacagcaat atattaaaga caataaagat          800
```

```
tcccaaagga aaaacatgcc aacctacttt ccaactctcc aaagctgaaa         850
aatttgtctt ttctggatgc tcaagtactc agagttacaa acccactttt         900
tgtggaatat gcttggataa agatgctgt atccctaata agtctaaaat          950
gattactatt caatttgatt gcccaaatga ggggtcattt aaatggaaga         1000
tgctgtggat tacatcttgt gtgtgtcaga gaaactgcag agaacctgga         1050
gatatatttt ctgagctcaa gattctgtaa aaccaagcaa atgggggaaa         1100
agttagtcaa tcctgtcata taataaaaaa attagtgagt aaaaaaaaaa         1150
aaaaaaaaaa aaaaaaaaaa aaaaaaaaaa aaaaaaaaaa agaaaaaaaa         1200
aaaaaaaaaa aa                                                   1212

<210> SEQ ID NO 35
<211> LENGTH: 1212
<212> TYPE: DNA
<213> ORGANISM: Homo sapiens

<400> SEQUENCE: 35
tttttttttt tttttttttt cttttttttt tttttttttt tttttttttt           50
tttttttttt tttttttttt ttactcacta atttttttat tatatgacag          100
gattgactaa cttttccccc atttgcttgg ttttacagaa tcttgagctc          150
agaaaatata tctccaggtt ctctgcagtt tctctgacac acacaagatg          200
taatccacag catcttccat ttaaatgacc cctcatttgg gcaatcaaat          250
tgaatagtaa tcattttaga cttattaggg atacagcatc tcttatccaa          300
gcatattcca caaaaagtgg gtttgtaact ctgagtactt gagcatccag          350
aaaagacaaa ttttcagct ttggagagtt ggaaagtagg ttggcatgtt           400
tttcctttgg gaatctttat tgtctttaat atattgctgt cgcaaggctg          450
aatgtaacac agtcttttct cttttctcat ttcacagttg ctgttttcat          500
tggtcaccct gttagatatt cccatcccac atgttctgga gcagggagtc          550
cattttgttg cttgcacaag acattttttt ttccaaataa gtgggagatt          600
tctataagct ggcattgttt tgtagcttgt tgaaagctgc tgtagtaatg          650
gttccaggct acagtttgac tgatcagact tctttccacc tttagctcca          700
gagcagtgac tgccagccag ctttggtatg aacagaggtg tgcatccaat          750
ggccccactc acacagaggc agctgaacaa ggggttgggc tgaaacactt          800
ggccattatg ataatgtacc tggttgaact cgcacccaac agctacaagg          850
tatgcacaca ctccagtctc gtacctaggc ctgtctactg agtagtcaca          900
atacagccct ttgtgtgggt cacagaggtc agcttcattg cagatttccc          950
ctggttgctt ggcacagatt ttacagcatc cacagccatc tctcaccagg         1000
ctcactccag gagggcaacg gggcttctgc tgagggcatt tgcagggcca         1050
gtgacaaaac tgtttacgct gaggtgcatc tgacacttct ccaggccttc         1100
cttcaggtgt tgtatctaat ggtccagtgc cctgtaccct gcagcagaac         1150
tgtgccaggc cagcaagcag aagagtggag aagaggagcc cctgcatgtc         1200
gctgggaccg tg                                                  1212

<210> SEQ ID NO 36
```

```
<211> LENGTH: 339
<212> TYPE: PRT
<213> ORGANISM: Homo sapiens

<400> SEQUENCE: 36

Gln Phe Cys Cys Arg Val Gln Gly Thr Gly Pro Leu Asp Thr Thr
 1               5                  10                  15

Pro Glu Gly Arg Pro Gly Glu Val Ser Asp Ala Pro Gln Arg Lys
                20                  25                  30

Gln Phe Cys His Trp Pro Cys Lys Cys Pro Gln Gln Lys Pro Arg
                35                  40                  45

Cys Pro Pro Gly Val Ser Leu Val Arg Asp Gly Cys Gly Cys Cys
                50                  55                  60

Lys Ile Cys Ala Lys Gln Pro Gly Glu Ile Cys Asn Glu Ala Asp
                65                  70                  75

Leu Cys Asp Pro His Lys Gly Leu Tyr Cys Asp Tyr Ser Val Asp
                80                  85                  90

Arg Pro Arg Tyr Glu Thr Gly Val Cys Ala Tyr Leu Val Ala Val
                95                 100                 105

Gly Cys Glu Phe Asn Gln Val His Tyr His Asn Gly Gln Val Phe
               110                 115                 120

Gln Pro Asn Pro Leu Phe Ser Cys Leu Cys Val Ser Gly Ala Ile
               125                 130                 135

Gly Cys Thr Pro Leu Phe Ile Pro Lys Leu Ala Gly Ser His Cys
               140                 145                 150

Ser Gly Ala Lys Gly Gly Lys Ser Asp Gln Ser Asn Cys Ser
               155                 160                 165

Leu Glu Pro Leu Leu Gln Leu Ser Thr Ser Tyr Lys Thr Met
               170                 175                 180

Pro Ala Tyr Arg Asn Leu Pro Leu Ile Trp Lys Lys Cys Leu
               185                 190                 195

Val Gln Ala Thr Lys Trp Thr Pro Cys Ser Arg Thr Cys Gly Met
               200                 205                 210

Gly Ile Ser Asn Arg Val Thr Asn Glu Asn Ser Asn Cys Glu Met
               215                 220                 225

Arg Lys Glu Lys Arg Leu Cys Tyr Ile Gln Pro Cys Asp Ser Asn
               230                 235                 240

Ile Leu Lys Thr Ile Lys Ile Pro Lys Gly Lys Thr Cys Gln Pro
               245                 250                 255

Thr Phe Gln Leu Ser Lys Ala Glu Lys Phe Val Phe Ser Gly Cys
               260                 265                 270

Ser Ser Thr Gln Ser Tyr Lys Pro Thr Phe Cys Gly Ile Cys Leu
               275                 280                 285

Asp Lys Arg Cys Cys Ile Pro Asn Lys Ser Lys Met Ile Thr Ile
               290                 295                 300

Gln Phe Asp Cys Pro Asn Glu Gly Ser Phe Lys Trp Lys Met Leu
               305                 310                 315

Trp Ile Thr Ser Cys Val Cys Gln Arg Asn Cys Arg Glu Pro Gly
               320                 325                 330

Asp Ile Phe Ser Glu Leu Lys Ile Leu
               335                 339

<210> SEQ ID NO 37
<211> LENGTH: 354
<212> TYPE: PRT
```

-continued

<213> ORGANISM: Homo sapiens

<400> SEQUENCE: 37

```
Met Gln Gly Leu Leu Phe Ser Thr Leu Leu Ala Gly Leu Ala
 1               5                  10                  15

Gln Phe Cys Cys Arg Val Gln Gly Thr Gly Pro Leu Asp Thr Thr
                 20                  25                  30

Pro Glu Gly Arg Pro Gly Glu Val Ser Asp Ala Pro Gln Arg Lys
             35                  40                      45

Gln Phe Cys His Trp Pro Cys Lys Cys Pro Gln Gln Lys Pro Arg
             50                  55                      60

Cys Pro Pro Gly Val Ser Leu Val Arg Asp Gly Cys Gly Cys Cys
             65                      70                  75

Lys Ile Cys Ala Lys Gln Pro Gly Glu Ile Cys Asn Glu Ala Asp
             80                      85                  90

Leu Cys Asp Pro His Lys Gly Leu Tyr Cys Asp Tyr Ser Val Asp
             95                     100                 105

Arg Pro Arg Tyr Glu Thr Gly Val Cys Ala Tyr Leu Val Ala Val
            110                     115                 120

Gly Cys Glu Phe Asn Gln Val His Tyr His Asn Gly Gln Val Phe
            125                     130                 135

Gln Pro Asn Pro Leu Phe Ser Cys Leu Cys Val Ser Gly Ala Ile
            140                     145                 150

Gly Cys Thr Pro Leu Phe Ile Pro Lys Leu Ala Gly Ser His Cys
            155                     160                 165

Ser Gly Ala Lys Gly Lys Lys Ser Asp Gln Ser Asn Cys Ser
            170                     175                 180

Leu Glu Pro Leu Leu Gln Gln Leu Ser Thr Ser Tyr Lys Thr Met
            185                     190                 195

Pro Ala Tyr Arg Asn Leu Pro Leu Ile Trp Lys Lys Cys Leu
            200                     205                 210

Val Gln Ala Thr Lys Trp Thr Pro Cys Ser Arg Thr Cys Gly Met
            215                     220                 225

Gly Ile Ser Asn Arg Val Thr Asn Glu Asn Ser Asn Cys Glu Met
            230                     235                 240

Arg Lys Glu Lys Arg Leu Cys Tyr Ile Gln Pro Cys Asp Ser Asn
            245                     250                 255

Ile Leu Lys Thr Ile Lys Ile Pro Lys Gly Lys Thr Cys Gln Pro
            260                     265                 270

Thr Phe Gln Leu Ser Lys Ala Glu Lys Phe Val Phe Ser Gly Cys
            275                     280                 285

Ser Ser Thr Gln Ser Tyr Lys Pro Thr Phe Cys Gly Ile Cys Leu
            290                     295                 300

Asp Lys Arg Cys Cys Ile Pro Asn Lys Ser Lys Met Ile Thr Ile
            305                     310                 315

Gln Phe Asp Cys Pro Asn Glu Gly Ser Phe Lys Trp Lys Met Leu
            320                     325                 330

Trp Ile Thr Ser Cys Val Cys Gln Arg Asn Cys Arg Glu Pro Gly
            335                     340                 345

Asp Ile Phe Ser Glu Leu Lys Ile Leu
            350                 354
```

<210> SEQ ID NO 38
<211> LENGTH: 738

```
<212> TYPE: DNA
<213> ORGANISM: Homo sapiens

<400> SEQUENCE: 38
ccgaagaccc acctcctggc cttctccctc ctctgcctcc tctcaaaggt       50
gcgtacccag ctgtgcccga caccatgtac ctgcccctgg ccacctcccc      100
gatgcccgct gggagtaccc ctggtgctgg atggctgtgg ctgctgccgg      150
gtatgtgcac ggcggctggg ggagccctgc gaccaactcc acgtctgcga      200
cgccagccag ggcctggtct gccagcccgg gcaggaccc ggtggccggg       250 gggccctgtg cctcttggca gaggacgaca gcagctgtga ggtgaacggc      300
cgcctgtatc gggaagggga gaccttccag ccccactgca gcatccgctg      350
ccgctgcgag gacggcggct tcacctgcgt gccgctgtgc agcgaggatg      400
tgcggctgcc cagctgggac tgcccccacc ccaggagggt cgaggtcctg      450
ggcaagtgct gccctgagtg ggtgtgcggc aaggagggg gactggggac       500 ccagcccctt ccagcccaag gacccagtt ttctggcctt gtctcttccc       550
tgccccctgg tgtcccctgc ccagaatgga gcacggcctg gggaccctgc      600
tcgaccacct gtgggctggg catggccacc cgggtgtcca accagaaccg      650
cttctgccga ctggagaccc agcgccgcct gtgcctgtcc aggccctgcc      700
cacccTccag gggtcgcagt ccacaaaaca gtgccttc                   738

<210> SEQ ID NO 39
<211> LENGTH: 841
<212> TYPE: DNA
<213> ORGANISM: Artificial sequence
<220> FEATURE:
<221> NAME/KEY: misc_feature
<222> LOCATION: 1-841
<223> OTHER INFORMATION: Sequence is synthesized.

<400> SEQUENCE: 39
ctgcagggga catgagaggc acaccgaaga cccacctcct ggccttctcc       50
ctcctctgcc tcctctcaaa ggtgcgtacc cagctgtgcc cgacaccatg      100
tacctgcccc tggccacctc cccgatgccc gctgggagta cccctggtgg      150
tggatggctg tggctgctgc cgggtatgtg cacggcggct gggggagccc      200
tgcgaccaac tccacgtctg cgacgccagc cagggcctgg tctgccagcc      250
cggggcagga cccggtggcc ggggggcccT gtgcctcttg gcagaggacg      300
acagcagctg tgaggtgaac ggccgcctgt atcgggaagg ggagaccttc      350
cagccccact gcagcatccg ctgccgctgc gaggacggcg gcttcacctg      400
cgtgccgctg tgcagcgagg atgtgcggct gcccagctgg gactgccccc      450
acccccagga ggtcgaggtc ctgggcaagt gctgccctga gtgggtgtgc      500
ggccaaggag ggggactggg gaccagccct ccagcccaa ggaccccagt       550 tttctggcct tgtctcttcc ctgccccctg tgtcccctg cccagaatgg       600 agcacggcct ggggaccctg ctcgaccacc tgtgggctgg gcatggccac      650
ccgggtgtcc aaccagaacc gcttctgccg actggagacc cagcgccgcc      700
tgtgcctgtc caggccctgc ccacccTcca ggggtcgcag tccacaaaac      750
agtgccttct agagccgggc tgggaatggg gacacggtgt ccaccatccc      800
```
cagctggtgg ccctgtgcct gggccctggg ctgatggaag a                    841

<210> SEQ ID NO 40
<211> LENGTH: 14
<212> TYPE: DNA
<213> ORGANISM: Artificial sequence
<220> FEATURE:
<221> NAME/KEY: misc_feature
<222> LOCATION: 1-14
<223> OTHER INFORMATION: Sequence is synthesized.

<400> SEQUENCE: 40
ttttgtacaa gctt                                                  14

<210> SEQ ID NO 41
<211> LENGTH: 44
<212> TYPE: DNA
<213> ORGANISM: Artificial sequence
<220> FEATURE:
<221> NAME/KEY: misc_feature
<222> LOCATION: 1-44
<223> OTHER INFORMATION: Sequence is synthesized.

<400> SEQUENCE: 41
ctaatacgac tcactatagg gctcgagcgg ccgcccgggc aggt                  44

<210> SEQ ID NO 42
<211> LENGTH: 43
<212> TYPE: DNA
<213> ORGANISM: Artificial sequence
<220> FEATURE:
<221> NAME/KEY: misc_feature
<222> LOCATION: 1-43
<223> OTHER INFORMATION: Sequence is synthesized

<400> SEQUENCE: 42
tgtagcgtga agacgacaga aagggcgtgg tgcggagggc ggt                   43

<210> SEQ ID NO 43
<211> LENGTH: 10
<212> TYPE: DNA
<213> ORGANISM: Artificial Sequence
<220> FEATURE:
<221> NAME/KEY: misc_feature
<222> LOCATION: 1-10
<223> OTHER INFORMATION: Sequence is synthesized

<400> SEQUENCE: 43
acctgcccgg                                                       10

<210> SEQ ID NO 44
<211> LENGTH: 11
<212> TYPE: DNA
<213> ORGANISM: Artificial sequence
<220> FEATURE:
<221> NAME/KEY: misc_feature
<222> LOCATION: 1-11
<223> OTHER INFORMATION: Sequence is synthesized

<400> SEQUENCE: 44
accgccctcc g                                                     11

<210> SEQ ID NO 45
<211> LENGTH: 22
<212> TYPE: DNA
<213> ORGANISM: Artificial sequence
<220> FEATURE:
<221> NAME/KEY: misc_feature

```
<222> LOCATION: 1-22
<223> OTHER INFORMATION: Sequence is synthesized

<400> SEQUENCE: 45
ctaatacgac tcactatagg gc                                              22

<210> SEQ ID NO 46
<211> LENGTH: 21
<212> TYPE: DNA
<213> ORGANISM: Artificial sequence
<220> FEATURE:
<221> NAME/KEY: misc_feature
<222> LOCATION: 1-21
<223> OTHER INFORMATION: Sequence is synthesized

<400> SEQUENCE: 46
tgtagcgtga agacgacaga a                                               21

<210> SEQ ID NO 47
<211> LENGTH: 22
<212> TYPE: DNA
<213> ORGANISM: Artificial sequence
<220> FEATURE:
<221> NAME/KEY: misc_feature
<222> LOCATION: 1-22
<223> OTHER INFORMATION: Sequence is synthesized

<400> SEQUENCE: 47
tcgagcggcc gcccgggcag gt                                              22

<210> SEQ ID NO 48
<211> LENGTH: 22
<212> TYPE: DNA
<213> ORGANISM: Artificial sequence
<220> FEATURE:
<221> NAME/KEY: misc_feature
<222> LOCATION: 1-22
<223> OTHER INFORMATION: Sequence is synthesized

<400> SEQUENCE: 48
agggcgtggt gcggagggcg gt                                              22

<210> SEQ ID NO 49
<211> LENGTH: 20
<212> TYPE: DNA
<213> ORGANISM: Artificial sequence
<220> FEATURE:
<221> NAME/KEY: misc_feature
<222> LOCATION: 1-20
<223> OTHER INFORMATION: Sequence is synthesized

<400> SEQUENCE: 49
accacagtcc atgccatcac                                                 20

<210> SEQ ID NO 50
<211> LENGTH: 20
<212> TYPE: DNA
<213> ORGANISM: Artificial sequence
<220> FEATURE:
<221> NAME/KEY: misc_feature
<222> LOCATION: 1-20
<223> OTHER INFORMATION: Sequence is synthesized

<400> SEQUENCE: 50
tccaccaccc tgttgctgta                                                 20

<210> SEQ ID NO 51
```

<211> LENGTH: 163
<212> TYPE: DNA
<213> ORGANISM: Artificial sequence
<220> FEATURE:
<221> NAME/KEY: misc_feature
<222> LOCATION: 1-163
<223> OTHER INFORMATION: Sequence is synthesized

<400> SEQUENCE: 51

| tgtaatacga ctcactatag ggcgaattgg gcccgacgtc gcatgctccc | 50 |
| ggccgccatg gccgcgggat tatcactagt gcggccgcct gcaggtcgac | 100 |
| catatgggag agctcccaac gcgttggatg catagcttga gtattctata | 150 |
| gtgtcaccta aat | 163 |

<210> SEQ ID NO 52
<211> LENGTH: 163
<212> TYPE: DNA
<213> ORGANISM: Artificial sequence
<220> FEATURE:
<221> NAME/KEY: misc_feature
<222> LOCATION: 1-163
<223> OTHER INFORMATION: Sequence is synthesized

<400> SEQUENCE: 52

| atttaggtga cactatagaa tactcaagct atgcatccaa cgcgttggga | 50 |
| gctctcccat atggtcgacc tgcaggcggc cgcactagtg attatcccgc | 100 |
| ggccatggcg gccgggagca tgcgacgtcg ggcccaattc gccctatagt | 150 |
| gagtcgtatt aca | 163 |

<210> SEQ ID NO 53
<211> LENGTH: 10325
<212> TYPE: DNA
<213> ORGANISM: Artificial sequence
<220> FEATURE:
<221> NAME/KEY: misc_feature
<222> LOCATION: 1-10325
<223> OTHER INFORMATION: Sequence is synthesized.

<400> SEQUENCE: 53

| ttcgagctcg cccgacattg attattgact agagtcgatc accggttatt | 50 |
| aatagtaatc aattacgggg tcatagttca tagcccatat atggagttcc | 100 |
| gcgttacata acttacggta aatggcccgc ctggctgacc gcccaacgac | 150 |
| ccccgcccat tgacgtcaat aatgacgtat gttcccatag taacgccaat | 200 |
| agggactttc cattgacgtc aatgggtgga gtatttacgg taaactgccc | 250 |
| acttggcagt acatcaagtg tatcatatgc caagtacgcc ccctattgac | 300 |
| gtcaatgacg gtaaatggcc cgcctggcat tatgcccagt acatgacctt | 350 |
| atgggacttt cctacttggc agtacatcta cgtattagtc atcgctatta | 400 |
| ccatggtgat gcggttttgg cagtacatca atgggcgtgg atagcggttt | 450 |
| gactcacggg gatttccaag tctccacccc attgacgtca atgggagttt | 500 |
| gttttggcac caaaatcaac gggactttcc aaaatgtcgt aacaactccg | 550 |
| ccccattgac gcaaatgggc ggtaggcgtg tacggtggga ggtctatata | 600 |
| agcagagctc gtttagtgaa ccgtcagatc gcctggagac gccatccacg | 650 |
| ctgttttgac ctgggcccgg ccgaggccgc ctcggcctct gagctattcc | 700 |
| agaagtagtg aggaggcttt tttggaggcc taggcttttg caaaaagcta | 750 |

-continued

```
gcttatccgg ccgggaacgg tgcattggaa cgcggattcc ccgtgccaag        800
agtgacgtaa gtaccgccta tagagcgact agtccaccat gaccgagtac        850
aagcccacgg tgcgcctcgc cacccgcgac gacgtcccgc gggccgtacg        900
caccctcgcc gccgcgttcg ccgactaccc cgccacgcgc cacaccgtag        950
acccggaccg ccacatcgag cgggtcaccg agctgcaaga actcttcctc       1000
acgcgcgtcg ggctcgacat cggcaaggtg tgggtcgcgg acgacggcgc       1050
cgcggtggcg gtctggacca cgccggagag cgtcgaagcg ggggcggtgt       1100 tcgcccgagat cggcccgcgc atggccgagt tgagcggttc ccggctggcc       1150
gcgcagcaac agatggaagg cctcctggcg ccgcaccggc ccaaggagcc       1200
cgcgtggttc ctggccaccg tcggcgtctc gcccgaccac cagggcaagg       1250
gtctgggcag cgccgtcgtg ctccccggag tggaggcggc cgagcgcgcc       1300
ggggtgcccg ccttcctgga gacctccgcg ccccgcaacc tccccttcta       1350
cgagcggctc ggcttcaccg tcaccgccga cgtcgagtgc ccgaaggacc       1400
gcgcgacctg gtgcatgacc cgcaagcccg tgccaacat ggttcgacca        1450 ttgaactgca tcgtcgccgt gtcccaaaat atggggattg caagaacgg        1500 agacctaccc tgccctccgc tcaggaacgc gttcaagtac ttccaaagaa       1550
tgaccacaac ctcttcagtg gaaggtaaac agaatctggt gattatgggt       1600
aggaaaacct ggttctccat tcctgagaag aatcgacctt taaaggacag       1650
aattaatata gttctcagta gagaactcaa agaaccacca cgaggagctc       1700
attttcttgc caaaagtttg gatgatgcct taagacttat tgaacaaccg       1750
gaattggcaa gtaaagtaga catggtttgg atagtcggag gcagttctgt       1800
ttaccaggaa gccatgaatc aaccaggcca ccttagactc tttgtgacaa       1850
ggatcatgca ggaatttgaa agtgacacgt ttttcccaga aattgatttg       1900
gggaaatata aacctctccc agaatacccc ggcgtcctct ctgaggtcca       1950
ggaggaaaaa ggcatcaagt ataagtttga agtctacgag aagaaagact       2000
aacgttaact gctcccctcc taaagctatg cattttttata agaccatggg       2050 acttttgctg gctttagatc cccttggctt cgttagaacg cagctacaat       2100
taatacataa ccttatgtat catacacata cgatttaggt gacactatag       2150
ataacatcca ctttgccttt ctctccacag gtgtccactc ccaggtccaa       2200
ctgcacctcg gttctatcga ttgaattccc cggggatcct ctagagtcga       2250
cctgcagaag cttcgatggc cgccatggcc caacttgttt attgcagctt       2300
ataatggtta caaataaagc aatagcatca caaatttcac aaataaagca       2350
tttttttcac tgcattctag ttgtggtttg tccaaactca tcaatgtatc       2400
ttatcatgtc tggatcgatc gggaattaat tcggcgcagc accatggcct       2450
gaaataacct ctgaaagagg aacttggtta ggtaccgact agtcgcgtta       2500
cataacttac ggtaaatggc ccgcctggct gaccgcccaa cgacccccgc       2550
ccattgacgt caataatgac gtatgttccc atagtaacgc caatagggac       2600
tttccattga cgtcaatggg tggagtattt acggtaaact gcccacttgg       2650
cagtacatca agtgtatcat atgccaagta cgccccctat tgacgtcaat       2700
```

```
gacggtaaat ggcccgcctg gcattatgcc cagtacatga ccttatggga      2750
ctttcctact tggcagtaca tctacgtatt agtcatcgct attaccatgg      2800
tgatgcggtt ttggcagtac atcaatgggc gtggatagcg gtttgactca      2850
cggggatttc caagtctcca ccccattgac gtcaatggga gtttgttttg      2900
actagtagca aggtcgccac gcacaagatc aatattaaca atcagtcatc      2950
tctctttagc aataaaaagg tgaaaaatta cattttaaaa atgacaccat      3000
agacgatgta tgaaaataat ctacttggaa ataaatctag gcaaagaagt      3050
gcaagactgt tacccagaaa acttacaaat tgtaaatgag aggttagtga      3100
agatttaaat gaatgaagat ctaaataaac ttataaattg tgagagaaat      3150
taatgaatgt ctaagttaat gcagaaacgg agagacatac tatattcatg      3200
aactaaaaga cttaatattg tgaaggtata ctttcttttc acataaattt      3250
gtagtcaata tgttcacccc aaaaaagctg tttgttaact tgtcaacctc      3300
atttcaaaat gtatatagaa agcccaaaga caataacaaa atatattcttg     3350 tagaacaaaa tgggaaagaa tgttccacta aatatcaaga tttagagcaa      3400
agcatgagat gtgtggggat agacagtgag gctgataaaa tagagtagag      3450
ctcagaaaca gacccattga tatatgtaag tgacctatga aaaaaatatg      3500
gcattttaca atgggaaaat gatgatcttt ttctttttta gaaaaacagg      3550
gaaatatatt tatatgtaaa aaataaaagg gaacccatat gtcataccat      3600
acacacaaaa aaattccagt gaattataag tctaaatgga gaaggcaaaa      3650 cttaaatct tttagaaaat aatatagaag catgccatca tgacttcagt        3700
gtagagaaaa atttcttatg actcaaagtc ctaaccacaa agaaaagatt      3750
gttaattaga ttgcatgaat attaagactt attttttaaaa ttaaaaaacc     3800 attaagaaaa gtcaggccat agaatgacag aaaatatttg caacaccccca     3850 gtaaagagaa ttgtaatatg cagattataa aaagaagtct tacaaatcag      3900
taaaaaataa aactagacaa aaatttgaac agatgaaaga gaaactctaa      3950
ataatcatta cacatgagaa actcaatctc agaaatcaga gaactatcat     4000
tgcatataca ctaaattaga gaaatattaa aaggctaagt aacatctgtg      4050
gcaatattga tggtatataa ccttgatatg atgtgatgag aacagtactt      4100
taccccatgg gcttcctccc caaacccctta ccccagtata aatcatgaca     4150
aatatacttt aaaaaccatt accctatatc taaccagtac tcctcaaaac      4200
tgtcaaggtc atcaaaaata agaaagtct gaggaactgt caaaactaag       4250
aggaacccaa ggagacatga gaattatatg taatgtggca ttctgaatga      4300
gatcccagaa cagaaaaaga acagtagcta aaaaactaat gaaatataaa      4350
taaagtttga actttagttt tttttaaaaa agagtagcat taacacggca      4400
aagtcatttt catatttttc ttgaacatta agtacaagtc tataattaaa      4450
aattttttaa atgtagtctg gaacattgcc agaaacagaa gtacagcagc      4500
tatctgtgct gtcgcctaac tatccatagc tgattggtct aaaatgagat      4550
acatcaacgc tcctccatgt ttttttgtttt cttttttaaat gaaaaacttt    4600 attttttaag aggagtttca ggttcatagc aaaattgaga ggaaggtaca      4650
ttcaagctga ggaagttttc ctctattcct agtttactga gagattgcat      4700
```

-continued

```
catgaatggg tgttaaattt tgtcaaatgc tttttctgtg tctatcaata       4750
tgaccatgtg attttcttct ttaacctgtt gatgggacaa attacgttaa       4800
ttgattttca aacgttgaac caccottaca tatctggaat aaattctact       4850
tggttgtggt gtatatttt tgatacattc ttggattctt tttgctaata       4900
ttttgttgaa aatgtttgta tctttgttca tgagagatat tggtctgttg       4950
ttttcttttc ttgtaatgtc attttctagt tccggtatta aggtaatgct       5000
ggcctagttg aatgatttag gaagtattcc ctctgcttct gtcttctgag       5050
gtaccgcggc cgcccgtcgt tttacaacgt cgtgactggg aaaaccctgg       5100
cgttacccaa cttaatcgcc ttgcagcaca tcccccttc gccagctggc        5150 gtaatagcga agaggcccgc accgatcgcc cttcccaaca gttgcgcagc       5200
ctgaatggcg aatggcgcct gatgcggtat tttctcctta cgcatctgtg       5250
cggtatttca caccgcatac gtcaaagcaa ccatagtacg cgccctgtag       5300
cggcgcatta agcgcggcgg gtgtggtggt tacgcgcagc gtgaccgcta       5350
cacttgccag cgccctagcg cccgctcctt tcgctttctt cccttccttt       5400
ctcgccacgt tcgccggctt tccccgtcaa gctctaaatc gggggctccc       5450
tttagggttc cgatttagtg ctttacggca cctcgacccc aaaaaacttg       5500
atttgggtga tggttcacgt agtgggccat cgccctgata acggtttttt      5550 cgcccttga cgttggagtc cacgttcttt aatagtggac tcttgttcca        5600
aactggaaca cactcaacc ctatctcggg ctattctttt gatttataag        5650
ggattttgcc gatttcggcc tattggttaa aaaatgagct gatttaacaa       5700
aaatttaacg cgaattttaa caaaatatta acgtttacaa ttttatggtg       5750
cactctcagt acaatctgct ctgatgccgc atagttaagc cagccccgac       5800
acccgccaac acccgctgac gcgccctgac gggcttgtct gctcccggca       5850
tccgcttaca gacaagctgt gaccgtctcc gggagctgca tgtgtcagag       5900
gttttcaccg tcatcaccga aacgcgcgag acgaaaggc ctcgtgatac        5950 gcctattttt ataggttaat gtcatgataa taatggtttc ttagacgtca      6000
ggtggcactt ttcggggaaa tgtgcgcgga accctatt gtttattttt        6050 ctaaatacat tcaaatatgt atccgctcat gagacaataa ccctgataaa      6100
tgcttcaata atattgaaaa aggaagagta tgagtattca acatttccgt      6150
gtcgccctta ttcccttttt tgcggcattt tgccttcctg tttttgctca      6200
cccagaaacg ctggtgaaag taaaagatgc tgaagatcag ttgggtgcac      6250
gagtgggtta catcgaactg gatctcaaca gcggtaagat ccttgagagt      6300
tttcgccccg aagaacgttt tccaatgatg agcactttta agttctgct       6350 atgtggcgcg gtattatccc gtattgacgc cgggcaagag caactcggtc      6400
gccgcataca ctattctcag aatgacttgg ttgagtactc accagtcaca      6450
gaaaagcatc ttacgatgg catgacagta agagaattat gcagtgctgc       6500
cataaccatg agtgataaca ctgcggccaa cttacttctg acaacgatcg      6550
gaggaccgaa ggagctaacc gcttttttgc acaacatggg ggatcatgta      6600
actcgccttg atcgttggga accggagctg aatgaagcca taccaaacga     6650
```

-continued

| | |
|---|---|
| cgagcgtgac accacgatgc ctgtagcaat ggcaacaacg ttgcgcaaac | 6700 |
| tattaactgg cgaactactt actctagctt cccggcaaca attaatagac | 6750 |
| tggatggagg cggataaagt tgcaggacca cttctgcgct cggcccttcc | 6800 |
| ggctggctgg tttattgctg ataaatctgg agccggtgag cgtgggtctc | 6850 |
| gcggtatcat tgcagcactg gggccagatg gtaagccctc ccgtatcgta | 6900 |
| gttatctaca cgacggggag tcaggcaact atggatgaac gaaatagaca | 6950 |
| gatcgctgag ataggtgcct cactgattaa gcattggtaa ctgtcagacc | 7000 |
| aagtttactc atatatactt tagattgatt taaaacttca ttttttaattt | 7050 |
| aaaaggatct aggtgaagat cctttttgat aatctcatga ccaaaatccc | 7100 |
| ttaacgtgag ttttcgttcc actgagcgtc agaccccgta gaaaagatca | 7150 |
| aaggatcttc ttgagatcct tttttctgc gcgtaatctg ctgcttgcaa | 7200 |
| acaaaaaaac caccgctacc agcggtggtt tgtttgccgg atcaagagct | 7250 |
| accaactctt tttccgaagg taactggctt cagcagagcg cagataccaa | 7300 |
| atactgtcct tctagtgtag ccgtagttag gccaccactt caagaactct | 7350 |
| gtagcaccgc ctacatacct cgctctgcta atcctgttac cagtggctgc | 7400 |
| tgccagtggc gataagtcgt gtcttaccgg gttggactca agacgatagt | 7450 |
| taccggataa ggcgcagcgg tcgggctgaa cggggggttc gtgcacacag | 7500 |
| cccagcttgg agcgaacgac ctacaccgaa ctgagatacc tacagcgtga | 7550 |
| gctatgagaa agcgccacgc ttcccgaagg gagaaaggcg gacaggtatc | 7600 |
| cggtaagcgg cagggtcgga acaggagagc gcacagggga gcttccaggg | 7650 |
| ggaaacgcct ggtatcttta tagtcctgtc gggtttcgcc acctctgact | 7700 |
| tgagcgtcga ttttttgtgat gctcgtcagg gggcggagc ctatggaaaa | 7750 |
| acgccagcaa cgcggccttt ttacggttcc tggccttttg ctggcctttt | 7800 |
| gctcacatgt tctttcctgc gttatcccct gattctgtgg ataaccgtat | 7850 |
| taccgccttt gagtgagctg ataccgctcg ccgcagccga acgaccgagc | 7900 |
| gcagcgagtc agtgagcgag gaagcggaag agcccgcggg caaggtcgcc | 7950 |
| acgcacaaga tcaatattaa caatcagtca tctctcttta gcaataaaaa | 8000 |
| ggtgaaaaat tacatttttaa aaatgacacc atagacgatg tatgaaaata | 8050 |
| atctacttgg aaataaatct aggcaaagaa gtgcaagact gttacccaga | 8100 |
| aaacttacaa attgtaaatg agaggttagt gaagatttaa atgaatgaag | 8150 |
| atctaaataa acttataaat tgtgagagaa attaatgaat gtctaagtta | 8200 |
| atgcagaaac ggagagacat actatattca tgaactaaaa gacttaatat | 8250 |
| tgtgaaggta tactttcttt tcacataaat ttgtagtcaa tatgttcacc | 8300 |
| ccaaaaaagc tgtttgttaa cttgtcaacc tcatttcaaa atgtatatag | 8350 |
| aaagcccaaa gacaataaca aaaatattct tgtagaacaa aatgggaaag | 8400 |
| aatgttccac taaatatcaa gatttagagc aaagcatgag atgtgtgggg | 8450 |
| atagacagtg aggctgataa aatagagtag agctcagaaa cagacccatt | 8500 |
| gatatatgta agtgacctat gaaaaaaata tggcattta caatgggaaa | 8550 |
| atgatgatct ttttcttttt tagaaaaaca gggaaatata tttatatgta | 8600 |
| aaaaataaaa gggaacccat atgtcatacc atacacacaa aaaaattcca | 8650 |

| | |
|---|---|
| gtgaattata agtctaaatg gagaaggcaa aactttaaat cttttagaaa | 8700 |
| ataatataga agcatgccat catgacttca gtgtagagaa aaatttctta | 8750 |
| tgactcaaag tcctaaccac aaagaaaaga ttgttaatta gattgcatga | 8800 |
| atattaagac ttattttaa aattaaaaaa ccattaagaa aagtcaggcc | 8850 |
| atagaatgac agaaaatatt tgcaacaccc cagtaaagag aattgtaata | 8900 |
| tgcagattat aaaagaagt cttacaaatc agtaaaaaat aaaactagac | 8950 |
| aaaaatttga acagatgaaa gagaaactct aaataatcat tacacatgag | 9000 |
| aaactcaatc tcagaaatca gagaactatc attgcatata cactaaatta | 9050 |
| gagaaatatt aaaaggctaa gtaacatctg tggcaatatt gatggtatat | 9100 |
| aaccttgata tgatgtgatg agaacagtac tttaccccat gggcttcctc | 9150 |
| cccaaaccct tacccagta taatcatga caaatatact ttaaaaacca | 9200 |
| ttaccctata tctaaccagt actcctcaaa actgtcaagg tcatcaaaaa | 9250 |
| taagaaaagt ctgaggaact gtcaaaacta agaggaaccc aaggagacat | 9300 |
| gagaattata tgtaatgtgg cattctgaat gagatcccag aacagaaaaa | 9350 |
| gaacagtagc taaaaaacta atgaaatata aataaagttt gaactttagt | 9400 |
| ttttttttaaa aagagtagc attaacacgg caaagtcatt ttcatattt | 9450 |
| tcttgaacat taagtacaag tctataatta aaaattttt aaatgtagtc | 9500 |
| tggaacattg ccagaaacag aagtacagca gctatctgtg ctgtcgccta | 9550 |
| actatccata gctgattggt ctaaaatgag atacatcaac gctcctccat | 9600 |
| gttttttgtt ttcttttaa atgaaaaact ttattttta agaggagttt | 9650 |
| caggttcata gcaaaattga gaggaaggta cattcaagct gaggaagttt | 9700 |
| tcctctattc ctagtttact gagagattgc atcatgaatg ggtgttaaat | 9750 |
| tttgtcaaat gcttttctg tgtctatcaa tatgaccatg tgattttctt | 9800 |
| cttaacctg ttgatgggac aaattacgtt aattgatttt caaacgttga | 9850 |
| accacccta catatctgga ataaattcta cttggttgtg gtgtatattt | 9900 |
| tttgatacat tcttggattc tttttgctaa tatttgttg aaaatgtttg | 9950 |
| tatctttgtt catgagagat attggtctgt tgttttcttt tcttgtaatg | 10000 |
| tcattttcta gttccggtat taaggtaatg ctggcctagt tgaatgattt | 10050 |
| aggaagtatt ccctctgctt ctgtcttctg aagcggaaga gcgcccaata | 10100 |
| cgcaaaccgc ctctccccgc gcgttggccg attcattaat gcagctggca | 10150 |
| cgacaggttt cccgactgga aagcgggcag tgagcgcaac gcaattaatg | 10200 |
| tgagttagct cactcattag gcaccccagg ctttacactt tatgcttccg | 10250 |
| gctcgtatgt tgtgtggaat tgtgagcgga taacaatttc acacaggaaa | 10300 |
| cagctatgac atgattacga attaa | 10325 |

<210> SEQ ID NO 54
<211> LENGTH: 10379
<212> TYPE: DNA
<213> ORGANISM: Artificial sequence
<220> FEATURE:
<221> NAME/KEY: misc-feature
<222> LOCATION: 1-10379
<223> OTHER INFORMATION: Sequence is synthesized.

-continued

```
<400> SEQUENCE: 54
aagctttact cgtaaagcga gttgaaggat catatttagt tgcgtttatg        50
agataagatt gaaagcacgt gtaaaatgtt tcccgcgcgt tggcacaact       100
atttacaatg cggccaagtt ataaaagatt ctaatctgat atgttttaaa       150
acacctttgc ggcccgagtt gtttgcgtac gtgactagcg aagaagatgt       200
gtggaccgca gaacagatag taaaacaaaa ccctagtatt ggagcaataa       250
tcgatttaac caacacgtct aaatattatg atggtgtgca ttttttgcgg       300
gcgggcctgt tatacaaaaa aattcaagta cctggccaga cttttgccgcc      350
tgaaagcata gttcaagaat ttattgacac ggtaaaagaa tttacagaaa       400
agtgtcccgg catgttggtg ggcgtgcact gcacacacgg tattaatcgc       450
accggttaca tggtgtgcag atatttaatg cacaccctgg gtattgcgcc       500
gcaggaagcc atagatagat cgaaaaagc cagaggtcac aaaattgaaa        550
gacaaaatta cgttcaagat ttattaattt aattaatatt atttgcattc       600
tttaacaaat actttatcct attttcaaat tgttgcgctt cttccagcga       650
accaaaacta tgcttcgctt gctccgttta gcttgtagcc gatcagtggc       700
gttgttccaa tcgacggtag gattaggccg gatattctcc accacaatgt       750
tggcaacgtt gatgttacgt ttatgctttt ggttttccac gtacgtcttt       800
tggccggtaa tagccgtaaa cgtagtgccg tcgcgcgtca cgcacaacac       850
cggatgtttg cgcttgtccg cggggtattg aaccgcgcga tccgacaaat       900
ccaccacttt ggcaactaaa tcggtgacct gcgcgtcttt tttctgcatt       950
atttcgtctt tcttttgcat ggtttcctgg aagccggtgt acatgcggtt      1000
tagatcagtc atgacgcgcg tgacctgcaa atctttggcc tcgatctgct      1050
tgtccttgat ggcaacgatg cgttcaataa actcttgttt tttaacaagt      1100
tcctcggttt tttgcgccac caccgcttgc agcgcgtttg tgtgctcggt      1150
gaatgtcgca atcagcttag tcaccaactg tttgctctcc tcctcccgtt      1200
gtttgatcgc gggatcgtac ttgccggtgc agagcacttg aggaattact      1250
tcttctaaaa gccattcttg taattctatg gcgtaaggca atttggactt      1300
cataatcagc tgaatcacgc cggatttagt aatgagcact gtatgcggct      1350
gcaaatacag cgggtcgccc cttttcacga cgctgttaga ggtagggccc      1400
ccattttgga tggtctgctc aaataacgat ttgtatttat tgtctacatg      1450
aacacgtata gctttatcac aaactgtata ttttaaactg ttagcgacgt      1500
ccttggccac gaaccggacc tgttggtcgc gctctagcac gtaccgcagg      1550
ttgaacgtat cttctccaaa tttaaattct ccaatttaaa cgcgagccat      1600
tttgatacac gtgtgtcgat tttgcaacaa ctattgtttt ttaacgcaaa      1650
ctaaacttat tgtggtaagc aataattaaa tatggggggaa catgcgccgc     1700
tacaacactc gtcgttatga acgcagacgg cgccggtctc ggcgcaagcg      1750
gctaaaacgt gttgcgcgtt caacgcggca acatcgcaa aagccaatag       1800
tacagttttg atttgcatat taacggcgat tttttaaatt atcttattta      1850
ataaatagtt atgacgccta caactccccg cccgcgttga ctcgctgcac      1900
ctcgagcagt tcgttgacgc cttcctccgt gtggccgaac acgtcgagcg      1950
```

-continued

```
ggtggtcgat gaccagcggc gtgccgcacg cgacgcacaa gtatctgtac      2000
accgaatgat cgtcgggcga aggcacgtcg gcctccaagt ggcaatattg      2050
gcaaattcga aaatatatac agttgggttg tttgcgcata tctatcgtgg      2100
cgttgggcat gtacgtccga acgttgattt gcatgcaagc cgaaattaaa      2150
tcattgcgat tagtgcgatt aaaacgttgt acatcctcgc ttttaatcat      2200
gccgtcgatt aaatcgcgca atcgagtcaa gtgatcaaag tgtggaataa      2250
tgttttcttt gtattcccga gtcaagcgca gcgcgtattt taacaaacta      2300
gccatcttgt aagttagttt catttaatgc aactttatcc aataatatat      2350
tatgtatcgc acgtcaagaa ttaacaatgc gcccgttgtc gcatctcaac      2400
acgactatga tagagatcaa ataaagcgcg aattaaatag cttgcgacgc      2450
aacgtgcacg atctgtgcac gcgttccggc acgagctttg attgtaataa      2500 gttttttacga agcgatgaca tgaccccgt agtgacaacg atcacgccca      2550
aaagaactgc cgactacaaa attaccgagt atgtcggtga cgttaaaact      2600
attaagccat ccaatcgacc gttagtcgaa tcaggaccgc tggtgcgaga      2650
agccgcgaag tatggcgaat gcatcgtata acgtgtggag tccgctcatt      2700
agagcgtcat gtttagacaa gaaagctaca tatttaattg atcccgatga      2750
ttttattgat aaattgaccc taactccata cacggtattc tacaatggcg      2800
gggttttggt caaaatttcc ggactgcgat tgtacatgct gttaacggct      2850
ccgcccacta ttaatgaaat taaaaattcc aattttaaaa aacgcagcaa      2900
gagaaacatt tgtatgaaag aatgcgtaga aggaaagaaa aatgtcgtcg      2950
acatgctgaa caacaagatt aatatgcctc cgtgtataaa aaaaatattg      3000
aacgatttga agaaaacaa tgtaccgcgc ggcggtatgt acaggaagag      3050
gtttatacta aactgttaca ttgcaaacgt ggtttcgtgt gccaagtgtg      3100
aaaaccgatg tttaatcaag gctctgacgc atttctacaa ccacgactcc      3150
aagtgtgtgg gtgaagtcat gcatcttta atcaaatccc aagatgtgta      3200
taaaccacca aactgccaaa aaatgaaaac tgtcgacaag ctctgtccgt      3250
ttgctggcaa ctgcaagggt ctcaatccta tttgtaatta ttgaataata      3300
aaacaattat aaatgctaaa tttgttttt attaacgata caaaccaaac      3350
gcaacaagaa catttgtagt attatctata attgaaaacg cgtagttata      3400
atcgctgagg taatatttaa aatcattttc aaatgattca cagttaattt      3450
gcgacaatat aattttattt tcacataaac tagacgcctt gtcgtcttct      3500
tcttcgtatt ccttctcttt tcatttttc tcctcataaa aattaacata      3550
gttattatcg tatccatata tgtatctatc gtatagagta aatttttgt      3600 tgtcataaat atatatgtct tttttaatgg ggtgtatagt accgctgcgc      3650 atagttttc tgtaatttac aacagtgcta ttttctggta gttcttcgga      3700
gtgtgttgct ttaattatta aatttatata atcaatgaat ttgggatcgt      3750
cggttttgta caatatgttg ccggcatagt acgcagcttc ttctagttca      3800
attacaccat ttttagcag caccggatta acataacttt ccaaaatgtt      3850
gtacgaaccg ttaaacaaaa acagttcacc tcccttttct atactattgt      3900
```

-continued

| | |
|---|---|
| ctgcgagcag ttgtttgttg ttaaaaataa cagccattgt aatgagacgc | 3950 |
| acaaactaat atcacaaact ggaaatgtct atcaatatat agttgctgat | 4000 |
| atcatggaga taattaaaat gataaccatc tcgcaaataa ataagtattt | 4050 |
| tactgttttc gtaacagttt tgtaataaaa aaacctataa atattccgga | 4100 |
| ttattcatac cgtcccacca tcgggcgcgg atccgcggcc gcgaattcta | 4150 |
| aaccaccatg gctagcaggc ctgacaaaac tcacacatgc ccaccgtgcc | 4200 |
| cagcacctga actcctgggg ggaccgtcag tcttcctctt cccccaaaa | 4250 |
| cccaaggaca ccctcatgat ctcccggacc cctgaggtca catgcgtggt | 4300 |
| ggtggacgtg agccacgaag accctgaggt caagttcaac tggtacgtgg | 4350 |
| acggcgtgga ggtgcataat gccaagacaa agccgcggga ggagcagtac | 4400 |
| aacagcacgt accgtgtggt cagcgtcctc accgtcctgc accaggactg | 4450 |
| gctgaatggc aaggagtaca agtgcaaggt ctccaacaaa gccctcccag | 4500 |
| cccccatcga gaaaaccatc tccaaagcca agggcagcc cgagaaccac | 4550 |
| caggtgtaca ccctgccccc atcccgggaa gagatgacca agaaccaggt | 4600 |
| cagcctgacc tgcctggtca aaggcttcta tcccagcgac atcgccgtgg | 4650 |
| agtgggagag caatgggcag ccggagaaca actacaagac cacgcctccc | 4700 |
| gtgctggact ccgacggctc cttcttcctc tacagcaagc tcaccgtgga | 4750 |
| caagagcagg tggcagcagg ggaacgtctt ctcatgctcc gtgatgcatg | 4800 |
| aggctctgca caaccactac acgcagaaga gcctctccct gtctccgggt | 4850 |
| aaatgacata gggcatcatc atcatcatca tcatcattaa ttctagacta | 4900 |
| gtctgcagat ctgatccttt cctgggaccc ggcaagaacc aaaaactcac | 4950 |
| tctcttcaag gaaatccgta atgttaaacc cgacacgatg aagcttgtcg | 5000 |
| ttggatggaa aggaaaagag ttctacaggg aaacttggac ccgcttcatg | 5050 |
| gaagacagct tccccattgt taacgaccaa gaagtgatgg atgttttcct | 5100 |
| tgttgtcaac atgcgtccca ctagacccaa ccgttgttac aaattcctgg | 5150 |
| cccaacacgc tctgcgttgc gaccccgact atgtacctca tgacgtgatt | 5200 |
| aggatcgtcg agccttcatg ggtgggcagc aacaacgagt accgcatcag | 5250 |
| cctggctaag aagggcggcg gctgcccaat aatgaaccttc cactctgagt | 5300 |
| acaccaactc gttcgaacag ttcatcgatc gtgtcatctg ggagaacttc | 5350 |
| tacaagccca tcgtttacat cggtaccgac tctgctgaag aggaggaaat | 5400 |
| tctccttgaa gtttccctgg tgttcaaagt aaaggagttt gcaccagacg | 5450 |
| cacctctgtt cactggtccg gcgtattaaa acacgataca ttgttattag | 5500 |
| tacatttatt aagcgctaga ttctgtgcgt tgttgattta cagacaattg | 5550 |
| ttgtacgtat tttaataatt cattaaattt ataatcttta gggtggtatg | 5600 |
| ttagagcgaa atcaaatga ttttcagcgt ctttatatct gaatttaaat | 5650 |
| attaaatcct caatagattt gtaaaatagg tttcgattag tttcaaacaa | 5700 |
| gggttgtttt tccgaaccga tggctggact atctaatgga ttttcgctca | 5750 |
| acgccacaaa acttgccaaa tcttgtagca gcaatctagc tttgtcgata | 5800 |
| ttcgtttgtg ttttgttttg taataaaggt tcgacgtcgt tcaaaatatt | 5850 |
| atgcgctttt gtatttcttt catcactgtc gttagtgtac aattgactcg | 5900 |

| | |
|---|---|
| acgtaaacac gttaaataaa gcttggacat atttaacatc gggcgtgtta | 5950 |
| gctttattag gccgattatc gtcgtcgtcc caaccctcgt cgttagaagt | 6000 |
| tgcttccgaa gacgattttg ccatagccac acgacgccta ttaattgtgt | 6050 |
| cggctaacac gtccgcgatc aaatttgtag ttgagctttt tggaattatt | 6100 |
| tctgattgcg ggcgtttttg ggcgggtttc aatctaactg tgcccgattt | 6150 |
| taattcagac aacacgttag aaagcgatgg tgcaggcggt ggtaacattt | 6200 |
| cagacggcaa atctactaat ggcggcggtg gtggagctga tgataaatct | 6250 |
| accatcggtg gaggcgcagg cggggctggc ggcggaggcg gaggcggagg | 6300 |
| tggtggcggt gatgcagacg gcggtttagg ctcaaatgtc tctttaggca | 6350 |
| acacagtcgg cacctcaact attgtactgg tttcgggcgc cgttttggt | 6400 |
| ttgaccggtc tgagacgagt gcgattttttt tcgtttctaa tagcttccaa | 6450 |
| caattgttgt ctgtcgtcta aaggtgcagc gggttgaggt tccgtcggca | 6500 |
| ttggtggagc gggcggcaat tcagacatcg atggtggtgg tggtggtgga | 6550 |
| ggcgctggaa tgttaggcac gggagaaggt ggtggcggcg gtgccgccgg | 6600 |
| tataatttgt tctggtttag tttgttcgcg cacgattgtg ggcaccggcg | 6650 |
| caggcgccgc tggctgcaca acggaaggtc gtctgcttcg aggcagcgct | 6700 |
| tggggtggtg gcaattcaat attataattg gaatacaaat cgtaaaaatc | 6750 |
| tgctataagc attgtaattt cgctatcgtt taccgtgccg atatttaaca | 6800 |
| accgctcaat gtaagcaatt gtattgtaaa gagattgtct caagctccgc | 6850 |
| acgccgataa caagcctttt cattttact acagcattgt agtggcgaga | 6900 |
| cacttcgctg tcgtcgacgt acatgtatgc tttgttgtca aaaacgtcgt | 6950 |
| tggcaagctt taaaatattt aaaagaacat ctctgttcag caccactgtg | 7000 |
| ttgtcgtaaa tgttgttttt gataatttgc gcttccgcag tatcgacacg | 7050 |
| ttcaaaaaat tgatgcgcat caattttgtt gttcctatta ttgaataaat | 7100 |
| aagattgtac agattcatat ctacgattcg tcatggccac cacaaatgct | 7150 |
| acgctgcaaa cgctggtaca attttacgaa aactgcaaaa acgtcaaaac | 7200 |
| tcggtataaa ataatcaacg ggcgcttttgg caaaatatct attttatcgc | 7250 |
| acaagcccac tagcaaattg tatttgcaga aaacaatttc ggcgcacaat | 7300 |
| tttaacgctg acgaaataaa agttcaccag ttaatgagcg accacccaaa | 7350 |
| ttttataaaa atctatttta atcacggttc catcaacaac caagtgatcg | 7400 |
| tgatggacta cattgactgt cccgatttat ttgaaacact acaaattaaa | 7450 |
| ggcgagcttt cgtaccaact tgttagcaat attattagac agctgtgtga | 7500 |
| agcgctcaac gatttgcaca agcacaattt catacacaac gacataaaac | 7550 |
| tcgaaaatgt cttatatttc gaagcacttg atcgcgtgta tgtttgcgat | 7600 |
| tacggattgt gcaaacacga aaactcactt agcgtgcacg acggcacgtt | 7650 |
| ggagtatttt agtccggaaa aaattcgaca cacaactatg cacgtttcgt | 7700 |
| ttgactggta cgcggcgtgt taacatacaa gttgctaacc ggcggttcgt | 7750 |
| aatcatggtc atagctgttt cctgtgtgaa attgttatcc gctcacaatt | 7800 |
| ccacacaaca tacgagccgg aagcataaag tgtaaagcct ggggtgccta | 7850 |

```
atgagtgagc taactcacat taattgcgtt gcgctcactg cccgctttcc      7900
agtcgggaaa cctgtcgtgc cagctgcatt aatgaatcgg ccaacgcgcg      7950
gggagaggcg gtttgcgtat tgggcgctct tccgcttcct cgctcactga      8000
ctcgctgcgc tcggtcgttc ggctgcggcg agcggtatca gctcactcaa      8050
aggcggtaat acggttatcc acagaatcag gggataacgc aggaaagaac      8100
atgtgagcaa aaggccagca aaaggccagg aaccgtaaaa aggccgcgtt      8150
gctggcgttt ttccataggc tccgcccccc tgacgagcat cacaaaaatc      8200
gacgctcaag tcagaggtgg cgaaacccga caggactata agataccag       8250
gcgtttcccc ctggaagctc cctcgtgcgc tctcctgttc cgaccctgcc      8300
gcttaccgga tacctgtccg cctttctccc ttcgggaagc gtggcgcttt      8350
ctcatagctc acgctgtagg tatctcagtt cggtgtaggt cgttcgctcc      8400
aagctgggct gtgtgcacga accccccgtt cagcccgacc gctgcgcctt      8450
atccggtaac tatcgtcttg agtccaaccc ggtaagacac gacttatcgc      8500
cactggcagc agccactggt aacaggatta gcagagcgag gtatgtaggc      8550
ggtgctacag agttcttgaa gtggtggcct aactacggct acactagaag      8600
gacagtattt ggtatctgcg ctctgctgaa gccagttacc ttcggaaaaa      8650
gagttggtag ctcttgatcc ggcaaacaaa ccaccgctgg tagcggtggt      8700
ttttttgttt gcaagcagca gattacgcgc agaaaaaaag gatctcaaga      8750
agatcctttg atcttttcta cggggtctga cgctcagtgg aacgaaaact      8800
cacgttaagg gattttggtc atgagattat caaaaaggat cttcacctag      8850
atccttttaa attaaaaatg aagttttaaa tcaatctaaa gtatatatga      8900
gtaaacttgg tctgacagtt accaatgctt aatcagtgag gcacctatct      8950
cagcgatctg tctatttcgt tcatccatag ttgcctgact ccccgtcgtg      9000
tagataacta cgatacggga gggcttacca tctggcccca gtgctgcaat      9050
gataccgcga gacccacgct caccggctcc agatttatca gcaataaacc      9100
agccagccgg aagggccgag cgcagaagtg gtcctgcaac tttatccgcc      9150
tccatccagt ctattaattg ttgccgggaa gctagagtaa gtagttcgcc      9200
agttaatagt ttgcgcaacg ttgttgccat tgctacaggc atcgtggtgt      9250
cacgctcgtc gtttggtatg gcttcattca gctccggttc ccaacgatca      9300
aggcgagtta catgatcccc catgttgtgc aaaaaagcgg ttagctcctt      9350
cggtcctccg atcgttgtca gaagtaagtt ggccgcagtg ttatcactca      9400
tggttatggc agcactgcat aattctctta ctgtcatgcc atccgtaaga      9450
tgcttttctg tgactggtga gtactcaacc aagtcattct gagaatagtg      9500
tatgcggcga ccgagttgct cttgcccggc gtcaatacgg gataataccg      9550
cgccacatag cagaacttta aaagtgctca tcattggaaa acgttcttcg      9600
gggcgaaaac tctcaaggat cttaccgctg ttgagatcca gttcgatgta      9650
acccactcgt gcacccaact gatcttcagc atcttttact ttcaccagcg      9700
tttctgggtg agcaaaaaca ggaaggcaaa atgccgcaaa aaagggaata      9750
agggcgacac ggaaatgttg aatactcata ctcttccttt ttcaatatta      9800
ttgaagcatt tatcagggtt attgtctcat gagcggatac atatttgaat      9850
```

-continued

| | |
|---|---|
| gtatttagaa aaataaacaa atagggggttc cgcgcacatt tccccgaaaa | 9900 |
| gtgccacctg acgtctaaga aaccattatt atcatgacat taacctataa | 9950 |
| aaataggcgt atcacgaggc cctttcgtct cgcgcgtttc ggtgatgacg | 10000 |
| gtgaaaacct ctgacacatg cagctcccgg agacggtcac agcttgtctg | 10050 |
| taagcggatg ccgggagcag acaagcccgt cagggcgcgt cagcgggtgt | 10100 |
| tggcgggtgt cggggctggc ttaactatgc ggcatcagag cagattgtac | 10150 |
| tgagagtgca ccatatatgc ggtgtgaaat accgcacaga tgcgtaagga | 10200 |
| gaaaataccg catcaggcgc cattcgccat tcaggctgcg caactgttgg | 10250 |
| gaagggcgat cggtgcgggc ctcttcgcta ttacgccagc tggcgaaagg | 10300 |
| gggatgtgct gcaaggcgat taagttgggt aacgccaggg ttttcccagt | 10350 |
| cacgacgttg taaaacgacg gccagtgcc | 10379 |

<210> SEQ ID NO 55
<211> LENGTH: 9690
<212> TYPE: DNA
<213> ORGANISM: Artificial sequence
<220> FEATURE:
<221> NAME/KEY: misc_feature
<222> LOCATION: 1-9690
<223> OTHER INFORMATION: Sequence is synthesized.

<400> SEQUENCE: 55

| | |
|---|---|
| aagctttact cgtaaagcga gttgaaggat catatttagt tgcgtttatg | 50 |
| agataagatt gaaagcacgt gtaaaatgtt tcccgcgcgt tggcacaact | 100 |
| atttacaatg cggccaagtt ataaaagatt ctaatctgat atgttttaaa | 150 |
| acacctttgc ggcccgagtt gtttgcgtac gtgactagcg aagaagatgt | 200 |
| gtggaccgca gaacagatag taaaacaaaa ccctagtatt ggagcaataa | 250 |
| tcgatttaac caacacgtct aaatattatg atggtgtgca ttttttgcgg | 300 |
| gcgggcctgt tatacaaaaa aattcaagta cctggccaga cttttgccgcc | 350 |
| tgaaagcata gttcaagaat ttattgacac ggtaaaagaa tttacagaaa | 400 |
| agtgtcccgg catgttggtg ggcgtgcact gcacacacgg tattaatcgc | 450 |
| accggttaca tggtgtgcag atatttaatg cacaccctgg gtattgcgcc | 500 |
| gcaggaagcc atagatagat tcgaaaaagc cagaggtcac aaaattgaaa | 550 |
| gacaaaatta cgttcaagat ttattaattt aattaatatt atttgcattc | 600 |
| tttaacaaat actttatcct attttcaaat tgttgcgctt cttccagcga | 650 |
| accaaaacta tgcttcgctt gctccgttta gcttgtagcc gatcagtggc | 700 |
| gttgttccaa tcgacggtag gattaggccg gatattctcc accacaatgt | 750 |
| tggcaacgtt gatgttacgt ttatgctttt ggttttccac gtacgtcttt | 800 |
| tggccggtaa tagccgtaaa cgtagtgccg tcgcgcgtca cgcacaacac | 850 |
| cggatgtttg cgcttgtccg cggggtattg aaccgcgcga tccgacaaat | 900 |
| ccaccacttt ggcaactaaa tcggtgacct gcgcgtcttt tttctgcatt | 950 |
| atttcgtctt tcttttgcat ggtttcctgg aagccggtgt acatgcggtt | 1000 |
| tagatcagtc atgacgcgcg tgacctgcaa atctttggcc tcgatctgct | 1050 |
| tgtccttgat ggcaacgatg cgttcaataa actcttgttt tttaacaagt | 1100 |

-continued

```
tcctcggttt tttgcgccac caccgcttgc agcgcgtttg tgtgctcggt      1150
gaatgtcgca atcagcttag tcaccaactg tttgctctcc tcctcccgtt      1200
gtttgatcgc gggatcgtac ttgccggtgc agagcacttg aggaattact      1250
tcttctaaaa gccattcttg taattctatg gcgtaaggca atttggactt      1300
cataatcagc tgaatcacgc cggatttagt aatgagcact gtatgcggct      1350
gcaaatacag cgggtcgccc cttttcacga cgctgttaga ggtagggccc      1400
ccattttgga tggtctgctc aaataacgat ttgtatttat tgtctacatg      1450
aacacgtata gctttatcac aaactgtata ttttaaactg ttagcgacgt      1500
ccttggccac gaaccggacc tgttggtcgc gctctagcac gtaccgcagg      1550
ttgaacgtat cttctccaaa tttaaattct ccaatttaa cgcgagccat       1600 tttgatacac gtgtgtcgat tttgcaacaa ctattgtttt taacgcaaa       1650 ctaaacttat tgtggtaagc aataattaaa tatgggggaa catgcgccgc      1700
tacaacactc gtcgttatga acgcagacgg cgccggtctc ggcgcaagcg      1750
gctaaaacgt gttgcgcgtt caacgcggca acatcgcaa aagccaatag       1800 tacagttttg atttgcatat taacggcgat tttttaaatt atcttattta      1850
ataaatagtt atgacgccta caactcccg cccgcgttga ctcgctgcac       1900
ctcgagcagt tcgttgacgc cttcctccgt gtggccgaac acgtcgagcg      1950
ggtggtcgat gaccagcggc gtgccgcacg cgacgcacaa gtatctgtac      2000
accgaatgat cgtcgggcga aggcacgtcg gcctccaagt ggcaatattg      2050
gcaaattcga aaatatatac agttgggttg tttgcgcata tctatcgtgg      2100
cgttgggcat gtacgtccga acgttgattt gcatgcaagc cgaaattaaa      2150
tcattgcgat tagtgcgatt aaaacgttgt acatcctcgc ttttaatcat      2200
gccgtcgatt aaatcgcgca atcgagtcaa gtgatcaaag tgtggaataa      2250
tgttttcttt gtattcccga gtcaagcgca gcgcgtattt taacaaacta      2300
gccatcttgt aagttagttt catttaatgc aactttatcc aataatatat      2350
tatgtatcgc acgtcaagaa ttaacaatgc gcccgttgtc gcatctcaac      2400
acgactatga tagagatcaa ataaagcgcg aattaaatag cttgcgacgc      2450
aacgtgcacg atctgtgcac gcgttccggc acgagctttg attgtaataa      2500 gttttttacga agcgatgaca tgaccccgt agtgacaacg atcacgccca      2550
aaagaactgc cgactacaaa attaccgagt atgtcggtga cgttaaaact      2600
attaagccat ccaatcgacc gttagtcgaa tcaggaccgc tggtgcgaga      2650
agccgcgaag tatggcgaat gcatcgtata acgtgtggag tccgctcatt      2700
agagcgtcat gtttagacaa gaaagctaca tatttaattg atcccgatga      2750
ttttattgat aaattgaccc taactccata cacggtattc tacaatggcg      2800
gggttttggt caaaatttcc ggactgcgat tgtacatgct gttaacggct      2850
ccgcccacta ttaatgaaat taaaaattcc aattttaaaa aacgcagcaa      2900
gagaaacatt tgtatgaaag aatgcgtaga aggaaagaaa aatgtcgtcg      2950
acatgctgaa caacaagatt aatatgcctc cgtgtataaa aaaatatttg      3000
aacgatttga agaaaacaa tgtaccgcgc ggcggtatgt acaggaagag        3050
gtttatacta aactgttaca ttgcaaacgt ggtttcgtgt gccaagtgtg      3100
```

-continued

| | |
|---|---|
| aaaaccgatg tttaatcaag gctctgacgc atttctacaa ccacgactcc | 3150 |
| aagtgtgtgg gtgaagtcat gcatctttta atcaaatccc aagatgtgta | 3200 |
| taaaccacca aactgccaaa aaatgaaaac tgtcgacaag ctctgtccgt | 3250 |
| ttgctggcaa ctgcaagggt ctcaatccta tttgtaatta ttgaataata | 3300 |
| aaacaattat aaatgctaaa tttgtttttt attaacgata caaaccaaac | 3350 |
| gcaacaagaa catttgtagt attatctata attgaaaacg cgtagttata | 3400 |
| atcgctgagg taatatttaa aatcattttc aaatgattca cagttaattt | 3450 |
| gcgacaatat aattttattt tcacataaac tagacgcctt gtcgtcttct | 3500 |
| tcttcgtatt ccttctcttt ttcattttc tcctcataaa aattaacata | 3550 |
| gttattatcg tatccatata tgtatctatc gtatagagta aattttttgt | 3600 |
| tgtcataaat atatatgtct tttttaatgg ggtgtatagt accgctgcgc | 3650 |
| atagttttc tgtaatttac aacagtgcta ttttctggta gttcttcgga | 3700 |
| gtgtgttgct ttaattatta aatttatata atcaatgaat ttgggatcgt | 3750 |
| cggttttgta caatatgttg ccggcatagt acgcagcttc ttctagttca | 3800 |
| attacaccat tttttagcag caccggatta acataacttt ccaaaatgtt | 3850 |
| gtacgaaccg ttaaacaaaa acagttcacc tcccttttct atactattgt | 3900 |
| ctgcgagcag ttgtttgttg ttaaaaataa cagccattgt aatgagacgc | 3950 |
| acaaactaat atcacaaact ggaaatgtct atcaatatat agttgctgat | 4000 |
| atcatggaga taattaaaat gataaccatc tcgcaaataa ataagtattt | 4050 |
| tactgttttc gtaacagttt tgtaataaaa aaacctataa atattccgga | 4100 |
| ttattcatac cgtcccacca tcgggcgcgg atccgcggcc gcgaattcta | 4150 |
| aaccaccatg ggcagctgcc cgggcatcat catcatcatc atcatcatta | 4200 |
| attctagact agtctgcaga tctgatcctt tcctgggacc cggcaagaac | 4250 |
| caaaaactca ctctcttcaa ggaaatccgt aatgttaaac ccgacacgat | 4300 |
| gaagcttgtc gttggatgga aaggaaaaga gttctacagg gaaacttgga | 4350 |
| cccgcttcat ggaagacagc ttccccattg ttaacgacca agaagtgatg | 4400 |
| gatgttttcc ttgttgtcaa catgcgtccc actagaccca accgttgtta | 4450 |
| caaattcctg gcccaacacg ctctgcgttg cgaccccgac tatgtacctc | 4500 |
| atgacgtgat taggatcgtc gagccttcat gggtgggcag caacaacgag | 4550 |
| taccgcatca gcctggctaa gaagggcggc ggctgcccaa taatgaacct | 4600 |
| tcactctgag tacaccaact cgttcgaaca gttcatcgat cgtgtcatct | 4650 |
| gggagaactt ctacaagccc atcgtttaca tcggtaccga ctctgctgaa | 4700 |
| gaggaggaaa ttctccttga gtttccctg tgttcaaag taaggagtt | 4750 |
| tgcaccagac gcacctctgt tcactggtcc ggcgtattaa aacacgatac | 4800 |
| attgttatta gtacatttat taagcgctag attctgtgcg ttgttgattt | 4850 |
| acagacaatt gttgtacgta ttttaataat tcattaaatt tataatcttt | 4900 |
| agggtggtat gttagagcga aaatcaaatg attttcagcg tctttatatc | 4950 |
| tgaatttaaa tattaaatcc tcaatagatt tgtaaaatag gttcgatta | 5000 |
| gtttcaaaca aggttgttt ttccgaaccg atggctggac tatctaatgg | 5050 |

```
attttcgctc aacgccacaa aacttgccaa atcttgtagc agcaatctag      5100
ctttgtcgat attcgtttgt gttttgtttt gtaataaagg ttcgacgtcg      5150
ttcaaaatat tatgcgcttt tgtatttctt tcatcactgt cgttagtgta      5200
caattgactc gacgtaaaca cgttaaataa agcttggaca tatttaacat      5250
cgggcgtgtt agctttatta ggccgattat cgtcgtcgtc ccaaccctcg      5300
tcgttagaag ttgcttccga agacgatttt gccatagcca cacgacgcct      5350
attaattgtg tcggctaaca cgtccgcgat caaatttgta gttgagcttt      5400
ttggaattat ttctgattgc gggcgttttt gggcgggttt caatctaact      5450
gtgcccgatt ttaattcaga caacacgtta gaaagcgatg gtgcaggcgg      5500
tggtaacatt tcagacggca aatctactaa tggcggcggt ggtggagctg      5550
atgataaatc taccatcggt ggaggcgcag gcggggctgg cggcggaggc      5600
ggaggcggag gtggtggcgg tgatgcagac ggcggtttag gctcaaatgt      5650
ctctttaggc aacacagtcg gcacctcaac tattgtactg gtttcgggcg      5700 ccgttttttgg tttgaccggt ctgagacgag tgcgattttt ttcgtttcta     5750
atagcttcca acaattgttg tctgtcgtct aaaggtgcag cgggttgagg      5800
ttccgtcggc attggtggag cgggcggcaa ttcagacatc gatggtggtg      5850
gtggtggtgg aggcgctgga atgttaggca cgggagaagg tggtggcggc      5900
ggtgccgccg gtataaattg ttctggttta gtttgttcgc gcacgattgt      5950
gggcaccggc gcaggcgccg ctggctgcac aacggaaggt cgtctgcttc      6000
gaggcagcgc ttggggtggt ggcaattcaa tattataatt ggaatacaaa      6050
tcgtaaaaat ctgctataag cattgtaatt tcgctatcgt ttaccgtgcc      6100
gatatttaac aaccgctcaa tgtaagcaat tgtattgtaa agagattgtc      6150
tcaagctccg cacgccgata acaagccttt tcattttttac tacagcattg     6200 tagtggcgag acacttcgct gtcgtcgacg tacatgtatg ctttgttgtc      6250
aaaaacgtcg ttggcaagct ttaaaatatt taaaagaaca tctctgttca      6300
gcaccactgt gttgtcgtaa atgttgtttt tgataatttg cgcttccgca      6350
gtatcgacac gttcaaaaaa ttgatgcgca tcaattttgt tgttcctatt      6400
attgaataaa taagattgta cagattcata tctacgattc gtcatggcca      6450
ccacaaatgc tacgctgcaa acgctggtac aattttacga aaactgcaaa      6500
aacgtcaaaa ctcggtataa aataatcaac gggcgctttg gcaaaatatc      6550
tattttatcg cacaagccca ctagcaaatt gtatttgcag aaaacaattt      6600
cggcgcacaa ttttaacgct gacgaaataa aagttcacca gttaatgagc      6650
gaccacccaa attttataaa aatctatttt aatcacggtt ccatcaacaa      6700
ccaagtgatc gtgatggact acattgactg tcccgattta tttgaaacac      6750
tacaaattaa aggcgagctt tcgtaccaac ttgttagcaa tattattaga      6800
cagctgtgtg aagcgctcaa cgatttgcac aagcacaatt tcatacacaa      6850
cgacataaaa ctcgaaaatg tcttatattt cgaagcactt gatcgcgtgt      6900
atgtttgcga ttacggattg tgcaaacacg aaaactcact tagcgtgcac      6950
gacggcacgt tggagtattt tagtccggaa aaaattcgac acacaactat      7000
gcacgtttcg tttgactggt acgcggcgtg ttaacataca agttgctaac      7050
```

| | |
|---|---|
| cggcggttcg taatcatggt catagctgtt tcctgtgtga aattgttatc | 7100 |
| cgctcacaat tccacacaac atacgagccg gaagcataaa gtgtaaagcc | 7150 |
| tggggtgcct aatgagtgag ctaactcaca ttaattgcgt tgcgctcact | 7200 |
| gcccgctttc cagtcgggaa acctgtcgtg ccagctgcat taatgaatcg | 7250 |
| gccaacgcgc ggggagaggc ggtttgcgta ttgggcgctc ttccgcttcc | 7300 |
| tcgctcactg actcgctgcg ctcggtcgtt cggctgcggc gagcggtatc | 7350 |
| agctcactca aaggcggtaa tacggttatc cacagaatca ggggataacg | 7400 |
| caggaaagaa catgtgagca aaaggccagc aaaaggccag gaaccgtaaa | 7450 |
| aaggccgcgt tgctggcgtt tttccatagg ctccgccccc ctgacgagca | 7500 |
| tcacaaaaat cgacgctcaa gtcagaggtg gcgaaacccg acaggactat | 7550 |
| aaagatacca ggcgtttccc cctggaagct ccctcgtgcg ctctcctgtt | 7600 |
| ccgaccctgc cgcttaccgg atacctgtcc gcctttctcc cttcgggaag | 7650 |
| cgtggcgctt tctcatagct cacgctgtag gtatctcagt tcggtgtagg | 7700 |
| tcgttcgctc caagctgggc tgtgtgcacg aaccccccgt tcagcccgac | 7750 |
| cgctgcgcct tatccggtaa ctatcgtctt gagtccaacc cggtaagaca | 7800 |
| cgacttatcg ccactggcag cagccactgg taacaggatt agcagagcga | 7850 |
| ggtatgtagg cggtgctaca gagttcttga agtggtggcc taactacggc | 7900 |
| tacactagaa ggacagtatt tggtatctgc gctctgctga agccagttac | 7950 |
| cttcggaaaa agagttggta gctcttgatc cggcaaacaa accaccgctg | 8000 |
| gtagcggtgg ttttttgtt tgcaagcagc agattacgcg cagaaaaaaa | 8050 |
| ggatctcaag aagatccttt gatcttttct acggggtctg acgctcagtg | 8100 |
| gaacgaaaac tcacgttaag ggattttggt catgagatta tcaaaaagga | 8150 |
| tcttcaccta gatcctttta aattaaaaat gaagttttaa atcaatctaa | 8200 |
| agtatatatg agtaaacttg gtctgacagt taccaatgct taatcagtga | 8250 |
| ggcacctatc tcagcgatct gtctatttcg ttcatccata gttgcctgac | 8300 |
| tccccgtcgt gtagataact acgatacggg agggcttacc atctggcccc | 8350 |
| agtgctgcaa tgataccgcg agacccacgc tcaccggctc cagatttatc | 8400 |
| agcaataaac cagccagccg gaagggccga gcgcagaagt ggtcctgcaa | 8450 |
| ctttatccgc ctccatccag tctattaatt gttgccggga agctagagta | 8500 |
| agtagttcgc cagttaatag tttgcgcaac gttgttgcca ttgctacagg | 8550 |
| catcgtggtg tcacgctcgt cgtttggtat ggcttcattc agctccggtt | 8600 |
| cccaacgatc aaggcgagtt acatgatccc ccatgttgtg caaaaaagcg | 8650 |
| gttagctcct tcggtcctcc gatcgttgtc agaagtaagt tggccgcagt | 8700 |
| gttatcactc atggttatgg cagcactgca taattctctt actgtcatgc | 8750 |
| catccgtaag atgcttttct gtgactggtg agtactcaac caagtcattc | 8800 |
| tgagaatagt gtatgcggcg accgagttgc tcttgcccgg cgtcaatacg | 8850 |
| ggataatacc gcgccacata gcagaacttt aaaagtgctc atcattggaa | 8900 |
| aacgttcttc ggggcgaaaa ctctcaagga tcttaccgct gttgagatcc | 8950 |
| agttcgatgt aacccactcg tgcacccaac tgatcttcag catcttttac | 9000 |

-continued

| | |
|---|---|
| tttcaccagc gtttctgggt gagcaaaaac aggaaggcaa aatgccgcaa | 9050 |
| aaaagggaat aagggcgaca cggaaatgtt gaatactcat actcttcctt | 9100 |
| tttcaatatt attgaagcat ttatcagggt tattgtctca tgagcggata | 9150 |
| catatttgaa tgtatttaga aaaataaaca aatagggggtt ccgcgcacat | 9200 |
| ttccccgaaa agtgccacct gacgtctaag aaaccattat tatcatgaca | 9250 |
| ttaacctata aaataggcg tatcacgagg cccttccgtc tcgcgcgttt | 9300 |
| cggtgatgac ggtgaaaacc tctgacacat gcagctcccg gagacggtca | 9350 |
| cagcttgtct gtaagcggat gccgggagca gacaagcccg tcagggcgcg | 9400 |
| tcagcgggtg ttggcgggtg tcggggctgg cttaactatg cggcatcaga | 9450 |
| gcagattgta ctgagagtgc accatatatg cggtgtgaaa taccgcacag | 9500 |
| atgcgtaagg agaaaatacc gcatcaggcg ccattcgcca ttcaggctgc | 9550 |
| gcaactgttg ggaagggcga tcggtgcggg cctcttcgct attacgccag | 9600 |
| ctggcgaaag ggggatgtgc tgcaaggcga ttaagttggg taacgccagg | 9650 |
| gttttcccag tcacgacgtt gtaaaacgac ggccagtgcc | 9690 |

<210> SEQ ID NO 56
<211> LENGTH: 249
<212> TYPE: PRT
<213> ORGANISM: Homo sapiens

<400> SEQUENCE: 56

Arg Gly Thr Pro Lys Thr His Leu Leu Ala P he Ser Leu Leu Cys
 1               5                  10                  15

Leu Leu Ser Lys Val Arg Thr Gln Leu Cys P ro Thr Pro Cys Thr
                20                  25                  30

Cys Pro Trp Pro Pro Arg Cys Pro Leu G ly Val Pro Leu Val
                35                  40                  45

Leu Asp Gly Cys Gly Cys Cys Arg Val Cys A la Arg Arg Leu Gly
                50                  55                  60

Glu Pro Cys Asp Gln Leu His Val Cys Asp A la Ser Gln Gly Leu
 65                  70                  75

Val Cys Gln Pro Gly Ala Gly Pro Gly Gly A rg Gly Ala Leu Cys
                80                  85                  90

Leu Leu Ala Glu Asp Asp Ser Ser Cys Glu V al Asn Gly Arg Leu
                95                  100                 105

Tyr Arg Glu Gly Glu Thr Phe Gln Pro His C ys Ser Ile Arg Cys
                110                 115                 120

Arg Cys Glu Asp Gly Gly Phe Thr Cys Val P ro Leu Cys Ser Glu
                125                 130                 135

Asp Val Arg Leu Pro Ser Trp Asp Cys Pro H is Pro Arg Arg Val
                140                 145                 150

Glu Val Leu Gly Lys Cys Cys Pro Glu Trp V al Cys Gly Gln Gly
                155                 160                 165

Gly Gly Leu Gly Thr Gln Pro Leu Pro Ala G ln Gly Pro Gln Phe
                170                 175                 180

Ser Gly Leu Val Ser Ser Leu Pro Pro Gly V al Pro Cys Pro Glu
                185                 190                 195

Trp Ser Thr Ala Trp Gly Pro Cys Ser Thr T hr Cys Gly Leu Gly
                200                 205                 210

Met Ala Thr Arg Val Ser Asn Gln Asn Arg P he Cys Arg Leu Glu

```
                    215                 220                 225
Thr Gln Arg Arg Leu Cys Leu Ser Arg Pro C ys Pro Pro Ser Arg
                230                 235                 240
Gly Arg Ser Pro Gln Asn Ser Ala Phe
                245                 249

<210> SEQ ID NO 57
<211> LENGTH: 248
<212> TYPE: PRT
<213> ORGANISM: Homo sapiens

<400> SEQUENCE: 57

Gly Thr Pro Lys Thr His Leu Leu Ala Phe S er Leu Leu Cys Leu
  1               5                  10                  15

Leu Ser Lys Val Arg Thr Gln Leu Cys Pro T hr Pro Cys Thr Cys
                 20                  25                  30

Pro Trp Pro Pro Arg Cys Pro Leu Gly V al Pro Leu Val Leu
                 35                  40                  45

Asp Gly Cys Gly Cys Arg Val Cys Ala A rg Arg Leu Gly Glu
                 50                  55                  60

Pro Cys Asp Gln Leu His Val Cys Asp Ala S er Gln Gly Leu Val
                 65                  70                  75

Cys Gln Pro Gly Ala Gly Pro Gly Gly Arg G ly Ala Leu Cys Leu
                 80                  85                  90

Leu Ala Glu Asp Ser Ser Cys Glu Val A sn Gly Arg Leu Tyr
                 95                 100                 105

Arg Glu Gly Glu Thr Phe Gln Pro His Cys S er Ile Arg Cys Arg
                110                 115                 120

Cys Glu Asp Gly Gly Phe Thr Cys Val Pro L eu Cys Ser Glu Asp
                125                 130                 135

Val Arg Leu Pro Ser Trp Asp Cys Pro His P ro Arg Arg Val Glu
                140                 145                 150

Val Leu Gly Lys Cys Cys Pro Glu Trp Val C ys Gly Gln Gly Gly
                155                 160                 165

Gly Leu Gly Thr Gln Pro Leu Pro Ala Gln G ly Pro Gln Phe Ser
                170                 175                 180

Gly Leu Val Ser Ser Leu Pro Pro Gly Val P ro Cys Pro Glu Trp
                185                 190                 195

Ser Thr Ala Trp Gly Pro Cys Ser Thr Thr C ys Gly Leu Gly Met
                200                 205                 210

Ala Thr Arg Val Ser Asn Gln Asn Arg Phe C ys Arg Leu Glu Thr
                215                 220                 225

Gln Arg Arg Leu Cys Leu Ser Arg Pro Cys P ro Pro Ser Arg Gly
                230                 235                 240

Arg Ser Pro Gln Asn Ser Ala Phe
                245                 248

<210> SEQ ID NO 58
<211> LENGTH: 247
<212> TYPE: PRT
<213> ORGANISM: Homo sapiens

<400> SEQUENCE: 58

Thr Pro Lys Thr His Leu Leu Ala Phe Ser L eu Leu Cys Leu Leu
  1               5                  10                  15

Ser Lys Val Arg Thr Gln Leu Cys Pro Thr P ro Cys Thr Cys Pro
```

-continued

```
                 20                  25                  30

Trp Pro Pro Arg Cys Pro Leu Gly Val Pro Leu Val Leu Asp
                 35                  40                  45

Gly Cys Gly Cys Cys Arg Val Cys Ala Arg Arg Leu Gly Glu Pro
                 50                  55                  60

Cys Asp Gln Leu His Val Cys Asp Ala Ser Gln Gly Leu Val Cys
                 65                  70                  75

Gln Pro Gly Ala Gly Pro Gly Arg Gly Ala Leu Cys Leu Leu
                 80                  85                  90

Ala Glu Asp Asp Ser Ser Cys Glu Val Asn Gly Arg Leu Tyr Arg
                 95                 100                 105

Glu Gly Glu Thr Phe Gln Pro His Cys Ser Ile Arg Cys Arg Cys
                110                 115                 120

Glu Asp Gly Gly Phe Thr Cys Val Pro Leu Cys Ser Glu Asp Val
                125                 130                 135

Arg Leu Pro Ser Trp Asp Cys Pro His Pro Arg Arg Val Glu Val
                140                 145                 150

Leu Gly Lys Cys Cys Pro Glu Trp Val Cys Gly Gln Gly Gly Gly
                155                 160                 165

Leu Gly Thr Gln Pro Leu Pro Ala Gln Gly Pro Gln Phe Ser Gly
                170                 175                 180

Leu Val Ser Ser Leu Pro Pro Gly Val Pro Cys Pro Glu Trp Ser
                185                 190                 195

Thr Ala Trp Gly Pro Cys Ser Thr Thr Cys Gly Leu Gly Met Ala
                200                 205                 210

Thr Arg Val Ser Asn Gln Asn Arg Phe Cys Arg Leu Glu Thr Gln
                215                 220                 225

Arg Arg Leu Cys Leu Ser Arg Pro Cys Pro Pro Ser Arg Gly Arg
                230                 235                 240

Ser Pro Gln Asn Ser Ala Phe
                245     247

<210> SEQ ID NO 59
<211> LENGTH: 246
<212> TYPE: PRT
<213> ORGANISM: Homo sapiens

<400> SEQUENCE: 59

Pro Lys Thr His Leu Leu Ala Phe Ser Leu Leu Cys Leu Leu Ser
  1               5                  10                  15

Lys Val Arg Thr Gln Leu Cys Pro Thr Pro Cys Thr Cys Pro Trp
                 20                  25                  30

Pro Pro Pro Arg Cys Pro Leu Gly Val Pro Leu Val Leu Asp Gly
                 35                  40                  45

Cys Gly Cys Cys Arg Val Cys Ala Arg Arg Leu Gly Glu Pro Cys
                 50                  55                  60

Asp Gln Leu His Val Cys Asp Ala Ser Gln Gly Leu Val Cys Gln
                 65                  70                  75

Pro Gly Ala Gly Pro Gly Gly Arg Gly Ala Leu Cys Leu Leu Ala
                 80                  85                  90

Glu Asp Asp Ser Ser Cys Glu Val Asn Gly Arg Leu Tyr Arg Glu
                 95                 100                 105

Gly Glu Thr Phe Gln Pro His Cys Ser Ile Arg Cys Arg Cys Glu
                110                 115                 120
```

```
Asp Gly Gly Phe Thr Cys Val Pro Leu Cys S er Glu Asp Val Arg
                125                 130                 135

Leu Pro Ser Trp Asp Cys Pro His Pro Arg A rg Val Glu Val Leu
            140                 145                 150

Gly Lys Cys Cys Pro Glu Trp Val Cys Gly G ln Gly Gly Gly Leu
            155                 160                 165

Gly Thr Gln Pro Leu Pro Ala Gln Gly Pro G ln Phe Ser Gly Leu
            170                 175                 180

Val Ser Ser Leu Pro Pro Gly Val Pro Cys P ro Glu Trp Ser Thr
            185                 190                 195

Ala Trp Gly Pro Cys Ser Thr Thr Cys Gly L eu Gly Met Ala Thr
            200                 205                 210

Arg Val Ser Asn Gln Asn Arg Phe Cys Arg L eu Glu Thr Gln Arg
            215                 220                 225

Arg Leu Cys Leu Ser Arg Pro Cys Pro Pro S er Arg Gly Arg Ser
            230                 235                 240

Pro Gln Asn Ser Ala Phe
            245 246

<210> SEQ ID NO 60
<211> LENGTH: 245
<212> TYPE: PRT
<213> ORGANISM: Homo sapiens

<400> SEQUENCE: 60

Lys Thr His Leu Leu Ala Phe Ser Leu Leu C ys Leu Leu Ser Lys
  1               5                  10                  15

Val Arg Thr Gln Leu Cys Pro Thr Pro Cys T hr Cys Pro Trp Pro
                 20                  25                  30

Pro Pro Arg Cys Pro Leu Gly Val Pro Leu V al Leu Asp Gly Cys
             35                  40                  45

Gly Cys Cys Arg Val Cys Ala Arg Arg Leu G ly Glu Pro Cys Asp
             50                  55                  60

Gln Leu His Val Cys Asp Ala Ser Gln Gly L eu Val Cys Gln Pro
             65                  70                  75

Gly Ala Gly Pro Gly Gly Arg Gly Ala Leu C ys Leu Leu Ala Glu
             80                  85                  90

Asp Asp Ser Ser Cys Glu Val Asn Gly Arg L eu Tyr Arg Glu Gly
             95                 100                 105

Glu Thr Phe Gln Pro His Cys Ser Ile Arg C ys Arg Cys Glu Asp
            110                 115                 120

Gly Gly Phe Thr Cys Val Pro Leu Cys Ser G lu Asp Val Arg Leu
            125                 130                 135

Pro Ser Trp Asp Cys Pro His Pro Arg Arg V al Glu Val Leu Gly
            140                 145                 150

Lys Cys Cys Pro Glu Trp Val Cys Gly Gln G ly Gly Gly Leu Gly
            155                 160                 165

Thr Gln Pro Leu Pro Ala Gln Gly Pro Gln P he Ser Gly Leu Val
            170                 175                 180

Ser Ser Leu Pro Pro Gly Val Pro Cys Pro G lu Trp Ser Thr Ala
            185                 190                 195

Trp Gly Pro Cys Ser Thr Thr Cys Gly Leu G ly Met Ala Thr Arg
            200                 205                 210

Val Ser Asn Gln Asn Arg Phe Cys Arg Leu G lu Thr Gln Arg Arg
            215                 220                 225
```

```
Leu Cys Leu Ser Arg Pro Cys Pro Pro Ser Arg Gly Arg Ser Pro
                230                 235                 240

Gln Asn Ser Ala Phe
            245

<210> SEQ ID NO 61
<211> LENGTH: 244
<212> TYPE: PRT
<213> ORGANISM: Homo sapiens

<400> SEQUENCE: 61

Thr His Leu Leu Ala Phe Ser Leu Leu Cys Leu Leu Ser Lys Val
  1               5                  10                  15

Arg Thr Gln Leu Cys Pro Thr Pro Cys Thr Cys Pro Trp Pro Pro
                 20                  25                  30

Pro Arg Cys Pro Leu Gly Val Pro Leu Val Leu Asp Gly Cys Gly
                 35                  40                  45

Cys Cys Arg Val Cys Ala Arg Arg Leu Gly Glu Pro Cys Asp Gln
                 50                  55                  60

Leu His Val Cys Asp Ala Ser Gln Gly Leu Val Cys Gln Pro Gly
                 65                  70                  75

Ala Gly Pro Gly Gly Arg Gly Ala Leu Cys Leu Leu Ala Glu Asp
                 80                  85                  90

Asp Ser Ser Cys Glu Val Asn Gly Arg Leu Tyr Arg Glu Gly Glu
                 95                 100                 105

Thr Phe Gln Pro His Cys Ser Ile Arg Cys Arg Cys Glu Asp Gly
                110                 115                 120

Gly Phe Thr Cys Val Pro Leu Cys Ser Glu Asp Val Arg Leu Pro
                125                 130                 135

Ser Trp Asp Cys Pro His Pro Arg Arg Val Glu Val Leu Gly Lys
                140                 145                 150

Cys Cys Pro Glu Trp Val Cys Gly Gln Gly Gly Gly Leu Gly Thr
                155                 160                 165

Gln Pro Leu Pro Ala Gln Gly Pro Gln Phe Ser Gly Leu Val Ser
                170                 175                 180

Ser Leu Pro Pro Gly Val Pro Cys Pro Glu Trp Ser Thr Ala Trp
                185                 190                 195

Gly Pro Cys Ser Thr Thr Cys Gly Leu Gly Met Ala Thr Arg Val
                200                 205                 210

Ser Asn Gln Asn Arg Phe Cys Arg Leu Glu Thr Gln Arg Arg Leu
                215                 220                 225

Cys Leu Ser Arg Pro Cys Pro Pro Ser Arg Gly Arg Ser Pro Gln
                230                 235                 240

Asn Ser Ala Phe
            244

<210> SEQ ID NO 62
<211> LENGTH: 243
<212> TYPE: PRT
<213> ORGANISM: Homo sapiens

<400> SEQUENCE: 62

His Leu Leu Ala Phe Ser Leu Leu Cys Leu Leu Ser Lys Val Arg
  1               5                  10                  15

Thr Gln Leu Cys Pro Thr Pro Cys Thr Cys Pro Trp Pro Pro Pro
                 20                  25                  30
```

```
Arg Cys Pro Leu Gly Val Pro Leu Val Leu Asp Gly Cys Gly Cys
             35                  40                  45

Cys Arg Val Cys Ala Arg Arg Leu Gly Glu Pro Cys Asp Gln Leu
             50                  55                  60

His Val Cys Asp Ala Ser Gln Gly Leu Val Cys Gln Pro Gly Ala
             65                  70                  75

Gly Pro Gly Gly Arg Gly Ala Leu Cys Leu Leu Ala Glu Asp Asp
             80                  85                  90

Ser Ser Cys Glu Val Asn Gly Arg Leu Tyr Arg Glu Gly Glu Thr
             95                 100                 105

Phe Gln Pro His Cys Ser Ile Arg Cys Arg Cys Glu Asp Gly Gly
            110                 115                 120

Phe Thr Cys Val Pro Leu Cys Ser Glu Asp Val Arg Leu Pro Ser
            125                 130                 135

Trp Asp Cys Pro His Pro Arg Arg Val Glu Val Leu Gly Lys Cys
            140                 145                 150

Cys Pro Glu Trp Val Cys Gly Gln Gly Gly Gly Leu Gly Thr Gln
            155                 160                 165

Pro Leu Pro Ala Gln Gly Pro Gln Phe Ser Gly Leu Val Ser Ser
            170                 175                 180

Leu Pro Pro Gly Val Pro Cys Pro Glu Trp Ser Thr Ala Trp Gly
            185                 190                 195

Pro Cys Ser Thr Thr Cys Gly Leu Gly Met Ala Thr Arg Val Ser
            200                 205                 210

Asn Gln Asn Arg Phe Cys Arg Leu Glu Thr Gln Arg Arg Leu Cys
            215                 220                 225

Leu Ser Arg Pro Cys Pro Ser Arg Gly Arg Ser Pro Gln Asn
            230                 235                 240

Ser Ala Phe
        243

<210> SEQ ID NO 63
<211> LENGTH: 242
<212> TYPE: PRT
<213> ORGANISM: Homo sapiens

<400> SEQUENCE: 63

Leu Leu Ala Phe Ser Leu Leu Cys Leu Leu Ser Lys Val Arg Thr
 1               5                  10                  15

Gln Leu Cys Pro Thr Pro Cys Thr Cys Pro Trp Pro Pro Pro Arg
             20                  25                  30

Cys Pro Leu Gly Val Pro Leu Val Leu Asp Gly Cys Gly Cys Cys
             35                  40                  45

Arg Val Cys Ala Arg Arg Leu Gly Glu Pro Cys Asp Gln Leu His
             50                  55                  60

Val Cys Asp Ala Ser Gln Gly Leu Val Cys Gln Pro Gly Ala Gly
             65                  70                  75

Pro Gly Gly Arg Gly Ala Leu Cys Leu Leu Ala Glu Asp Asp Ser
             80                  85                  90

Ser Cys Glu Val Asn Gly Arg Leu Tyr Arg Glu Gly Glu Thr Phe
             95                 100                 105

Gln Pro His Cys Ser Ile Arg Cys Arg Cys Glu Asp Gly Gly Phe
            110                 115                 120

Thr Cys Val Pro Leu Cys Ser Glu Asp Val Arg Leu Pro Ser Trp
```

```
                    125                 130                 135
Asp Cys Pro His Pro Arg Arg Val Glu Val Leu Gly Lys Cys Cys
                140                 145                 150
Pro Glu Trp Val Cys Gly Gln Gly Gly Leu Gly Thr Gln Pro
                155                 160                 165
Leu Pro Ala Gln Gly Pro Gln Phe Ser Gly Leu Val Ser Ser Leu
                170                 175                 180
Pro Pro Gly Val Pro Cys Pro Glu Trp Ser Thr Ala Trp Gly Pro
                185                 190                 195
Cys Ser Thr Thr Cys Gly Leu Gly Met Ala Thr Arg Val Ser Asn
                200                 205                 210
Gln Asn Arg Phe Cys Arg Leu Glu Thr Gln Arg Arg Leu Cys Leu
                215                 220                 225
Ser Arg Pro Cys Pro Pro Ser Arg Gly Arg Ser Pro Gln Asn Ser
                230                 235                 240
Ala Phe
    242

<210> SEQ ID NO 64
<211> LENGTH: 241
<212> TYPE: PRT
<213> ORGANISM: Homo sapiens

<400> SEQUENCE: 64

Leu Ala Phe Ser Leu Leu Cys Leu Leu Ser Lys Val Arg Thr Gln
 1               5                  10                  15
Leu Cys Pro Thr Pro Cys Thr Cys Pro Trp Pro Pro Pro Arg Cys
                20                  25                  30
Pro Leu Gly Val Pro Leu Val Leu Asp Gly Cys Gly Cys Cys Arg
                35                  40                  45
Val Cys Ala Arg Arg Leu Gly Glu Pro Cys Asp Gln Leu His Val
                50                  55                  60
Cys Asp Ala Ser Gln Gly Leu Val Cys Gln Pro Gly Ala Gly Pro
                65                  70                  75
Gly Gly Arg Gly Ala Leu Cys Leu Leu Ala Glu Asp Asp Ser Ser
                80                  85                  90
Cys Glu Val Asn Gly Arg Leu Tyr Arg Glu Gly Glu Thr Phe Gln
                95                  100                 105
Pro His Cys Ser Ile Arg Cys Arg Cys Glu Asp Gly Gly Phe Thr
                110                 115                 120
Cys Val Pro Leu Cys Ser Glu Asp Val Arg Leu Pro Ser Trp Asp
                125                 130                 135
Cys Pro His Pro Arg Arg Val Glu Val Leu Gly Lys Cys Cys Pro
                140                 145                 150
Glu Trp Val Cys Gly Gln Gly Gly Gly Leu Gly Thr Gln Pro Leu
                155                 160                 165
Pro Ala Gln Gly Pro Gln Phe Ser Gly Leu Val Ser Ser Leu Pro
                170                 175                 180
Pro Gly Val Pro Cys Pro Glu Trp Ser Thr Ala Trp Gly Pro Cys
                185                 190                 195
Ser Thr Thr Cys Gly Leu Gly Met Ala Thr Arg Val Ser Asn Gln
                200                 205                 210
Asn Arg Phe Cys Arg Leu Glu Thr Gln Arg Arg Leu Cys Leu Ser
                215                 220                 225
```

```
Arg Pro Cys Pro Pro Ser Arg Gly Arg Ser Pro Gln Asn Ser Ala
                230                 235                 240

Phe
241

<210> SEQ ID NO 65
<211> LENGTH: 240
<212> TYPE: PRT
<213> ORGANISM: Homo sapiens

<400> SEQUENCE: 65

Ala Phe Ser Leu Leu Cys Leu Leu Ser Lys Val Arg Thr Gln Leu
  1               5                  10                  15

Cys Pro Thr Pro Cys Thr Cys Pro Trp Pro Pro Arg Cys Pro
                 20                  25                  30

Leu Gly Val Pro Leu Val Leu Asp Gly Cys Gly Cys Cys Arg Val
                 35                  40                  45

Cys Ala Arg Arg Leu Gly Glu Pro Cys Asp Gln Leu His Val Cys
                 50                  55                  60

Asp Ala Ser Gln Gly Leu Val Cys Gln Pro Gly Ala Gly Pro Gly
                 65                  70                  75

Gly Arg Gly Ala Leu Cys Leu Leu Ala Glu Asp Asp Ser Ser Cys
                 80                  85                  90

Glu Val Asn Gly Arg Leu Tyr Arg Glu Gly Glu Thr Phe Gln Pro
                 95                 100                 105

His Cys Ser Ile Arg Cys Arg Cys Glu Asp Gly Gly Phe Thr Cys
                110                 115                 120

Val Pro Leu Cys Ser Glu Asp Val Arg Leu Pro Ser Trp Asp Cys
                125                 130                 135

Pro His Pro Arg Arg Val Glu Val Leu Gly Lys Cys Cys Pro Glu
                140                 145                 150

Trp Val Cys Gly Gln Gly Gly Gly Leu Gly Thr Gln Pro Leu Pro
                155                 160                 165

Ala Gln Gly Pro Gln Phe Ser Gly Leu Val Ser Ser Leu Pro Pro
                170                 175                 180

Gly Val Pro Cys Pro Glu Trp Ser Thr Ala Trp Gly Pro Cys Ser
                185                 190                 195

Thr Thr Cys Gly Leu Gly Met Ala Thr Arg Val Ser Asn Gln Asn
                200                 205                 210

Arg Phe Cys Arg Leu Glu Thr Gln Arg Arg Leu Cys Leu Ser Arg
                215                 220                 225

Pro Cys Pro Pro Ser Arg Gly Arg Ser Pro Gln Asn Ser Ala Phe
                230                 235                 240

SEQ ID NO 66
LENGTH: 239

<212> TYPE: PRT
<213> ORGANISM: Homo sapiens

<400> SEQUENCE: 66

Phe Ser Leu Leu Cys Leu Leu Ser Lys Val Arg Thr Gln Leu Cys
  1               5                  10                  15

Pro Thr Pro Cys Thr Cys Pro Trp Pro Pro Arg Cys Pro Leu
                 20                  25                  30

Gly Val Pro Leu Val Leu Asp Gly Cys Gly Cys Cys Arg Val Cys
                 35                  40                  45
```

```
Ala Arg Arg Leu Gly Glu Pro Cys Asp Gln Leu His Val Cys Asp
                50                  55                  60

Ala Ser Gln Gly Leu Val Cys Gln Pro Gly Ala Gly Pro Gly Gly
            65                  70                  75

Arg Gly Ala Leu Cys Leu Leu Ala Glu Asp Asp Ser Ser Cys Glu
        80                  85                  90

Val Asn Gly Arg Leu Tyr Arg Glu Gly Glu Thr Phe Gln Pro His
    95                 100                 105

Cys Ser Ile Arg Cys Arg Cys Glu Asp Gly Gly Phe Thr Cys Val
           110                 115                 120

Pro Leu Cys Ser Glu Asp Val Arg Leu Pro Ser Trp Asp Cys Pro
       125                 130                 135

His Pro Arg Arg Val Glu Val Leu Gly Lys Cys Cys Pro Glu Trp
   140                 145                 150

Val Cys Gly Gln Gly Gly Gly Leu Gly Thr Gln Pro Leu Pro Ala
            155                 160                 165

Gln Gly Pro Gln Phe Ser Gly Leu Val Ser Ser Leu Pro Pro Gly
       170                 175                 180

Val Pro Cys Pro Glu Trp Ser Thr Ala Trp Gly Pro Cys Ser Thr
   185                 190                 195

Thr Cys Gly Leu Gly Met Ala Thr Arg Val Ser Asn Gln Asn Arg
            200                 205                 210

Phe Cys Arg Leu Glu Thr Gln Arg Arg Leu Cys Leu Ser Arg Pro
       215                 220                 225

Cys Pro Pro Ser Arg Gly Arg Ser Pro Gln Asn Ser Ala Phe
   230                 235                 239
```

<210> SEQ ID NO 67
<211> LENGTH: 238
<212> TYPE: PRT
<213> ORGANISM: Homo sapiens

<400> SEQUENCE: 67

```
Ser Leu Leu Cys Leu Leu Ser Lys Val Arg Thr Gln Leu Cys Pro
 1               5                  10                  15

Thr Pro Cys Thr Cys Pro Trp Pro Pro Arg Cys Pro Leu Gly
            20                  25                  30

Val Pro Leu Val Leu Asp Gly Cys Gly Cys Cys Arg Val Cys Ala
        35                  40                  45

Arg Arg Leu Gly Glu Pro Cys Asp Gln Leu His Val Cys Asp Ala
    50                  55                  60

Ser Gln Gly Leu Val Cys Gln Pro Gly Ala Gly Pro Gly Gly Arg
        65                  70                  75

Gly Ala Leu Cys Leu Leu Ala Glu Asp Asp Ser Ser Cys Glu Val
    80                  85                  90

Asn Gly Arg Leu Tyr Arg Glu Gly Glu Thr Phe Gln Pro His Cys
    95                 100                 105

Ser Ile Arg Cys Arg Cys Glu Asp Gly Gly Phe Thr Cys Val Pro
       110                 115                 120

Leu Cys Ser Glu Asp Val Arg Leu Pro Ser Trp Asp Cys Pro His
       125                 130                 135

Pro Arg Arg Val Glu Val Leu Gly Lys Cys Cys Pro Glu Trp Val
   140                 145                 150

Cys Gly Gln Gly Gly Gly Leu Gly Thr Gln Pro Leu Pro Ala Gln
```

```
                    155                 160                 165
Gly Pro Gln Phe Ser Gly Leu Val Ser Ser L eu Pro Pro Gly Val
                170                 175                 180

Pro Cys Pro Glu Trp Ser Thr Ala Trp Gly P ro Cys Ser Thr Thr
                185                 190                 195

Cys Gly Leu Gly Met Ala Thr Arg Val Ser A sn Gln Asn Arg Phe
                200                 205                 210

Cys Arg Leu Glu Thr Gln Arg Arg Leu Cys L eu Ser Arg Pro Cys
                215                 220                 225

Pro Pro Ser Arg Gly Arg Ser Pro Gln Asn S er Ala Phe
                230                 235         238

<210> SEQ ID NO 68
<211> LENGTH: 237
<212> TYPE: PRT
<213> ORGANISM: Homo sapiens

<400> SEQUENCE: 68

Leu Leu Cys Leu Leu Ser Lys Val Arg Thr G ln Leu Cys Pro Thr
  1               5                  10                  15

Pro Cys Thr Cys Pro Trp Pro Pro Arg C ys Pro Leu Gly Val
                 20                  25                  30

Pro Leu Val Leu Asp Gly Cys Gly Cys A rg Val Cys Ala Arg
                 35                  40                  45

Arg Leu Gly Glu Pro Cys Asp Gln Leu His V al Cys Asp Ala Ser
                 50                  55                  60

Gln Gly Leu Val Cys Gln Pro Gly Ala Gly P ro Gly Gly Arg Gly
                 65                  70                  75

Ala Leu Cys Leu Leu Ala Glu Asp Asp Ser S er Cys Glu Val Asn
                 80                  85                  90

Gly Arg Leu Tyr Arg Glu Gly Glu Thr Phe G ln Pro His Cys Ser
                 95                 100                 105

Ile Arg Cys Arg Cys Glu Asp Gly Gly Phe T hr Cys Val Pro Leu
                110                 115                 120

Cys Ser Glu Asp Val Arg Leu Pro Ser Trp A sp Cys Pro His Pro
                125                 130                 135

Arg Arg Val Glu Val Leu Gly Lys Cys Cys P ro Glu Trp Val Cys
                140                 145                 150

Gly Gln Gly Gly Gly Leu Gly Thr Gln Pro L eu Pro Ala Gln Gly
                155                 160                 165

Pro Gln Phe Ser Gly Leu Val Ser Ser Leu P ro Pro Gly Val Pro
                170                 175                 180

Cys Pro Glu Trp Ser Thr Ala Trp Gly Pro C ys Ser Thr Thr Cys
                185                 190                 195

Gly Leu Gly Met Ala Thr Arg Val Ser Asn G ln Asn Arg Phe Cys
                200                 205                 210

Arg Leu Glu Thr Gln Arg Arg Leu Cys Leu S er Arg Pro Cys Pro
                215                 220                 225

Pro Ser Arg Gly Arg Ser Pro Gln Asn Ser A la Phe
                230                 235         237

<210> SEQ ID NO 69
<211> LENGTH: 236
<212> TYPE: PRT
<213> ORGANISM: Homo sapiens
```

```
<400> SEQUENCE: 69

Leu Cys Leu Leu Ser Lys Val Arg Thr Gln L eu Cys Pro Thr Pro
  1               5                  10                  15

Cys Thr Cys Pro Trp Pro Pro Arg Cys P ro Leu Gly Val Pro
             20                  25                  30

Leu Val Leu Asp Gly Cys Gly Cys Cys Arg V al Cys Ala Arg Arg
                 35                  40                  45

Leu Gly Glu Pro Cys Asp Gln Leu His Val C ys Asp Ala Ser Gln
                 50                  55                  60

Gly Leu Val Cys Gln Pro Gly Ala Gly Pro G ly Gly Arg Gly Ala
                 65                  70                  75

Leu Cys Leu Leu Ala Glu Asp Asp Ser Ser C ys Glu Val Asn Gly
                 80                  85                  90

Arg Leu Tyr Arg Glu Gly Glu Thr Phe Gln P ro His Cys Ser Ile
                 95                 100                 105

Arg Cys Arg Cys Glu Asp Gly Gly Phe Thr C ys Val Pro Leu Cys
                110                 115                 120

Ser Glu Asp Val Arg Leu Pro Ser Trp Asp C ys Pro His Pro Arg
                125                 130                 135

Arg Val Glu Val Leu Gly Lys Cys Cys Pro G lu Trp Val Cys Gly
                140                 145                 150

Gln Gly Gly Gly Leu Gly Thr Gln Pro Leu P ro Ala Gln Gly Pro
                155                 160                 165

Gln Phe Ser Gly Leu Val Ser Ser Leu Pro P ro Gly Val Pro Cys
                170                 175                 180

Pro Glu Trp Ser Thr Ala Trp Gly Pro Cys S er Thr Thr Cys Gly
                185                 190                 195

Leu Gly Met Ala Thr Arg Val Ser Asn Gln A sn Arg Phe Cys Arg
                200                 205                 210

Leu Glu Thr Gln Arg Arg Leu Cys Leu Ser A rg Pro Cys Pro Pro
                215                 220                 225

Ser Arg Gly Arg Ser Pro Gln Asn Ser Ala P he
                230                 235 236

<210> SEQ ID NO 70
<211> LENGTH: 235
<212> TYPE: PRT
<213> ORGANISM: Homo sapiens

<400> SEQUENCE: 70

Cys Leu Leu Ser Lys Val Arg Thr Gln Leu C ys Pro Thr Pro Cys
  1               5                  10                  15

Thr Cys Pro Trp Pro Pro Arg Cys Pro L eu Gly Val Pro Leu
             20                  25                  30

Val Leu Asp Gly Cys Gly Cys Cys Arg Val C ys Ala Arg Arg Leu
                 35                  40                  45

Gly Glu Pro Cys Asp Gln Leu His Val Cys A sp Ala Ser Gln Gly
                 50                  55                  60

Leu Val Cys Gln Pro Gly Ala Gly Pro Gly G ly Arg Gly Ala Leu
                 65                  70                  75

Cys Leu Leu Ala Glu Asp Asp Ser Ser Cys G lu Val Asn Gly Arg
                 80                  85                  90

Leu Tyr Arg Glu Gly Glu Thr Phe Gln Pro H is Cys Ser Ile Arg
                 95                 100                 105
```

-continued

Cys Arg Cys Glu Asp Gly Gly Phe Thr Cys Val Pro Leu Cys Ser
            110                 115                 120

Glu Asp Val Arg Leu Pro Ser Trp Asp Cys Pro His Pro Arg Arg
            125                 130                 135

Val Glu Val Leu Gly Lys Cys Cys Pro Glu Trp Val Cys Gly Gln
            140                 145                 150

Gly Gly Gly Leu Gly Thr Gln Pro Leu Pro Ala Gln Gly Pro Gln
            155                 160                 165

Phe Ser Gly Leu Val Ser Ser Leu Pro Pro Gly Val Pro Cys Pro
            170                 175                 180

Glu Trp Ser Thr Ala Trp Gly Pro Cys Ser Thr Thr Cys Gly Leu
            185                 190                 195

Gly Met Ala Thr Arg Val Ser Asn Gln Asn Arg Phe Cys Arg Leu
            200                 205                 210

Glu Thr Gln Arg Arg Leu Cys Leu Ser Arg Pro Cys Pro Pro Ser
            215                 220                 225

Arg Gly Arg Ser Pro Gln Asn Ser Ala Phe
            230                 235

<210> SEQ ID NO 71
<211> LENGTH: 234
<212> TYPE: PRT
<213> ORGANISM: Homo sapiens

<400> SEQUENCE: 71

Leu Leu Ser Lys Val Arg Thr Gln Leu Cys Pro Thr Pro Cys Thr
  1               5                  10                 15

Cys Pro Trp Pro Pro Arg Cys Pro Leu Gly Val Pro Leu Val
            20                  25                 30

Leu Asp Gly Cys Gly Cys Cys Arg Val Cys Ala Arg Arg Leu Gly
            35                  40                 45

Glu Pro Cys Asp Gln Leu His Val Cys Asp Ala Ser Gln Gly Leu
            50                  55                 60

Val Cys Gln Pro Gly Ala Gly Pro Gly Gly Arg Gly Ala Leu Cys
            65                  70                 75

Leu Leu Ala Glu Asp Asp Ser Ser Cys Glu Val Asn Gly Arg Leu
            80                  85                 90

Tyr Arg Glu Gly Glu Thr Phe Gln Pro His Cys Ser Ile Arg Cys
            95                 100                 105

Arg Cys Glu Asp Gly Gly Phe Thr Cys Val Pro Leu Cys Ser Glu
            110                 115                 120

Asp Val Arg Leu Pro Ser Trp Asp Cys Pro His Pro Arg Arg Val
            125                 130                 135

Glu Val Leu Gly Lys Cys Cys Pro Glu Trp Val Cys Gly Gln Gly
            140                 145                 150

Gly Gly Leu Gly Thr Gln Pro Leu Pro Ala Gln Gly Pro Gln Phe
            155                 160                 165

Ser Gly Leu Val Ser Ser Leu Pro Pro Gly Val Pro Cys Pro Glu
            170                 175                 180

Trp Ser Thr Ala Trp Gly Pro Cys Ser Thr Thr Cys Gly Leu Gly
            185                 190                 195

Met Ala Thr Arg Val Ser Asn Gln Asn Arg Phe Cys Arg Leu Glu
            200                 205                 210

Thr Gln Arg Arg Leu Cys Leu Ser Arg Pro Cys Pro Pro Ser Arg
            215                 220                 225

```
Gly Arg Ser Pro Gln Asn Ser Ala Phe
            230             234
```

<210> SEQ ID NO 72
<211> LENGTH: 233
<212> TYPE: PRT
<213> ORGANISM: Homo sapiens

<400> SEQUENCE: 72

```
Leu Ser Lys Val Arg Thr Gln Leu Cys Pro T hr Pro Cys Thr Cys
 1               5                  10                  15

Pro Trp Pro Pro Arg Cys Pro Leu Gly V al Pro Leu Val Leu
                20                  25                  30

Asp Gly Cys Gly Cys Arg Val Cys Ala A rg Arg Leu Gly Glu
                35                  40                  45

Pro Cys Asp Gln Leu His Val Cys Asp Ala S er Gln Gly Leu Val
                50                  55                  60

Cys Gln Pro Gly Ala Gly Pro Gly Arg G ly Ala Leu Cys Leu
                65                  70                  75

Leu Ala Glu Asp Asp Ser Ser Cys Glu Val A sn Gly Arg Leu Tyr
                80                  85                  90

Arg Glu Gly Glu Thr Phe Gln Pro His Cys S er Ile Arg Cys Arg
                95                  100                 105

Cys Glu Asp Gly Gly Phe Thr Cys Val Pro L eu Cys Ser Glu Asp
                110                 115                 120

Val Arg Leu Pro Ser Trp Asp Cys Pro His P ro Arg Arg Val Glu
                125                 130                 135

Val Leu Gly Lys Cys Cys Pro Glu Trp Val C ys Gly Gln Gly Gly
                140                 145                 150

Gly Leu Gly Thr Gln Pro Leu Pro Ala Gln G ly Pro Gln Phe Ser
                155                 160                 165

Gly Leu Val Ser Ser Leu Pro Pro Gly Val P ro Cys Pro Glu Trp
                170                 175                 180

Ser Thr Ala Trp Gly Pro Cys Ser Thr Thr C ys Gly Leu Gly Met
                185                 190                 195

Ala Thr Arg Val Ser Asn Gln Asn Arg Phe C ys Arg Leu Glu Thr
                200                 205                 210

Gln Arg Arg Leu Cys Leu Ser Arg Pro C ys P ro Pro Ser Arg Gly
                215                 220                 225

Arg Ser Pro Gln Asn Ser Ala Phe
            230             233
```

<210> SEQ ID NO 73
<211> LENGTH: 232
<212> TYPE: PRT
<213> ORGANISM: Homo sapiens

<400> SEQUENCE: 73

```
Ser Lys Val Arg Thr Gln Leu Cys Pro Thr P ro Cys Thr Cys Pro
 1               5                  10                  15

Trp Pro Pro Arg Cys Pro Leu Gly Val P ro Leu Val Leu Asp
                20                  25                  30

Gly Cys Gly Cys Arg Val Cys Ala Arg A rg Leu Gly Glu Pro
                35                  40                  45

Cys Asp Gln Leu His Val Cys Asp Ala Ser G ln Gly Leu Val Cys
                50                  55                  60
```

```
Gln Pro Gly Ala Gly Pro Gly Arg Gly A la Leu Cys Leu Leu
                65                  70                  75

Ala Glu Asp Asp Ser Ser Cys Glu Val Asn G ly Arg Leu Tyr Arg
                80                  85                  90

Glu Gly Glu Thr Phe Gln Pro His Cys Ser I le Arg Cys Arg Cys
                95                 100                 105

Glu Asp Gly Gly Phe Thr Cys Val Pro Leu C ys Ser Glu Asp Val
               110                 115                 120

Arg Leu Pro Ser Trp Asp Cys Pro His Pro A rg Arg Val Glu Val
               125                 130                 135

Leu Gly Lys Cys Cys Pro Glu Trp Val Cys G ly Gln Gly Gly Gly
               140                 145                 150

Leu Gly Thr Gln Pro Leu Pro Ala Gln Gly P ro Gln Phe Ser Gly
               155                 160                 165

Leu Val Ser Ser Leu Pro Pro Gly Val Pro C ys Pro Glu Trp Ser
               170                 175                 180

Thr Ala Trp Gly Pro Cys Ser Thr Thr Cys G ly Leu Gly Met Ala
               185                 190                 195

Thr Arg Val Ser Asn Gln Asn Arg Phe Cys A rg Leu Glu Thr Gln
               200                 205                 210

Arg Arg Leu Cys Leu Ser Arg Pro Cys Pro P ro Ser Arg Gly Arg
               215                 220                 225

Ser Pro Gln Asn Ser Ala Phe
               230     232

<210> SEQ ID NO 74
<211> LENGTH: 231
<212> TYPE: PRT
<213> ORGANISM: Homo sapiens

<400> SEQUENCE: 74

Lys Val Arg Thr Gln Leu Cys Pro Thr Pro C ys Thr Cys Pro Trp
  1                 5                  10                  15

Pro Pro Pro Arg Cys Pro Leu Gly Val Pro L eu Val Leu Asp Gly
                20                  25                  30

Cys Gly Cys Cys Arg Val Cys Ala Arg Leu  L eu Gly Glu Pro Cys
                35                  40                  45

Asp Gln Leu His Val Cys Asp Ala Ser Gln G ly Leu Val Cys Gln
                50                  55                  60

Pro Gly Ala Gly Pro Gly Gly Arg Gly Ala L eu Cys Leu Leu Ala
                65                  70                  75

Glu Asp Asp Ser Ser Cys Glu Val Asn Gly A rg Leu Tyr Arg Glu
                80                  85                  90

Gly Glu Thr Phe Gln Pro His Cys Ser Ile A rg Cys Arg Cys Glu
                95                 100                 105

Asp Gly Gly Phe Thr Cys Val Pro Leu Cys S er Glu Asp Val Arg
               110                 115                 120

Leu Pro Ser Trp Asp Cys Pro His Pro Arg A rg Val Glu Val Leu
               125                 130                 135

Gly Lys Cys Cys Pro Glu Trp Val Cys Gly G ln Gly Gly Leu
               140                 145                 150

Gly Thr Gln Pro Leu Pro Ala Gln Gly Pro G ln Phe Ser Gly Leu
               155                 160                 165

Val Ser Ser Leu Pro Pro Gly Val Pro Cys P ro Glu Trp Ser Thr
```

```
                    170                 175                 180
Ala Trp Gly Pro Cys Ser Thr Thr Cys Gly Leu Gly Met Ala Thr
                185                 190                 195
Arg Val Ser Asn Gln Asn Arg Phe Cys Arg Leu Glu Thr Gln Arg
            200                 205                 210
Arg Leu Cys Leu Ser Arg Pro Cys Pro Pro Ser Arg Gly Arg Ser
        215                 220                 225
Pro Gln Asn Ser Ala Phe
            230 231

<210> SEQ ID NO 75
<211> LENGTH: 230
<212> TYPE: PRT
<213> ORGANISM: Homo sapiens

<400> SEQUENCE: 75

Val Arg Thr Gln Leu Cys Pro Thr Pro Cys Thr Cys Pro Trp Pro
  1               5                  10                  15
Pro Pro Arg Cys Pro Leu Gly Val Pro Leu Val Leu Asp Gly Cys
                 20                  25                  30
Gly Cys Cys Arg Val Cys Ala Arg Arg Leu Gly Glu Pro Cys Asp
                 35                  40                  45
Gln Leu His Val Cys Asp Ala Ser Gln Gly Leu Val Cys Gln Pro
                 50                  55                  60
Gly Ala Gly Pro Gly Gly Arg Gly Ala Leu Cys Leu Leu Ala Glu
             65                  70                  75
Asp Asp Ser Ser Cys Glu Val Asn Gly Arg Leu Tyr Arg Glu Gly
                 80                  85                  90
Glu Thr Phe Gln Pro His Cys Ser Ile Arg Cys Arg Cys Glu Asp
                 95                 100                 105
Gly Gly Phe Thr Cys Val Pro Leu Cys Ser Glu Asp Val Arg Leu
                110                 115                 120
Pro Ser Trp Asp Cys Pro His Pro Arg Arg Val Glu Val Leu Gly
                125                 130                 135
Lys Cys Cys Pro Glu Trp Val Cys Gly Gln Gly Gly Gly Leu Gly
                140                 145                 150
Thr Gln Pro Leu Pro Ala Gln Gly Pro Gln Phe Ser Gly Leu Val
                155                 160                 165
Ser Ser Leu Pro Pro Gly Val Pro Cys Pro Glu Trp Ser Thr Ala
                170                 175                 180
Trp Gly Pro Cys Ser Thr Thr Cys Gly Leu Gly Met Ala Thr Arg
                185                 190                 195
Val Ser Asn Gln Asn Arg Phe Cys Arg Leu Glu Thr Gln Arg Arg
            200                 205                 210
Leu Cys Leu Ser Arg Pro Cys Pro Pro Ser Arg Gly Arg Ser Pro
        215                 220                 225
Gln Asn Ser Ala Phe
            230

<210> SEQ ID NO 76
<211> LENGTH: 229
<212> TYPE: PRT
<213> ORGANISM: Homo sapiens

<400> SEQUENCE: 76

Arg Thr Gln Leu Cys Pro Thr Pro Cys Thr Cys Pro Trp Pro Pro
```

```
                1               5                  10                 15
          Pro Arg Cys Pro Leu Gly Val Pro Leu Val Leu Asp Gly Cys Gly
                              20                 25                 30
          Cys Cys Arg Val Cys Ala Arg Leu Gly Glu Pro Cys Asp Gln
                              35                 40                 45
          Leu His Val Cys Asp Ala Ser Gln Gly Leu Val Cys Gln Pro Gly
                              50                 55                 60
          Ala Gly Pro Gly Gly Arg Gly Ala Leu Cys Leu Leu Ala Glu Asp
                              65                 70                 75
          Asp Ser Ser Cys Glu Val Asn Gly Arg Leu Tyr Arg Glu Gly Glu
                              80                 85                 90
          Thr Phe Gln Pro His Cys Ser Ile Arg Cys Arg Cys Glu Asp Gly
                              95                 100                105
          Gly Phe Thr Cys Val Pro Leu Cys Ser Glu Asp Val Arg Leu Pro
                              110                115                120
          Ser Trp Asp Cys Pro His Pro Arg Arg Val Glu Val Leu Gly Lys
                              125                130                135
          Cys Cys Pro Glu Trp Val Cys Gly Gln Gly Gly Leu Gly Thr
                              140                145                150
          Gln Pro Leu Pro Ala Gln Gly Pro Gln Phe Ser Gly Leu Val Ser
                              155                160                165
          Ser Leu Pro Pro Gly Val Pro Cys Pro Glu Trp Ser Thr Ala Trp
                              170                175                180
          Gly Pro Cys Ser Thr Thr Cys Gly Leu Gly Met Ala Thr Arg Val
                              185                190                195
          Ser Asn Gln Asn Arg Phe Cys Arg Leu Glu Thr Gln Arg Arg Leu
                              200                205                210
          Cys Leu Ser Arg Pro Cys Pro Pro Ser Arg Gly Arg Ser Pro Gln
                              215                220                225
          Asn Ser Ala Phe
                              229

<210> SEQ ID NO 77
<211> LENGTH: 228
<212> TYPE: PRT
<213> ORGANISM: Homo sapiens

<400> SEQUENCE: 77

Thr Gln Leu Cys Pro Thr Pro Cys Thr Cys Pro Trp Pro Pro Pro
            1               5                  10                 15
          Arg Cys Pro Leu Gly Val Pro Leu Val Leu Asp Gly Cys Gly Cys
                              20                 25                 30
          Cys Arg Val Cys Ala Arg Leu Gly Glu Pro Cys Asp Gln Leu
                              35                 40                 45
          His Val Cys Asp Ala Ser Gln Gly Leu Val Cys Gln Pro Gly Ala
                              50                 55                 60
          Gly Pro Gly Gly Arg Gly Ala Leu Cys Leu Leu Ala Glu Asp Asp
                              65                 70                 75
          Ser Ser Cys Glu Val Asn Gly Arg Leu Tyr Arg Glu Gly Glu Thr
                              80                 85                 90
          Phe Gln Pro His Cys Ser Ile Arg Cys Arg Cys Glu Asp Gly Gly
                              95                 100                105
          Phe Thr Cys Val Pro Leu Cys Ser Glu Asp Val Arg Leu Pro Ser
                              110                115                120
```

-continued

```
Trp Asp Cys Pro His Pro Arg Arg Val Glu Val Leu Gly Lys Cys
            125                 130                 135

Cys Pro Glu Trp Val Cys Gly Gln Gly Gly Leu Gly Thr Gln
            140                 145                 150

Pro Leu Pro Ala Gln Gly Pro Gln Phe Ser Gly Leu Val Ser Ser
            155                 160                 165

Leu Pro Gly Val Pro Cys Pro Glu Trp Ser Thr Ala Trp Gly
            170                 175                 180

Pro Cys Ser Thr Thr Cys Gly Leu Gly Met Ala Thr Arg Val Ser
            185                 190                 195

Asn Gln Asn Arg Phe Cys Arg Leu Glu Thr Gln Arg Arg Leu Cys
            200                 205                 210

Leu Ser Arg Pro Cys Pro Pro Ser Arg Gly Arg Ser Pro Gln Asn
            215                 220                 225

Ser Ala Phe
       228

<210> SEQ ID NO 78
<211> LENGTH: 250
<212> TYPE: PRT
<213> ORGANISM: Homo sapiens

<400> SEQUENCE: 78

Arg Gly Asn Pro Leu Ile His Leu Leu Ala Ile Ser Phe Leu Cys
 1               5                  10                  15

Ile Leu Ser Met Val Tyr Ser Gln Leu Cys Pro Ala Pro Cys Ala
                20                  25                  30

Cys Pro Trp Thr Pro Pro Gln Cys Pro Pro Gly Val Pro Leu Val
                35                  40                  45

Leu Asp Gly Cys Gly Cys Cys Arg Val Cys Ala Arg Arg Leu Gly
                50                  55                  60

Glu Ser Cys Asp His Leu His Val Cys Asp Pro Ser Gln Gly Leu
                65                  70                  75

Val Cys Gln Pro Gly Ala Gly Pro Ser Gly Arg Gly Ala Val Cys
                80                  85                  90

Leu Phe Glu Glu Asp Asp Gly Ser Cys Glu Val Asn Gly Arg Arg
                95                  100                 105

Tyr Leu Asp Gly Glu Thr Phe Lys Pro Asn Cys Arg Val Leu Cys
                110                 115                 120

Arg Cys Asp Asp Gly Gly Phe Thr Cys Leu Pro Leu Cys Ser Glu
                125                 130                 135

Asp Val Arg Leu Pro Ser Trp Asp Cys Pro Arg Pro Arg Arg Ile
                140                 145                 150

Gln Val Pro Gly Arg Cys Cys Pro Glu Trp Val Cys Asp Gln Ala
                155                 160                 165

Val Met Gln Pro Ala Ile Gln Pro Ser Ala Gln Gly His Gln
                170                 175                 180

Leu Ser Ala Leu Val Thr Pro Ala Ser Ala Asp Gly Pro Cys Pro
                185                 190                 195

Asn Trp Ser Thr Ala Trp Gly Pro Cys Ser Thr Thr Cys Gly Leu
                200                 205                 210

Gly Ile Ala Thr Arg Val Ser Asn Gln Asn Arg Phe Cys Gln Leu
                215                 220                 225

Glu Ile Gln Arg Arg Leu Cys Leu Ser Arg Pro Cys Leu Ala Ser
                230                 235                 240
```

-continued

```
Arg Ser His Gly Ser Trp Asn Ser Ala Phe
            245                 250

<210> SEQ ID NO 79
<211> LENGTH: 249
<212> TYPE: PRT
<213> ORGANISM: Homo sapiens

<400> SEQUENCE: 79

Gly Asn Pro Leu Ile His Leu Leu Ala Ile Ser Phe Leu Cys Ile
  1               5                  10                  15

Leu Ser Met Val Tyr Ser Gln Leu Cys Pro Ala Pro Cys Ala Cys
                 20                  25                  30

Pro Trp Thr Pro Pro Gln Cys Pro Pro Gly Val Pro Leu Val Leu
                 35                  40                  45

Asp Gly Cys Gly Cys Cys Arg Val Cys Ala Arg Arg Leu Gly Glu
                 50                  55                  60

Ser Cys Asp His Leu His Val Cys Asp Pro Ser Gln Gly Leu Val
                 65                  70                  75

Cys Gln Pro Gly Ala Gly Pro Ser Gly Arg Gly Ala Val Cys Leu
                 80                  85                  90

Phe Glu Glu Asp Asp Gly Ser Cys Glu Val Asn Gly Arg Arg Tyr
                 95                 100                 105

Leu Asp Gly Glu Thr Phe Lys Pro Asn Cys Arg Val Leu Cys Arg
                110                 115                 120

Cys Asp Asp Gly Gly Phe Thr Cys Leu Pro Leu Cys Ser Glu Asp
                125                 130                 135

Val Arg Leu Pro Ser Trp Asp Cys Pro Arg Pro Arg Arg Ile Gln
                140                 145                 150

Val Pro Gly Arg Cys Cys Pro Glu Trp Val Cys Asp Gln Ala Val
                155                 160                 165

Met Gln Pro Ala Ile Gln Pro Ser Ser Ala Gln Gly His Gln Leu
                170                 175                 180

Ser Ala Leu Val Thr Pro Ala Ser Ala Asp Gly Pro Cys Pro Asn
                185                 190                 195

Trp Ser Thr Ala Trp Gly Pro Cys Ser Thr Thr Cys Gly Leu Gly
                200                 205                 210

Ile Ala Thr Arg Val Ser Asn Gln Asn Arg Phe Cys Gln Leu Glu
                215                 220                 225

Ile Gln Arg Arg Leu Cys Leu Ser Arg Pro Cys Leu Ala Ser Arg
                230                 235                 240

Ser His Gly Ser Trp Asn Ser Ala Phe
            245                 249

<210> SEQ ID NO 80
<211> LENGTH: 248
<212> TYPE: PRT
<213> ORGANISM: Homo sapiens

<400> SEQUENCE: 80

Asn Pro Leu Ile His Leu Leu Ala Ile Ser Phe Leu Cys Ile Leu
  1               5                  10                  15

Ser Met Val Tyr Ser Gln Leu Cys Pro Ala Pro Cys Ala Cys Pro
                 20                  25                  30

Trp Thr Pro Pro Gln Cys Pro Pro Gly Val Pro Leu Val Leu Asp
                 35                  40                  45
```

```
Gly Cys Gly Cys Cys Arg Val Cys Ala Arg Arg Leu Gly Glu Ser
                50                  55                  60

Cys Asp His Leu His Val Cys Asp Pro Ser Gln Gly Leu Val Cys
             65                  70                  75

Gln Pro Gly Ala Gly Pro Ser Gly Arg Gly Ala Val Cys Leu Phe
             80                  85                  90

Glu Glu Asp Asp Gly Ser Cys Glu Val Asn Gly Arg Arg Tyr Leu
             95                 100                 105

Asp Gly Glu Thr Phe Lys Pro Asn Cys Arg Val Leu Cys Arg Cys
            110                 115                 120

Asp Asp Gly Gly Phe Thr Cys Leu Pro Leu Cys Ser Glu Asp Val
            125                 130                 135

Arg Leu Pro Ser Trp Asp Cys Pro Arg Pro Arg Arg Ile Gln Val
            140                 145                 150

Pro Gly Arg Cys Cys Pro Glu Trp Val Cys Asp Gln Ala Val Met
            155                 160                 165

Gln Pro Ala Ile Gln Pro Ser Ser Ala Gln Gly His Gln Leu Ser
            170                 175                 180

Ala Leu Val Thr Pro Ala Ser Ala Asp Gly Pro Cys Pro Asn Trp
            185                 190                 195

Ser Thr Ala Trp Gly Pro Cys Ser Thr Thr Cys Gly Leu Gly Ile
            200                 205                 210

Ala Thr Arg Val Ser Asn Gln Asn Arg Phe Cys Gln Leu Glu Ile
            215                 220                 225

Gln Arg Arg Leu Cys Leu Ser Arg Pro Cys Leu Ala Ser Arg Ser
            230                 235                 240

His Gly Ser Trp Asn Ser Ala Phe
            245             248

<210> SEQ ID NO 81
<211> LENGTH: 247
<212> TYPE: PRT
<213> ORGANISM: Homo sapiens

<400> SEQUENCE: 81

Pro Leu Ile His Leu Leu Ala Ile Ser Phe Leu Cys Ile Leu Ser
  1               5                  10                  15

Met Val Tyr Ser Gln Leu Cys Pro Ala Pro Cys Ala Cys Pro Trp
             20                  25                  30

Thr Pro Pro Gln Cys Pro Pro Gly Val Pro Leu Val Leu Asp Gly
             35                  40                  45

Cys Gly Cys Cys Arg Val Cys Ala Arg Arg Leu Gly Glu Ser Cys
             50                  55                  60

Asp His Leu His Val Cys Asp Pro Ser Gln Gly Leu Val Cys Gln
             65                  70                  75

Pro Gly Ala Gly Pro Ser Gly Arg Gly Ala Val Cys Leu Phe Glu
             80                  85                  90

Glu Asp Asp Gly Ser Cys Glu Val Asn Gly Arg Arg Tyr Leu Asp
             95                 100                 105

Gly Glu Thr Phe Lys Pro Asn Cys Arg Val Leu Cys Arg Cys Asp
            110                 115                 120

Asp Gly Gly Phe Thr Cys Leu Pro Leu Cys Ser Glu Asp Val Arg
            125                 130                 135

Leu Pro Ser Trp Asp Cys Pro Arg Pro Arg Arg Ile Gln Val Pro
```

```
                    140                 145                 150
Gly Arg Cys Cys Pro Glu Trp Val Cys Asp Gln Ala Val Met Gln
                155                 160                 165
Pro Ala Ile Gln Pro Ser Ser Ala Gln Gly His Gln Leu Ser Ala
                170                 175                 180
Leu Val Thr Pro Ala Ser Ala Asp Gly Pro Cys Pro Asn Trp Ser
                185                 190                 195
Thr Ala Trp Gly Pro Cys Ser Thr Thr Cys Gly Leu Gly Ile Ala
                200                 205                 210
Thr Arg Val Ser Asn Gln Asn Arg Phe Cys Gln Leu Glu Ile Gln
                215                 220                 225
Arg Arg Leu Cys Leu Ser Arg Pro Cys Leu Ala Ser Arg Ser His
                230                 235                 240
Gly Ser Trp Asn Ser Ala Phe
                245     247

<210> SEQ ID NO 82
<211> LENGTH: 246
<212> TYPE: PRT
<213> ORGANISM: Homo sapiens

<400> SEQUENCE: 82

Leu Ile His Leu Leu Ala Ile Ser Phe Leu Cys Ile Leu Ser Met
  1               5                  10                  15
Val Tyr Ser Gln Leu Cys Pro Ala Pro Cys Ala Cys Pro Trp Thr
                 20                  25                  30
Pro Pro Gln Cys Pro Pro Gly Val Pro Leu Val Leu Asp Gly Cys
                 35                  40                  45
Gly Cys Cys Arg Val Cys Ala Arg Arg Leu Gly Glu Ser Cys Asp
                 50                  55                  60
His Leu His Val Cys Asp Pro Ser Gln Gly Leu Val Cys Gln Pro
                 65                  70                  75
Gly Ala Gly Pro Ser Gly Arg Gly Ala Val Cys Leu Phe Glu Glu
                 80                  85                  90
Asp Asp Gly Ser Cys Glu Val Asn Gly Arg Arg Tyr Leu Asp Gly
                 95                 100                 105
Glu Thr Phe Lys Pro Asn Cys Arg Val Leu Cys Arg Cys Asp Asp
                110                 115                 120
Gly Gly Phe Thr Cys Leu Pro Leu Cys Ser Glu Asp Val Arg Leu
                125                 130                 135
Pro Ser Trp Asp Cys Pro Arg Pro Arg Arg Ile Gln Val Pro Gly
                140                 145                 150
Arg Cys Cys Pro Glu Trp Val Cys Asp Gln Ala Val Met Gln Pro
                155                 160                 165
Ala Ile Gln Pro Ser Ser Ala Gln Gly His Gln Leu Ser Ala Leu
                170                 175                 180
Val Thr Pro Ala Ser Ala Asp Gly Pro Cys Pro Asn Trp Ser Thr
                185                 190                 195
Ala Trp Gly Pro Cys Ser Thr Thr Cys Gly Leu Gly Ile Ala Thr
                200                 205                 210
Arg Val Ser Asn Gln Asn Arg Phe Cys Gln Leu Glu Ile Gln Arg
                215                 220                 225
Arg Leu Cys Leu Ser Arg Pro Cys Leu Ala Ser Arg Ser His Gly
                230                 235                 240
```

```
Ser Trp Asn Ser Ala Phe
            245 246

<210> SEQ ID NO 83
<211> LENGTH: 245
<212> TYPE: PRT
<213> ORGANISM: Homo sapiens

<400> SEQUENCE: 83

Ile His Leu Leu Ala Ile Ser Phe Leu Cys Ile Leu Ser Met Val
  1               5                  10                  15

Tyr Ser Gln Leu Cys Pro Ala Pro Cys Cys Pro Trp Thr Pro
                 20                  25                  30

Pro Gln Cys Pro Pro Gly Val Pro Leu Val Leu Asp Gly Cys Gly
                 35                  40                  45

Cys Cys Arg Val Cys Ala Arg Arg Leu Gly Glu Ser Cys Asp His
                 50                  55                  60

Leu His Val Cys Asp Pro Ser Gln Gly Leu Val Cys Gln Pro Gly
                 65                  70                  75

Ala Gly Pro Ser Gly Arg Gly Ala Val Cys Leu Phe Glu Glu Asp
                 80                  85                  90

Asp Gly Ser Cys Glu Val Asn Gly Arg Arg Tyr Leu Asp Gly Glu
                 95                 100                 105

Thr Phe Lys Pro Asn Cys Arg Val Leu Cys Arg Cys Asp Asp Gly
                110                 115                 120

Gly Phe Thr Cys Leu Pro Leu Cys Ser Glu Asp Val Arg Leu Pro
                125                 130                 135

Ser Trp Asp Cys Pro Arg Pro Arg Arg Ile Gln Val Pro Gly Arg
                140                 145                 150

Cys Cys Pro Glu Trp Val Cys Asp Gln Ala Val Met Gln Pro Ala
                155                 160                 165

Ile Gln Pro Ser Ser Ala Gln Gly His Gln Leu Ser Ala Leu Val
                170                 175                 180

Thr Pro Ala Ser Ala Asp Gly Pro Cys Pro Asn Trp Ser Thr Ala
                185                 190                 195

Trp Gly Pro Cys Ser Thr Thr Cys Gly Leu Gly Ile Ala Thr Arg
                200                 205                 210

Val Ser Asn Gln Asn Arg Phe Cys Gln Leu Glu Ile Gln Arg Arg
                215                 220                 225

Leu Cys Leu Ser Arg Pro Cys Leu Ala Ser Arg Ser His Gly Ser
                230                 235                 240

Trp Asn Ser Ala Phe
                245

<210> SEQ ID NO 84
<211> LENGTH: 244
<212> TYPE: PRT
<213> ORGANISM: Homo sapiens

<400> SEQUENCE: 84

His Leu Leu Ala Ile Ser Phe Leu Cys Ile Leu Ser Met Val Tyr
  1               5                  10                  15

Ser Gln Leu Cys Pro Ala Pro Cys Ala Cys Pro Trp Thr Pro Pro
                 20                  25                  30

Gln Cys Pro Pro Gly Val Pro Leu Val Leu Asp Gly Cys Gly Cys
                 35                  40                  45
```

```
Cys Arg Val Cys Ala Arg Arg Leu Gly Glu Ser Cys Asp His Leu
                50                  55                  60

His Val Cys Asp Pro Ser Gln Gly Leu Val Cys Gln Pro Gly Ala
            65                  70                  75

Gly Pro Ser Gly Arg Gly Ala Val Cys Leu Phe Glu Glu Asp Asp
        80                  85                  90

Gly Ser Cys Glu Val Asn Gly Arg Arg Tyr Leu Asp Gly Glu Thr
            95                  100                 105

Phe Lys Pro Asn Cys Arg Val Leu Cys Arg Cys Asp Asp Gly Gly
                110                 115                 120

Phe Thr Cys Leu Pro Leu Cys Ser Glu Asp Val Arg Leu Pro Ser
            125                 130                 135

Trp Asp Cys Pro Arg Pro Arg Arg Ile Gln Val Pro Gly Arg Cys
            140                 145                 150

Cys Pro Glu Trp Val Cys Asp Gln Ala Val Met Gln Pro Ala Ile
            155                 160                 165

Gln Pro Ser Ser Ala Gln Gly His Gln Leu Ser Ala Leu Val Thr
            170                 175                 180

Pro Ala Ser Ala Asp Gly Pro Cys Pro Asn Trp Ser Thr Ala Trp
            185                 190                 195

Gly Pro Cys Ser Thr Thr Cys Gly Leu Gly Ile Ala Thr Arg Val
            200                 205                 210

Ser Asn Gln Asn Arg Phe Cys Gln Leu Glu Ile Gln Arg Arg Leu
            215                 220                 225

Cys Leu Ser Arg Pro Cys Leu Ala Ser Arg Ser His Gly Ser Trp
            230                 235                 240

Asn Ser Ala Phe
            244

<210> SEQ ID NO 85
<211> LENGTH: 243
<212> TYPE: PRT
<213> ORGANISM: Homo sapiens

<400> SEQUENCE: 85

Leu Leu Ala Ile Ser Phe Leu Cys Ile Leu Ser Met Val Tyr Ser
  1               5                   10                  15

Gln Leu Cys Pro Ala Pro Cys Ala Cys Pro Trp Thr Pro Pro Gln
            20                  25                  30

Cys Pro Pro Gly Val Pro Leu Val Leu Asp Gly Cys Gly Cys Cys
            35                  40                  45

Arg Val Cys Ala Arg Arg Leu Gly Glu Ser Cys Asp His Leu His
            50                  55                  60

Val Cys Asp Pro Ser Gln Gly Leu Val Cys Gln Pro Gly Ala Gly
        65                  70                  75

Pro Ser Gly Arg Gly Ala Val Cys Leu Phe Glu Glu Asp Asp Gly
        80                  85                  90

Ser Cys Glu Val Asn Gly Arg Arg Tyr Leu Asp Gly Glu Thr Phe
            95                  100                 105

Lys Pro Asn Cys Arg Val Leu Cys Arg Cys Asp Asp Gly Gly Phe
            110                 115                 120

Thr Cys Leu Pro Leu Cys Ser Glu Asp Val Arg Leu Pro Ser Trp
            125                 130                 135

Asp Cys Pro Arg Pro Arg Arg Ile Gln Val Pro Gly Arg Cys Cys
            140                 145                 150
```

```
Pro Glu Trp Val Cys Asp Gln Ala Val Met Gln Pro Ala Ile Gln
            155                 160                 165

Pro Ser Ser Ala Gln Gly His Gln Leu Ser Ala Leu Val Thr Pro
            170                 175                 180

Ala Ser Ala Asp Gly Pro Cys Pro Asn Trp Ser Thr Ala Trp Gly
            185                 190                 195

Pro Cys Ser Thr Thr Cys Gly Leu Gly Ile Ala Thr Arg Val Ser
            200                 205                 210

Asn Gln Asn Arg Phe Cys Gln Leu Glu Ile Gln Arg Arg Leu Cys
            215                 220                 225

Leu Ser Arg Pro Cys Leu Ala Ser Arg Ser His Gly Ser Trp Asn
            230                 235                 240

Ser Ala Phe
        243

<210> SEQ ID NO 86
<211> LENGTH: 242
<212> TYPE: PRT
<213> ORGANISM: Homo sapiens

<400> SEQUENCE: 86

Leu Ala Ile Ser Phe Leu Cys Ile Leu Ser Met Val Tyr Ser Gln
 1               5                  10                  15

Leu Cys Pro Ala Pro Cys Ala Cys Pro Trp Thr Pro Pro Gln Cys
                20                  25                  30

Pro Pro Gly Val Pro Leu Val Leu Asp Gly Cys Gly Cys Cys Arg
                35                  40                  45

Val Cys Ala Arg Arg Leu Gly Glu Ser Cys Asp His Leu His Val
                50                  55                  60

Cys Asp Pro Ser Gln Gly Leu Val Cys Gln Pro Gly Ala Gly Pro
                65                  70                  75

Ser Gly Arg Gly Ala Val Cys Leu Phe Glu Glu Asp Asp Gly Ser
                80                  85                  90

Cys Glu Val Asn Gly Arg Arg Tyr Leu Asp Gly Glu Thr Phe Lys
                95                  100                 105

Pro Asn Cys Arg Val Leu Cys Arg Cys Asp Asp Gly Gly Phe Thr
                110                 115                 120

Cys Leu Pro Leu Cys Ser Glu Asp Val Arg Leu Pro Ser Trp Asp
                125                 130                 135

Cys Pro Arg Pro Arg Arg Ile Gln Val Pro Gly Arg Cys Cys Pro
                140                 145                 150

Glu Trp Val Cys Asp Gln Ala Val Met Gln Pro Ala Ile Gln Pro
                155                 160                 165

Ser Ser Ala Gln Gly His Gln Leu Ser Ala Leu Val Thr Pro Ala
                170                 175                 180

Ser Ala Asp Gly Pro Cys Pro Asn Trp Ser Thr Ala Trp Gly Pro
                185                 190                 195

Cys Ser Thr Thr Cys Gly Leu Gly Ile Ala Thr Arg Val Ser Asn
                200                 205                 210

Gln Asn Arg Phe Cys Gln Leu Glu Ile Gln Arg Arg Leu Cys Leu
                215                 220                 225

Ser Arg Pro Cys Leu Ala Ser Arg Ser His Gly Ser Trp Asn Ser
                230                 235                 240

Ala Phe
```

```
<210> SEQ ID NO 87
<211> LENGTH: 241
<212> TYPE: PRT
<213> ORGANISM: Homo sapiens

<400> SEQUENCE: 87
```

Ala Ile Ser Phe Leu Cys Ile Leu Ser Met Val Tyr Ser Gln Leu
 1               5                  10                  15

Cys Pro Ala Pro Cys Ala Cys Pro Trp Thr Pro Pro Gln Cys Pro
                20                  25                  30

Pro Gly Val Pro Leu Val Leu Asp Gly Cys Gly Cys Cys Arg Val
                35                  40                  45

Cys Ala Arg Arg Leu Gly Glu Ser Cys Asp His Leu His Val Cys
                50                  55                  60

Asp Pro Ser Gln Gly Leu Val Cys Gln Pro Gly Ala Gly Pro Ser
                65                  70                  75

Gly Arg Gly Ala Val Cys Leu Phe Glu Glu Asp Asp Gly Ser Cys
                80                  85                  90

Glu Val Asn Gly Arg Arg Tyr Leu Asp Gly Glu Thr Phe Lys Pro
                95                 100                 105

Asn Cys Arg Val Leu Cys Arg Cys Asp Asp Gly Gly Phe Thr Cys
               110                 115                 120

Leu Pro Leu Cys Ser Glu Asp Val Arg Leu Pro Ser Trp Asp Cys
               125                 130                 135

Pro Arg Pro Arg Arg Ile Gln Val Pro Gly Arg Cys Cys Pro Glu
               140                 145                 150

Trp Val Cys Asp Gln Ala Val Met Gln Pro Ala Ile Gln Pro Ser
               155                 160                 165

Ser Ala Gln Gly His Gln Leu Ser Ala Leu Val Thr Pro Ala Ser
               170                 175                 180

Ala Asp Gly Pro Cys Pro Asn Trp Ser Thr Ala Trp Gly Pro Cys
               185                 190                 195

Ser Thr Thr Cys Gly Leu Gly Ile Ala Thr Arg Val Ser Asn Gln
               200                 205                 210

Asn Arg Phe Cys Gln Leu Glu Ile Gln Arg Arg Leu Cys Leu Ser
               215                 220                 225

Arg Pro Cys Leu Ala Ser Arg Ser His Gly Ser Trp Asn Ser Ala
               230                 235                 240

Phe
241

```
<210> SEQ ID NO 88
<211> LENGTH: 240
<212> TYPE: PRT
<213> ORGANISM: Homo sapiens

<400> SEQUENCE: 88
```

Ile Ser Phe Leu Cys Ile Leu Ser Met Val Tyr Ser Gln Leu Cys
 1               5                  10                  15

Pro Ala Pro Cys Ala Cys Pro Trp Thr Pro Pro Gln Cys Pro Pro
                20                  25                  30

Gly Val Pro Leu Val Leu Asp Gly Cys Gly Cys Cys Arg Val Cys
                35                  40                  45

Ala Arg Arg Leu Gly Glu Ser Cys Asp His Leu His Val Cys Asp

```
                    50                  55                  60
Pro Ser Gln Gly Leu Val Cys Gln Pro Gly Ala Gly Pro Ser Gly
                65                  70                  75
Arg Gly Ala Val Cys Leu Phe Glu Glu Asp Asp Gly Ser Cys Glu
                80                  85                  90
Val Asn Gly Arg Arg Tyr Leu Asp Gly Glu Thr Phe Lys Pro Asn
                95                 100                 105
Cys Arg Val Leu Cys Arg Cys Asp Asp Gly Gly Phe Thr Cys Leu
               110                 115                 120
Pro Leu Cys Ser Glu Asp Val Arg Leu Pro Ser Trp Asp Cys Pro
               125                 130                 135
Arg Pro Arg Arg Ile Gln Val Pro Gly Arg Cys Cys Pro Glu Trp
               140                 145                 150
Val Cys Asp Gln Ala Val Met Gln Pro Ala Ile Gln Pro Ser Ser
               155                 160                 165
Ala Gln Gly His Gln Leu Ser Ala Leu Val Thr Pro Ala Ser Ala
               170                 175                 180
Asp Gly Pro Cys Pro Asn Trp Ser Thr Ala Trp Gly Pro Cys Ser
               185                 190                 195
Thr Thr Cys Gly Leu Gly Ile Ala Thr Arg Val Ser Asn Gln Asn
               200                 205                 210
Arg Phe Cys Gln Leu Glu Ile Gln Arg Arg Leu Cys Leu Ser Arg
               215                 220                 225
Pro Cys Leu Ala Ser Arg Ser His Gly Ser Trp Asn Ser Ala Phe
               230                 235                 240

<210> SEQ ID NO 89
<211> LENGTH: 239
<212> TYPE: PRT
<213> ORGANISM: Homo sapiens

<400> SEQUENCE: 89

Ser Phe Leu Cys Ile Leu Ser Met Val Tyr Ser Gln Leu Cys Pro
 1               5                  10                  15
Ala Pro Cys Ala Cys Pro Trp Thr Pro Pro Gln Cys Pro Pro Gly
                20                  25                  30
Val Pro Leu Val Leu Asp Gly Cys Gly Cys Cys Arg Val Cys Ala
                35                  40                  45
Arg Arg Leu Gly Glu Ser Cys Asp His Leu His Val Cys Asp Pro
                50                  55                  60
Ser Gln Gly Leu Val Cys Gln Pro Gly Ala Gly Pro Ser Gly Arg
                65                  70                  75
Gly Ala Val Cys Leu Phe Glu Glu Asp Asp Gly Ser Cys Glu Val
                80                  85                  90
Asn Gly Arg Arg Tyr Leu Asp Gly Glu Thr Phe Lys Pro Asn Cys
                95                 100                 105
Arg Val Leu Cys Arg Cys Asp Asp Gly Gly Phe Thr Cys Leu Pro
               110                 115                 120
Leu Cys Ser Glu Asp Val Arg Leu Pro Ser Trp Asp Cys Pro Arg
               125                 130                 135
Pro Arg Arg Ile Gln Val Pro Gly Arg Cys Cys Pro Glu Trp Val
               140                 145                 150
Cys Asp Gln Ala Val Met Gln Pro Ala Ile Gln Pro Ser Ser Ala
               155                 160                 165
```

```
Gln Gly His Gln Leu Ser Ala Leu Val Thr Pro Ala Ser Ala Asp
                170                 175                 180

Gly Pro Cys Pro Asn Trp Ser Thr Ala Trp Gly Pro Cys Ser Thr
            185                 190                 195

Thr Cys Gly Leu Gly Ile Ala Thr Arg Val Ser Asn Gln Asn Arg
            200                 205                 210

Phe Cys Gln Leu Glu Ile Gln Arg Arg Leu Cys Leu Ser Arg Pro
            215                 220                 225

Cys Leu Ala Ser Arg Ser His Gly Ser Trp Asn Ser Ala Phe
            230                 235             239

<210> SEQ ID NO 90
<211> LENGTH: 238
<212> TYPE: PRT
<213> ORGANISM: Homo sapiens

<400> SEQUENCE: 90

Phe Leu Cys Ile Leu Ser Met Val Tyr Ser Gln Leu Cys Pro Ala
  1               5                  10                  15

Pro Cys Ala Cys Pro Trp Thr Pro Pro Gln Cys Pro Pro Gly Val
                 20                  25                  30

Pro Leu Val Leu Asp Gly Cys Gly Cys Cys Arg Val Cys Ala Arg
                 35                  40                  45

Arg Leu Gly Glu Ser Cys Asp His Leu His Val Cys Asp Pro Ser
                 50                  55                  60

Gln Gly Leu Val Cys Gln Pro Gly Ala Gly Pro Ser Gly Arg Gly
                 65                  70                  75

Ala Val Cys Leu Phe Glu Glu Asp Asp Gly Ser Cys Glu Val Asn
                 80                  85                  90

Gly Arg Arg Tyr Leu Asp Gly Glu Thr Phe Lys Pro Asn Cys Arg
                 95                 100                 105

Val Leu Cys Arg Cys Asp Asp Gly Gly Phe Thr Cys Leu Pro Leu
                110                 115                 120

Cys Ser Glu Asp Val Arg Leu Pro Ser Trp Asp Cys Pro Arg Pro
                125                 130                 135

Arg Arg Ile Gln Val Pro Gly Arg Cys Cys Pro Glu Trp Val Cys
                140                 145                 150

Asp Gln Ala Val Met Gln Pro Ala Ile Gln Pro Ser Ser Ala Gln
                155                 160                 165

Gly His Gln Leu Ser Ala Leu Val Thr Pro Ala Ser Ala Asp Gly
                170                 175                 180

Pro Cys Pro Asn Trp Ser Thr Ala Trp Gly Pro Cys Ser Thr Thr
                185                 190                 195

Cys Gly Leu Gly Ile Ala Thr Arg Val Ser Asn Gln Asn Arg Phe
                200                 205                 210

Cys Gln Leu Glu Ile Gln Arg Arg Leu Cys Leu Ser Arg Pro Cys
                215                 220                 225

Leu Ala Ser Arg Ser His Gly Ser Trp Asn Ser Ala Phe
                230                 235             238

<210> SEQ ID NO 91
<211> LENGTH: 237
<212> TYPE: PRT
<213> ORGANISM: Homo sapiens

<400> SEQUENCE: 91
```

```
Leu Cys Ile Leu Ser Met Val Tyr Ser Gln Leu Cys Pro Ala Pro
  1               5                  10                  15

Cys Ala Cys Pro Trp Thr Pro Pro Gln Cys Pro Pro Gly Val Pro
                 20                  25                  30

Leu Val Leu Asp Gly Cys Gly Cys Cys Arg Val Cys Ala Arg Arg
                 35                  40                  45

Leu Gly Glu Ser Cys Asp His Leu His Val Cys Asp Pro Ser Gln
                 50                  55                  60

Gly Leu Val Cys Gln Pro Gly Ala Gly Pro Ser Gly Arg Gly Ala
                 65                  70                  75

Val Cys Leu Phe Glu Glu Asp Asp Gly Ser Cys Glu Val Asn Gly
                 80                  85                  90

Arg Arg Tyr Leu Asp Gly Glu Thr Phe Lys Pro Asn Cys Arg Val
                 95                 100                 105

Leu Cys Arg Cys Asp Asp Gly Gly Phe Thr Cys Leu Pro Leu Cys
                110                 115                 120

Ser Glu Asp Val Arg Leu Pro Ser Trp Asp Cys Pro Arg Pro Arg
                125                 130                 135

Arg Ile Gln Val Pro Gly Arg Cys Cys Pro Glu Trp Val Cys Asp
                140                 145                 150

Gln Ala Val Met Gln Pro Ala Ile Gln Pro Ser Ser Ala Gln Gly
                155                 160                 165

His Gln Leu Ser Ala Leu Val Thr Pro Ala Ser Ala Asp Gly Pro
                170                 175                 180

Cys Pro Asn Trp Ser Thr Ala Trp Gly Pro Cys Ser Thr Thr Cys
                185                 190                 195

Gly Leu Gly Ile Ala Thr Arg Val Ser Asn Gln Asn Arg Phe Cys
                200                 205                 210

Gln Leu Glu Ile Gln Arg Arg Leu Cys Leu Ser Arg Pro Cys Leu
                215                 220                 225

Ala Ser Arg Ser His Gly Ser Trp Asn Ser Ala Phe
                230                 235     237

<210> SEQ ID NO 92
<211> LENGTH: 236
<212> TYPE: PRT
<213> ORGANISM: Homo sapiens

<400> SEQUENCE: 92

Cys Ile Leu Ser Met Val Tyr Ser Gln Leu Cys Pro Ala Pro Cys
  1               5                  10                  15

Ala Cys Pro Trp Thr Pro Pro Gln Cys Pro Pro Gly Val Pro Leu
                 20                  25                  30

Val Leu Asp Gly Cys Gly Cys Cys Arg Val Cys Ala Arg Arg Leu
                 35                  40                  45

Gly Glu Ser Cys Asp His Leu His Val Cys Asp Pro Ser Gln Gly
                 50                  55                  60

Leu Val Cys Gln Pro Gly Ala Gly Pro Ser Gly Arg Gly Ala Val
                 65                  70                  75

Cys Leu Phe Glu Glu Asp Asp Gly Ser Cys Glu Val Asn Gly Arg
                 80                  85                  90

Arg Tyr Leu Asp Gly Glu Thr Phe Lys Pro Asn Cys Arg Val Leu
                 95                 100                 105

Cys Arg Cys Asp Asp Gly Gly Phe Thr Cys Leu Pro Leu Cys Ser
                110                 115                 120
```

```
Glu Asp Val Arg Leu Pro Ser Trp Asp Cys Pro Arg Pro Arg Arg
            125                 130                 135

Ile Gln Val Pro Gly Arg Cys Cys Pro Glu Trp Val Cys Asp Gln
            140                 145                 150

Ala Val Met Gln Pro Ala Ile Gln Pro Ser Ser Ala Gln Gly His
            155                 160                 165

Gln Leu Ser Ala Leu Val Thr Pro Ala Ser Ala Asp Gly Pro Cys
            170                 175                 180

Pro Asn Trp Ser Thr Ala Trp Gly Pro Cys Ser Thr Thr Cys Gly
            185                 190                 195

Leu Gly Ile Ala Thr Arg Val Ser Asn Gln Asn Arg Phe Cys Gln
            200                 205                 210

Leu Glu Ile Gln Arg Arg Leu Cys Leu Ser Arg Pro Cys Leu Ala
            215                 220                 225

Ser Arg Ser His Gly Ser Trp Asn Ser Ala Phe
            230                 235 236

<210> SEQ ID NO 93
<211> LENGTH: 235
<212> TYPE: PRT
<213> ORGANISM: Homo sapiens

<400> SEQUENCE: 93

Ile Leu Ser Met Val Tyr Ser Gln Leu Cys Pro Ala Pro Cys Ala
 1               5                  10                  15

Cys Pro Trp Thr Pro Pro Gln Cys Pro Pro Gly Val Pro Leu Val
            20                  25                  30

Leu Asp Gly Cys Gly Cys Cys Arg Val Cys Ala Arg Arg Leu Gly
            35                  40                  45

Glu Ser Cys Asp His Leu His Val Cys Asp Pro Ser Gln Gly Leu
            50                  55                  60

Val Cys Gln Pro Gly Ala Gly Pro Ser Gly Arg Gly Ala Val Cys
            65                  70                  75

Leu Phe Glu Glu Asp Asp Gly Ser Cys Glu Val Asn Gly Arg Arg
            80                  85                  90

Tyr Leu Asp Gly Glu Thr Phe Lys Pro Asn Cys Arg Val Leu Cys
            95                  100                 105

Arg Cys Asp Asp Gly Gly Phe Thr Cys Leu Pro Leu Cys Ser Glu
            110                 115                 120

Asp Val Arg Leu Pro Ser Trp Asp Cys Pro Arg Pro Arg Arg Ile
            125                 130                 135

Gln Val Pro Gly Arg Cys Cys Pro Glu Trp Val Cys Asp Gln Ala
            140                 145                 150

Val Met Gln Pro Ala Ile Gln Pro Ser Ser Ala Gln Gly His Gln
            155                 160                 165

Leu Ser Ala Leu Val Thr Pro Ala Ser Ala Asp Gly Pro Cys Pro
            170                 175                 180

Asn Trp Ser Thr Ala Trp Gly Pro Cys Ser Thr Thr Cys Gly Leu
            185                 190                 195

Gly Ile Ala Thr Arg Val Ser Asn Gln Asn Arg Phe Cys Gln Leu
            200                 205                 210

Glu Ile Gln Arg Arg Leu Cys Leu Ser Arg Pro Cys Leu Ala Ser
            215                 220                 225

Arg Ser His Gly Ser Trp Asn Ser Ala Phe
            230                 235
```

```
                        230                 235

<210> SEQ ID NO 94
<211> LENGTH: 234
<212> TYPE: PRT
<213> ORGANISM: Homo sapiens

<400> SEQUENCE: 94

Leu Ser Met Val Tyr Ser Gln Leu Cys Pro Ala Pro Cys Ala Cys
  1               5                  10                  15

Pro Trp Thr Pro Pro Gln Cys Pro Pro Gly Val Pro Leu Val Leu
                 20                  25                  30

Asp Gly Cys Gly Cys Arg Val Cys Ala Arg Arg Leu Gly Glu
             35                  40                  45

Ser Cys Asp His Leu His Val Cys Asp Pro Ser Gln Gly Leu Val
             50                  55                  60

Cys Gln Pro Gly Ala Gly Pro Ser Gly Arg Gly Ala Val Cys Leu
             65                  70                  75

Phe Glu Glu Asp Asp Gly Ser Cys Glu Val Asn Gly Arg Arg Tyr
             80                  85                  90

Leu Asp Gly Glu Thr Phe Lys Pro Asn Cys Arg Val Leu Cys Arg
             95                 100                 105

Cys Asp Asp Gly Gly Phe Thr Cys Leu Pro Leu Cys Ser Glu Asp
            110                 115                 120

Val Arg Leu Pro Ser Trp Asp Cys Pro Arg Pro Arg Arg Ile Gln
            125                 130                 135

Val Pro Gly Arg Cys Cys Pro Glu Trp Val Cys Asp Gln Ala Val
            140                 145                 150

Met Gln Pro Ala Ile Gln Pro Ser Ser Ala Gln Gly His Gln Leu
            155                 160                 165

Ser Ala Leu Val Thr Pro Ala Ser Ala Asp Gly Pro Cys Pro Asn
            170                 175                 180

Trp Ser Thr Ala Trp Gly Pro Cys Ser Thr Thr Cys Gly Leu Gly
            185                 190                 195

Ile Ala Thr Arg Val Ser Asn Gln Asn Arg Phe Cys Gln Leu Glu
            200                 205                 210

Ile Gln Arg Arg Leu Cys Leu Ser Arg Pro Cys Leu Ala Ser Arg
            215                 220                 225

Ser His Gly Ser Trp Asn Ser Ala Phe
            230                 234

<210> SEQ ID NO 95
<211> LENGTH: 233
<212> TYPE: PRT
<213> ORGANISM: Homo sapiens

<400> SEQUENCE: 95

Ser Met Val Tyr Ser Gln Leu Cys Pro Ala Pro Cys Ala Cys Pro
  1               5                  10                  15

Trp Thr Pro Pro Gln Cys Pro Pro Gly Val Pro Leu Val Leu Asp
                 20                  25                  30

Gly Cys Gly Cys Cys Arg Val Cys Ala Arg Arg Leu Gly Glu Ser
             35                  40                  45

Cys Asp His Leu His Val Cys Asp Pro Ser Gln Gly Leu Val Cys
             50                  55                  60

Gln Pro Gly Ala Gly Pro Ser Gly Arg Gly Ala Val Cys Leu Phe
```

```
                65                  70                  75
Glu Glu Asp Asp Gly Ser Cys Glu Val Asn Gly Arg Arg Tyr Leu
                    80                  85                  90
Asp Gly Glu Thr Phe Lys Pro Asn Cys Arg Val Leu Cys Arg Cys
                    95                 100                 105
Asp Asp Gly Gly Phe Thr Cys Leu Pro Leu Cys Ser Glu Asp Val
                   110                 115                 120
Arg Leu Pro Ser Trp Asp Cys Pro Arg Arg Arg Ile Gln Val
                   125                 130                 135
Pro Gly Arg Cys Cys Pro Glu Trp Val Cys Asp Gln Ala Val Met
                   140                 145                 150
Gln Pro Ala Ile Gln Pro Ser Ser Ala Gln Gly His Gln Leu Ser
                   155                 160                 165
Ala Leu Val Thr Pro Ala Ser Ala Asp Gly Pro Cys Pro Asn Trp
                   170                 175                 180
Ser Thr Ala Trp Gly Pro Cys Ser Thr Thr Cys Gly Leu Gly Ile
                   185                 190                 195
Ala Thr Arg Val Ser Asn Gln Asn Arg Phe Cys Gln Leu Glu Ile
                   200                 205                 210
Gln Arg Arg Leu Cys Leu Ser Arg Pro Cys Leu Ala Ser Arg Ser
                   215                 220                 225
His Gly Ser Trp Asn Ser Ala Phe
                   230         233

<210> SEQ ID NO 96
<211> LENGTH: 232
<212> TYPE: PRT
<213> ORGANISM: Homo sapiens

<400> SEQUENCE: 96

Met Val Tyr Ser Gln Leu Cys Pro Ala Pro Cys Ala Cys Pro Trp
  1               5                  10                  15
Thr Pro Pro Gln Cys Pro Pro Gly Val Pro Leu Val Leu Asp Gly
                    20                  25                  30
Cys Gly Cys Cys Arg Val Cys Ala Arg Arg Leu Gly Glu Ser Cys
                    35                  40                  45
Asp His Leu His Val Cys Asp Pro Ser Gln Gly Leu Val Cys Gln
                    50                  55                  60
Pro Gly Ala Gly Pro Ser Gly Arg Gly Ala Val Cys Leu Phe Glu
                    65                  70                  75
Glu Asp Asp Gly Ser Cys Glu Val Asn Gly Arg Arg Tyr Leu Asp
                    80                  85                  90
Gly Glu Thr Phe Lys Pro Asn Cys Arg Val Leu Cys Arg Cys Asp
                    95                 100                 105
Asp Gly Gly Phe Thr Cys Leu Pro Leu Cys Ser Glu Asp Val Arg
                   110                 115                 120
Leu Pro Ser Trp Asp Cys Pro Arg Pro Arg Arg Ile Gln Val Pro
                   125                 130                 135
Gly Arg Cys Cys Pro Glu Trp Val Cys Asp Gln Ala Val Met Gln
                   140                 145                 150
Pro Ala Ile Gln Pro Ser Ser Ala Gln Gly His Gln Leu Ser Ala
                   155                 160                 165
Leu Val Thr Pro Ala Ser Ala Asp Gly Pro Cys Pro Asn Trp Ser
                   170                 175                 180
```

-continued

```
Thr Ala Trp Gly Pro Cys Ser Thr Thr Cys Gly Leu Gly Ile Ala
                185                 190                 195

Thr Arg Val Ser Asn Gln Asn Arg Phe Cys Gln Leu Glu Ile Gln
                200                 205                 210

Arg Arg Leu Cys Leu Ser Arg Pro Cys Leu Ala Ser Arg Ser His
                215                 220                 225

Gly Ser Trp Asn Ser Ala Phe
                230     232

<210> SEQ ID NO 97
<211> LENGTH: 231
<212> TYPE: PRT
<213> ORGANISM: Homo sapiens

<400> SEQUENCE: 97

Val Tyr Ser Gln Leu Cys Pro Ala Pro Ala Cys Pro Trp Thr
  1               5                  10                  15

Pro Pro Gln Cys Pro Pro Gly Val Pro Leu Val Leu Asp Gly Cys
                 20                  25                  30

Gly Cys Cys Arg Val Cys Ala Arg Arg Leu Gly Glu Ser Cys Asp
                 35                  40                  45

His Leu His Val Cys Asp Pro Ser Gln Gly Leu Val Cys Gln Pro
                 50                  55                  60

Gly Ala Gly Pro Ser Gly Arg Gly Ala Val Cys Leu Phe Glu Glu
                 65                  70                  75

Asp Asp Gly Ser Cys Glu Val Asn Gly Arg Arg Tyr Leu Asp Gly
                 80                  85                  90

Glu Thr Phe Lys Pro Asn Cys Arg Val Leu Cys Arg Cys Asp Asp
                 95                 100                 105

Gly Gly Phe Thr Cys Leu Pro Leu Cys Ser Glu Asp Val Arg Leu
                110                 115                 120

Pro Ser Trp Asp Cys Pro Arg Pro Arg Arg Ile Gln Val Pro Gly
                125                 130                 135

Arg Cys Cys Pro Glu Trp Val Cys Asp Gln Ala Val Met Gln Pro
                140                 145                 150

Ala Ile Gln Pro Ser Ser Ala Gln Gly His Gln Leu Ser Ala Leu
                155                 160                 165

Val Thr Pro Ala Ser Ala Asp Gly Pro Cys Pro Asn Trp Ser Thr
                170                 175                 180

Ala Trp Gly Pro Cys Ser Thr Thr Cys Gly Leu Gly Ile Ala Thr
                185                 190                 195

Arg Val Ser Asn Gln Asn Arg Phe Cys Gln Leu Glu Ile Gln Arg
                200                 205                 210

Arg Leu Cys Leu Ser Arg Pro Cys Leu Ala Ser Arg Ser His Gly
                215                 220                 225

Ser Trp Asn Ser Ala Phe
                230 231

<210> SEQ ID NO 98
<211> LENGTH: 230
<212> TYPE: PRT
<213> ORGANISM: Homo sapiens

<400> SEQUENCE: 98

Tyr Ser Gln Leu Cys Pro Ala Pro Cys Ala Cys Pro Trp Thr Pro
  1               5                  10                  15
```

Pro Gln Cys Pro Pro Gly Val Pro Leu Val Leu Asp Gly Cys Gly
                20                  25                  30

Cys Cys Arg Val Cys Ala Arg Arg Leu Gly Glu Ser Cys Asp His
            35                  40                  45

Leu His Val Cys Asp Pro Ser Gln Gly Leu Val Cys Gln Pro Gly
            50                  55                  60

Ala Gly Pro Ser Gly Arg Gly Ala Val Cys Leu Phe Glu Glu Asp
            65                  70                  75

Asp Gly Ser Cys Glu Val Asn Gly Arg Arg Tyr Leu Asp Gly Glu
            80                  85                  90

Thr Phe Lys Pro Asn Cys Arg Val Leu Cys Arg Cys Asp Asp Gly
            95                 100                 105

Gly Phe Thr Cys Leu Pro Leu Cys Ser Glu Asp Val Arg Leu Pro
           110                 115                 120

Ser Trp Asp Cys Pro Arg Pro Arg Arg Ile Gln Val Pro Gly Arg
           125                 130                 135

Cys Cys Pro Glu Trp Val Cys Asp Gln Ala Val Met Gln Pro Ala
           140                 145                 150

Ile Gln Pro Ser Ser Ala Gln Gly His Gln Leu Ser Ala Leu Val
           155                 160                 165

Thr Pro Ala Ser Ala Asp Gly Pro Cys Pro Asn Trp Ser Thr Ala
           170                 175                 180

Trp Gly Pro Cys Ser Thr Thr Cys Gly Leu Gly Ile Ala Thr Arg
           185                 190                 195

Val Ser Asn Gln Asn Arg Phe Cys Gln Leu Glu Ile Gln Arg Arg
           200                 205                 210

Leu Cys Leu Ser Arg Pro Cys Leu Ala Ser Arg Ser His Gly Ser
           215                 220                 225

Trp Asn Ser Ala Phe
           230

<210> SEQ ID NO 99
<211> LENGTH: 229
<212> TYPE: PRT
<213> ORGANISM: Homo sapiens

<400> SEQUENCE: 99

Ser Gln Leu Cys Pro Ala Pro Cys Ala Cys Pro Trp Thr Pro Pro
 1               5                  10                  15

Gln Cys Pro Pro Gly Val Pro Leu Val Leu Asp Gly Cys Gly Cys
                20                  25                  30

Cys Arg Val Cys Ala Arg Arg Leu Gly Glu Ser Cys Asp His Leu
            35                  40                  45

His Val Cys Asp Pro Ser Gln Gly Leu Val Cys Gln Pro Gly Ala
            50                  55                  60

Gly Pro Ser Gly Arg Gly Ala Val Cys Leu Phe Glu Glu Asp Asp
            65                  70                  75

Gly Ser Cys Glu Val Asn Gly Arg Arg Tyr Leu Asp Gly Glu Thr
            80                  85                  90

Phe Lys Pro Asn Cys Arg Val Leu Cys Arg Cys Asp Asp Gly Gly
            95                 100                 105

Phe Thr Cys Leu Pro Leu Cys Ser Glu Asp Val Arg Leu Pro Ser
           110                 115                 120

Trp Asp Cys Pro Arg Pro Arg Arg Ile Gln Val Pro Gly Arg Cys
           125                 130                 135

```
Cys Pro Glu Trp Val Cys Asp Gln Ala Val Met Gln Pro Ala Ile
            140                 145                 150

Gln Pro Ser Ser Ala Gln Gly His Gln Leu Ser Ala Leu Val Thr
            155                 160                 165

Pro Ala Ser Ala Asp Gly Pro Cys Pro Asn Trp Ser Thr Ala Trp
            170                 175                 180

Gly Pro Cys Ser Thr Thr Cys Gly Leu Gly Ile Ala Thr Arg Val
            185                 190                 195

Ser Asn Gln Asn Arg Phe Cys Gln Leu Glu Ile Gln Arg Arg Leu
            200                 205                 210

Cys Leu Ser Arg Pro Cys Leu Ala Ser Arg Ser His Gly Ser Trp
            215                 220                 225

Asn Ser Ala Phe
            229

<210> SEQ ID NO 100
<211> LENGTH: 22
<212> TYPE: DNA
<213> ORGANISM: Artificial sequence
<220> FEATURE:
<221> NAME/KEY: misc_feature
<222> LOCATION: 1-22
<223> OTHER INFORMATION: Sequence is synthesized.

<400> SEQUENCE: 100
ccagccagag gaggccacga ac                                    22

<210> SEQ ID NO 101
<211> LENGTH: 24
<212> TYPE: DNA
<213> ORGANISM: Artificial sequence
<220> FEATURE:
<221> NAME/KEY: misc_feature
<222> LOCATION: 1-24
<223> OTHER INFORMATION: Sequence is synthesized.

<400> SEQUENCE: 101
gtacttgggt cggtaggtgc gtgt                                  24

<210> SEQ ID NO 102
<211> LENGTH: 23
<212> TYPE: DNA
<213> ORGANISM: Artificial sequence
<220> FEATURE:
<221> NAME/KEY: misc_feature
<222> LOCATION: 1-23
<223> OTHER INFORMATION: Sequence is synthesized.

<400> SEQUENCE: 102
gtggcccatg ctctggcaga ggg                                   23

<210> SEQ ID NO 103
<211> LENGTH: 24
<212> TYPE: DNA
<213> ORGANISM: Artificial sequence
<220> FEATURE:
<221> NAME/KEY: misc_feature
<222> LOCATION: 1-24
<223> OTHER INFORMATION: Sequence is synthesized.

<400> SEQUENCE: 103
gactggagca aggtcgtcct cgcc                                  24
```

```
<210> SEQ ID NO 104
<211> LENGTH: 24
<212> TYPE: DNA
<213> ORGANISM: Artificial sequence
<220> FEATURE:
<221> NAME/KEY: misc_feature
<222> LOCATION: 1-24
<223> OTHER INFORMATION: Sequence is synthesized.

<400> SEQUENCE: 104
gcaccaccca caaggaagcc atcc                                              24

<210> SEQ ID NO 105
<211> LENGTH: 24
<212> TYPE: DNA
<213> ORGANISM: Artificial sequence
<220> FEATURE:
<221> NAME/KEY: misc_feature
<222> LOCATION: 1-24
<223> OTHER INFORMATION: Sequence is synthesized.

<400> SEQUENCE: 105
gacgaaaggg aagccggcat cacc                                              24

<210> SEQ ID NO 106
<211> LENGTH: 24
<212> TYPE: DNA
<213> ORGANISM: Artificial sequence
<220> FEATURE:
<221> NAME/KEY: misc_feature
<222> LOCATION: 1-24
<223> OTHER INFORMATION: Sequence is synthesized.

<400> SEQUENCE: 106
gagaaggtcg tgttcgagca aacc                                              24

<210> SEQ ID NO 107
<211> LENGTH: 24
<212> TYPE: DNA
<213> ORGANISM: Artificial sequence
<220> FEATURE:
<221> NAME/KEY: misc_feature
<222> LOCATION: 1-24
<223> OTHER INFORMATION: Sequence is synthesized.

<400> SEQUENCE: 107
cttctcgtgt acttcctgtg cctg                                              24

<210> SEQ ID NO 108
<211> LENGTH: 24
<212> TYPE: DNA
<213> ORGANISM: Artificial sequence
<220> FEATURE:
<221> NAME/KEY: misc_feature
<222> LOCATION: 1-24
<223> OTHER INFORMATION: Sequence is synthesized.

<400> SEQUENCE: 108
cacgtcagct ggcgttgcca gctc                                              24

<210> SEQ ID NO 109
<211> LENGTH: 23
<212> TYPE: PRT
<213> ORGANISM: Artificial sequence
<220> FEATURE:
<221> NAME/KEY: misc_feature
<222> LOCATION: 1-23
<223> OTHER INFORMATION: Sequence is synthesized.
```

-continued

<400> SEQUENCE: 109

Gln Pro Glu Glu Ala Thr Asn Phe Thr Leu Ala Gly Cys Val Ser
1               5                   10                  15

Thr Arg Thr Tyr Arg Pro Lys Tyr
            20          23

<210> SEQ ID NO 110
<211> LENGTH: 24
<212> TYPE: DNA
<213> ORGANISM: Artificial sequence
<220> FEATURE:
<221> NAME/KEY: misc_feature
<222> LOCATION: 1-24
<223> OTHER INFORMATION: Sequence is synthesized.

<400> SEQUENCE: 110
ggccctggcc tgccagaagt gtgg                                      24

<210> SEQ ID NO 111
<211> LENGTH: 24
<212> TYPE: DNA
<213> ORGANISM: Artificial sequence
<220> FEATURE:
<221> NAME/KEY: misc_feature
<222> LOCATION: 1-24
<223> OTHER INFORMATION: Sequence is synthesized.

<400> SEQUENCE: 111
gtgtgccttt cctgatctga gaac                                      24

<210> SEQ ID NO 112
<211> LENGTH: 50
<212> TYPE: DNA
<213> ORGANISM: Artificial sequence
<220> FEATURE:
<221> NAME/KEY: misc_feature
<222> LOCATION: 1-50
<223> OTHER INFORMATION: Sequence is synthesized.

<400> SEQUENCE: 112
gtgattccat ctcttcatgt tcccagaaaa ttcttcccag ccgggcaggg           50

<210> SEQ ID NO 113
<211> LENGTH: 70
<212> TYPE: DNA
<213> ORGANISM: Artificial sequence
<220> FEATURE:
<221> NAME/KEY: misc_feature
<222> LOCATION: 1-70
<223> OTHER INFORMATION: Sequence is synthesized.

<400> SEQUENCE: 113
ccagccagag gaggccacga acttcactct cgcaggctgt gtcagcacac           50
gcacctaccg acccaagtac                                           70

<210> SEQ ID NO 114
<211> LENGTH: 50
<212> TYPE: DNA
<213> ORGANISM: Artificial sequence
<220> FEATURE:
<221> NAME/KEY: misc_feature
<222> LOCATION: 1-50
<223> OTHER INFORMATION: Sequence is synthesized.

<400> SEQUENCE: 114 gccctggag cccttgctcc accagctgcg gcctggggt ctccactcgg             50

<210> SEQ ID NO 115
<211> LENGTH: 23
<212> TYPE: DNA
<213> ORGANISM: Artificial sequence
<220> FEATURE:
<221> NAME/KEY: misc_feature
<222> LOCATION: 1-23
<223> OTHER INFORMATION: Sequence is synthesized.

<400> SEQUENCE: 115
aaaggtgcgt acccagctgt gcc                                          23

<210> SEQ ID NO 116
<211> LENGTH: 24
<212> TYPE: DNA
<213> ORGANISM: Artificial sequence
<220> FEATURE:
<221> NAME/KEY: misc_feature
<222> LOCATION: 1-24
<223> OTHER INFORMATION: Sequence is synthesized.

<400> SEQUENCE: 116
ggtcttggcg aagacggctg acct                                         24

<210> SEQ ID NO 117
<211> LENGTH: 51
<212> TYPE: DNA
<213> ORGANISM: Artificial sequence
<220> FEATURE:
<221> NAME/KEY: misc_feature
<222> LOCATION: 1-51
<223> OTHER INFORMATION: Sequence is synthesized.

<400> SEQUENCE: 117
cctggtgctg gatggctgtg gctgctgccg ggtatgtgca cggcggctgg             50
g                                                                  51

<210> SEQ ID NO 118
<211> LENGTH: 28
<212> TYPE: DNA
<213> ORGANISM: Artificial sequence
<220> FEATURE:
<221> NAME/KEY: misc_feature
<222> LOCATION: 1-28
<223> OTHER INFORMATION: Sequence is synthesized.

<400> SEQUENCE: 118
gtcttgtgca agcaacaaaa tggactcc                                     28

<210> SEQ ID NO 119
<211> LENGTH: 27
<212> TYPE: DNA
<213> ORGANISM: Artificial sequence
<220> FEATURE:
<221> NAME/KEY: misc_feature
<222> LOCATION: 1-27
<223> OTHER INFORMATION: Sequence is synthesized.

<400> SEQUENCE: 119
gctgtcgcaa ggctgaatgt aacacag                                      27

<210> SEQ ID NO 120
<211> LENGTH: 50
<212> TYPE: DNA
<213> ORGANISM: Artificial sequence
<220> FEATURE:

<221> NAME/KEY: misc_feature
<222> LOCATION: 1-50
<223> OTHER INFORMATION: Sequence is synthesized.

<400> SEQUENCE: 120
gctccagaac atgtgggatg ggaatatcta acagggtgac caatgaaaac          50

<210> SEQ ID NO 121
<211> LENGTH: 23
<212> TYPE: DNA
<213> ORGANISM: Artificial sequence
<220> FEATURE:
<221> NAME/KEY: misc_feature
<222> LOCATION: 1-23
<223> OTHER INFORMATION: Sequence is synthesized.

<400> SEQUENCE: 121
cctggagtga gcctggtgag aga                                       23

<210> SEQ ID NO 122
<211> LENGTH: 27
<212> TYPE: DNA
<213> ORGANISM: Artificial sequence
<220> FEATURE:
<221> NAME/KEY: misc_feature
<222> LOCATION: 1-27
<223> OTHER INFORMATION: Sequence is synthesized.

<400> SEQUENCE: 122
acaatacagc cctttgtgtg ggtcaca                                   27

<210> SEQ ID NO 123
<211> LENGTH: 44
<212> TYPE: DNA
<213> ORGANISM: Artificial sequence
<220> FEATURE:
<221> NAME/KEY: misc_feature
<222> LOCATION: 1-44
<223> OTHER INFORMATION: Sequence is synthesized.

<400> SEQUENCE: 123
tggttgcttg gcacagattt tacagcatcc acagccatct ctca                44

<210> SEQ ID NO 124
<211> LENGTH: 27
<212> TYPE: DNA
<213> ORGANISM: Artificial sequence
<220> FEATURE:
<221> NAME/KEY: misc_feature
<222> LOCATION: 1-27
<223> OTHER INFORMATION: Sequence is synthesized.

<400> SEQUENCE: 124
tgacttccag gcatgaggtg gctcctg                                   27

<210> SEQ ID NO 125
<211> LENGTH: 34
<212> TYPE: DNA
<213> ORGANISM: Artificial sequence
<220> FEATURE:
<221> NAME/KEY: misc_feature
<222> LOCATION: 1-34
<223> OTHER INFORMATION: Sequence is synthesized.

<400> SEQUENCE: 125
attggcaatc tcttcgaagt cagggtaaga ttcc                           34

```
<210> SEQ ID NO 126
<211> LENGTH: 40
<212> TYPE: DNA
<213> ORGANISM: Artificial sequence
<220> FEATURE:
<221> NAME/KEY: misc_feature
<222> LOCATION: 1-40
<223> OTHER INFORMATION: Sequence is synthesized.

<400> SEQUENCE: 126
ggtacgtcta gactaattgg caatctcttc gaagtcaggg                          40

<210> SEQ ID NO 127
<211> LENGTH: 42
<212> TYPE: DNA
<213> ORGANISM: Artificial sequence
<220> FEATURE:
<221> NAME/KEY: misc_feature
<222> LOCATION: 1-42
<223> OTHER INFORMATION: Sequence is synthesized.

<400> SEQUENCE: 127 tttcccttttg gatcctaaac caacatgagg tggctcctgc cc                      42

<210> SEQ ID NO 128
<211> LENGTH: 20
<212> TYPE: DNA
<213> ORGANISM: Artificial sequence
<220> FEATURE:
<221> NAME/KEY: misc_feature
<222> LOCATION: 1-20
<223> OTHER INFORMATION: Sequence is synthesized.

<400> SEQUENCE: 128
cagattggtg ctggatatgc                                                20

<210> SEQ ID NO 129
<211> LENGTH: 20
<212> TYPE: DNA
<213> ORGANISM: Artificial sequence
<220> FEATURE:
<221> NAME/KEY: misc_feature
<222> LOCATION: 1-20
<223> OTHER INFORMATION: Sequence is synthesized.

<400> SEQUENCE: 129
actgccttga ttactcctac                                                20

<210> SEQ ID NO 130
<211> LENGTH: 18
<212> TYPE: DNA
<213> ORGANISM: Artificial sequence
<220> FEATURE:
<221> NAME/KEY: misc_feature
<222> LOCATION: 1-18
<223> OTHER INFORMATION: Sequence is synthesized.

<400> SEQUENCE: 130
agttgcagat gtggctct                                                  18

<210> SEQ ID NO 131
<211> LENGTH: 18
<212> TYPE: DNA
<213> ORGANISM: Artificial sequence
<220> FEATURE:
<221> NAME/KEY: misc_feature
<222> LOCATION: 1-18
<223> OTHER INFORMATION: Sequence is synthesized.
```

```
<400> SEQUENCE: 131
agtccaagag tctcagca                                                    18

<210> SEQ ID NO 132
<211> LENGTH: 18
<212> TYPE: DNA
<213> ORGANISM: Artificial sequence
<220> FEATURE:
<221> NAME/KEY: misc_feature
<222> LOCATION: 1-18
<223> OTHER INFORMATION: Sequence is synthesized.

<400> SEQUENCE: 132
acaactggaa gcactgga                                                    18

<210> SEQ ID NO 133
<211> LENGTH: 18
<212> TYPE: DNA
<213> ORGANISM: Artificial sequence
<220> FEATURE:
<221> NAME/KEY: misc_feature
<222> LOCATION: 1-18
<223> OTHER INFORMATION: Sequence is synthesized.

<400> SEQUENCE: 133
tcttattcca gaggaacc                                                    18

<210> SEQ ID NO 134
<211> LENGTH: 22
<212> TYPE: DNA
<213> ORGANISM: Artificial sequence
<220> FEATURE:
<221> NAME/KEY: misc_feature
<222> LOCATION: 1-22
<223> OTHER INFORMATION: Sequence is synthesized.

<400> SEQUENCE: 134
tccctgtacg cttctggtcg ta                                               22

<210> SEQ ID NO 135
<211> LENGTH: 22
<212> TYPE: DNA
<213> ORGANISM: Artificial sequence
<220> FEATURE:
<221> NAME/KEY: misc_feature
<222> LOCATION: 1-22
<223> OTHER INFORMATION: Sequence is synthesized.

<400> SEQUENCE: 135
tctcaaagtc caaagccaca ta                                               22

<210> SEQ ID NO 136
<211> LENGTH: 18
<212> TYPE: DNA
<213> ORGANISM: Artificial sequence
<220> FEATURE:
<221> NAME/KEY: misc_feature
<222> LOCATION: 1-18
<223> OTHER INFORMATION: Sequence is synthesized.

<400> SEQUENCE: 136
cacagttcca gcaaatac                                                    18

<210> SEQ ID NO 137
<211> LENGTH: 18
<212> TYPE: DNA
<213> ORGANISM: Artificial sequence
```

```
<220> FEATURE:
<221> NAME/KEY: misc_feature
<222> LOCATION: 1-18
<223> OTHER INFORMATION: Sequence is synthesized.

<400> SEQUENCE: 137
ggaatcaggc ggtacagt                                                  18

<210> SEQ ID NO 138
<211> LENGTH: 31
<212> TYPE: DNA
<213> ORGANISM: Artificial sequence
<220> FEATURE:
<221> NAME/KEY: misc_feature
<222> LOCATION: 1-31
<223> OTHER INFORMATION: Sequence is synthesized.

<400> SEQUENCE: 138
agcctttcca agtcactaga agtcctgctg g                                   31

<210> SEQ ID NO 139
<211> LENGTH: 21
<212> TYPE: DNA
<213> ORGANISM: Artificial sequence
<220> FEATURE:
<221> NAME/KEY: misc_feature
<222> LOCATION: 1-21
<223> OTHER INFORMATION: Sequence is synthesized.

<400> SEQUENCE: 139
ctggactaca cccaagcctg a                                              21

<210> SEQ ID NO 140
<211> LENGTH: 23
<212> TYPE: DNA
<213> ORGANISM: Artificial sequence
<220> FEATURE:
<221> NAME/KEY: misc_feature
<222> LOCATION: 1-23
<223> OTHER INFORMATION: Sequence is synthesized.

<400> SEQUENCE: 140
catttcttgg gatttaggca aga                                            23

<210> SEQ ID NO 141
<211> LENGTH: 19
<212> TYPE: DNA
<213> ORGANISM: Artificial sequence
<220> FEATURE:
<221> NAME/KEY: misc_feature
<222> LOCATION: 1-19
<223> OTHER INFORMATION: Sequence is synthesized.

<400> SEQUENCE: 141
tctagcccac tccctgcct                                                 19

<210> SEQ ID NO 142
<211> LENGTH: 21
<212> TYPE: DNA
<213> ORGANISM: Artificial sequence
<220> FEATURE:
<221> NAME/KEY: misc_feature
<222> LOCATION: 1-21
<223> OTHER INFORMATION: Sequence is synthesized.

<400> SEQUENCE: 142
gaagtcggag agaaagctcg c                                              21
```

<210> SEQ ID NO 143
<211> LENGTH: 30
<212> TYPE: DNA
<213> ORGANISM: Artificial sequence
<220> FEATURE:
<221> NAME/KEY: misc_feature
<222> LOCATION: 1-30
<223> OTHER INFORMATION: Sequence is synthesized.

<400> SEQUENCE: 143
cacacacagc ctatatcaaa catgcacacg                              30

<210> SEQ ID NO 144
<211> LENGTH: 38
<212> TYPE: DNA
<213> ORGANISM: Artificial sequence
<220> FEATURE:
<221> NAME/KEY: misc_feature
<222> LOCATION: 1-38
<223> OTHER INFORMATION: Sequence is synthesized.

<400> SEQUENCE: 144
cttgagactg aaagatttag ccataatgta aactgcct                     38

<210> SEQ ID NO 145
<211> LENGTH: 22
<212> TYPE: DNA
<213> ORGANISM: Artificial sequence
<220> FEATURE:
<221> NAME/KEY: misc_feature
<222> LOCATION: 1-22
<223> OTHER INFORMATION: Sequence is synthesized.

<400> SEQUENCE: 145
caaatgcaac ctcacaacct tg                                      22

<210> SEQ ID NO 146
<211> LENGTH: 24
<212> TYPE: DNA
<213> ORGANISM: Artificial sequence
<220> FEATURE:
<221> NAME/KEY: misc_feature
<222> LOCATION: 1-24
<223> OTHER INFORMATION: Sequence is synthesized.

<400> SEQUENCE: 146
ttcttttatg cccaaagtcc aatt                                    24

<210> SEQ ID NO 147
<211> LENGTH: 48
<212> TYPE: DNA
<213> ORGANISM: Artificial sequence
<220> FEATURE:
<221> NAME/KEY: misc_feature
<222> LOCATION: 1-48
<223> OTHER INFORMATION: Sequence is synthesized.

<400> SEQUENCE: 147
ggattctaat acgactcact atagggcgtc cctggccagt gctgtgag          48

<210> SEQ ID NO 148
<211> LENGTH: 48
<212> TYPE: DNA
<213> ORGANISM: Artificial sequence
<220> FEATURE:
<221> NAME/KEY: misc_feature
<222> LOCATION: 1-48
<223> OTHER INFORMATION: Sequence is synthesized.

<400> SEQUENCE: 148
ctatgaaatt aaccctcact aaagggaggg ccaggctttg cttccatt    48

<210> SEQ ID NO 149
<211> LENGTH: 47
<212> TYPE: DNA
<213> ORGANISM: Artificial sequence
<220> FEATURE:
<221> NAME/KEY: misc_feature
<222> LOCATION: 1-47
<223> OTHER INFORMATION: Sequence is synthesized.

<400> SEQUENCE: 149
ggattctaat acgactcact atagggctgg aggcatggca caggaac    47

<210> SEQ ID NO 150
<211> LENGTH: 48
<212> TYPE: DNA
<213> ORGANISM: Artificial sequence
<220> FEATURE:
<221> NAME/KEY: misc_feature
<222> LOCATION: 1-48
<223> OTHER INFORMATION: Sequence is synthesized.

<400> SEQUENCE: 150
ctatgaaatt aaccctcact aaagggatcc ggatcaggct tgggtgta    48

<210> SEQ ID NO 151
<211> LENGTH: 48
<212> TYPE: DNA
<213> ORGANISM: Artificial sequence
<220> FEATURE:
<221> NAME/KEY: misc_feature
<222> LOCATION: 1-48
<223> OTHER INFORMATION: Sequence is synthesized.

<400> SEQUENCE: 151
ggattctaat acgactcact atagggcagc ttgggatgga ggtctttc    48

<210> SEQ ID NO 152
<211> LENGTH: 44
<212> TYPE: DNA
<213> ORGANISM: Artificial sequence
<220> FEATURE:
<221> NAME/KEY: misc_feature
<222> LOCATION: 1-44
<223> OTHER INFORMATION: Sequence is synthesized.

<400> SEQUENCE: 152
ctatgaaatt aaccctcact aaagggaggg cactggggtg gtgt    44

<210> SEQ ID NO 153
<211> LENGTH: 45
<212> TYPE: DNA
<213> ORGANISM: Artificial sequence
<220> FEATURE:
<221> NAME/KEY: misc_feature
<222> LOCATION: 1-45
<223> OTHER INFORMATION: Sequence is synthesized.

<400> SEQUENCE: 153
ggattctaat acgactcact atagggcgcg aggacggcgg cttca    45

<210> SEQ ID NO 154
<211> LENGTH: 48
<212> TYPE: DNA

```
<213> ORGANISM: Artificial sequence
<220> FEATURE:
<221> NAME/KEY: misc_feature
<222> LOCATION: 1-48
<223> OTHER INFORMATION: Sequence is synthesized.

<400> SEQUENCE: 154
ctatgaaatt aaccctcact aaagggaaga gtcgcggccg ccctttt            48

<210> SEQ ID NO 155
<211> LENGTH: 48
<212> TYPE: DNA
<213> ORGANISM: Artificial sequence
<220> FEATURE:
<221> NAME/KEY: misc_feature
<222> LOCATION: 1-48
<223> OTHER INFORMATION: Sequence is synthesized.

<400> SEQUENCE: 155
ggattctaat acgactcact atagggcggg gctcctcttc tccactct            48

<210> SEQ ID NO 156
<211> LENGTH: 48
<212> TYPE: DNA
<213> ORGANISM: Artificial sequence
<220> FEATURE:
<221> NAME/KEY: misc_feature
<222> LOCATION: 1-48
<223> OTHER INFORMATION: Sequence is synthesized.

<400> SEQUENCE: 156
ctatgaaatt aaccctcact aaagggagct gtcgcaaggc tgaatgta            48
```

WISP POLYPEPTIDES AND NUCLEIC ACIDS ENCODING SAME

RELATED APPLICATIONS

This is a non-provisional application claiming priority to provisional application No. 60/063,704, filed Oct. 29, 1997, to provisional application No. 60/073,612, filed Feb. 4, 1998, and to provisional application No. 60/081,695, filed Apr. 14, 1998, the entire disclosure of which applications are hereby incorporated by reference.

GOVERNMENT LICENSE RIGHTS

This invention was made with government support under grant no. 5P01 CA41086, awarded by the National Institutes of Health, National Cancer Institute. The government has certain rights in the invention.

FIELD OF THE INVENTION

The present invention relates generally to the identification and isolation of novel DNA and to the recombinant production of novel polypeptides having homology to connective tissue growth factor, designated herein as Wnt-1-Induced Secreted Proteins (WISPs).

BACKGROUND OF THE INVENTION

Malignant tumors (cancers) are the second leading cause of death in the United States, after heart disease. Boring et al., *CA Cancer J. Clin.,* 43: 7 (1993).

Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites (metastasis). In a cancerous state a cell proliferates under conditions in which normal cells would not grow. Cancer manifests itself in a wide variety of forms, characterized by different degrees of invasiveness and aggressiveness.

Alteration of gene expression is intimately related to the uncontrolled cell growth and de-differentiation which are a common feature of all cancers. The genomes of certain well studied tumors have been found to show decreased expression of recessive genes, usually referred to as tumor suppression genes, which would normally function to prevent malignant cell growth, and/or overexpression of certain dominant genes, such as oncogenes, that act to promote malignant growth. Each of these genetic changes appears to be responsible for importing some of the traits that, in aggregate, represent the full neoplastic phenotype. Hunter, *Cell,* 64: 1129 (1991); Bishop, *Cell,* 64: 235–248 (1991).

A well-known mechanism of gene (e.g., oncogene) overexpression in cancer cells is gene amplification. This is a process where in the chromosome of the ancestral cell multiple copies of a particular gene are produced. The process involves unscheduled replication of the region of chromosome comprising the gene, followed by recombination of the replicated segments back into the chromosome. Alitalo et al., *Adv. Cancer Res.,* 47: 235–281 (1986). It is believed that the overexpression of the gene parallels gene amplification, i.e., is proportionate to the number of copies made.

Proto-oncogenes that encode growth factors and growth factor receptors have been identified to play important roles in the pathogenesis of various human malignancies, including breast cancer. For example, it has been found that the human ErbB2 gene (erbB2, also known as her2, or c-erbB-2), which encodes a 185-kd transmembrane glycoprotein receptor (p185$^{HER2}$; HER2) related to the epidermal growth factor receptor (EGFR), is overexpressed in about 25% to 30% of human breast cancer. Slamon et al., *Science,* 235:177–182 (1987); Slamon et al., *Science,* 244:707–712 (1989). It has been reported that gene amplification of a protooncogen is an event typically involved in the more malignant forms of cancer, and could act as a predictor of clinical outcome. Schwab et al., *Genes Chromosomes Cancer,* 1: 181–193 (1990); Alitalo et al., supra. Thus, erbB2 overexpression is commonly regarded as a predictor of a poor prognosis, especially in patients with primary disease that involves axillary lymph nodes (Slamon et al., (1987) and (1989), supra; Ravdin and Chamness, *Gene,* 159:19–27 (1995); and Hynes and Stern, *Biochim Biophys Acta,* 1198:165–184 (1994)), and has been linked to sensitivity and/or resistance to hormone therapy and chemotherapeutic regimens, including CMF (cyclophosphamide, methotrexate, and fluoruracil) and anthracyclines. Baselga et al., *Oncology,* 11(3 Suppl 1):43–48 (1997). However, despite the association of erbB2 overexpression with poor prognosis, the odds of HER2-positive patients responding clinically to treatment with taxanes were greater than three times those of HER2-negative patients. Baselga et al., supra. A recombinant humanized anti-ErbB2 (anti-HER2) monoclonal antibody (a humanized version of the murine anti-ErbB2 antibody 4D5, referred to as rhuMAb HER2 or HERCEPTIN®) has been clinically active in patients with ErbB2-overexpressing metastatic breast cancers that had received extensive prior anticancer therapy. Baselga et al., *J. Clin. Oncol.,* 14:737–744 (1996).

Cytokines have been implicated in the pathogenesis of a number of brain diseases in which neurological dysfunction has been attributed to a change in amino acid neurotransmitter metabolism. In particular, members of the transforming growth factor-β (TGF-β) family have been implicated. TGF peptides are small polypeptides that were first identified by their ability to induce proliferation and transformation in noncancerous cells in culture. Although initially defined as a growth factor, TGF-β also inhibits proliferation of epithelial, endothelial, lymphoid, and hematopoietic cells. This cytokine is thought to play an important role in regulating the duration of the inflammatory response, allowing the healing process to proceed. It is also a potent immunomodulator, which has many pleiotrophic effects, including regulating many other cytokines.

The TGF-β superfamily includes bone morphogenetic proteins (BMP-2, BMP-4, BMP-5, BMP-6, BMP-7), activins A & B, decapentaplegic (dpp), 60A, OP-2, dorsalin, growth differentiation factors (GDFs), nodal, MIS, Inhibin-α, TGF-β1, TGF-β2, TGF-β3, TGF-β5, and glial-derived neurotrophic factor (GDNF). Atrisano, et al., *J. Biochemica et Biophysica Acta,* 1222:71–80 (1994). Of particular interest are the growth differentiation factors, for as their name implies, these factors are implicated in the differentiation of cells.

Connective tissue growth factor (CTGF) is a growth factor induced in fibroblasts by many factors, including TGF-β, and is essential for the ability of TGF-β to induce anchorage-independent growth (AIG), a property of transformed cells. CTGF was discovered in an attempt to identify the type of platelet-derived growth factor (PDGF) dimers present in the growth media of cultured endothelial cells, and is related immunologically and biologically to PDGF. See U.S. Pat. No. 5,408,040. CTGF also is mitogenic and chemotactic for cells, and hence growth factors in this family are believed to play a role in the normal development, growth, and repair of human tissue.

Seven proteins related to CTGF, including the chicken ortholog for Cyr61, CEF10, human, mouse, and Xenopus laevis CTGF, and human, chicken, and Xenopus laevis Nov have been isolated, cloned, sequenced, and characterized as belonging to the CTGF gene family. Oemar and Luescher, *Arterioscler. Thromb. Vasc. Biol.,* 17: 1483–1489 (1997). The gene encoding Cyr61 has been found to promote angiogenesis, tumor growth, and vascularization. Babic et al., *Proc. Natl. Acad. Sci. USA,* 95: 6355–6360 (1998). The nov gene is expressed in the kidney essentially at the embryonic stage, and alterations of nov expression, relative to the normal kidney, have been detected in both avian nephroblastomas and human Wilms' tumors. Martinerie et al., *Oncoaene,* 9: 2729–2732 (1994). Wt1 downregulates human nov expression, which downregulation might represent a key element in normal and tumoral nephrogenesis. Martinerie et al., *Oncogene,* 12: 1479–1492 (1996). It has recently been proposed that the CTGF, nov, and cyr61 genes, which encode secreted proteins that contain conserved sequences and IGFBP motifs in their N-termini and bind IGFs with low affinity, represent more members of the IGFBP superfamily, along with the low-affinity mac25/IGFBP-7 (Yamanaka et al., *J. Biol. Chem.,* 272: 30729–30734 (1997)) and the high-affinity IGFBPs 1–6. CTGF under this proposal would be designated IGFBP-8. Kim et al., *Proc. Natl. Acad. Sci. USA,* 94: 12981–12986 (1997).

Recently, a protein was found in the mouse designated ELM1 that is expressed in low metastatic cells. Hashimoto et al., *J. Exp. Med.,* 187: 289–296 (1998). The elm1 gene, a mouse homologue of WISP-1 disclosed below, is another member of the CTGF, Cyr61/Cef10, and neuroblastoma overexpressed-gene family and suppresses in vivo tumor growth and metastasis of K-1735 murine melanoma cells. Another recent article on rCop-1, the rat orthologue of WISP-2 described below describes the loss of expression of this gene after cell transformation. Zhang et al., *Mol. Cell. Biol.,* 18:6131–6141 (1998).

CTGF family members (with the exception of nov) are immediate early growth-responsive genes that are thought to regulate cell proliferation, differentiation, embryogenesis, and wound healing. Sequence homology among members of the CTGF gene family is high; however, functions of these proteins in vitro range from growth stimulatory (i.e., human CTGF) to growth inhibitory (i.e., chicken Nov and also possibly hCTGF). Further, some molecules homologous to CTGF are indicated to be useful in the prevention of desmoplasia, the formation of highly cellular, excessive connective tissue stroma associated with some cancers, and fibrotic lesions associated with various skin disorders such as scleroderma, keloid, eosinophilic fasciitis, nodular fasciitis, and Dupuytren's contracture. Moreover, CTGF expression has recently been demonstrated in the fibrous stoma of mammary tumors, suggesting cancer stroma formation involves the induction of similar fibroproliferative growth factors as wound repair. Human CTGF is also expressed at very high levels in advanced atherosclerotic lesions, but not in normal arteries, suggesting it may play a role in atherosclerosis. Oemar and Luescher, supra. Therefore, molecules homologous to CTGF are of importance.

Extracellular and membrane-bound proteins play important roles in the formation, differentiation, and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones), which are, in turn, received and interpreted by diverse cell receptors or membrane-bound proteins. These secreted polypeptides or signaling molecules normally pass through the cellular secretory pathway to reach their site of action in the extracellular environment, usually at a membrane-bound receptor protein.

Secreted proteins have various industrial applications, including use as pharmaceuticals, diagnostics, biosensors, and bioreactors. In fact, most protein drugs available at present, such as thrombolytic agents, interferons, interleukins, erythropoietins, colony stimulating factors, and various other cytokines, are secreted proteins. Their receptors, which are membrane-bound proteins, also have potential as therapeutic or diagnostic agents. Receptor immunoadhesins, for instance, can be employed as therapeutic agents to block receptor-ligand interaction. Membrane-bound proteins can also be employed for screening of potential peptide or small molecule inhibitors of the relevant receptor/ligand interaction. Such membrane-bound proteins and cell receptors include, but are not limited to, cytokine receptors, receptor kinases, receptor phosphatases, receptors involved in cell-cell interactions, and cellular adhesin molecules like selectins and integrins. Transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Efforts are being undertaken by both industry and academia to identify new, native secreted and membrane-bound receptor proteins, particularly those having homology to CTGF. Many efforts are focused on the screening of mammalian recombinant DNA libraries to identify the coding sequences for novel secreted and membrane-bound receptor proteins. Examples of screening methods and techniques are described in the literature. See, for example, Klein et al., *Proc. Natl. Acad. Sci.,* 93:7108–7113 (1996); and U.S. Pat. No. 5,536,637.

Wnts are encoded by a large gene family whose members have been found in round worms, insects, cartilaginous fish, and vertebrates. Holland et al., *Dev. Suppl.,* 125–133 (1994). Wnts are thought to function in a variety of developmental and physiological processes since many diverse species have multiple conserved Wnt genes. McMahon, *Trends Genet.,* 8: 236–242 (1992); Nusse and Varmus, *Cell,* 69: 1073–1087 (1992). Wnt genes encode secreted glycoproteins that are thought to function as paracrine or autocrine signals active in several primitive cell types. McMahon, supra (1992); Nusse and Varmus, supra (1992). The Wnt growth factor family includes more than ten genes identified in the mouse (Wnt-1, -2, -3A, -3B, -4, -5A, -5B, -6, -7A, -7B, -8A, -8B, -10B, -11, -12, and -13) (see, e.g., Gavin et al., *Genes Dev.,* 4: 2319–2332 (1990); Lee et al., *Proc. Natl. Acad. Sci. USA,* 92: 2268–2272 (1995); Christiansen et al., *Mech. Dev.,* 51: 341–350 (1995)) and at least nine genes identified in the human (Wnt-1, -2, -3, -5A, -7A, -7B, -8B, -10B, and -11) by cDNA cloning. See, e.g., Vant Veer et al., *Mol.Cell.Biol.,* 4: 2532–2534 (1984).

The Wnt-1 proto-oncogene (int-1) was originally identified from mammary tumors induced by mouse mammary tumor virus (MMTV) due to an insertion of viral IDNA sequence. Nusse and Varmus, Cell, 31: 99–109 (1982). In adult mice, the expression level of Wnt-1 mRNA is detected only in the testis during later stages of sperm development. Wnt-1 protein is about 42 KDa and contains an amino-terminal hydrophobic region, which may function as a signal sequence for secretion (Nusse and Varmus, supra, 1992). The expression of Wnt-2/irp is detected in mouse fetal and adult tissues and its distribution does not overlap with the expression pattern for Wnt-1. Wnt-3 is associated with mouse mammary tumorigenesis. The expression of Wnt-3 in mouse embryos is detected in the neural tubes and in the limb buds. Wnt-5a transcripts are detected in the developing fore- and hind limbs at 9.5 through 14.5 days and highest levels are concentrated in apical ectoderm at the distal tip of limbs. Nusse and Varmus, supra (1992). Recently, a Wnt growth factor, termed Wnt-x, was described (WO95/17416) along with the detection of Wnt-x expression in bone tissues and in bone-derived cells. Also described was the role of Wnt-x in the maintenance of mature osteoblasts and the use of the Wnt-x growth factor as a therapeutic agent or in the development of other therapeutic agents to treat bone-related diseases.

Wnts may play a role in local cell signaling. Biochemical studies have shown that much of the secreted Wnt protein can be found associated with the cell surface or extracellular matrix rather than freely diffusible in the medium. Papkoff and Schryver, Mol. Cell. Biol., 10: 2723–2730 (1990); Bradley and Brown, EMBO J., 9: 1569–1575 (1990).

Studies of mutations in Wnt genes have indicated a role for Wnts in growth control and tissue patterning. In Drosophila, wingless (wg) encodes a Wnt-related gene (Rijsewik et al., Cell, 50: 649–657 (1987)) and wg mutations alter the pattern of embryonic ectoderm, neurogenesis, and imaginal disc outgrowth. Morata and Lawerence, Dev. Biol., 56: 227–240 (1977); Baker, Dev. Biol., 125: 96–108 (1988); Klingensmith and Nusse, Dev. Biol., 166: 396–414 (1994). In Caenorhabditis elegans, lin-44 encodes a Wnt homolog which is required for asymmetric cell divisions. Herman and Horvitz, Development, 120: 1035–1047 (1994). Knock-out mutations in mice have shown Wnts to be essential for brain development (McMahon and Bradley, Cell, 62: 1073–1085 (1990); Thomas and Cappechi, Nature, 346: 847–850 (1990)), and the outgrowth of embryonic primordia for kidney (Stark et al., Nature, 372: 679–683 (1994)), tail bud (Takada et al., Genes Dev., 8: 174–189 (1994)), and limb bud. Parr and McMahon, Nature, 374: 350–353 (1995). Overexpression of Wnts in the mammary gland can result in mammary hyperplasia (McMahon, supra (1992); Nusse and Varmus, supra (1992)), and precocious alveolar development. Bradbury et al., Dev. Biol., 170: 553–563 (1995).

Wnt-5a and Wnt-5b are expressed in the posterior and lateral mesoderm and the extraembryonic mesoderm of the day 7–8 murine embryo. Gavin et al., supra (1990). These embryonic domains contribute to the AGM region and yolk sac tissues from which multipotent hematopoietic precursors and HSCs are derived. Dzierzak and Medvinsky, Trends Genet., 11: 359–366 (1995); Zon et al., in Gluckman and Coulombel, ed., Colloque, INSERM, 235: 17–22 (1995), presented at the Joint International Workshop on Foetal and Neonatal Hematopoiesis and Mechanism of Bone Marrow Failure, Paris France, Apr. 3–6, 1995; Kanatsu and Nishikawa, Development, 122: 823–830 (1996). Wnt-5a, Wnt-10b, and other Wnts have been detected in limb buds, indicating possible roles in the development and patterning of the early bone microenvironment as shown for Wnt-7b. Gavin et al., supra (1990); Christiansen et al., Mech. Devel., 51: 341–350 (1995); Parr and McMahon, supra (1995).

The Wnt/Wg signal transduction pathway plays an important role in the biological development of the organism and has been implicated in several human cancers. This pathway also includes the tumor suppressor gene, APC. Mutations in the APC gene are associated with the development of sporadic and inherited forms of human colorectal cancer. The Wnt/Wg signal leads to the accumulation of beta-catenin/Armadillo in the cell, resulting in the formation of a bipartite transcription complex consisting of beta-catenin and a member of the lymphoid enhancer binding factor/T cell factor (LEF/TCF)HMG box transcription factor family. This complex translocates to the nucleus where it can activate expression of genes downstream of the Wnt/Wg signal, such as the engrailed and Ultrabithorax genes in Drosophila. The downstream target genes of Wnt-1 signaling in vertebrates that presumably function in tumorigenesis, however, are currently unknown.

For a most recent review on Wnt, see Cadigan and Nusse, Genes & Dev., 11: 3286–3305 (1997).

There is a need to elucidate the further members of the above families, including cell-surface molecules that may be tumor-specific antigens or proteins that serve a regulatory function in initiating the Wnt pathway of tumorigenesis. These would also include downstream components of the Wnt signaling pathway that are important to the transformed phenotype and the development of cancer.

SUMMARY OF THE INVENTION

Several putative Wnt-1-induced genes have been identified at the mRNA level in a high-throughput cDNA substraction experiment. Thus, applicants have identified novel cDNA clones (WISP1, WISP2, and WISP3) that encode novel polypeptides of the WISP family, designated as WISP-1, WISP-2, and WISP-3, respectively. This class of polypeptides was formerly referred to as Wnt-1-Induced Gene (WIG) polypeptides, with WISP-1 and WISP-2 formerly designated as WIG-1 and WIG-2, respectively. One of the cDNA clones encodes a novel polypeptide, human WISP-2, having homology to CTGF, wherein the polypeptide is designated in the present application as "human WISP-2" or "PRO261". The WISP-1 and WISP-3 molecules also have homology to CTGF.

In one embodiment, this invention provides isolated nucleic acid comprising DNA having at least about 600 nucleotides and at least about a 75% sequence identity to (a) a DNA molecule encoding a human WISP-1 polypeptide comprising the sequence of amino acids 23 to 367 of FIGS. 3A–3C (SEQ ID NO:3), or (b) the complement of the DNA molecule of (a). Preferably, this nucleic acid has at least one WISP biological activity. In a more preferred embodiment, this nucleic acid has at least about a 95% sequence identity to (a) a DNA molecule encoding a human WISP-1 polypeptide comprising the sequence of amino acids 23 to 367 of FIGS. 3A–3C (SEQ ID NO: 3), or (b) the complement of the DNA molecule of (a).

More preferred is the nucleic acid comprising DNA encoding a human WISP-1 polypeptide having amino acid residues 23 to 367 of FIGS. 3A–3C (SEQ ID NO:3), or DNA encoding a human WISP-1 polypeptide having amino acid residues 1 to 367 of FIGS. 3A–3C (SEQ ID NO:4), or the complement of either of the encoding DNAs. Further preferred is this nucleic acid comprising DNA encoding a human WISP-1 polypeptide having amino acid residues 23 to 367 or 1 to 367 of FIGS. 3A–3C except for an isoleucine residue at position 184 rather than a valine residue or a serine residue at position 202 rather than an alanine residue (SEQ ID NOS:5–8, respectively). Further preferred also is this nucleic acid comprising DNA encoding a human WISP-1 polypeptide having amino acid residues 23 to 367 or 1 to 367 of FIGS. 3A–3C except for an isoleucine residue at position 184 rather than a valine residue and a serine residue at position 202 rather than an alanine residue (SEQ ID NOS:21–22, respectively).

Also preferred is this nucleic acid comprising DNA encoding a mouse WISP-1 polypeptide having amino acid residues 23 to 367 of FIG. 1A–1B (SEQ ID NO:11), or DNA encoding a mouse WISP-1 polypeptide having amino acid residues 1 to 367 of FIGS. 1A–1B (SEQ ID NO:12), or the complement of either of the encoding DNAs.

Also provided by this invention is isolated nucleic acid comprising DNA having at least about 600 nucleotides and at least about a 85% sequence identity to (a) a DNA molecule encoding a mouse WISP-1 polypeptide comprising the sequence of amino acids 23 to 367 of FIGS. 1A–1B (SEQ ID NO:11), or (b) the complement of the DNA molecule of (a). Preferably, this nucleic acid has at least one WISP biological activity. More preferably, this nucleic acid comprises DNA having at least about a 95% sequence identity to (a) a DNA molecule encoding a mouse WISP-1 polypeptide comprising the sequence of amino acids 23 to 367 of FIGS. 1A–1B (SEQ ID NO:11), or (b) the complement of the DNA molecule of (a). Preferably, this nucleic acid has at least one WISP biological activity. More preferably, this nucleic acid comprises DNA having at least about a 95% sequence identity to (a) a DNA molecule encoding a mouse WISP-1 polypeptide comprising the sequence of amino acids 23 to 367 of FIGS. 1A–1B (SEQ ID NO:11), or (b) the complement of the DNA molecule of (a).

In another preferred embodiment, the invention provides an isolated nucleic acid comprising DNA having at least about 600 nucleotides and at least about a 75% sequence identity to (a) a DNA molecule encoding the same full-length polypeptide encoded by the human WISP-1 polypeptide cDNA in ATCC Deposit No. 209533_(pRK5E.h.WISP-1.568.38), or (b) the complement of the DNA molecule of (a). This nucleic acid preferably comprises DNA having at least about 600 nucleotides and at least about a 95% sequence identity to (a) a DNA molecule encoding the same full-length polypeptide encoded by the human WISP-1 polypeptide cDNA in ATCC Deposit No. 209533 (pRK5E.h.WISP-1.568.38), or (b) the complement of the DNA molecule of (a).

In another aspect, the invention provides a process for producing a WISP-1 polypeptide comprising culturing a host cell comprising the above nucleic acid under conditions suitable for expression of the WISP-1 polypeptide and recovering the WISP-1 polypeptide from the cell culture. Additionally provided is an isolated WISP-1 polypeptide encoded by the above nucleic acid, including where the polypeptide is human WISP-1 or mouse WISP-1.

In another embodiment, the invention provides isolated nucleic acid comprising SEQ ID NO:23, 24, 25, 26, 27, 28, or 29, and an isolated WISP-1 polypeptide encoded by such a nucleic acid.

Also provided by this invention is an isolated nucleic acid having at least about 600 nucleotides and produced by hybridizing a test DNA molecule under stringent conditions with (a) a DNA molecule encoding a human WISP-1 polypeptide comprising the sequence of amino acids 23 to 367 of FIGS. 3A–3C (SEQ ID NO:3), or (b) the complement of the DNA molecule of (a), and, if the test DNA molecule has at least about a 75% sequence identity to (a) or (b), isolating the test DNA molecule.

Further provided is a polypeptide produced by (i) hybridizing a test DNA molecule under stringent conditions with (a) a DNA molecule encoding a human WISP-1 polypeptide comprising the sequence of amino acids 23 to 367 of FIGS. 3A–3C (SEQ ID NO:3), or (b) the complement of the DNA molecule of (a), and if the test DNA molecule has at least about a 75% sequence identity to (a) or (b), (ii) culturing a host cell comprising the test DNA molecule under conditions suitable for expression of the polypeptide, and (iii) recovering the polypeptide from the cell culture.

In another aspect, the invention provides isolated nucleic acid comprising DNA having at least about an 80% sequence identity to (a) a DNA molecule encoding a human WISP-2 polypeptide comprising the sequence of amino acids 24 to 250 of FIGS. 4A–4B (SEQ ID NO:15), or (b) the complement of the DNA molecule of (a). Preferably, this nucleic acid has at least one WISP biological activity. Also, preferably this nucleic acid comprises DNA having at least about a 95% sequence identity to (a) a DNA molecule encoding a human WISP-2 polypeptide comprising the sequence of amino acids 24 to 250 of FIGS. 4A–4B (SEQ ID NO:15), or (b) the complement of the DNA molecule of (a). In another preferred embodiment, this nucleic acid comprises DNA encoding a human WISP-2 polypeptide having amino acid residues 24 to 250 of FIGS. 4A–4B (SEQ ID NO:15), or DNA encoding a human WISP-2 polypeptide having amino acid residues 1 to 250 of FIGS. 4A–4B (SEQ ID NO:16), or a complement of either of the encoding DNAs.

In another aspect, the invention provides isolated nucleic acid comprising DNA having at least about an 80% sequence identity to (a) a DNA molecule encoding a human WISP-2 polypeptide comprising the sequence of amino acids 1 to 250 of FIGS. 4A–4B (SEQ ID NO:16), or (b) the complement of the DNA molecule of (a).

In another aspect, the invention provides isolated nucleic acid comprising DNA having at least about 500 nucleotides and at least about an 80% sequence identity to (a) a DNA molecule encoding a mouse WISP-2 polypeptide comprising the sequence of amino acids 24 to 251 of FIGS. 2A–2B (SEQ ID NO:19), or (b) the complement of the DNA molecule of (a). In a preferred embodiment, this nucleic acid comprises DNA having at least about a 95% sequence identity to (a) a DNA molecule encoding a mouse WISP-2 polypeptide comprising the sequence of amino acids 24 to 251 of FIGS. 2A–2B (SEQ ID NO:19), or (b) the complement of the DNA molecule of (a). More preferably, the nucleic acid comprises DNA encoding a mouse WISP-2 polypeptide having amino acid residues 24 to 251 of FIGS. 2A–2B (SEQ ID NO:19), or DNA encoding a mouse WISP-2 polypeptide having amino acid residues 1 to 251 of FIGS. 2A–2B (SEQ ID NO:20), or the complement of either of these encoding DNAs.

In a further aspect, the invention provides isolated nucleic acid comprising DNA having at least about 500 nucleotides and at least about an 80% sequence identity to (a) a DNA molecule encoding a mouse WISP-2 polypeptide comprising the sequence of amino acids 1 to 251 of FIGS. 2A–2B (SEQ ID NO:20), or (b) the complement of the DNA molecule of (a).

In yet another aspect, the invention provides an isolated nucleic acid comprising DNA having at least about 400 nucleotides and at least about a 75% sequence identity to (a) a DNA molecule encoding the same full-length polypeptide encoded by the human WISP-2 polypeptide cDNA in ATCC Deposit No. 209391 (DNA33473), or (b) the complement of the DNA molecule of (a). Preferably, this nucleic acid comprises DNA having at least about a 95% sequence identity to (a) a DNA molecule encoding the same full-length polypeptide encoded by the human WISP-2 polypeptide cDNA in ATCC Deposit No. 209391 (DNA33473), or (b) the complement of the DNA molecule of (a).

In another embodiment, this invention provides an isolated nucleic acid comprising the nucleotide sequence of the full-length coding sequence of clone UNQ228 (DNA33473) deposited under accession number ATCC 209391.

In another aspect, the invention provides a process for producing a WISP-2 polypeptide comprising culturing a host cell comprising the above nucleic acid under conditions suitable for expression of the WISP-2 polypeptide and recovering the WISP-2 polypeptide from the cell culture. Additionally provided is a WISP-2 polypeptide encoded by the isolated nucleic acid, including where the polypeptide is human WISP-2 or mouse WISP-2. In a specific embodiment of this, the invention provides isolated native-sequence human WISP-2 polypeptide comprising amino acid residues 1 to 250 of FIGS. 4A–4B (SEQ ID NO:16) or comprising amino acid residues 24 to 250 of FIGS. 4A–4B (SEQ ID NO:15).

In a further embodiment, the invention provides an isolated nucleic acid having at least about 400 nucleotides and produced by hybridizing a test DNA molecule under stringent conditions with (a) a DNA molecule encoding a human WISP-2 polypeptide comprising the sequence of amino acids 24 to 250 of FIGS. 4A–4B (SEQ ID NO:15), or (b) the complement of the DNA molecule of (a), and, if the test DNA molecule has at least about a 75% sequence identity to (a) or (b), isolating the test DNA molecule.

In a still further embodiment, the invention provides a polypeptide produced by (i) hybridizing a test DNA molecule under stringent conditions with (a) a DNA molecule encoding a human WISP-2 polypeptide comprising the sequence of amino acids 24 to 250 of FIGS. 4A–4B (SEQ ID NO:15), or (b) the complement of the DNA molecule of (a), and if the test DNA molecule has at least about a 75% sequence identity to (a) or (b), (ii) culturing a host cell comprising the test DNA molecule under conditions suitable for expression of the polypeptide, and (iii) recovering the polypeptide from the cell culture.

In yet another embodiment, the invention provides isolated nucleic acid comprising DNA having a 100% sequence identity in more than about 500 nucleotides to (a) a DNA molecule encoding a human WISP-3 polypeptide comprising the sequence of amino acids 34 to 372 of FIGS. 6A–6C (SEQ ID NO:32), or (b) the complement of the DNA molecule of (a). Preferably, this nucleic acid has at least one WISP biological activity. Preferably, this nucleic acid comprises DNA encoding a human WISP-3 polypeptide having amino acid residues 34 to 372 of FIGS. 6A–6C (SEQ ID NO:32) or amino acids 1 to 372 of FIGS. 6A–6C (SEQ ID NO:33), or the complement thereof.

In a still further embodiment, the invention provides an isolated nucleic acid comprising DNA having a 100% sequence identity in more than about 500 nucleotides to (a) a DNA molecule encoding the same full-length polypeptide encoded by the human WISP-3 polypeptide cDNA in ATCC Deposit No. 209706 (DNA56350-1176-2), or (b) the complement of the DNA molecule of (a). A still further aspect of the invention involves a process for producing a WISP-3 polypeptide comprising culturing a host cell comprising WISP-3-encoding nucleic acid under conditions suitable for expression of the WISP-3 polypeptide and recovering the WISP-3 polypeptide from the cell culture.

Further provided is an isolated WISP-3 polypeptide encoded by the WISP-3-encoding nucleic acid. Preferably, this polypeptide is human WISP-3.

In another embodiment, the invention provides an isolated nucleic acid produced by hybridizing a test DNA molecule under stringent conditions with (a) a DNA molecule encoding a human WISP-3 polypeptide comprising the sequence of amino acids 34 to 372 of FIGS. 6A–6C (SEQ ID NO:32), or (b) the complement of the DNA molecule of (a), and, if the test DNA molecule has a 100% sequence identity to (a) or (b) in more than about 500 nucleotides, isolating the test DNA molecule.

Also provided is a polypeptide produced by (i) hybridizing a test DNA molecule under stringent conditions with (a) a DNA molecule encoding a human WISP-3 polypeptide comprising the sequence of amino acids 34 to 372 of FIGS. 6A–6C (SEQ ID NO:32), or (b) the complement of the DNA molecule of (a), and if the test DNA molecule has a 100% sequence identity to (a) or (b) in more than about 500 nucleotides, (ii) culturing a host cell comprising the test DNA molecule under conditions suitable for expression of the polypeptide, and (iii) recovering the polypeptide from the cell culture.

In yet another embodiment, the invention provides isolated nucleic acid comprising DNA having a 100% sequence identity in more than about 400 nucleotides to (a) a DNA molecule encoding a human WISP-3 polypeptide comprising the sequence of amino acids 16 to 355 of FIGS. 7A–7C (SEQ ID NO:36), or (b) the complement of the DNA molecule of (a). Preferably, this nucleic acid has at least one WISP biological activity. Preferably, this nucleic acid comprises DNA encoding a human WISP-3 polypeptide having amino acid residues 16 to 355 of FIGS. 7A–7C (SEQ ID NO:36), or amino acid residues 1 to 355 of FIGS. 7A–7C (SEQ ID NO:37) or the complement thereof.

In a still further embodiment, the invention provides an isolated nucleic acid comprising DNA having a 100% sequence identity in more than about 400 nucleotides to (a) a DNA molecule encoding the same full-length polypeptide encoded by the human WISP-3 polypeptide cDNA in ATCC Deposit No. 209707 (DNA58800-1176-2), or (b) the complement of the DNA molecule of (a).

A still further aspect of the invention involves a process for producing a WISP-3 polypeptide of FIGS. 7A–7C comprising culturing a host cell comprising WISP-3-encoding nucleic acid under conditions suitable for expression of the WISP-3 polypeptide and recovering the WISP-3 polypeptide from the cell culture.

Further provided is an isolated WISP-3 polypeptide of FIGS. 7A–7C encoded by the WISP-3-encoding nucleic acid. Preferably, this polypeptide is human WISP-3.

In another embodiment, the invention provides an isolated nucleic acid produced by hybridizing a test DNA molecule under stringent conditions with (a) a DNA molecule encoding a human WISP-3 polypeptide comprising the sequence of amino acids 16 to 355 of FIGS. 7A–7C (SEQ ID NO:36), or (b) the complement of the DNA molecule of (a), and, if the test DNA molecule has a 100% sequence identity to (a) or (b) in more than about 400 nucleotides, isolating the test DNA molecule.

Also provided is a polypeptide produced by (i) hybridizing a test DNA molecule under stringent conditions with (a) a DNA molecule encoding a human WISP-3 polypeptide comprising the sequence of amino acids 16 to 355 of FIGS. 7A–7C (SEQ ID NO:36), or (b) the complement of the DNA molecule of (a), and if the test DNA molecule has a 100% sequence identity to (a) or (b) in more than about 400 nucleotides, (ii) culturing a host cell comprising the test DNA molecule under conditions suitable for expression of the polypeptide, and (iii) recovering the polypeptide from the cell culture.

Preferably the complements of the DNA molecules herein remain stably bound to the primary sequence under at least moderate, and optionally, under high stringency conditions.

Also provided are vectors comprising the above nucleic acids, host cells comprising the vector, preferably wherein the cell is a Chinese hamster ovary (CHO) cell, an *E. coli* cell, a baculovirus-infected cell, or a yeast cell.

Additionally provided are a chimeric molecule comprising one of the above polypeptides or an inactivated variant thereof, fused to a heterologous amino acid sequence, wherein the heterologous amino acid sequence may be, for example, an epitope tag sequence, a polyamino acid such as poly-histidine, or an immunoglobulin constant region (Fc). Also provided is an antibody which specifically binds to one of the above polypeptides, wherein the antibody can be a monoclonal antibody.

Further provided are a composition comprising one of the above polypeptides and a carrier therefor, and a composition comprising an antagonist to one of the polypeptides and a carrier therefor. In one such embodiment, the invention provides a composition comprising a WISP-1, WISP-2, or WISP-3 polypeptide and a pharmaceutically acceptable carrier. Preferably, the polypeptide is a human polypeptide. Also, preferably, these compositions may also comprise a chemotherapeutic agent or growth-inhibitory agent.

In another aspect, the invention provides a pharmaceutical product comprising:

(a) the composition comprising WISP-1, WISP-2, or WISP-3 polypeptide and a pharmaceutically acceptable carrier;

(b) a container containing said composition; and (c) a label affixed to said container, or a package insert included in said pharmaceutical product referring to the use of said WISP-1, WISP-2, or WISP-3 polypeptide in the treatment of a WISP-related disorder.

In yet another embodiment, the invention provides a method for treating a WISP-related disorder in a mammal comprising administering to the mammal an effective amount of any of the above compositions, including the composition of a WISP-1, WISP-2, or WISP-3 polypeptide in a pharmaceutically acceptable carrier, and including the composition of an antagonist to a WISP-1, WISP-2, or WISP-3 polypeptide in a pharmaceutically acceptable carrier. Preferably, the disorder is a malignant disorder or arteriosclerosis. More preferably, the malignant disorder is breast cancer, ovarian cancer, colon cancer, or melanoma. Also, preferably the mammal is human. In another preferred embodiment, the WISP-1, WISP-2, or WISP-3 polypeptide is administered in combination with a chemotherapeutic agent, a growth inhibitory agent, or a cytotoxic agent.

In another embodiment, the invention supplies a process for diagnosing a disease or a susceptibility to a disease related to a mutation in a nucleic acid sequence encoding a WISP-1, WISP-2, or WISP-3 polypeptide comprising:

(a) isolating a nucleic acid sequence encoding a WISP-1, WISP-2, or WISP-3 polypeptide from a sample derived from a host; and (b) determining a mutation in the nucleic acid sequence encoding a WISP-1, WISP-2, or WISP-3 polypeptide.

In another embodiment, the invention provides a method of diagnosing a WISP-related disorder in a mammal comprising detecting the level of expression of a gene encoding a WISP-1, WISP-2, or WISP-3 polypeptide (a) in a test sample of tissue cells obtained from the mammal, and (b) in a control sample of known normal tissue cells of the same cell type, wherein a higher or lower expression level in the test sample indicates the presence of a WISP-related dysfunction in the mammal from which the test tissue cells were obtained. Preferably, such a disorder is a type of cancer and a higher expression level in the test sample indicates the presence of a tumor in the mammal.

In a still further embodiment, the invention provides an isolated antibody binding a WISP-1, WISP-2, or WISP-3 polypeptide. Preferably, the antibody induces death of a cell overexpressing a WISP-1, WISP-2, or WISP-3 polypeptide, more preferably a cancer cell. Also preferred is an antibody that binds to a human WISP-1, WISP-2, or WISP-3 polypeptide, and is a human or humanized antibody. More preferred is a monoclonal antibody, still more preferred, a monoclonal antibody that has complementary-determining regions and constant immunoglobulin regions, and in other embodiments is an antibody fragment, a single-chain antibody, or an anti-idiotypic antibody. In addition, the antibody is suitably labeled with a detectable label or immobilized on a solid support.

Also provided is a composition comprising an antibody to a WISP-1, WISP-2, or WISP-3 polypeptide in admixture with a pharmaceutically accetable carrier. Preferably, the antibody is to a human WISP-1, WISP-2, or WISP-3 polypeptide, and is a human or humanized antibody, most preferably a monoclonal antibody against human WISP-1. Further, the composition may comprise a growth-inhibitory amount of said antibody.

In another embodiment, the invention provides a method for treating cancer in a mammal comprising administering to the mammal an effective amount of the above antibody composition. In a preferred aspect of this method, the cancer is colon cancer, the antibody is against human WISP-1 and is a humanized or human monoclonal antibody, and the mammal is human.

In another aspect, the invention provides a method for treating a WISP-related disorder in a mammal comprising administering to the mammal an effective amount of a composition comprising an antagonist to a WISP-1, WISP-2, or WISP-3 polypeptide in a pharmaceutically acceptable carrier.

In a further aspect, the invention provides a method for inhibiting the growth of tumor cells comprising exposing a cell that overexpresses a Wnt-1-induced gene to an effective amount of an antagonist that inhibits the expression or activity of a WISP-1, WISP-2, or WISP-3 polypeptide.

A further aspect entails a method for inhibiting the growth of tumor cells comprising exposing said cells to an effective amount of the composition with the growth-inhibiting amount of an anti-WISP-1, anti-WISP-2, or anti-WISP-3 antibody in admixture with the carrier. In a preferred aspect of this method, the tumor cells are colon cancer cells, the antibody is against human WISP-1 and is a humanized or human monoclonal antibody, and the mammal is human.

Also provided herein is a kit comprising one of the above WISP polypeptides or WISP antagonists, such as anti-WISP antibodies, and instructions for using the polypeptide or antagonist to detect or treat a WISP-related disorder, such as cancer induced by Wnt. One such preferred kit is a cancer diagnostic kit comprising an anti-WISP-1, anti-WISP-2, or anti-WISP-3 antibody and a carrier in suitable packaging.

Preferably, this kit further comprises instructions for using said antibody to detect the WISP-1, WISP-2, or WISP-3 polypeptide.

Also provided is a method for inducing cell death comprising exposing a cell which is induced by Wnt to an effective amount of one of the above WISP polypeptides or WISP antagonists, such as anti-WISP antibodies. Preferably, such cell is a cancer cell. More preferably, the cell is in a mammal, more preferably a human. In addition, an effective amount of another chemotherapeutic antibody is used in the exposure of the cell, such as an anti-ErbB2 antibody. Further, optionally the method comprises exposing the cell to a chemotherapeutic agent, a growth-inhibitory agent, or radiation. Optionally, the cell is exposed to the growth-inhibitory agent prior to exposure to the antibody.

In a further aspect, the invention provides an article of manufacture, comprising:
  a container;
  a label on the container; and
  a composition comprising an active agent contained within the container;
wherein the composition is effective for inducing cell death or inhibiting the growth of tumor cells, the label on the container indicates that the composition can be used for treating conditions characterized by overinduction of Wnt or a WISP-related disorder or by overexpression of a WISP-1, WISP-2, or WISP-3 polypeptide, and the active agent in the composition is an antagonist to one of the polypeptides, that is, an agent that inhibits the expression and/or activity of the WISP-1, WISP-2, or WISP-3 polypeptide. Preferably, the active agent in such article of manufacture is an anti-WISP-1, anti-WISP-2, or anti-WISP-3 antibody, and the label on the container indicates that the composition can be used for treating a WISP-related disorder.

In another embodiment, the invention provides a process for identifying agonists to a WISP-1, WISP-2, or WISP-3 polypeptide comprising:
  (a) contacting cells and a compound to be screened under conditions suitable for the stimulation of cell proliferation by the polypeptide; and
  (b) measuring the proliferation of the cells to determine if the compound is an effective agonist.

Additionally, the invention provides an agonist to a WISP-1, WISP-2, or WISP-3 polypeptide identified by the above process.

Further, the invention provides a method for identifying a compound that inhibits the expression or activity of a WISP-1, WISP-2, or WISP-3 polypeptide, comprising contacting a candidate compound with a WISP-1, WISP-2, or WISP-3 polypeptide under conditions and for a time sufficient to allow the compound and polypeptide to interact. In a preferred embodiment, this method comprises the steps of:
  (a) contacting cells and a compound to be screened in the presence of the WISP-1, WISP-2, or WISP-3 polypeptide under conditions suitable for the stimulation of cell proliferation by polypeptide; and
  (b) measuring the proliferation of the cells to determine if the compound is an effective antagonist.

Further, a compound identified by this method is provided.

In another aspect, this invention provides a compound that inhibits the expression or activity of a WISP-1, WISP-2, or WISP-3 polypeptide.

In another embodiment, the invention provides a method for determining the presence of a WISP-1, WISP-2, or WISP-3 polypeptide comprising exposing a cell suspected of containing the WISP-1, WISP-2, or WISP-3 polypeptide to an anti-WISP-1, anti-WISP-2, or anti-WISP-3 antibody and determining binding of said antibody to said cell.

In another preferred embodiment, the invention provides a method of diagnosing a WISP-related disorder in a mammal comprising (a) contacting an anti-WISP-1, anti-WISP-2, or anti-WISP-3 antibody with a test sample of tissue cells obtained from the mammal, and (b) detecting the formation of a complex between the anti-WISP-1, anti-WISP-2, or anti-WISP-3 antibody and the WISP-1, WISP-2, or WISP-3 polypeptide in the test sample. Preferably, said test sample is obtained from an individual suspected to have neoplastic cell growth or proliferation. Also, preferably the antibody is labeled with a detectable label and/or is immobilized on a solid support.

BRIEF DESCRIPTION OF THE DRAWINGS

FIGS. 1A–1B show the derived amino acid sequence of a native-sequence mouse WISP-1 protein from amino acids 1 to 367 (SEQ ID NO:12) and the nucleotide sequence (and complementary sequence) encoding the protein (SEQ ID NOS:9 and 10, respectively). There is a 1104-bp coding region and 584 bp of 3' untranslated region. In the Figure, amino acids 1 through 22 form a putative signal sequence, amino acids 23 through 367 are the putative mature protein (SEQ ID NO:11), with amino acids 86 to 88, 143 to 145, 284 to 286, and 343 to 345 being potential glycosylation sites. Potential protein kinase C phosphorylation sites are at amino acids 43–45, 159–161, 235–237, 292–294, 295–297, and 345–347. Potential casein kinase II phosphorylation sites are at amino acids 44–47, 131–134, 145–148, and 358–361. Potential N-myristoylation sites are at amino acids 18–23, 72–77, 127–132, 149–154, 231–236, and 289–294. A potential amidation site is at amino acids 269–272. A potential prokaryotic membrane lipoprotein lipid attachment site is at amino acids 113–123. A potential von Willebrand C1 domain is at amino acids 130–146. A potential thrombospondin 1 domain is at amino acids 223–237. A potential CT module is at amino acids 301–312. A potential IGF binding protein consensus site is at amino acids 72–80.

FIGS. 2A–2B shows the derived amino acid sequence of a native-sequence mouse WISP-2 protein from amino acids 1 to 251 (SEQ ID NO:20) and the nucleotide sequence (and complementary sequence) encoding the protein (SEQ ID NOS:17 and 18, respectively) from a clone 1367.3. There are 756 bp of coding nucleotides and 722 bp of 3' untranslated region. In the Figure, amino acids 1 through 23 form a putative signal sequence; amino acids 24 through 251 are the putative mature protein (SEQ ID NO:19). A potential N-glycosylation site is at amino acids 197–200. A potential glycosaminoglycan attachment site is at amino acids 85–88. Potential protein kinase C phosphorylation sites are at amino acids 85–87 and 112–114. Potential N-myristoylation sites are at amino acids 49–54, 81–86, 126–131, 210–215, and 245–250. A potential amidation site is at amino acids 103–106. A potential phospholipase A2 aspartic acid active site is at amino acids 120–130. A potential IGF binding protein consensus signature is at amino acids 49–64. A potential von Willebrand C1 domain is at amino acids 107–123. A potential thrombospondin 1 domain is at amino acids 202–216. A potential IGF binding protein consensus site is at amino acids 49–57.

FIGS. 3A–3E show the derived amino acid sequence of a native-sequence human WISP-1 protein from amino acids 1 to 367 (SEQ ID NO:4) and the nucleotide sequence (and complementary sequence) encoding the protein (SEQ ID NOS:1 and 2, respectively). There are 1104 bp of coding region in this human clone 568.38, and 1638 bp of 3' untranslated region. In the Figure, amino acids 1 through 22 form a putative signal sequence, amino acids 23 through 367 are the putative mature protein (SEQ ID NO:3), with amino acids 85 to 87, 143 to 145, 284 to 286, and 343 to 345 being potential glycosylation sites. A potential cAMP- and cGMP-dependent protein kinase phosphorylation site is from amino acids 171 to 174; potential protein kinase C phosphorylation sites are at amino acids 43–45, 235–237, 292–294, and 345–347. Potential casein kinase II phosphorylation sites are at amino acids 30–33, 145–148, and 358–361. Potential N-myristoylation sites are at amino acids 72–77, 127–132, 149–154, 201–206, 231–236, 289–294, and 327–332. A potential amidation site is at amino acids 269–272. A potential prokaryotic membrane lipoprotein lipid attachment site is at amino acids 113–123. A potential von Willebrand C1 domain is at amino acids 130–146. A potential thrombospondin 1 domain is at amino acids 223–237. A potential CT (C-Terminal) module is at amino acids 301–312. A potential IGF binding protein consensus site is at amino acids 72–80.

FIGS. 4A–4B show the derived amino acid sequence of a native-sequence human WISP-2 protein from amino acids 1 to 250 (SEQ ID NO:16) and the nucleotide sequence (and complementary sequence) encoding the protein (SEQ ID NOS:13 and 14, respectively). The coding region is 753 bp and the 3' untranslated region is 519 bp. The putative signal sequence is from amino acid residues 1 through 23 and the putative mature region is from 24 through 250 (SEQ ID NO: 15). The clone designated herein as "UNQ228" and/or "DNA33473-seqmin" (SEQ ID NO:38) begins at nucleotide 34 of SEQ ID NO:13. Potential protein kinase C phosphorylation sites are at amino acids 4–6, 118–120, and 227–229. A potential casein kinase II phosphorylation site is at amino acids 98–101. A potential N-myristoylation site is at amino acids 3–8, 49–54, 81–86, 85–90, 126–131, 164–169, 166–171, 167–172, 183–188, and 209–214. A potential IGF binding protein consensus signature is at amino acids 49–64. A potential von Willebrand C1 domain is at amino acids 107–123. A potential thrombospondin 1 domain is at amino acids 201–215. A potential IGF binding protein consensus site is at amino acids 49–57.

FIG. 5 shows a 841-bp consensus nucleotide sequence designated "DNA30843" (SEQ ID NO:39) derived from the nucleotide sequences of twenty different expressed sequence tags from Incyte. When aligned with the other sequences, DNA30843 has 3 gaps. It has 441 bp orf (+1). DNA30843 was used to design probes for isolation of human WISP-2.

FIGS. 6A–6C show the derived amino acid sequence of a native-sequence human WISP-3 protein from amino acids 1 to 372 (SEQ ID NO:33) and the nucleotide sequence (and complementary sequence) encoding the protein (SEQ ID NOS:30 and 31, respectively). In the Figure, amino acids 1 through 33 form a putative signal sequence, amino acids 34 through 372 are the putative mature protein (SEQ ID NO:32), with amino acids 196 to 198 and 326 to 328 being potential glycosylation sites. Potential protein kinase C phosphorylation sites are at amino acids 209–211, 246–248, 277–279, 308–310, and 342–344. Potential casein kinase II phosphorylation sites are at amino acids 47–50, 254–257, and 293–296. Potential N-myristoylation sites are at amino acids 21–26, 89–94, 139–144, 166–171, 180–185, 185–190, 188–193, 242–247, and 302–307. A potential amidation site is at amino acids 188–191. Potential prokaryotic membrane lipoprotein lipid attachment sites are at amino acids 130–140 and 160–170. A potential IGF binding protein signature site is at amino acids 89–104. A potential IGF binding protein site (less stringent than prosite's) is at amino acids 89–97.

FIGS. 7A–7C show the derived amino acid sequence of a native-sequence human WISP-3 protein from amino acids 1 to 355 (SEQ ID NO:37) and the nucleotide sequence (and complementary sequence) encoding the protein (SEQ ID NOS:34 and 35, respectively). This protein is believed to be a splice variant of the nucleotide sequence shown in FIG. 6 with a shorter 5' end. In the Figure, amino acids 1 through 15 form a putative signal sequence, amino acids 16 through 355 are the putative mature protein (SEQ ID NO:36), with amino acids 178 to 180 and 308 to 310 being potential glycosylation sites. Potential protein kinase C phosphorylation sites are at amino acids 191–193, 228–230, 259–261, 290–292, and 324–326. Potential casein kinase II phosphorylation sites are at amino acids 29–32, 236–239, and 275–278. Potential N-myristoylation sites are at amino acids 3–8, 71–76, 121–126, 148–153, 162–167, 167–172, 170–175, 224–229, and 284–289. A potential amidation site is at amino acids 170–173. Potential prokaryotic membrane lipoprotein lipid attachment sites are at amino acids 112–122 and 142–152. A potential IGF binding protein signature site is at amino acids 71–87. A potential IGF binding protein site (less stringent than prosite's) is at amino acids 71–79.

FIG. 8 shows an alignment of the full-length amino acid sequences of the human and mouse WISP-1 (SEQ ID NOS:4 and 12, respectively).

FIG. 9 shows an alignment of the full-length amino acid sequences of the human and mouse WISP-2 (SEQ ID NOS:16 and 20, respectively).

FIG. 10 shows an alignment of the amino acid sequences of the two clones of human WISP-3 (SEQ ID NOS: 33 and 37, respectively).

FIGS. 11A–11C show an alignment of the nucleotide sequences of human WISP-1 (SEQ ID NO:1) and the human WISP-3 (SEQ ID NO:30).

FIG. 12 shows an alignment of the amino acid sequences of human WISP-1 (SEQ ID NO:4) and the human WISP-3 (SEQ ID NO:33).

FIG. 13 shows a map of the vector pBabe puro (5.1 kb) used to transform cells for purposes of differential expression. The vector includes both unique restriction sites and multiple restriction sites. It is shown here in modified form for Wnt-1 cloning wherein the HindIII site after the SV40 promoter in the original pBabe puro vector has been removed and a HindIII site added to the multiple cloning site of the original pBabe puro vector. Wnt-1 is cloned from EcoRI-HindIII in the multiple cloning site. Constructs derived from this vector are selected in ampicillin (100 µg/ml) and the cells infected in culture are selected in 1.0–2.5 µg/ml puromycin.

FIG. 14 shows the sequences of the PCR-Select® cDNA synthesis primer (SEQ ID NO:40), adaptors 1 and 2 (SEQ ID NOS:41 and 42, respectively) and complementary sequences for the adaptors (SEQ ID NOS:43 and 44, respectively), PCR primer 1 (SEQ ID NO:45), PCR primer 2 (SEQ ID NO:46), nested PCR primer 1 (SEQ ID NO:47), nested PCR primer 2 (SEQ ID NO:48), control primer G3PDH 5' primer (SEQ ID NO:49), and control primer G3PDH 3' primer (SEQ ID NO:50) used for suppression subtractive hybridization for identifying WISP clones. When the adaptors are ligated to RsaI-digested cDNA, the RsaI site is restored.

FIG. 15 shows the cloning site region of the plasmid pGEM-T used to clone all of the WISP sequences herein (SEQ ID NOS:51 and 52 for 5' and 3' sequences, respectively).

FIGS. 16A–16D show the sequence (SEQ ID NO:53) of a plasmid that is used to prepare an expression plasmid for expression of mouse WISP-1 in mammalian cells, the latter being designated pRK5.CMV.puro-dhfR.mWISP-1.6His.

FIGS. 17A–17D show the sequence (SEQ ID NO:54) of plasmid pb.PH.IgG, which is used to prepare an expression plasmid for expression of mouse WISP-1 DNA in baculovirus-infected insect cells.

FIGS. 18A–18D show the sequence (SEQ ID NO:55) of plasmid pbPH.His.c, which is used to prepare an expression plasmid for expression of mouse WISP-1 DNA in baculovirus-infected insect cells, the latter being designated pbPH.mu.568.8his.baculo.

FIGS. 19A–19D show graphs of the delta CT in nine colon cancer cell lines and DNA from the blood of ten normal human donors (Nor Hu) as control, for human TNF, human WISP-1, Lyra, and human Apo2 ligand, respectively, using the ABI Prism 7700™ Sequence Detection System procedure for testing genomic amplification.

FIGS. 20A–20D show graphs of the delta CT in nine colon cancer cell lines and Nor Hu as control, for human DCR1, huFAS, human WISP-2, and Apo3, respectively, using the ABI Prism 7700™ Sequence Detection System procedure for testing genomic amplification.

FIGS. 21A–21D show graphs of the delta CT in nine colon cancer cell lines and Nor Hu as control, for three different runs of human WISP-1 (designated in the figure as huWISP-1c, 1b, and -1a) and the average of these three runs of human WISP-1, respectively, using the ABI Prism 7700™ Sequence Detection System procedure for testing genomic amplification.

FIGS. 22A–22D show graphs of the delta CT in nine colon cancer cell lines and Nor Hu as control, for three different runs of human WISP-2 (designated in the figure as huWISP-2c, -2b, and -2a; FIGS. 22A, C, and D, respectively) and the average of these three runs of human WISP-2 (FIG. 22B), using the ABI Prism 7700™ Sequence Detection System procedure for testing genomic amplification.

FIGS. 23A–23C show graphs of the delta CT in nine colon cancer cell lines and Nor Hu as control, for two different runs of human DR5 (DR5a and DR5b) and the average of these two runs of DR5, respectively, using the ABI Prism 7700™ Sequence Detection System procedure for testing genomic amplification.

FIGS. 24A–24D show graphs of the delta CT in nine colon cancer cell lines and Nor Hu as control, for four different runs of c-myc (c-myc(a1), c-myc(b1), c-myc(b), and c-myc(a)), respectively, using the ABI Prism 7700™ Sequence Detection System procedure for testing genomic amplification.

FIGS. 25A–25D show graphs of the delta CT in nine colon cancer cell lines and Nor Hu as control, for two different runs of human WISP-1 (designated in the figure as huWISP-1(a) and huWISP-1(b)) and for two different runs of human WISP-2 (designated in the figure as huWISP-2(a) and huWISP-2(b)), respectively, using the ABI Prism 7700™ Sequence Detection System procedure for testing genomic amplification.

FIG. 26 shows the sequence (SEQ ID NO:23) of clone 568.13, a potential splice variant of human WISP-1 obtained by screening with a probe derived from clone 568.15A, which is the initial clone isolated from a human lung library in the process to obtain full-length human WISP-1 DNA.

FIG. 27 shows the sequence (SEQ ID NO:24) of clone 568.1A, a potential human WISP-1 splice variant, 5' end only, obtained by screening with a probe derived from clone 568.15A.

FIG. 28 shows the sequence (SEQ ID NO:25) of clone 568.39, a potential human WISP-1 splice variant, 5' end only, obtained by screening with a probe derived from clone 568.15A.

FIG. 29 shows the sequence (SEQ ID NO:26) of clone 568.4A, a potential human WISP-1 splice variant obtained by screening with a probe derived from clone 568.15A.

FIG. 30 shows the sequence (SEQ ID NO:27) of clone 568.5A, a potential human WISP-1 splice variant, 5' end only, obtained by screening with a probe derived from clone 568.15A.

FIG. 31 shows the sequence (SEQ ID NO:28) of clone 568.6B, a potential human WISP-1 splice variant, 5' end only, obtained by screening with a probe derived from clone 568.15A.

FIG. 32 shows the sequence (SEQ ID NO:29) of clone 568.7, a potential human WISP-1 splice variant, 5' end only, obtained by screening with a probe derived from clone 568.15A.

DETAILED DESCRIPTION OF THE PREFERRED EMBODIMENTS

I. Definitions

The term "WISP polypeptide" refers to the family of native-sequence human and mouse WISP proteins and variants described herein whose genes are induced at least by Wnt-1. This term includes WISP-1, WISP-2, and WISP-3.

The terms "WISP-1 polypeptide", "WISP-1 homologue" and grammatical variants thereof, as used herein, encompass native-sequence WISP-1 protein and variants (which are further defined herein). The WISP-1 polypeptide may be isolated from a variety of sources, such as from human tissue types or from another source, or prepared by recombinant or synthetic methods, or by any combination of these and similar techniques.

The terms "WISP-2 polypeptide", "WISP-2 homologue", "PRO261", and "PRO261 polypeptide" and grammatical variants thereof, as used herein, encompass native-sequence WISP-2 protein and variants (which are further defined herein). The WISP-2 polypeptide may be isolated from a variety of sources, such as from human tissue types or from another source, or prepared by recombinant or synthetic methods, or by any combination of these and similar techniques.

The terms "WISP-3 polypeptide", "WISP-3 homologue", and grammatical variants thereof, as used herein, encompass native-sequence WISP-3 protein and variants (which are further defined herein). The WISP-3 polypeptide may be isolated from a variety of sources, such as from human tissue types or from another source, or prepared by recombinant or synthetic methods, or by any combination of these and similar techniques.

A "native-sequence WISP-1 polypeptide" comprises a polypeptide having the same amino acid sequence as a WISP-1 polypeptide derived from nature. Such native-sequence WISP-1 polypeptides can be isolated from nature or can be produced by recombinant or synthetic means. The term "native-sequence WISP-1 polypeptide" specifically encompasses naturally occurring truncated or secreted forms of a WISP-1 polypeptide disclosed herein, naturally occurring variant forms (e.g., alternatively spliced forms or splice variants), and naturally occurring allelic variants of a WISP-1 polypeptide. In one embodiment of the invention, the native-sequence WISP-1 polypeptide is a mature or full-length native-sequence human WISP-1 polypeptide comprising amino acids 23 to 267 of FIGS. 3A and 3B (SEQ ID NO:3) or amino acids 1 to 267 of FIGS. 3A–3C (SEQ ID NO:4), respectively, with or without the N-terminal methionine.

In another embodiment of the invention, the native-sequence WISP-1 polypeptide is the full-length or mature native-sequence human WISP-1 polypeptide comprising amino acids 23 to 267 or 1 to 267 of FIGS. 3A–3C wherein the valine residue at position 184 or the alanine residue at position 202 has/have been changed to an isoleucine or serine residue, respectively, (SEQ ID NOS:5–8) with or without the N-terminal methionine. In another embodiment of the invention, the native-sequence WISP-1 polypeptide is the full-length or mature native-sequence human WISP-1 polypeptide comprising amino acids 23 to 267 or 1 to 267 of FIGS. 3A–3C wherein the valine residue at position 184 and the alanine residue at position 202 has/have been changed to an isoleucine or serine residue, respectively, (SEQ ID NOS:21 and 22, respectively) with or without the N-terminal methionine. In another embodiment of the invention, the native-sequence WISP-1 polypeptide is a mature or full-length native-sequence mouse WISP-1 polypeptide comprising amino acids 23 to 367 of FIGS. 1A–1B (SEQ ID NO:11), or amino acids 1 to 367 of FIGS. 1A–1B (SEQ ID NO:12), respectively, with or without the N-terminal methionine.

In another embodiment of the invention, the native-sequence WISP-1 polypeptide is one which is encoded by a nucleotide sequence comprising one of the human WISP-1 splice or other native-sequence variants, including SEQ ID NOS:23, 24, 25, 26, 27, 28, or 29, with or without an N-terminal methionine.

A "native-sequence WISP-2 polypeptide" or a "native-sequence PRO261 polypeptide" comprises a polypeptide having the same amino acid sequence as a WISP-2 polypeptide derived from nature. Such native-sequence WISP-2 polypeptides can be isolated from nature or can be produced by recombinant or synthetic means. The term "native-sequence WISP-2 polypeptide" specifically encompasses naturally occurring truncated or secreted forms of a WISP-2 polypeptide disclosed herein, naturally occurring variant forms (e.g., alternatively spliced forms or splice variants), and naturally occurring allelic variants of a WISP-2 polypeptide. In one embodiment of the invention, the native-sequence WISP-2 polypeptide is a mature or full-length native-sequence human WISP-2 polypeptide comprising amino acids 1–24 up to 250 of FIGS. 4A–4B (SEQ ID NOS:15, 16, and 56–77), including amino acids 24 to 250 and amino acids 1 to 250 of FIGS. 4A–4B (SEQ ID NOS:15 and 16, respectively), with or without the N-terminal methionine. In another embodiment of the invention, the native-sequence WISP-2 polypeptide is a mature or full-length native-sequence mouse WISP-2 polypeptide comprising amino acids 1–24 up to 251 of FIGS. 2A–2B (SEQ ID NOS:19, 20, and 78–99), including amino acids 24 to 251 and amino acids 1 to 251 of FIGS. 2A–2B (SEQ ID NOS:19 and 20, respectively), with or without the N-terminal methionine.

A "native-sequence WISP-3 polypeptide" comprises a polypeptide having the same amino acid sequence as a WISP-3 polypeptide derived from nature. Such native-sequence WISP-3 polypeptides can be isolated from nature or can be produced by recombinant or synthetic means. The term "native-sequence WISP-3 polypeptide" specifically encompasses naturally occurring truncated or other forms of a WISP-3 polypeptide disclosed herein, naturally occurring variant forms (e.g., alternatively spliced forms or splice variants), and naturally occurring allelic variants of a WISP-3 polypeptide. In one embodiment of the invention, the native-sequence WISP-3 polypeptide is a mature or full-length, native-sequence human WISP-3 polypeptide comprising amino acids 34 to 372 of FIGS. 6A–6C (SEQ ID NO:32) or amino acids 1 to 372 of FIGS. 6A=6C (SEQ ID NO:33), respectively, with or without the N-terminal methionine. In another embodiment of the invention, the native-sequence WISP-3 polypeptide is a mature or full-length, native-sequence human WISP-3 polypeptide comprising amino acids 16 to 355 of FIGS. 7A–7C (SEQ ID NO:36) or amino acids 1 to 355 of FIGS. 7A–7C (SEQ ID NO:37), respectively, with or without the N-terminal methionine.

The term "WISP-1 variant" means an active WISP-1 polypeptide as defined below having at least about 80%, preferably at least about 85%, more preferably at least about 90%, most preferably at least about 95% amino acid sequence identity with human mature WISP-1 having the deduced amino acid sequence shown in FIGS. 3A–3C (SEQ ID NO:3), and/or with human full-length WISP-1 having the deduced amino acid sequence shown in FIGS. 3A–3C (SEQ ID NO:4), and/or with mouse mature WISP-1 having the deduced amino acid sequence shown in FIGS. 1A–1B (SEQ ID NO:11), and/or with mouse full-length WISP-2 having the deduced amino acid sequence shown in FIGS. 1A–1B (SEQ ID NO:12). Such variants include, for instance, WISP-1 polypeptides wherein one or more amino acid residues are added to, or deleted from, the N- or C-terminus of the full-length or mature sequences of FIGS. 3A–3C and 1A–1B (SEQ ID NOS:4, 3, 12, and 11, respectively), including variants from other species, but excludes a native-sequence WISP-1 polypeptide.

The term "WISP-2 variant" or "PRO261 variant" means an active WISP-2 polypeptide as defined below having at least about 80%, preferably at least about 85%, more preferably at least about 90%, most preferably at least about 95% amino acid sequence identity with human mature WISP-2 having the putative deduced amino acid sequence shown in FIGS. 4A–4B (SEQ ID NO:15), and/or with human full-length WISP-2 having the deduced amino acid sequence shown in FIGS. 4A–4B (SEQ ID NO:16), and/or with mouse mature WISP-2 having the putative deduced amino acid sequence shown in FIGS. 2A–2B (SEQ ID NO:19), and/or with mouse full-length WISP-2 having the deduced amino acid sequence shown in FIGS. 2A–2B (SEQ ID NO:20). Such variants include, for instance, WISP-2 polypeptides wherein one or more amino acid residues are added to, or deleted from, the N- or C-terminus of the full-length and putative mature sequences of FIGS. 4A–4B and 2A–2B (SEQ ID NOS:16, 15, 20, and 19, respectively), including variants from other species, but excludes a native-sequence WISP-2 polypeptide.

The term "WISP-3 variant" means an active WISP-3 polypeptide as defined below having at least about 80%, preferably at least about 85%, more preferably at least about 90%, most preferably at least about 95% amino acid sequence identity with human mature WISP-3 having the deduced amino acid sequence shown in FIGS. 6A–6C (SEQ ID NO:32), and/or with human full-length WISP-3 having the deduced amino acid sequence shown in FIGS. 6A–6C (SEQ ID NO:33), and/or with human mature WISP-3 having the deduced amino acid sequence shown in FIGS. 7A–7C (SEQ ID NO:36), or with human full-length WISP-3 having the deduced amino acid sequence shown in FIGS. 7A–7C (SEQ ID NO:37). Such variants include, for instance, WISP-3 polypeptides wherein one or more amino acid residues are added to, or deleted from, the N- or C-terminus of the full-length or mature sequences of FIGS. 6A–6C and 7A–7C (SEQ ID NOS:32, 33, 36, and 37, respectively), including variants from other species, but excludes a native-sequence WISP-3 polypeptide.

"Percent (%) amino acid sequence identity" with respect to the WISP sequences identified herein is defined as the percentage of amino acid residues in a candidate sequence that are identical with the amino acid residues in a WISP polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN, or Megalign (DNASTAR™) software. Those skilled in the art can determine appropriate parameters for measuring alignment, including any algorithms needed to achieve maximal alignment over the full length of the sequences being compared.

"Percent (%) nucleic acid sequence identity" with respect to the coding region of the WISP sequences identified herein, including UNQ228 (DNA34387-seq min) sequence, and the coding region therein, is defined as the percentage of nucleotides in a candidate sequence that are identical with the nucleotides in the coding region of the WISP sequence of interest, e.g., in the UNQ228 (DNA34387-seq min) sequence (SEQ ID NO:38) or coding region therein (SEQ ID NO:16), after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared.

"Stringent conditions" are those that (1) employ low ionic strength and high temperature for washing, for example, 0.015 M sodium chloride/0.0015 M sodium citrate/0.1% sodium dodecyl sulfate at 50° C.; (2) employ during hybridization a denaturing agent, such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS; or (4) employ a buffer of 10% dextran sulfate, 2×SSC (sodium chloride/sodium citrate), and 50% formamide at 55° C., followed by a high-stringency wash consisting of 0.1×SSC containing EDTA at 55° C.

"Moderately stringent conditions" are described in Sambrook et al., *Molecular Cloning: A Laboratory Manual* (New York: Cold Spring Harbor Laboratory Press, 1989), and include the use of a washing solution and hybridization conditions (e.g., temperature, ionic strength, and percent SDS) less stringent than described above. An example of moderately stringent conditions is a condition such as overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc., as necessary to accommodate factors such as probe length and the like.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the WISP natural environment will not be present. Ordinarily, however, isolated polypeptide will be prepared by at least one purification step.

An "isolated" nucleic acid encoding a WISP polypeptide or "isolated" DNA33473 or "isolated" PRO261 polypeptide-encoding nucleic acid molecule is a nucleic acid molecule that is identified and separated from at least one contaminant nucleic acid molecule with which it is ordinarily associated in the natural source of the respective nucleic acid. Isolated DNA33473 or an isolated WISP-encoding nucleic acid molecule is other than in the form or setting in which it is found in nature. An isolated WISP-encoding or DNA33473 nucleic acid molecule therefore is distinguished from the WISP-encoding or DNA33473 nucleic acid molecule, respectively, as it exists in natural cells. However, an isolated WISP-encoding or DNA33473 nucleic acid molecule includes a nucleic acid molecule contained in cells that ordinarily express WISP-encoding DNA or DNA33473, respectively, where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-WISP polypeptide, such as anti-PRO261, monoclonal antibodies (including agonist, antagonist, and neutralizing antibodies), and anti-WISP polypeptide, such as anti-PRO261, and antibody compositions with polyepitopic specificity. The term "monoclonal antibody" as used herein refers to an antibody obtained from a population of substantially homogeneous antibodies, i.e., the individual antibodies comprising the population are identical except for possible naturally occurring mutations that may be present in minor amounts.

"Active" or "activity" or "WISP biological activity", for purposes herein, describes form(s) of a WISP polypeptide, such as PRO261, including its variants, or its antagonists, which retain the biologic and/or immunologic activities of a native or naturally occurring (native-sequence) WISP polypeptide, such as PRO261, or its antagonist. Preferred "activities" for a WISP polypeptide or its antagonist include the ability to inhibit proliferation of tumor cells or to stimulate proliferation of normal cells and to treat arteriosclerosis, including atherosclerosis, as well as to induce wound repair and hematopoiesis, prevent desmoplasia, prevent fibrotic lesions associated with skin disorders such as scleroderma, keloid, eosinophilic fasciitis, nodular fasciitis, and Dupuytren's contracture, to treat bone-related diseases such as osteoporosis, to regulate anabolism including promotion of growth, to treat immune disorders, to treat Wilms' tumor and kidney-related disorders, to treat testis-related disorders, to treat lung-related disorders, and to treat cardiac disorders.

An "antagonist" of a WISP polypeptide is a molecule that inhibits an activity of a WISP polypeptide. Preferred antagonists are those which interfere with or block an undesirable biological activity of a WISP polypeptide, such as where a WISP polypeptide might act to stimulate cancer cells and the antagonist would serve to inhibit the growth of those cells. In some cases, such as with WISP-1, WISP-2, and WISP-3, the antagonist may be useful to inhibit the binding of a WISP polypeptide to an IGF. Such molecules include antibodies and small molecules that have such inhibitory capability, as well as WISP polypeptide variants of, and receptors for, WISP polypeptide (if available) or portions thereof that bind to WISP. For example, antagonists can be derived from receptors of WISP-1, WISP-2, and WISP-3 using the predicted family of receptors for WISPs-1, -2, and -3 (the CTGF receptors). Thus, the receptor can be expression cloned from the family; then a soluble form of the receptor is made by identifying the extracellular domain and excising the transmembrane domain therefrom. The soluble form of the receptor can then be used as an antagonist, or the receptor can be used to screen for small molecules that would antagonize WISP polypeptide activity.

Alternatively, using the murine sequences shown in FIGS. 1A–1B and 2A–2B (SEQ ID NOS:11, 12, 19, and 20, respectively) or the human sequences shown in FIGS. 3A–3C, 4A–4B, (SEQ ID NOS: 3, 4, 15, and 16, respectively), 6A–6C, and 7A–7C, variants of native WISP-1, WISP-2, or WISP-3, are made that act as antagonists. Using knowledge from the CTGF receptor family, the receptor binding sites of WISP-1, WISP-2, and WISP-3 polypeptides can be determined by binding studies and one of them eliminated by standard techniques (deletion or radical substitution) so that the molecule acts as an antagonist.

Antagonist activity can be determined by several means, including standard assays for induction of cell death such as that described herein, e.g., $^3$H-thymidine proliferation assays, or other mitogenic assays, such as an assay measuring the capability of the candidate antagonist of inducing EGF-potentiated anchorage independent growth of target cell lines (Volckaert et al., Gene, 15:215–223 (1981)) and/or growth inhibition of neoplastic cell lines. Roberts et al., Proc. Natl. Acad. Sci. USA, 82:119–123 (1985). Anchorage-independent growth refers to the ability of WISP polypeptide-treated, or TGF-β-treated and EGF-treated non-neoplastic target cells to form colonies in soft agar, a characteristic ascribed to transformation of the cells. In this assay, the candidate is incubated together with an equimolar amount of a WISP polypeptide otherwise detectable in the EGF-potentiated anchorage-independent target cell growth assay, and the culture observed for failure to induce anchorage-independent growth. In addition, an antagonist may be an IGF such as IGF-I or a peptide mimic of IGF-I or a receptor to IGF or a receptor to an IGFBP.

"Treatment" refers to both therapeutic treatment and prophylactic or preventative measures. Those in need of treatment include those already with the disorder or condition as well as those in which the disorder or condition is to be prevented.

"Mammal" for purposes of treatment refers to any animal classified as a mammal, including humans, domestic, and farm animals, and zoo, sports, or pet animals, such as dogs, horses, cats, sheep, pigs, cows, etc. Preferably, the mammal is human.

A "disorder" or "WISP-related disorder" is any condition that would benefit from treatment with the WISP polypeptides or WISP antagonists herein. This includes chronic and acute disorders, as well as those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal, and blastocoelic disorders; hematopoiesis-related disorders; tissue-growth disorders; skin disorders; desmoplasia, fibrotic lesions; kidney disorders; bone-related disorders; trauma such as burns, incisions, and other wounds; catabolic states; testicular-related disorders; and inflammatory, angiogenic, and immunologic disorders, including arteriosclerosis. A "Wnt-related disorder" is one caused at least by the upregulation of the Wnt gene pathway, including Wnt-1 and Wnt-4, but preferably Wnt-1, and may include cancer.

The terms "cancer", "cancerous", and "malignant" refer to or describe the physiological condition in mammals that is typically characterized by unregulated cell growth. Examples of cancer include but are not limited to, carcinoma including adenocarcinorma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. The preferred cancers for treatment herein are breast, colon, lung, and melanoma.

The term "cytotoxic agent" as used herein refers to a substance that inhibits or prevents the function of cells and/or causes destruction of cells. The term is intended to include radioactive isotopes (e.g., $^{131}$I, $^{125}$I, $^{90}$Y, and $^{186}$Re), chemotherapeutic agents, and toxins such as enzymatically active toxins of bacterial, fungal, plant, or animal origin, or fragments thereof.

A "chemotherapeutic agent" is a chemical compound useful in the treatment of cancer. Examples of chemotherapeutic agents include Adriamycin, Doxorubicin, 5-Fluorouracil, Cytosine arabinoside ("Ara-C"), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan, and other related nitrogen mustards. Also included in this definition are hormonal agents that act to regulate or inhibit hormone action on tumors, such as tamoxifen and onapristone.

A "growth-inhibitory agent" when used herein refers to a compound or composition which inhibits growth of a cell, such as an Wnt-overexpressing cancer cell, either in vitro or in vivo. Thus, the growth-inhibitory agent is one which significantly reduces the percentage of malignant cells in S phase. Examples of growth-inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The 4D5 antibody (and functional equivalents thereof) can also be employed for this purpose if the cancer involves ErbB2-overexpressing cancer cells. See, e.g., WO 92/22653.

"Northern analysis" or "Northern blot" is a method used to identify RNA sequences that hybridize to a known probe such as an oligonucleotide, DNA fragment, cDNA or fragment thereof, or RNA fragment. The probe is labeled with a radioisotope such as $^{32}$P, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences. specific DNA sequences from total genomic DNA, and cDNA transcribed from total cellular RNA, bacteriophage, or plasmid sequences, etc. See generally Mullis et al. , *Cold Soring Harbor Symp. Quant.* *Biol.,* 51: 263 (1987); Erlich, ed., *PCR Technology,* (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

II. Compositions and Methods of the Invention

A. Full-length WISP Polypeptide

The present invention provides newly-identified and isolated nucleotide sequences encoding a polypeptide referred to in the present application as a WISP polypeptide, including a WISP-1, WISP-2, or WISP-3 polypeptide. In particular, cDNAs have been identified and isolated encoding novel murine and human WISP-1 and WISP-2, and human WISP-3 splice variants as disclosed in further detail in the Examples below.

Using BLAST and FastA sequence alignment computer programs, it was found that the coding sequences of mouse and human WISP-1 and -2, as well as the two coding sequences of human WISP-3 disclosed herein, show significant homology to DNA sequences disclosed in the GenBank database, including those published by Adams et al., *Nature,* 377: 3–174 (1995).

Further, using BLAST and FastA sequence alignment computer programs, it was found that various portions of the coding sequences of mouse and human WISP-1 and WISP-2 show significant homology to CTGF, cef-10, Cyr61, and/or Nov protein. In this regard, mouse WISP-1 is 47% homologous to mouse CTGF and 46% homologous to human CTGF, mouse WISP-2 is 46% homologous to chick cef-10 protein precursor and 42% homologous to human Cyr61 protein, human WISP-1 is 47% homologous to mouse CTGF and 48% homologous to human CTGF, and human WISP-2 is 48% homologous to mouse CTGF, 49% homologous to human CTGF precursor, 46% homologous to mouse Nov protein homolog precursor, 49% homologous to human CTGF, and 48% homologous to mouse CTGF precursor. Further, apparently the amino acid sequences of mouse WISP-1 and mouse ELM1 (Hashimoto et al., supra) are identical, and the amino acid sequences of human WISP-1 and mouse ELM1 are 84% identical.

Since these factors have also been correlated with IGFBPs, it is presently believed that the WISP-1 and WISP-2 polypeptides disclosed in the present application are newly identified members of the CTGF or IGFBP family and possess activity relating to development of normal, injured, and cancerous cells and tissue. More specifically, WISP-1 and WISP-2 may be involved in breast cancer, lung cancer, melanoma, and colon cancer, as well as in wound repair. Further, they may be involved in atherosclerosis.

Further, using BLAST and FastA sequence alignment computer programs, it was found that various portions of the coding sequences of the two splice variants of human WISP-3 show significant homology to mouse ELM1 and CTGF proteins. In this regard, both splice variants of WISP-3 are 45% homologous to mouse ELM1 and 42% homologous to mouse and human CTGF and its precursor, with the longer variant of FIG. 6 being 43% homologous to Xenopus CTGF and the shorter variant of FIG. 7 being 42% homologous to Xenopus CTGF.

B. WISP Polypeptide Variants

In addition to the full-length native-sequence WISP polypeptides described herein, it is contemplated that variants of these sequences can be prepared. WISP variants can be prepared by introducing appropriate nucleotide changes into the WISP-encoding DNA, or by synthesis of the desired variant WISP polypeptides. Those skilled in the art will appreciate that amino acid changes may alter post-translational processes of the WISP polypeptide, such as changing the number or position of glycosylation sites or altering the membrane-anchoring characteristics, if the native WISP polypeptide is membrane bound.

Variations in the native full-length WISP sequences, or in various domains of the WISP polypeptides described herein, can be made, for example, using any of the techniques and guidelines for conservative and non-conservative mutations set forth, for instance, in U.S. Pat. No. 5,364,934. Variations may be a substitution, deletion, or insertion of one or more codons encoding the WISP polypeptide that results in a change in the amino acid sequence as compared with the native-sequence WISP polypeptide. Optionally the variation is by substitution of at least one amino acid with any other amino acid in any portion of the WISP polypeptide. Guidance in determining which amino acid residue may be inserted, substituted, or deleted without adversely affecting the desired activity may be found by comparing the sequence of the WISP polypeptide with that of homologous known CTGF protein molecules, in the case of WISP-1, WISP-2, and WISP-3, and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to about 5 amino acids. The variation allowed may be determined by systematically making insertions, deletions, or substitutions of amino acids in the sequence and testing the resulting variants for activity in in vitro assays for gene upregulation or downregulation and in transgenic or knockout animals.

The variations can be made on the cloned DNA to produce the WISP DNA or WISP polypeptide variant DNA using methods known in the art such as oligonucleotide-mediated (site-directed) mutagenesis (Carter et al., *Nucl. Acids Res.,* 13:4331 (1986); Zoller et al., *Nucl. Acids Res.,* 10:6487 (1987)), cassette mutagenesis (Wells et al., *Gene,* 34:315 (1985)), alanine scanning, PCR mutagenesis, restriction selection mutagenesis (Wells et al., *Philos. Trans. R. Soc. London SerA,* 317:415 (1986)), or other known techniques.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is Less likely to alter the main-chain conformation of the variant. Alanine is also typically preferred because it is the most common amino acid. Further, it is frequently found in both buried and exposed positions. T. E. Creighton, *Proteins: Structure and Molecular Properties* (W. H. Freeman & Co., San Francisco, 1983); Chothia, *J. Mol. Biol.,* 150:1 (1976). If alanine substitution does not yield adequate-amounts of variant, an isoteric amino acid can be used.

Further deletional variants of the full-length WISP polypeptide include variants from which the N-terminal signal peptide, if any (such as, for example, those putatively identified as amino acids 1 to 22 for WISP-1, 1 to 23 for WISP-2, 1–33 for the WISP-3 of FIGS. 6 and 1–15 for the WISP-3 of FIG. 7), and/or the initiating methionine has been deleted.

C. Modifications of the WISP Polypeptide

Covalent modifications of the WISP polypeptides are included within the scope of this invention. One type of covalent modification includes reacting targeted amino acid residues of a WISP polypeptide with an organic derivatizing agent that is capable of reacting with selected side chains or the N- or C-terminal residues. Derivatization with bifunctional agents is useful, for instance, for crosslinking a WISP polypeptide to a water-insoluble support matrix or surface for use in the method for purifying anti-WISP antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane, and agents such as methyl-3-((p-azidophenyi)dithio)propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the $\alpha$-amino groups of lysine, arginine, and histidine side chains (Creighton, supra, pp. 79–86), acetylation of the N-terminal amine, and amidation of any C-terminal carboxyl group.

Another type of covalent modification of the WISP polypeptide included within the scope of this invention comprises altering the native glycosylation pattern of the polypeptide. "Altering the native glycosylation pattern" is intended for purposes herein to mean deleting one or more carbohydrate moieties found in the native sequence (either by deleting the underlying glycosylation site or by removing the glycosylation moieties by chemical and/or enzymatic means) and/or adding one or more glycosylation sites that are not present in the native sequence. In addition, the phrase includes qualitative changes in the glycosylation of the native proteins, involving a change in the nature and proportion of the varicus sugar residues present.

Addition of glycosylation sites to the WISP polypeptide herein may be accomplished by altering the amino acid sequence. The alteration may be made, for example, by the addition of, or substitution by, one or more serine or threonine residues to the native sequence (for O-linked glycosylation sites). The amino acid sequence may optionally be altered through changes at the DNA level, particularly by mutating the DNA encoding the WISP polypeptide at preselected bases such that codons are generated that will translate into the desired amino acids. The DNA mutation(s) may be made using methods described above.

Another means of increasing the number of carbohydrate moieties on the WISP polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.,* pp. 259–306 (1981).

Removal of carbohydrate moieties present on the WISP polypeptide may be accomplished chemically or enzymatically or by mutational substitution of codons encoding amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Another type of covalent modification comprises linking the WISP polypeptide to one of a variety of nonproteinaceous polymers, e.g., polyethylene glycol, polypropylene glycol, or polyoxyalkylenes, in the manner set forth, e.g., in U.S. Pat. Nos. 4,640,835; 4,496,689; 4,301,144; 4,670,417; 4,791,192 or 4,179,337.

The WISP polypeptide of the present invention may also be modified in a way to form a chimeric molecule comprising a WISP polypeptide, or a fragment thereof, fused to a heterologous polypeptide or amino acid sequence. In one embodiment, such a chimeric molecule comprises a fusion of the WISP polypeptide with a tag polypeptide which provides an epitope to which an anti-tag antibody can selectively bind. The epitope tag is generally placed at the amino- or carboxyl-terminus of a native or variant WISP molecule. The presence of such epitope-tagged forms can be detected using an antibody against the tag polypeptide. Also, provision of the epitope tag enables the WISP polypeptides to be readily purified by affinity purification using an anti-tag antibody or another type of affinity matrix that binds to the epitope tag. In an alternative embodiment, the chimeric molecule may comprise a fusion of the WISP polypeptides, or fragments thereof, with an immunoglobulin or a particular region of an immunoglobulin. For a bivalent form of the chimeric molecule, such a fusion could be to the Fc region of an Ig, such as an IgG molecule.

Various tag polypeptides and their respective antibodies are well known in the art. Examples include poly-histidine (poly-His) or poly-histidine-glycine (poly-His-Gly) tags; the flu HA tag polypeptide and its antibody 12CA5 (Field et al., *Mol. Cell. Biol.,* 8:2159–2165 (1988)); the c-myc tag and the 8F9, 3C7, 6E10, G4, B7, and 9E10 antibodies thereto (Evan et al., *Molecular and Cellular Bioloay,* 5:3610–3616 (1985)); and the Herpes Simplex virus glycoprotein D (gD) tag and its antibody. Paborsky et al., *Protein Engineering,* 3(6) :547–553 (1990). Other tag polypeptides include the Flag-peptide (Hopp et al., *BioTechnology,* 6:1204–1210 (1988)); the KT3 epitope peptide (Martin et al., *Science,* 255:192–194 (1992)); an α-tubulin epitope peptide (Skinner et al., *J. Biol. Chem.,* 266:15163–15166 (1991)); and the T7 gene 10 protein peptide tag. Lutz-Freyermuth et al., *Proc. Natl. Acad. Sci. USA,* 87:6393–6397 (1990).

D. Preparation of WISP Polypeptide

The description below relates primarily to production of WISP polypeptides by culturing cells transformed or transfected with a vector containing at least DNA encoding the mature or full-length sequences of human or mouse WISP-1 (SEQ ID NOS:3, 4, 11, or 12, respectively), or containing at least DNA encoding the mature or full-length sequences of human or mouse WISP-2 (SEQ ID NOS:15, 16, 19, or 20, respectively), or containing at least DNA encoding the mature or full-length sequences of human WISP-3 of FIGS. 6A–6C (SEQ ID NOS:32 or 33, respectively), or containing at least DNA encoding the mature or full-length sequences of human WISP-3 of FIG. 7A–7C (SEQ ID NOS:36 or 37, respectively).

It is, of course, contemplated that alternative methods, which are well known in the art, may be employed to prepare WISP polypeptides. For instance, the WISP polypeptide sequence, or portions thereof, may be produced by direct peptide synthesis using solid-phase techniques. See, e.g., Stewart et al., *Solid-Phase Peptide Synthesis* (W. H. Freeman Co.: San Francisco, Calif., 1969); Merrifield, *J. Am. Chem. Soc.,* 85:2149–2154 (1963). In vitro protein synthesis may be performed using manual techniques or by automation. Automated synthesis may be accomplished, for instance, using an Applied Biosystems peptide synthesizer (Foster City, Calif.) in accordance with manufacturer's instructions. Various portions of WISP polypeptides may be chemically synthesized separately and combined using chemical or enzymatic methods to produce a full-length WISP polypeptide.

1. Isolation of DNA Encoding WISP Polypeptide

DNA encoding a WISP polypeptide may be obtained from a cDNA library prepared from tissue believed to possess the mRNA for WISP polypeptide and to express it at a detectable level. Accordingly, DNA encoding human WISP polypeptide can be conveniently obtained from a cDNA library prepared from human tissue, such as a human fetal liver library or as otherwise described in the Examples. The gene encoding WISP polypeptide may also be obtained from a genomic library or by oligonucleotide synthesis.

A still alternative method of cloning WISP polypeptide is suppressive subtractive hybridization, which is a method for generating differentially regulated or tissue-specific cDNA probes and libraries. This is described, for example, in Diatchenko et al. , *Proc. Natl. Acad. Sci USA,* 93: 6025–6030 (1996). The procedure is based primarily on a technique called suppression PCR and combines normalization and subtraction in a single procedure. The normalization step equalizes the abundance of cDNAs within the target population and the subtraction step excludes the common sequences between the target and driver populations.

Libraries can be screened with probes (such as antibodies to a WISP polypeptide or oligonucleotides of at least about 20–80 bases) designed to identify the gene of interest or the protein encoded by it. Screening the cDNA or genomic library with the selected probe may be conducted using standard procedures, such as described in Sambrook et al., supra. An alternative means to isolate the gene encoding WISP polypeptide is to use PCR methodology. Sambrook et al., supra; Dieffenbach et al., *PCR Primer: A Laboratory Manual* (New York: Cold Spring Harbor Laboratory Press, 1995).

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation, or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, and INHERIT which employ various algorithms to measure homology.

Nucleic acid having polypeptide-coding sequence may be obtained by screening selected cDNA or genomic libraries using the deduced amino acid sequences disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for WISP polypeptide production and cultured in conventional nutrient media modified as appropriate for inducing promoters, selecting transformants, or amplifying the genes encoding the desired sequences. The culture conditions, such as media, temperature, pH, and the like, can be selected by the skilled artisan without undue experimentation. In general, principles, protocols, and practical techniques for maximizing the productivity of cell cultures can be found in *Mammalian Cell Biotechnology: a Practical Approach,* M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene,* 23:315 (1983) and WO 89/05859 published Jun. 29, 1989. For mammalian cells without such cell walls, the calcium phosphate precipitation method of Graham and van der Eb, *Virology,* 52:456–457 (1978) can be employed. General aspects of mammalian cell host system transformations have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci. (USA),* 76:3829 (1979). However, other methods for introducing DNA into cells, such as by nuclear microinjection, electroporation, bacterial protoplast fusion with intact cells, or polycations, e.g., polybrene or polyornithine, may also be used. For various techniques for transforming mammalian cells, see Keown et al., *Methods in Enzymology,* 185:527–537 (1990) and Mansour et al., *Nature,* 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as Escherichia, e.g., *E. coli,* Enterobacter, Erwinia, Klebsiella, Proteus, Salmonella, e.g., *Salmonella typhimurium,* Serratia, e.g., *Serratia marcescans,* and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa,* and Streptomyces. Various *E. coli* strains are publicly available, such as *E. coli* K12 strain MM294 (ATCC 31,446); *E. coli* X1776 (ATCC 31,537); *E. coli* strain W3110 (ATCC 27,325); and K5 772 (ATCC 53,635). These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for vectors containing nucleic acid encoding WISP polypeptide. *Saccharomyces cerevisiae* is a commonly used lower eukaryotic host microorganism. However, a number of other genera, species, and strains are commonly available and useful herein, such as *Schizosaccharomyces pombe* (Beach and Nurse, *Nature,* 290: 140 (1981); EP 139,383 published May 2, 1985); Kluyveromyces hosts (U.S. Pat. No. 4,943,529; Fleer et al., *Bio/Technology,* 9: 968–975 (1991)) such as, e.g., *K. lactis* (MW98–8C, CBS683, CBS4574; Louvencourt et al., *J. Bacteriol.,* 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technolocy,* 8: 135 (1990)), *K . thermotolerans,* and *K. marxianus; yarrowia* (EP 402,226); *Pichia pastoris* (EP 183,070; Sreekrishna et al.,*J. Basic Microbiol.,* 28: 265–278 (1988)); Candida; *Trichoderma reesia* (EP 244,234); *Neurospora crassa* (Case et al., *Proc. Natl. Acad. Sci. USA,* 76: 5259–5263 (1979)) ; Schwanniomyces such as *Schwanniomyces occidentalis* (EP 394,538 published Oct. 31, 1990); and filamentous fungi such as, e.g., Neurospora, Penicillium, Tolypocladium (WO 91/00357 published Jan. 10, 1991), and Aspergillus hosts such as *A. nidulans* (Ballance et al., *Biochem. Biophys. Res. Commun.,* 112: 284–289 (1983); Tilburn et al., *Gene,* 26: 205–221 (1983); Yelton et al., *Proc. Natl. Acad. Sci. USA,* 81: 1470–1474 (1984)) and *A. niger* Kelly and Hynes, *EMBO J.,* 4: 475–479 (1985). Methylotropic yeasts are suitable herein and include, but are not limited to, yeast capable of growth on methanol selected from the genera consisting of Hansenula, Candida, Kloeckera, Pichia, Saccharomyces, Torulopsis, and Rhodotorula. A list of specific species that are exemplary of this class of yeasts may be found in C. Anthony, *The Biochemistry of Methylotrophs,* 269 (1982).

Suitable host cells for the expression of glycosylated WISP are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture (Graham et al., *J. Gen Virol.,* 36:59 (1977)); Chinese hamster ovary cells/-DHFR (CHO, Urlaub and Chasin, *Proc. Natl. Acad. Sci. USA,* 77:4216 (1980)); mouse sertoli cells (TM4, Mather, *Biol. Reprod.,* 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding the desired WISP polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The desired WISP polypeptide may be produced recombinantly not only directly, but also as a fusion polypeptide with a heterologous polypeptide, which may be a signal sequence, if the WISP polypeptide is conducive to being secreted, or other polypeptide having a specific cleavage site at the N-terminus of the mature or full-length protein or polypeptide. In general, the signal sequence may be a component of the vector, or it may be a part of the DNA encoding the WISP polypeptide that is inserted into the vector. The signal sequence may be a prokaryotic signal sequence such as, for example, the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders, and including signals from WISP polypeptides.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV, or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the nucleic acid encoding WISP polypeptide, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7. Stinchcomb et al., *Nature*, 282:39 (1979); Kingsman et al., *Gene*, 7:141 (1979); Tschemper et al., *Gene*, 10:157 (1980). The trp1 gene provides a selection marker for a mutant strain of yeast lacking the ability to grow in tryptophan, for example, ATCC No. 44076 or PEP4-1. Jones, *Genetics*, 85:12 (1977).

Expression and cloning vectors usually contain a promoter operably linked to the nucleic acid sequence encoding WISP polypeptide to direct mRNA synthesis. Promoters recognized by a variety of potential host cells are well known. Promoters suitable for use with prokaryotic hosts include the β-lactamase and lactose promoter systems (Chang et al., *Nature*, 275:615 (1978); Goeddel et al .,  *Nature*, 281:544 (1979)), alkaline phosphatase, a tryptophan (trp) promoter system (Goeddel, *Nucleic Acids Res.*, 8:4057 (1980); EP 36,776), and hybrid promoters such as the tac promoter. deBoer et al., *Proc. Natl. Acad. Sci. USA*, 80:21–25 (1983). Promoters for use in bacterial systems also will contain a Shine-Dalgarno (S.D.) sequence operably linked to the DNA encoding the WISP polypeptide.

Examples of suitable promoting sequences for use with yeast hosts include the promoters for 3-phosphoglycerate kinase (Hitzeman et al., *J. Biol. Chem.*, 255:2073 (1980)) or other glycolytic enzymes (Hess et al., *J. Adv. Enzyme Rea.*, 7:149 (1968); Holland, *Biochemistry*, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol clehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

WISP transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus, and Simian Virus 40 (SV40); from heterologous mammalian promoters, e.g., the actin promoter or an immunoglobulin promoter; and from heat-shock promoters, provided such promoters are compatible with the host cell systems.

Transcription of a DNA encoding a WISP polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin) Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the sequence coding for a WISP polypeptide, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding WISP polypeptide.

Still other methods, vectors, and host cells suitable for adaptation to the synthesis of WISP polypeptides in recombinant vertebrate cell culture are described in Gething et al., *Nature*, 293:620–625 (1981); Mantei et al., *Nature*, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA*, 77:5201–5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native-sequence WISP polypeptide or against a synthetic peptide based on the DNA sequences provided herein or against exogenous sequence fused to DNA encoding WISP polypeptide and encoding a specific antibody epitope.

5. Purification of Polypeptide

Forms of WISP polypeptide may be recovered from culture medium or from host cell lysates. If membrane-bound, it can be released from the membrane using a suitable detergent solution (e.g., Triton-X 100) or by enzymatic cleavage. Cells employed in expression of WISP polypeptides can be disrupted by various physical or chemical means, such as freeze-thaw cycling, sonication, mechanical disruption, or cell lysing agents.

It may be desired to purify WISP polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX™ G-75; protein A SEPHAROSE™ columns to remove contaminants such as IgG; and metal chelating columns to bind epitope-tagged forms of the WISP polypeptide. Various methods of protein purification may be employed, and such methods are known in the art and described, for example, in Deutscher, *Methods in Enzymology*, 182 (1990); and Scopes, *Protein Purification:Principles and Practice* (Springer-Verlag: New York, 1982).

In one specific example of purification, either a poly-His tag or the Fc portion of human IgG is added to the C-terminal coding region of the cDNA for WISP-1, WISP-2, or WISP-3 before expression. The conditioned media from the transfected cells are harvested by centrifugation to remove the cells and filtered. For the poly-His-tagged constructs, the protein may be purified using a Ni-NTA column. After loading, the column may be washed with additional equilibration buffer and the protein eluted with equilibration buffer containing 0.25 M imidazole. The highly purified protein may then be desalted into a storage buffer if desired.

Immunoadhesin (Fc-containing) constructs of the WISP-1, WISP-2, and WISP-3 proteins may be purified from the conditioned media by pumping them onto a 5-ml Protein A column which had been equilibrated in a phosphate buffer. After loading, the column may be washed extensively with equilibration buffer before elution with citric acid. The eluted protein may be immediately neutralized by collecting 1-ml fractions into tubes containing TRIS buffer. The highly purified protein may be subsequently desalted into storage buffer as described above for the poly-His-tagged proteins. The homogeneity of the protein may be assessed by SDS polyacrylamide gels and by N-terminal amino acid sequencing by Edman degradation.

The purification step(s) selected will depend, for example, on the nature of the production process used and the particular WISP polypeptide produced.

E. Uses For WISP Polypeptide and Its Nucleic Acid

Nucleotide sequences (or their complement) encoding WISP polypeptides have various applications in the art of molecular biology, including uses as hybridization probes, in chromosome and gene mapping, and in the generation of anti-sense RNA and DNA. Nucleic acid encoding WISP polypeptide will also be useful for the preparation of WISP polypeptides by the recombinant techniques described herein.

The full-length nucleotide sequences for mouse or human WISP-1 or WISP-2 (SEQ ID NOS:9, 1, 17, and 13, respectively), or portions thereof, or the full-length nucleotide sequences for human WISP-3 of FIG. 6 (SEQ ID NO:30) or for WISP-3 of FIG. 7 (SEQ ID NO:34) may be used as hybridization probes for a cDNA library to isolate or detect the full-length gene encoding the WISP polypeptide of interest or to isolate or detect still other genes (for instance, those encoding naturally occurring variants of WISP polypeptide, other WISP polypeptide family members, or WISP polypeptides from other species) which have a desired sequence identity to the WISP polypeptide sequences disclosed in FIGS. 1, 2, 3A and 3B, 4, 6A and 6B, and 7A and 7B (SEQ ID NOS:3, 4, 11, 12, 15, 16, 19, 20, 32, 33, 36, or 37). For example, such procedures as in situ hybridization, Northern and Southern blotting, and PCR analysis may be used to determine whether DNA and/or RNA encoding a different WISP is present in the cell type(s) being evaluated. Optionally, the length of the probes will be about 20 to about 50 bases. For example, the hybridization probes may be derived from the UNQ228 (DNA33473-seq min) nucleotide sequence (SEQ ID NO:38) or the full-length human WISP-2 nucleotide sequence (SEQ ID NO:13) as shown in FIG. 4 or from genomic sequences including promoters, enhancer elements, and introns of DNA encoding native-sequence WISP polypeptide.

By way of example, a screening method will comprise isolating the coding region of the WISP gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of any of the genes encoding WISP polypeptides of the present invention can be used to screen libraries of human cDNA, genomic DNA, or mRNA to determine to which members of such libraries the probe hybridizes. Hybridization techniques are described in further detail in the Examples below.

The probes may also be employed in PCR techniques to generate a pool of sequences for identification of closely related WISP sequences.

Nucleotide sequences encoding a WISP polypeptide can also be used to construct hybridization probes for mapping the gene which encodes that WISP polypeptide and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries. If the amplification of a given gene is functionally relevant, then that gene should be amplified more than neighboring genomic regions which are not important for tumor survival. To test this, the gene can be mapped to a particular chromosome, e.g. by radiation-hybrid analysis. The amplification level is then determined at the location identified, and at neighboring genomic region. Selective or preferential amplification at the genomic region to which to gene has been mapped is consistent with the possibility that the gene amplification observed promotes tumor growth or survival. Chromosome mapping includes both framework and epicenter mapping. For further details see e.g., Stewart et al., *Genome Research* 7, 422–433 (1997).

Nucleic acid encoding a WISP polypeptide may be used as a diagnostic to determine the extent and rate of the expression of the DNA encoding the WISP polypeptide in the cells of a patient. To accomplish such an assay, a sample of a patient's cells is treated, via in situ hybridization, or by other suitable means, and analyzed to determine whether the sample contains mRNA molecules capable of hybridizing with the nucleic acid molecule.

Nucleic acids which encode WISP polypeptides or any of their modified forms can also be used to generate either transgenic animals or "knock-out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a WISP polypeptide can be used to clone genomic DNA encoding the WISP polypeptide in accordance with established techniques and the genomic sequences used to generate transgenic animals that contain cells which express DNA encoding the WISP polypeptide.

Methods for generating transgenic animals, particularly animals such as mice or rats, have become conventional in the art and are described, for example, in U.S. Pat. Nos. 4,736,866 and 4,870,009 and WO 97/38086. Typically, particular cells would be targeted for WISP transgene incorporation with tissue-specific enhancers. Transgenic animals that include a copy of a transgene encoding the WISP polypeptide introduced into the germ line of the animal at an embryonic stage can be used to examine the effect of increased expression of DNA encoding the WISP polypeptide. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of WISP polypeptides can be used to construct a WISP polypeptide "knockout" animal which has a defective or altered gene encoding a WISP polypeptide as a result of homologous recombination between the endogenous gene encoding the WISP polypeptide and altered genomic DNA encoding the WISP polypeptide introduced into an embryonic cell of the animal. For example, cDNA encoding the WISP polypeptide can be used to clone genomic DNA encoding the WISP polypeptide in accordance with established techniques. A portion of the genomic DNA encoding the WISP polypeptide can be deleted or replaced with another gene, such as a gene encoding a selectable marker which can be used to monitor integration. Typically, several kilobases of unaltered flanking DNA (both at the 5' and 3' ends) are included in the vector. See e.g., Thomas and Capecchi, *Cell*, 51:503 (1987) for a description of homologous recombination vectors. The vector is introduced into an embryonic stem cell line (e.g., by electroporation) and cells in which the introduced DNA has homologously recombined with the endogenous DNA are selected. See e.g., Li et al., *Cell*, 69:915 (1992). The selected cells are then injected into a blastocyst of an animal (e.g., a mouse or rat) to form aggregation chimeras. See e.g., Bradley, in *Teratocarcinomas and Embryonic Stem Cells: A Practical Approach*, E. J. Robertson, ed. (IRL, Oxford, 1987), pp. 113–152. A chimeric embryo can then be implanted into a suitable pseudopregnant female foster animal and the embryo brought to term to create a "knockout" animal. Progeny harboring the homologously recombined DNA in their germ cells can be identified by standard techniques and used to breed animals in which all cells of the animal contain the homologously recombined DNA. Knockout animals can be characterized, for instance, by their ability to defend against certain pathological conditions and by their development of pathological conditions due to absence of the WISP polypeptide.

In particular, assays in which CTGF, IGFBPs, and other members of the CTGF superfamily and other growth factors are usually used are preferably performed with the WISP-1 and WISP-2 polypeptides. For example, an assay to determine whether TGF-$\beta$ induces the WISP polypeptide, indicating a role in cancer, may be performed as known in the art, as well as assays involving induction of cell death and $^3$H-thymidine proliferation assays. Mitogenic and tissue growth assays are also performed with the WISP polypeptide as set forth above. The results are applied accordingly.

The WISP polypeptides of the present invention may also be used to induce the formation of anti-WISP polypeptide antibodies, which are identified by routine screening as detailed below.

In addition to their uses above, the WISP-1, WISP-2, and WISP-3 polypeptides of the present invention are useful as the basis for assays of IGF activity. Importantly, since such an assay measures a physicologically significant binding event, i.e., that of an IGF to its IGFBP, triggering a detectable change {such as phosphorylation, cleavage, chemical modification, etc.), it is likely to be both more sensitive and more accurate than immunoassays, which detect the physiologically non-significant binding of an IGF to anti-WISP polypeptide antibody. Although more sensitive and accurate than antibodies, the WISP-1, WISP-2, and WISP-3 molecules of the invention can be used to assay IGF (such as IGF-I or IGF-II) levels in a sample in the same ways in which antibodies are used.

For diagnostic purposes, the WISP-1, WISP-2, or WISP-3 polypeptide can be used in accordance with immunoassay technology. Examples of immunoassays are provided by Wide at pages 199–206 of *Radioimmune Assay Method*, Kirkham and Huner, ed., E & S. Livingstone, Edinburgh. 1970.

Thus, in one embodiment, WISP-1, WISP-2, and WISP-3 polypeptides can be detectably labeled and incubated with a test sample containing IGF molecules (such as biological fluids, e.g., serum, sputum, urine, etc.), and the amount of WISP-1, WISP-2, or WISP-3 molecule bound to the sample ascertained.

Immobilization of reagents is required for certain assay methods. Immobilization entails separating the WISP-1, WISP-2, or WISP-3 polypeptide from any analyte that remains free in solution. This conventionally is accomplished by either insolubilizing the WISP-1, WISP-2, or WISP-3 polypeptide before the assay procedure, as by adsorption to a water-insoluble matrix or surface (Bennich et al . . . U.S. Pat. No. 3,720,760), by covalent coupling (for example, using glutaraldehyde cross-linking), or by insolubilizing the molecule afterward, e.g., by immunoprecipitation.

The foregoing are merely exemplary diagnostic assays for IGF. Other methods now or hereafter developed for the determination of these analytes are included within the scope hereof.

WISP-1, WISP-2, and WISP-3 polypeptides are also useful in radioimmunoassays to measure IGFs such as IGF-I or IGF-II. Such a radioimmunoassay would be conducted as described in the literature using the naturally purified or recombinant WISP-1, WISP-2, or WISP-3 as the WISP element.

In addition, WISP polypeptides are useful for screening for compounds that bind to them as defined above. Preferably, these compounds are small molecules such as organic or peptide molecules that exhibit one or more of the desired activities. Screening assays of this kind are conventional in the art, and any such screening procedure may be employed, whereby the test sample is contacted with the WISP polypeptide herein and the extent of binding and biological activity of the bound molecule are determined.

More specifically, this invention encompasses methods of screening compounds to identify those that mimic the WISP polypeptide (agonists) or prevent the effect of the WISP polypeptide (antagonists). Screening assays for antagonist drug candidates are designed to identify compounds that bind or complex with the WISP polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a WISP polypeptide encoded by a nucleic acid identified herein under conditions and for a time sufficient to allow these two components to interact.

In binding assays, the interaction is binding and the complex formed can be isolated or detected in the reaction mixture. In a particular embodiment, the WISP polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the WISP polypeptide and drying. Alternatively, an immobilized antibody, e.g., a monoclonal antibody, specific for the WISP polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular WISP polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature* (*London*), 340: 245–246 (1989); Chien et al., *Proc. Natl. Acad. Sci. USA*, 88: 9578–9582 (1991)) as disclosed by Chevray and Nathans, *Proc. Natl. Acad. Sci. USA*, 89: 5789–5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a WISP polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

If the WISP polypeptide has the ability to stimulate the proliferation of endothelial cells in the presence of the co-mitogen ConA, then one example of a screening method takes advantage of this ability. Specifically, in the proliferation assay, human umbilical vein endothelial cells are obtained and cultured in 96-well flat-bottomed culture plates (Costar, Cambridge, Mass.) and supplemented with a reaction mixture appropriate for facilitating proliferation of the cells, the mixture containing Con-A (Calbiochem, La Jolla, Calif.). Con-A and the compound to be screened are added and after incubation at 37° C., cultures are pulsed with $^{3-}$-H-thymidine and harvested onto glass fiber filters (phD; Cambridge Technology, Watertown, Mass.). Mean $^{3-}$(H) thymidine incorporation (cpm) of triplicate cultures is determined using a liquid scintillation counter (Beckman Instruments, Irvine, Calif.). Significant $^{3-}$(H)thymidine incorporation indicates stimulation of endothelial cell proliferation.

To assay for antagonists, the assay described above is performed; however, in this assay the WISP polypeptide is added along with the compound to be screened and the ability of the compound to inhibit $^{3-}$(H) thymidine incorporation in the presence of the WISP polypeptide indicates that the compound is an antagonist to the WISP polypeptide. Alternatively, antagonists may be detected by combining the WISP polypeptide and a potential antagonist with membrane-bound WISP polypeptide receptors or recombinant receptors under appropriate conditions for a competitive inhibition assay. The WISP polypeptide can be labeled, such as by radioactivity, such that the number of WISP polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the WISP polypeptide and a cDNA library created from this RNA is divided into pools and used to transfect COS cells or other cells that are not responsive to the WISP polypeptide. Transfected cells that are grown on glass slides are exposed to labeled WISP polypeptide. The WISP polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled WISP polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled WISP polypeptide in the presence of the candidate compound. The ability of the compound to enhance or block this interaction could then be measured.

The compositions useful in the treatment of WISP-related disorders include, without limitation, antibodies, small organic and inorganic molecules, peptides, phosphopeptides, antisense and ribozyme molecules, triple-helix molecules, etc., that inhibit the expression and/or activity of the target gene product.

More specific examples of potential antagonists include an oligonucleotide that binds to the WISP polypeptide, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the WISP polypeptide that recognizes the receptor but imparts no effect, thereby competitively inhibiting the action of the WISP polypeptide.

Another potential WISP polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature WISP polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6: 3073 (1979); Cooney et al., *Science*, 241: 456 (1988); Dervan et al., *Science*, 251: 1360 (1991)), thereby preventing transcription and the production of the WISP polypeptide. The antisense RNA oligonucleotide hybridizes to the mRNA in vivo and blocks translation of the mRNA molecule into the WISP polypeptide (antisense—Okano, *Neurochem.*, 56: 560 (1991); *Oliaodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the WISP polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the WISP polypeptide, thereby blocking the normal biological activity of the WISP polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4: 469–471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

WISP-1, WISP-2, and WISP-3 polypeptides are additionally useful in affinity purification of an IGF that binds to WISP-1, WISP-2, or WISP-3 (such as, for example. IGF-I) and in purifying antibodies thereto. The WISP-1, WISP-2, or WISP-3 is typically coupled to an immobilized resin such as Affi-Gel 10™ (Bio-Rad, Richmond. Calif.) or other such resins (support matrices) by means well known in the art. The resin is equilibrated in a buffer (such as one containing 150 mM NaCl, 20 mM HEPES, pH 7.4 supplemented to contain 20% glycerol and 0.5% NP-40) and the preparation to be purified is placed in contact with the resin, whereby the molecules are selectively adsorbed to the WISP-1, WISP-2, or WISP-3 on the resin.

The resin is then sequentially washed with suitable buffers to remove non-adsorbed material, including unwanted contaminants, from the mixture to be purified, using, e.g., 150 0.5 mM NaCl, 20 mM HEPES, pH 7.4, containing 0.5% NP-40; 150 mM NaCl, 20 mM HEPES, pH 7.4 containing 0.5 M NaCl and 0.1% NP-40; 150 mM NaCl, 20 mM HEPES, pH 7.4 containing 0.1% deoxycholate: 150 mM NaCl, 20 mM HEPES, pH 7.4 containing 0.1% NP-40; and a solution of 0.1% NP-40, 20% glycerol and 50 MM glycine, pH 3. The resin is then treated so as to elute the IGF using a buffer that will break the bond between the IGF and WISP-1, WISP-2. or WISP-3 (using, e.g., 50 mM glycine, pH 3, 0.1% NP-40, 20% glycerol, and 100 mM NaCl).

It is contemplated that the WISP polypeptides of the present invention may be used to treat various conditions, including those characterized by overexpression and/or activation of at least the Wnt pathway. Further, since the WISP-1, WISP-2, and WISP-3 molecules respond to hormone-expressed breast cancer in mice and are abnormally expressed in human cancer, and are over-amplified in various colon cancer cell lines, they are useful in diagnosing cancer, for example, as a marker for increased susceptibility to cancer or for having cancer. Exemplary conditions or disorders to be treated with the WISP polypeptides include benign or malignant tumors (e.g., renal, liver, kidney, bladder, testicular, breast, gastric, ovarian, colorectal, prostate, pancreatic, lung, esophageal, vulval, thyroid, hepatic carcinomas; sarcomas; glioblastomas; and various head and neck tumors); leukemias and lymphoid malignancies; other disorders such as neuronal, glial, astrocytal, hypothalamic, and other glandular, macrophagal, epithelial, stromal, and blastocoelic disorders; cardiac disorders; renal disorders; catabolic disorders; bone-related disorders such as osteoporosis; and inflammatory, angiogenic, and immunologic disorders, such as arteriosclerosis; as well as connective tissue disorders, including wound healing.

The WISP polypeptides of the invention are administered to a mammal, preferably a human, in accord with known methods, such as intravenous administration as a bolus or by continuous infusion over a period of time, by intramuscular, intraperitoneal, intracerebrospinal, subcutaneous, intraarticular, intrasynovial, intrathecal, oral, topical, or inhalation routes. Intravenous or subcutaneous administration of the polypeptide is preferred.

Therapeutic formulations of the WISP polypeptide are prepared for storage by mixing the polypeptide having the desired degree of purity with optional pharmaceutically acceptable carriers, excipients, or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose, or sorbitol; salt-forming counter-ions such as sodium; metal complexes (e.g., Zn-protein complexes); and/or non-ionic surfactants such as TWEEN™, PLURONICS™, or polyethylene glycol (PEG).

Other therapeutic regimens may be combined with the administration of the WISP polypeptides of the instant invention. For example, the patient to be treated with the polypeptides disclosed herein may also receive radiation therapy if the disorder is cancer. Alternatively, or in addition, a chemotherapeutic agent may be administered to the patient with cancer. Preparation and dosing schedules for such chemotherapeutic agents may be used according to manufacturers' instructions or as determined empirically by the skilled practitioner. Preparation and dosing schedules for such chemotherapy are also described in *Chemotherapy Service*, Ed., M. C. Perry (Williams & Wilkins: Baltimore, Md., 1992). The chemotherapeutic agent may precede or follow administration of the polypeptide or may be given simultaneously therewith. The polypeptide may be combined with an anti-oestrogen compound such as tamoxifen or an anti-progesterone such as onapristone (see, EP 616812) in dosages known for such molecules.

It may be desirable also to co-administer with the WISP polypeptide (or anti-WISP polypeptide) antibodies against other tumor-associated antigens, such as antibodies which bind to HER-2, EGFR, ErbB2, ErbB3, ErbB4, or vascular endothelial factor (VEGF). Alternatively, or in addition, two or more different anti-cancer antibodies, such as anti-ErbB2 antibodies, may be co-administered to the patient with the WISP polypeptide (or anti-WISP polypeptide antibody). Sometimes, it may be beneficial also to administer one or more cytokines to the patient.

In a preferred embodiment, the WISP polypeptide is co-administered with a growth-inhibitory agent to the cancer patient. For example, the growth-inhibitory agent may be administered first, followed by the WISP polypeptide. However, simultaneous administration or administration of the WISP polypeptide first is also contemplated. Suitable dosages for the growth-inhibitory agent are those presently used and may be lowered due to the combined action (synergy) of the growth-inhibitory agent and polypeptide. The antibodies, cytotoxic agents, cytokines, or growth-inhibitory agents are suitably present in combination in amounts that are effective for the purpose intended.

The active ingredients may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in *Remington's Pharmaceutical Sciences,* 16th edition, Osol, A. Ed. (1980), supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the polypeptide, which matrices are in the form of shaped articles, e.g., films, or microcapsules. Examples of sustained-release matrices include polyesters, hydrogels (for example, poly (2-hydroxyethyl-methacrylate), or poly (vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

For the prevention or treatment of disease or disorder, the appropriate dosage of WISP polypeptide will depend on the type of disorder to be treated, as defined above, the severity and course of the disorder, whether the polypeptide is administered for preventive or therapeutic purposes, previous therapy, the patient's clinical history and response to the polypeptide, the route of administration, the condition of the patient, and the discretion of the attending physician. The polypeptide is suitably administered to the patient at one time or over a series of treatments.

Depending on the type and severity of the disease, about 1 μg/kg to 15 mg/kg (e.g., 0.1–20 mg/kg) of WISP polypeptide is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of symptoms of the disorder occurs. However, other dosage regimens may be useful. The progress of this therapy is easily monitored by conventional techniques and assays. In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example, the container may be an intravenous solution bag or a vial having a stopper pierceable by a hypodermic injection needle). The active agent in the composition is the WISP polypeptide. The label on, or associated with, the container indicates that the composition is used for treating the condition or disorder of choice. The article of manufacture may further comprise a second container comprising a pharmaceutically acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

F. Anti-WISP Polypeptide Antibodies

The present invention further provides anti-WISP polypeptide antibodies. Exemplary antibodies include polyclonal, monoclonal, humanized, bispecific, and heteroconjugate antibodies.

1. Polyclonal Antibodies

The anti-WISP polypeptide antibodies of the present invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the WISP polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-WISP polypeptide antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the WISP polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as PEG, to form a hybridoma cell. Goding, *Monoclonal Antibodies: Principles and Practice* (Academic Press: New York, 1986) pp. 59–103. Immortalized cell lines are usually transformed mammalian cells, particularly myeloma cells of rodent, bovine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif., and the American Type Culture Collection, Manassas, Va. Human myeloma and mouse-human heteromyeloma cell lines also have been described for the production of human monoclonal antibodies. Kozbor, *J. Immunol.,* 133:3001 (1984); Brodeur et al., *Monoclonal Antibody Production Techniques and Applications* (Marcel Dekker, Inc.: New York, 1987) pp. 51–63.

The culture medium in which the hybridoma cells are cultured can then be assayed for the presence of monoclonal antibodies directed against a WISP polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980)

After the desired hybridoma cells are identified, the clones may be subcloned by limiting dilution procedures and grown by standard methods. Goding, supra. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, CHO cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., *Proc. Natl. Acad. Sci. USA,* 81: 6851–6855 (1984)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using routine techniques known in the art.

3. Humanized Antibodies

The anti-WISP antibodies of the invention may further comprise humanized antibodies or human antibodies. Humanized forms of non-human (e.g., murine) antibodies are chimeric immunoglobulins, immunoglobulin chains, or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementary-determining region (CDR) of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody preferably also will comprise at least a portion of an Fc, typically that of a human immunoglobulin. Jones et al., *Nature,* 321:522–525 (1986); Riechmann et al., *Nature,* 332:323–329 (1988); Presta, *Curr. OP. Struct. Biol.,* 2:593–596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522–525 (1986); Riechmann et al., *Nature,* 332:323–327 (1988); Verhoeyen et al., *Science,* 239:1534–1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage-d-splay libraries. Hoogenboom and Winter, *J. Mol. Biol.,* 227:381 (1991); Marks et al., *J. Mol. Biol.,* 222:581 (1991). The techniques of Cole et al. and Boerner et al. are also available for the preparation of human monoclonal antibodies. Cole et al., *Monoclonal Antibodies and Cancer Therapy,* Alan R. Liss, p. 77 (1985); Boerner et al., *J. Immunol.,* 147(1):86–95 (1991).

4. Bispecific Antibodies

Bispecific antibodies are monoclonal, preferably human or humanized, antibodies that have binding specificities for at least two different antigens. In the present case, one of the binding specificities is for a WISP polypeptide; the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities. Milstein and Cuello, *Nature*, 305:537–539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection. WO 91/00360; WO 92/200373; EP 03089. It is contemplated that the antibodies may be prepared in vitro using known methods in synthetic protein chemistry, including those involving cross-linking agents. For example, immunotoxins may be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses For Anti-WISP Polypeptide Antibodies

The antibodies of the invention may be used as affinity purification agents. In this process, the antibodies are immobilized on a solid phase such a SEPHADEX™ resin or filter paper, using methods well known in the art. The immobilized antibody is contacted with a sample containing the WISP polypeptide (or fragment thereof) to be purified, and thereafter the support is washed with a suitable solvent that will remove substantially all the material in the sample except the WISP protein, which is bound to the immobilized antibody. Finally, the support is washed with another suitable solvent, such as glycine buffer, pH 5.0, that will release the WISP polypeptide from the antibody.

Anti-WISP polypeptide antibodies may also be useful in diagnostic assays for WISP polypeptide, e.g., detecting its expression in specific cells, tissues, or serum. Thus, the antibodies may be used in the diagnosis of human malignancies (see, for example, U.S. Pat. No. 5,183,884).

For diagnostic applications, the antibody typically will be labeled with a detectable moiety. Numerous labels are available which can be preferably grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed., (Wiley-Interscience: New York, 1991), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin, and Texas Red are available. The fluorescent labels can be conjugated to the antibody using the techniques disclosed in *Current Protocols in Immunology*, supra, Coligen, ed., for example. Fluorescence can be quantified using a fluorimeter.

(c) Various enzyme-substrate labels are available, and U.S. Pat. No. 4,275,149 provides a review of some of these. The enzyme preferably catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.*, Vol. 73, Langone and Van Vunakis, eds. (New York: Academic Press, 1981), pp. 147–166.

Examples of enzyme-substrate combinations include:

(I) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (4-methylumbelliferyl-β-D-galactosidase).

Numerous other enzyme-substrate combinations are available to those skilled in the art. For a general review of these, see, for example, U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin, and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-WISP polypeptide antibody need not be labeled, and the presence thereof can be detected using a labeled antibody which binds to the anti-WISP polypeptide antibody.

The antibodies of the present invention may be employed in any known assay method, such as competitive binding assays, direct and indirect sandwich assays, and immunoprecipitation assays. Zola, *Monoclonal Antibodies: A Manual of Techniques* (New York: CRC Press, Inc., 1987), pp.147–158.

Competitive binding assays rely on the ability of a labeled standard to compete with the test sample analyte for binding with a limited amount of antibody. The amount of WISP protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Preferably, the antibody is labeled with a radionuclide (such as $^{111}In$, $^{99}Tc$, $^{14}C$, $^{131}I$, $^{125}I$, $^{3}H$, $^{32}P$ or $^{35}S$) so that the tumor can be localized using immunoscintiography.

Additionally, anti-WISP polypeptide antibodies may be useful as antagonists to WISP polypeptide functions where WISP polypeptide is upregulated in cancer cells or stimulates their prolilferation or is upregulated in atherosclerotic tissue. Hence, for example, the anti-WISP polypeptide antibodies may by themselves or with a chemotherapeutic agent or other cancer treatment or drug such as anti-HER-2 antibodies be effective in treating certain forms of cancer such as breast cancer, colon cancer, lung cancer, and melanoma. Further uses for the antibodies include inhibiting the binding of a WISP polypeptide to its receptor, if applicable, or to an IGF, if applicable. For therapeutic use, the antibodies can be used in the formulations, schedules, routes, and doses indicated above under uses for the WISP polypeptides. In addition, anti-WISP polypeptide antibody may be administered into the lymph as well as the blood stream.

As a matter of convenience, the anti-WISP antibody of the present invention can be provided as an article of manufacture such as a kit. An article of manufacture containing a WISP polypeptide or antagonists thereof useful for the diagnosis or treatment of the disorders described above comprises at least a container and a label. Suitable containers include, for example, bottles, vials, syringes, and test tubes. The containers may be formed from a variety of materials such as glass or plastic. The container holds a composition that is effective for diagnosing or treating the condition and may have a sterile access port (for example, the container may be an intravenous solution bag or a vial having a stopper pierceable by a hypodermic injection needle).

The active agent in the composition is the WISP polypeptide or an agonist or antagonist thereto. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use. The article of manufacture may also comprise a second or third container with another active agent as described above. A kit format generally is a packaged combination of reagents in predetermined amounts with instructions for performing the diagnostic or treatment assay.

If the active agent is an antibody that is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer), and the like. The relative amounts of the various reagents may be varied widely to provide for concentrations in solution of the reagents which substantially maximize the sensitivity of the assay. Particularly, the reagents may be provided as dry powders, usually lyophilized, including excipients which on dissolution will provide a reagent solution having the appropriate concentration.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, 10801 University Blvd., Manassas, Va.

Example 1
Isolation of cDNA Clones Encoding Mouse WISP-1

Several putative WISP genes have been identified at the mRNA level in a high-throughput PCR-select cDNA substraction experiment carried out using a mouse mammary cell line (C57MG), which has been transformed by a Wnt-1 retroviral vector and compared with the parental cell line. The WISP family disclosed herein, including the mouse WISP-1 gene, was induced only in the transformed cell line C57MGWnt-1.

1. Suppression Subtractive Hybridization

Mouse WISP-1 was isolated independently by Wnt-1 differential screening using suppression subtractive hybridization (SSH), as described by Diatchenko et al., *Proc. Natl. Acad. Sci. USA,* 93: 6025–6030 (1996). SSH was carried out using the PCR-SELECT® cDNA Subtraction Kit (Clontech Laboratories, Inc.) according to the manufacturer's protocol. Driver double-stranded (ds) cDNA was synthesized from 2 micrograms of polyA+ RNA isolated from a mouse mammary cell line (C57MG), obtainable from a mouse breast cancer myoepithelial cell line. This cell line is described in Brown et al., *Cell,* 46: 1001–1009 (1986); Olson and Papkoff, *Cell Growth and Differentiation,* 5: 197–206 (1994); Wong et al., *Mol. Cell. Biol.,* 14: 6278–6286 (1994); and Jue et al., *Mol. Cell. Biol.,* 12: 321–328 (1992), and is responsive to Wnt-1 but not to Wnt-4. Tester ds cDNA was synthesized from 2 micrograms of polyA+ RNA isolated from a transformed version of C57MG, called C57MG/wnt-1.

The C57MG/wnt-1 mouse mammary derivative cell line was prepared by first transforming the parent line with a Wnt-1 retroviral vector, pBabe Puro (5.1 kb). This vector has a 5' LTR, packaging elements, a multiple cloning site, the puromycin-resistance gene driven off the SV40 promoter, a 3' LTR, and the bacterial elements for replication and ampicillin selection. The vector was modified slightly for Wnt-1 cloning by removing the HindIII site after the SV40 promoter and adding a HindIII site to the multiple cloning site. Wnt-1 is cloned from EcoRI-HindIII in the multiple cloning site. FIG. 13 shows a map of the vector.

The transformed derivative cells were grown up in a conventional fashion, and the final cell population was selected in DMEM+10% FCS with 2.5 μg/ml puromycin to stabilize the expression vector.

PCR was performed using the Clontech kit, including the cDNA synthesis primer (SEQ ID NO:40), adaptors 1 and 2 (SEQ ID NOS:41 and 42, respectively) and complementary sequences for the adaptors (SEQ ID NOS:43 and 44, respectively), PCR primer 1 (SEQ ID NO:45), PCR primer 2 (SEQ ID NO:46), nested PCR primer 1 (SEQ ID NO:47), nested PCR primer 2 (SEQ ID NO:48), control primer G3PDH5' primer (SEQ ID NO:49), and control primer G3PDH3' primer (SEQ ID NO:50), shown in FIG. 14.

Products generated from the secondary PCR reaction were inserted into the cloning site region of pGEM-T vector (Promega), shown in FIG. 15 (SEQ ID NOS:51 and 52 for 5' and 3' sequences, respectively). Plasmid DNAs were prepared using the WIZARD MINIPREP™ Kit (Promega). DNA sequencing of the subcloned PCR fragments was performed manually by the chain termination reaction (SEQUENASE 2.0™ Kit, Pharmacia). Nucleic acid homology searches were performed using the BLAST program noted above.

A total of 1384 clones were sequenced out of greater than 5000 found. A total of 1996 DNA templates were prepared. A program was used to trim the vector off, and a different program used to cluster the clones into two or more identical clones or with an overlap of 50 bases the same. Then a BLAST was performed of a representative clone from the cluster. Primers were designed for RT-PCR to see if the clones were differentially expressed.

2. Semi-quantitative RT-PCR

One of the clones was clone 568 having 71 bp, which was identified as encoding mouse WISP-1. There were six clones in this cluster. The nucleotide sequence and putative amino acid sequence of full-length mouse WISP-1 are shown in FIGS. 1A–1B (SEQ ID NOS:9 and 12, respectively). RT-PCR primers were designed for confirming differential expression, screening for full-length mouse clone, and screening for the human clone. These primers were 568.PCR.top1 (nucleotides 909–932 of the full-length nucleotide sequence encoding mouse WISP-1 (SEQ ID NO:9) of FIGS. 1A–1B) and 568.PCR.bot1 (nucleotides 955–978 of the full-length complementary nucleotide sequence encoding mouse WISP-1 (SEQ ID NO: 10) of FIGS. 1A–1B), which are as follows:

568.PCR.top1: 5'-CCAGCCAGAGGAGGCCAC GAAC (SEQ ID NO:100)

568.PCR.bot1: 3'-TGTGCGTGGATGGCTGGG TTCATG (SEQ ID NO:101)

For the RT-PCR procedure, cell lines were grown to subconfluence before extracting the RNA. Total RNA was extracted using Stat-60™ (TEL-TEST™ B) per manufacturer's instructions. First-strand cDNA was prepared from 0.1 μg–3 μg of total RNA with the SUPERSCRIPT™ RT kit (Gibco, BRL). PCR amplification of 5 μl of first-strand cDNA was performed in a 50-μl PCR reaction. The above primers were used to amplify first-strand cDNA. As controls, primers corresponding to nucleotide positions 707–729 (sense; 5'-GTGGCCCATGCTCTGGCAGAGGG (SEQ ID NO:102)) or 836–859 (sense; 5'-GACTGGAGCAAGGTCGTCCTCGCC (SEQ ID NO:103)) and 1048–1071 (anti-sense; 5'-GCACCACCCACAAGGAAGCCATCC (SEQ ID NO:104)) of human triosephosphate isomerase (huTPI) (Maquat et al., *J. Biol. Chem.,* 260: 3748–3753 (1985); Brown et al., *Mol. Cell. Biol.,* 5: 1694–1706 (1985)) were used to amplify first-strand cDNA. For mouse triosephosphate isomerase, primers corresponding to nucleotide positions 433–456 (sense; 5'-GACGAAAGGGAAGCCGGCATCACC (SEQ ID NO: 105)) or 457–480 bp (sense; 5'-GAGAAGGTCGTGTTCGAGCAAACC (SEQ ID NO: 106)) and 577–600 bp (antisense; 5'-CTTCTCGTGTACTTCCTGTGCCTG (SEQ ID NO:107)) or 694–717 bp (antisense; 5'-CACGTCAGCTGGCGTTGCCAGCTC (SEQ ID NO:108)) were used for amplification.

Briefly, 4 μCi of ($^{32}$P-)CTP (3000 Ci/mmol) was added to each reaction with 2.5 U of TAKARA EX TAQ™ (Panvera, Madison, Wis.) and 0.2 μM of each dNTP. The reactions were amplified in a 480 PCR THERMOCYCLER™ (Perkin Elmer) using the following conditions: 94° C. for 1 min., 62° C. for 30 sec., 72° C. for 1 min, for 18–25 cycles. 5 μl of PCR products were electrophoresed on a 6% polyacrylamide gel. The gel was exposed to film. Densitometry measurements were obtained using ALPHA EASE VERSION 3.3a™ software (Alpha Innotech Corporation) to quantitate the WISP- or TPI-specific gene products.

3. Northern Blot Analysis

Adult multiple-tissue Northern blots (Clontech) and the Northern blot of the C57MG parent and C57MG/Wnt-1 derivative polyA+RNA (2 μg/lane) were hybridized with a 70-bp mouse WISP-1 probe (amino acids 278 through 300 of FIG. 1; QPEEATNFTLAGCVSTRTYRPKY; SEQ ID NO:109) generated using the primers 568.PCR.top1 and 568.pcr.bot1 noted above. The membranes were washed in 0.1×SSC at 55–65° C. and exposed for autoradiography. Blots were rehybridized with a 75-bp synthetic probe from the human actin gene. See Godowski et al., *Proc. Natl. Acad. Sci. USA*, 86: 8083–8087 (1989) for a method for making a probe with overlapping oligos, which is how the actin probe was prepared.

4. cDNA Library Screening

Clones encoding the full-length mouse WISP-1 were isolated by screening a λgt10 oligodT primed mouse embryo library (Clontech) with the primers 568.PCR.top1 and 568.PCR.bot1 noted above. The inserts of 13 of these clones were subcloned into pBLUESCRIPT™ IISK+ and their DNA sequences determined by dideoxy DNA sequencing on both strands.

5. Results

The recently described technique of SSH combines a high subtraction efficiency with an equalized representation of differentially expressed sequences. This method is based on specific PCR reactions that permit exponential amplification of cDNAs which differ in abundance, whereas amplification of sequences of identical abundance in two populations is suppressed. The SSH technique was used herein to isolate genes expressed in a mouse mammary myoepithelial cell transformed with Wnt-1 whose expression is reduced or absent in the parental myoepithelial cell. The polyA$^+$RNA extracted from both types of cells was used to synthesize tester and driver cDNAs. The degree of subtraction efficiency was monitored by Southern blot analysis of unsubtracted and subtracted PCR products using a β-actin probe. No β-actin mRNA was apparent in the subtracted PCR products, confirming the efficiency of the subtraction.

The subtracted cDNA library was subcloned into a pGEM-T vector for further analysis. A random sample of 1996 clones was sequenced from the transformed colonies obtained. To determine if the clones obtained were differentially expressed, PCR primers were designed for selected clones and semi-quantitative RT-PCR and Northern analyses were performed using mRNA from the mouse mammary cell line and its derivative. It was found that expression of Wnt-1 in C57MG cells leads to elongated cell morphology and loss of contact inhibition.

One clone (m568.19A) of those that fulfilled the criteria for differential expression was found to encode full-length mouse WISP-1. By both RT-PCR analysis and Northern analysis, it was found that this clone provided an about three-fold induction in the Wnt-1 cell line over the parent cell line.

The cDNA sequence of this clone and deduced amino acid sequence of full-length mouse WISP-1 are shown in FIGS. 1A–1B (SEQ ID NOS:9 and 12, respectively). The sequence alignment of human and mouse WISP-1 (SEQ ID NOS:4 and 12, respectively) is shown in FIG. 8. In-situ analysis of the clone is presented below, along with thymidine incorporation assay and angiostatic assay results.

This clone was placed in pRK5E, an *E. coli*-derived cloning vector having a human cytomegalovirus intermediate early gene promoter, an SV40 origin and polyA site, an sp6 transcription initiation site, a human immunoglobulin splice acceptor, and XhoI/NotI cDNA cloning sites. It is a progeny of pRK5D that has an added SceI site. Holmes et al., *Science*, 253:1278–1280 (1991). Upon transformation into JM109 cells, the plasmid rendered the cells ampicillin resistant. Upon digestion with XbaI and BamHI, a 1140-bp fragment was obtained, and the mouse insert size was 1122 base pairs, from the ATG to the stop codon, including a 3' tag of six histidines.

Example 2

Isolation of a cDNA Clone Encoding Mouse WISP-2

The cDNA for mouse WISP-2 was isolated independently by Wnt-1 differential screening using the procedure described in Example 1. The initial clone isolated was 318 bp in length and was designated clone 1367. There were four clones in this cluster. The clone was sequenced as described above and RT-PCR primers were designed as follows: 1367.pcr.top1: nucleotides 1604–1627 of FIGS. 2A–2B:

3'-GGTGTGAAGACCGTCCGGTCCCGG (SEQ ID NO:110)

and 1367.pcr.bot1: nucleotides 1438–1461 of FIGS. 2A–2B:

5'-GTGTGCCTTTCCTGATCTGAGAAC (SEQ ID NO:111)

After RT-PCR and Northern blot procedures were carried out as described in Example 1 to confirm differential expression, a five-fold induction in the Wnt-1 cell line was observed.

Clones encoding full-length mouse WISP-2 were isolated from RNA library 211: C57MG/Wnt-1. mRNA for construction of this library was isolated from the C57MG/Wnt-1 cell line described in Example 1. The RNA was used to generate an oligo-dT-primed cDNA library in the cloning vector pRK5E using reagents and protocols from Life Technologies, Gaithersburg, Md. (SUPERSCRIPT PLASMID SYSTEM™).

In this procedure, the double-stranded cDNA was primed with oligo dT containing a NotI site, linked with blunt-to-SalI hemikinased adaptors, cleaved with NotI, sized to greater than 1000 bp appropriately by gel electrophoresis, and cloned in a defined orientation into the XhoI/NotI-cleaved pRK5E vector. The library was screened by colony hybridization with a probe 1367.50mer.1 of bases 1463–1512 of FIGS. 2A–2B:

3'-GGGACGGGCCGACCCTTCTTAAAAGAC-
CCTTGTACTTCTCTACCTTAGTG (SEQ ID NO:112).

The full-length mouse WISP-2 clone was obtained, designated clone 1367.3.

The cDNA for mouse WISP-2, like the mouse WISP-1 molecule, encodes a novel secreted protein that belongs to the CTGF family and is the mouse homologue of SST DNA33473 of Example 4. (The alignment of human and mouse WISP-2 (SEQ ID NOS: 16 and 20, respectively) is shown in FIG. 9.) The mouse WISP-2 gene is 38% identical in sequence to mouse WISP-1, disclosed in Example 1, but lacks the C-terminal 95 amino acids thought to be involved in dimerization and receptor binding. Mouse WISP-2 was highly expressed in the lung. In-situ analysis of the clone is noted below. The nucleotide sequence and putative amino acid sequence of full-length mouse WISP-2 are shown in FIGS. 2A–2B (SEQ ID NOS:17 and 20, respectively). The putative signal sequence is from amino acid positions 1 to 23 of SEQ ID:20.

The clone was inserted into pRK5E, described above. Upon transformation of JM109 cells, the plasmid rendered the cells ampicillin resistant. Upon digestion with BamHI and NotI, a 1770-bp fragment was obtained, having a mouse insert of 756 bp from ATG to the stop codon.

Example 3

Isolation of a cDNA Clone Encoding Human WISP-1

To isolate the full-length human clone corresponding to m568.19A (mouse WISP-1), a human lung cDNA library (Clontech), treated with the SUPERSCRIPT™ kit using the pRK5E vector as described above, was screened with a 70-bp probe at low stringency (20% formamide, 1×SSC, 55° C. wash). The probe had the sequence from nucleotides 909–978 of the full-length mouse WISP-1 nucleotide sequence of FIGS. 1A–1B, i.e., the sequence:

5'-CCAGCCAGAGGAGGCCACGAACT-
TCACTCTCGCAGGCTGTGTCAGCACACGCACCTACC
GACCCAAGTAC (SEQ ID NO:113)

Only one clone was identified, hL.568.15A. The insert to this clone was subcloned into pBLUESCRIPT™ IISK+ and its DNA sequence determined by dideoxy DNA sequencing on both strands. This clone was found to be missing about 280 amino acids. Hence, a new probe (hu.568.50mer.1) was designed from clone 15A having the nucleotides 750–799 of the full-length human WISP-1 nucleotide sequence shown in FIGS. 3A and 3B, i.e.,

5'-GCCCCTGGAGCCCTTGCTCCACCAGCT-
GCGGCCTGGGGGTCTCCACTCGG (SEQ ID NO:114)

This probe was used to screen a human fetal kidney cDNA library (Clontech), treated with the SUPERSCRIPT™ kit using the pRK5E vector as described above, by colony hybridization. A number of clones were obtained by screening this human fetal kidney cDNA library (clones without the A or B designation) or by screening a human fetal kidney λgt10 library (clones with the A or B designation) using the same probes described above. The inserts of these clones were subcloned into pBLUESCRIPT™ IISK+ and their DNA sequences determined by dideoxy DNA sequencing on both strands.

Two of these clones, designated as 568.1A and 568.4A, have their respective sequences (SEQ ID NOS:24 and 26) shown in FIGS. 27 and 29. These clones are missing the von Willebrand C1 domain, the variable domain, and the thrombospondin 1 domain, and have a frameshift. Other clones, designated as 568.13, 568.39, 568.5A, 568.6B, and 568.7 (SEQ ID NOS:23, 25, 27, 28, and 29, respectively; FIGS. 26, 28, and 30–32, respectively), were obtained that lack one or more domains and/or short amino-acid stretches (e.g., an 8-amino-acid deletion) or contain additional short amino-acid stretches and may contain introns or alternative splice variants.

Two clones sharing a significant amount of sequence with the full-length clone 568.38 were identified: 568.23 and 568.35. Human clone 568.38 encoded the full-length human WISP-1. The nucleotide sequence and putative amino acid sequence for clone 568.38 are shown in FIGS. 3A–3C (SEQ ID NOS:1 and 4, respectively). The aligning sequences of clones 568.38 and 568.35 differ from the corresponding aligning sequences of clones 568.15A and 568.23 in that the respective sequences of the latter two clones have an isoleucine residue at amino acid position 184 of FIGS. 3A–3C, whereas the respective corresponding sequences of clones 568.38 and 568.35 have a valine residue at this position. Further, the aligning sequences of clones 568.35 and 568.38 differ from each other in that the sequence of clone 568.35 has a serine residue at amino acid position 202 of FIGS. 3A and 3B, whereas the corresponding sequence of clone 568.38 has an alanine residue at this position.

The human WISP-1 polypeptide, by homology searching, is also found to be a member of the CTGF family. The clone was placed in a pRK5E plasmid as described above and deposited with the ATCC. Upon transformation into JM109 cells, the plasmid rendered the cells ampicillin resistant. Digestion with ClaI and EcoRV yielded a 1435-bp fragment with an insert size of 1104 basepairs from ATG to the stop codon.

In situ hybridization of human WISP-1 was performed, with the results given below. Northern analysis of human WISP-1 showed high expression in adult heart tissue and ovary tissue, and in fetal kidney tissue. Also presented below are thymidine incorporation assay, gene amplification assay, and angiostatic assay results.

The chromosomal location of the human WISP genes was determined by radiation hybrid mapping using the Stanford G3™ and the MIT Genebridge 4 Radiation Hybrid™ panels. WISP-1 resides at approximately 3.48 cr from the meiotic marker AFM259xc5 (LOD score 16.31) on the Genebridge map. This places WISP-1 in band 8q24.1 to 8q24.3, roughly four megabases distal to c-myc located at chromosome band 8q24.12-8q24.13. Takahashi et al., *Cytogenet. Cell Genet.*, 57: 109–111 (1991). c-myc is a region that is a recurrent site of amplification in non-small cell lung carcinoma.

Example 4
Isolation of a cDNA Clone Encoding Human PRO261 (Designated Herein as Human WISP-2)

The extracellular domain (ECD) sequences (including the secretion signal, if any) of from about 950 known secreted proteins from the SWISS-PROT™ public protein database were used to search expressed sequence tag (EST) databases. The EST databases included public EST databases (e.g., GenBank) and a proprietary EST DNA database (LIFESEQ™, Incyte Pharmaceuticals, Palo Alto, Calif.). The search was performed using the computer program BLAST or BLAST2 (Altshul et al., *Methods in Enzymology* 266:460–480 (1996)) as a comparison of the ECD protein sequences to a 6-frame translation of the EST sequence. Those comparisons resulting in a BLAST score of 70 (or in some cases 90) or greater that did not encode known proteins were clustered and assembled into consensus DNA sequences with the program "phrap" (Phil Green, University of Washington, Seattle, Wash.: http:// bozeman.mbt.washington.edu/phrap.docs/phrap.html).

A consensus DNA sequence was assembled relative to other EST sequences using phrap. The EST sequences used (from Incyte) were Nos. 2633736, 2118874, 360014, 2316216, 1985573, 2599326, 1544634, 2659601, 1319684, 783649, 627240, 1962606, 2369125, 939761, 1666205, 692911, 984510, 1985843, 2104709, and 2120142. This consensus sequence is herein designated DNA30843 (see FIG. 5). Based on the DNA30843 consensus sequence, oligonucleotides were synthesized: 1) to identify by PCR a cDNA library that contained the sequence of interest, and 2) for use as probes to isolate a clone of the full-length coding sequence for PRO261 (human WISP-2). A pair of PCR primers, forward and reverse, were synthesized having the respective sequences:

5'-AAAGGTGCGTACCCAGCTGTGCC (SEQ ID NO:115)

and

3'-TCCAGTCGGCAGAAGCGGTTCTGG (SEQ ID NO:116).

Additionally, a synthetic oligonucleotide hybridization probe was constructed from the consensus DNA30843 sequence, which probe has the sequence:

5'-CCTGGTGCTGGATGGCTGTGGCTGCTGC-
CGGGTATGTGCACGGCGGCTGGG (SEQ ID NO:117).

For screening several libraries for a source of a full-length clone, DNA from the libraries was screened by PCR amplification, as per Ausubel et al., *Current Protocols in Molecular Biology* (Green Publishing Associates and Wiley Interscience, N.Y., 1989), with the PCR primer pair identified above. A positive library was then screened by colony hybridization to isolate clones encoding PRO261 (human WISP-2) using the probe oligonucleotide and one of the PCR primers.

RNA for construction of the cDNA libraries was isolated from human fetal lung tissue. The cDNA libraries used to isolate the cDNA clones were constructed by standard methods using commercially available reagents such as those from Invitrogen, San Diego, Calif. The cDNA was primed with oligo dT containing a NotI site, linked with blunt-to-SalI-hemikinased adaptors, cleaved with NotI, sized appropriately by gel electrophoresis, and cloned in a defined orientation into a suitable cloning vector (such as pRK5B or pRK5D; pRK5B is a precursor of pRK5D that does not contain the SfiI site; see Holmes et al., *Science*, 253:1278–1280 (1991)) in the unique XhoI and NotI sites.

DNA sequencing of the clones isolated as described above gave the DNA sequence for PRO261 (herein designated as UNQ228 (DNA33473-seq min); SEQ ID NO:38), which begins at nucleotide 13 of SEQ ID NO:13 (FIGS. 4A–4B) and the derived amino acid sequence for PRO261 (SEQ ID NO:16).

The entire nucleotide sequence encoding human WISP-2 is shown in FIGS. 4A–4B (SEQ ID NO:13). This sequence contains a single open reading frame with an apparent translational initiation site at nucleotide positions 22–24 of SEQ ID NO:13 and ending at the stop codon after nucleotide 770 of SEQ ID NO:13 (FIGS. 4A–4B). The predicted polypeptide precursor is 250 amino acids long (FIGS. 4A–4B). The putative signal sequence spans from amino acid positions 1 to 23 of SEQ ID NO:16. Clone UNQ228 (DNA33473-seq min) has been deposited with ATCC and is assigned ATCC deposit no. 209391.

Analysis of the amino acid sequence of the full-length PRO261 polypeptide suggests that portions of it possess significant homology to CTGF, thereby indicating that PRO261 is a novel growth factor.

In situ hybridization of human WISP-2 is given below. The chromosomal location of the human WISP-2 gene was determined as described above for human WISP-1. Specifically, WISP-2 is linked to the marker SHGC-33922, with a LOD score of 1000. This places WISP-2 in band 20q12-20q13.1. Human chromosome 20q12 is a frequent site of DNA amplification in human breast cancer. In a Xenopus assay, injection of human WISP-2 RNA partially induced axis duplication (see Example 11). Also presented below are thymidine incorporation assay, gene amplification assay, and angiostatic assay results for human WISP-2.

Example 5
Isolation of cDNA Clones Encoding Human WISP-3

In this example, the gene encoding WISP-3 was cloned twice essentially in parallel. First, it was determined whether the databases described above contained any new members of the WISP family. Two EST homologies to the WISPs were found and both were cloned. Full-length clones were isolated corresponding to each of these EST homologies. The efforts resulted in two full-length clones of the same gene (the original EST homologies had been from distinct regions of the same gene). The first clone obtained was designated as DNA56350 and the second as DNA58800.

DNA56350

Based on the sequence of INCYTE 3208053, a virtual DNA 48917 was obtained and oligonucleotides were synthesized for use as probes to isolate a clone of the full-length coding sequence for PRO956 (human WISP-3). A pair of PCR primers, forward and reverse, were synthesized having the sequences:

5'-GTCTTGTGCAAGCAACAAAATGGACTCC(SEQ ID NO:118)

3'-GACACAATGTAAGTCGGAACGCTGTCG (SEQ ID NO:119)

Additionally, a synthetic oligonucleotide hybridization probe was constructed from the INCYTE sequence, which probe has the sequence:

5'-GCTCCAGAACATGTGGGATGG-
GAATATCTAACAGGGTGACCAATGAAAA(SEQ ID NO:120)

A human fetal kidney library primed with oligo dT containing a Xho1-Not1 size cut greater than 3700 kb was screened for a source of a full-length clone by PCR amplification with the PCR primer pair identified above. The positive library was then used to isolate clones encoding PRO956 (human WISP-3) using the probe oligonucleotide and one of the PCR primers.

DNA sequencing of the clone isolated as described above gave the DNA sequence for PRO956 (herein designated as UNQ462 (SEQ ID NO:30), and the derived amino acid sequence for PRO956 (SEQ ID NO: 33).

The entire nucleotide sequence encoding human WISP-3 from this clone is shown in FIGS. 6A–6C (SEQ ID NO:30). This sequence contains a single open reading frame with an apparent translational initiation site at nucleotide positions 46–48 of SEQ ID NO:30 and ending at the stop codon after nucleotide 1161 of SEQ ID NO:30 (FIGS. 6A–6C). The predicted polypeptide precursor is 372 amino acids long (FIGS. 6A–6C). The putative signal sequence is from amino acid positions 1 to 33 of SEQ ID NO:33. Clone UNQ462 (DNA56350-1176-2) has been deposited with ATCC and is assigned ATCC deposit no. 209706.

Analysis of the amino acid sequence of the full-length PRO956 polypeptide suggests that portions of it possess significant homology to CTGF, thereby indicating that PRO956 is a novel growth factor. This clone has an additional methionine just 5' of the first methionine in this clone. The amino acid sequence of this clone is 42% homologous to that of human WISP-1, and 32% homologous to that of human WISP-2.

In situ hybridization of human WISP-3 is shown below. Using the mapping techniques set forth above, it was found that human WISP-3 was localized to chromosome 6q22-6q23 and was linked to the marker AFM211ze5 with a LOD score of 1000. WISP-3 is approximately 18 megabases proximal to CTGF and 23 megabases promimal to the human cellular oncogene MYB, which are also located at 6q22-6q23. Martinerie et al., *Oncogene*, 7: 2529–2534 (1992); Meese et al., *Genes Chromosomes Cancer*, 1: 88–94 (1989).

The clone was inserted into pRK5E, described above. Upon transformation of JM109 cells, the plasmid rendered the cells ampicillin resistant. Upon digestion with BamHI and NotI, a fragment was obtained having a human insert from ATG to the stop codon as indicated in FIG. 6.

DNA58800

Based on the sequence of HS142L7, a virtual DNA 56506 was obtained and oligonucleotides were synthesized for use as probes to isolate a clone of the full-length coding sequence for PRO790 (human WISP-3). To this end, a pair of PCR primers, forward and reverse, were synthesized having the sequences:

5'-CCTGGAGTGAGCCTGGTGAGAGA (SEQ ID NO:121)

3'-ACACTGGGTGTGTTTCCCGACATAACA (SEQ ID NO:122)

Additionally, a synthetic oligonucleotide hybridization probe was constructed from the HS142L7 sequence, which probe has the sequence:

5'-TGGTTGCTTGGCACAGATTTTACAG-
CATCCACAGCCATCTCTCA          (SEQ ID NO:123)

A human bone marrow library primed with oligo dT containing a Xho1-Not1 size cut of 1–3 kb was screened for a source of a full-length clone by PCR amplification with the PCR primer pair identified above. The positive library was then used to isolate clones encoding PRO790 (human WISP-3) using the probe oligonucleotide and one of the PCR primers.

DNA sequencing of the clone isolated as described above gave the DNA sequence for PRO790 (SEQ ID NO:34), and the derived amino acid sequence for PRO790 (SEQ ID NO:37).

The entire nucleotide sequence encoding human WISP-3 from this clone is shown in FIGS. 7A–7C (SEQ ID NO:34). This sequence contains a single open reading frame with an apparent translational initiation site at nucleotide positions 16–18 of SEQ ID NO:34 and ending at the stop codon after nucleotide 1077 of SEQ ID NO:34 (FIGS. 7A–7C). The predicted polypeptide precursor is 355 amino acids long (FIGS. 7A–7C). The putative signal sequence spans from amino acid positions 1 to 15 of SEQ ID NO:37. This clone DNA58800-1176-2 has been deposited with ATCC and is assigned ATCC deposit no. 209707.

Analysis of the amino acid sequence of the full-length PRO790 polypeptide suggests that portions of it possess significant homology to CTGF, thereby indicating that, like PRO956 which is a splice variant thereof, PRO790 is a novel growth factor.

In situ hybridization of human WISP-3 is shown below.

The clone was inserted into pRK5E, described above. Upon transformation of JM109 cells, the plasmid rendered the cells ampicillin resistant. Upon digestion with BamHI and NotI, a fragment was obtained having a human insert from ATG to the stop codon as indicated in FIGS. 7A–7C.

EXAMPLE 6
Use of WISP-Encoding DNA as a Hybridization Probe

The following method describes use of a nucleotide sequence encoding a WISP polypeptide as a hybridization probe.

DNA comprising the coding sequence of full-length or mature human WISP-1 (as shown in FIGS. 3A–3C, SEQ ID NOS:4 or 3, respectively), or full-length or mature mouse WISP-1 (as shown in FIGS. 1A–1B, SEQ ID NOS:12 or 11, respectively), or of full-length or putative mature human WISP-2 (as shown in FIGS. 4A–4B, SEQ ID NOS:16 or 15, respectively), or full-length or putative mature mouse WISP-2 (as shown in FIGS. 2A–2B, SEQ ID NOS:20 or 19, respectively) is employed as a probe to screen for homologous DNAs (such as those encoding naturally occurring variants of these particular WISP proteins in human tissue cDNA libraries or human tissue genomic libraries.

Hybridization and washing of filters containing either library DNAs is performed under the following high-stringency conditions. Hybridization of radiolabeled WISP-polypeptide-derived probe (such as UNQ228 (DNA33473-seq min)-derived probe) to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding a full-length, native-sequence WISP polypeptide can then be identified using standard techniques known in the art.

EXAMPLE 7
Expression of WISP Polypeptide in E. coli

This example illustrates preparation of an unglycosylated form of WISP polypeptide by recombinant expression in E. coli.

The DNA sequence encoding WISP polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR-amplified sequences are then ligated into the vector. The vector will preferably include sequences which encode an antibiotic-resistance gene, a trp promoter, a polyhis leader (including the first six STII codons, polyhis sequence, and enterokinase cleavage site), the WISP-coding region, lambda transcriptional terminator, and an argU gene.

The ligation mixture is then used to transform a selected E. coli strain using the methods described in Sambrook et al., supra. Transformants are identified by their ability to grow on LB plates, and antibiotic-resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger-scale culture. The cells are then grown to a desired optical density, during which the expression promoter is turned on.

After the cells are cultured for several more hours, the cells can be harvested by centrifugation. The cell pellet obtained by the centrifugation can be solubilized using various agents known in the art, and the WISP polypeptide can then be purified using a metal-chelating column under conditions that allow tight binding of the protein.

Example 8
Expression of WISP Polypeptide in Mammalian Cells

This example illustrates preparation of a potentially glycosylated form of WISP polypeptide by recombinant expression in mammalian cells.

The vector, pRK5E, was employed as the expression vector. The appropriate DNA encoding WISP polypeptide was ligated into pRK5E with selected restriction enzymes to allow insertion of the DNA for WISP polypeptide using ligation methods as described in Sambrook et al., supra. The resulting vectors were pRK5E.h.WIG-1.568.38, pRK5E.m.WIG-1.568.6his, pRK5E.m.WIG-2.1367.3, plasmid encoding human WISP-2, DNA56350-1176-2, and DNA58800-1176-2, all deposited at the ATCC. These vectors are conveniently referred to collectively as pRK5E.WISP in the general description below.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5E.WISP DNA is mixed with about 1 μg DNA encoding the VA RNA gene (Thimmappaya et al., Cell, 31:543 (1982)) and dissolved in 500 μl of 1 mM Tris-HCl, 0.1 mM EDTA, 0.227 M CaCl$_2$. To this mixture is added, dropwise, 500 μl of 50 mM HEPES (pH 7.35), 280 mM NaCl, 1.5 mM NaPO$_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in phosphate-buffered saline (PBS) is added for 30 seconds. The 293 cells are then washed with serum-free medium, fresh medium is added, and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12-hour incubation, the conditioned medium is collected, concentrated on a spin filter, and loaded onto a 15% SDS gel. The processed gel may be dried and exposed to film for a selected period of time to reveal the presence of the WISP polypeptide. The cultures containing transfected cells may undergo further incubation (in serum-free medium) and the medium is tested in selected bioassays.

In an alternative technique, the WISP polypeptide may be introduced into 293 cells transiently using the dextran sulfate method described by Somparyrac et al., *Proc. Natl. Acad. Sci.,* 12:7575 (1981). 293 cells are grown to maximal density in a spinner flask and 700 μg pRK5E.WISP DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin, and 0.1 μg/ml bovine transferrin. After about four days, the conditioned media are centrifuged and filtered to remove cells and debris. The sample containing expressed WISP polypeptide can then be concentrated and purified by any selected method, such as dialysis and/or column chromatography.

In another embodiment, the WISP polypeptide can be expressed in CHO cells. The pRK5E.WISP can be transfected into CHO cells using known reagents such as CaPO$_4$ or DEAE-dextran. As described above, the cell cultures can be incubated, and the medium replaced with culture medium (alone) or medium containing a radiolabel such as $^{35}$S-methionine. After determining the presence of the WISP polypeptide, the culture medium may be replaced with serum-free medium. Preferably, the cultures are incubated for about 6 days, and then the conditioned medium is harvested. The medium containing the expressed WISP polypeptide can then be concentrated and purified by any selected method.

Epitope-tagged WISP polypeptide may also be expressed in host CHO cells. The WISP polypeptide may be subcloned out of the pRK5 vector. Suva et al., *Science,* 237: 893–896 (1987); EP 307,247 published Mar. 15, 1989. The subclone insert can undergo PCR to fuse in-frame with a selected epitope tag such as a poly-his tag into a baculovirus expression vector. The poly-his-tagged WISP polypeptide insert can then be subcloned into a SV40-driven vector containing a selection marker such as DHFR for selection of stable clones. Finally, the CHO cells can be transfected (as described above) with the SV40-driven vector. Labeling may be performed, as described above, to verify expression. The culture medium containing the expressed poly-His-tagged WISP can then be concentrated and purified by any selected method, such as by Ni$^{24}$-chelate affinity chromatography.

In particular, mouse WISP-1 cDNA for insertion into mammalian expression vectors was created via PCR using clone m568.19A (see above) pure phage DNA as template and using as primers m.568.pcr.top4 (5'-TGACTTCCAGGCATGAGGTGGCTCCTG; SEQ ID NO:124) and m.568.pcr.bot3 (5'-ATTGGCAATCTCTTCGAAGTCAGGGTAAGATTCC; SEQ ID NO:125) for the 6-his version, or m.568.pcr.top4 (SEQ ID NO:124) and 568.pcr.bot5, which has a 3'-terminal XbaI site (5'-GGTACGTCTAGACTAATTGGCAPTCTCT-TCGAAGTCAGGG; SEQ ID NO: 126) for the non-his version. The insert integrity was confirmed by sequencing and analyzed. The PCR was run using Pfu polymerase and the conditions were:

| | temp. | time |
|---|---|---|
| denaturation | 94° C. | 1 min |
| annealing | 62° C. | 30 sec |
| extension | 72° C. | 1.5 min |
| # of cycles: 25 | | |

For transient expression in 293 cells analyzed by Western blot, the above inserts were ligated into the pRK5 vector referred to above at the BamHI/XbaI site using the BOEHRINGER MANNHEIM™ rapid ligation kit. The resulting plasmids were designated pRK5.mu.WISP-1.6his and pRK5.mu.WISP-1.nohis for the His-tagged and non-His-tagged inserts, respectively. Then the 293 cells were plated and allowed to reach approximately 85% confluency overnight (37° C./5% CO$_2$). The plated cells were transfected with plasmid DNA pRK5.mu.WISP-1.6his or pRK5.mu.WISP-1.nohis by using lipofectamine (Gibco BRL) at a 4.5:1 lipid:DNA ratio.

Transfection efficiency (>70% usually) was monitored using a GFP expression plasmid (pGREEN LANTERN™ from Gibco BRL). Approximately 5 hours post-transfection, the medium was changed to fresh SF media (50:50 with 1×L-Glu and 1×P/S) for protein production. The conditioned media was allowed to accumulate for specified amounts of time (depending on the experiment) before harvesting.

The medium was harvested and concentrated in the presence of 1 mM PMSF using the CENTRICON-10™ concentrator. The concentrated, conditioned media (usually 1.5 ml) was then bound to Ni$^{++}$NTA agarose beads (Qiagen) for 2 hours (for the His-tagged version only). Protein was eluted from the beads by boiling for 10 minutes in 2×SDS loading buffer (Novex) with or without beta-mercaptoethanol for reduced vs. non-reduced protein, respectively.

The protein was visualized by SDS-PAGE using 4–20% gradient TRIS-glycine gels, 10-wells, 1 mm thickness (Novex). Gels ran at 125 volts (constant) for 95 minutes. Western transfer was achieved using a NOVEX™ transfer apparatus to PVDF membranes (Novex) at 200 mA (constant) for 45 minutes. The blots were blocked for a minimum of 1 hour at room temperature in blocking buffer (PBS+TWEEN-20™ (0.5%), 5% dry milk, and 3% goat serum). Blots were incubated in primary antibody (for His-tagged protein: INVITROGEN™ anti-his(C-terminal)-HRP-conjugated antibody or for the non-His version: polyclonal anti-murine WISP-1 antibody prepared as described below) at a 1:2000 dilution in fresh blocking buffer for 1 hour at room temperature. The non-His-tagged protein blots were incubated in secondary antibody (PIERCE™ goat anti-rabbit IgG(H+L) HRP conjugated) diluted 1:2000 in fresh blocking buffer. The blots were incubated in chemiluminescent substrate (ECL™ from Amersham or SUPERSIGNAL™ from Pierce) for 1 minute before exposing to film.

For transient expression analyzed by antibody staining, 293 cells were cultured, plated, and transfected as described above. The cells were fixed to culture dishes for 2 minutes in 1:1 methanol:acetone solution. Fixed cells were then incubated in primary antibody (for His-tagged protein: INVITROGEN™ anti-his(C-term)-HRP-conjugated antibody or for the non-His version: polyclonal anti-murine WISP-1 antibody prepared as described below) diluted 1:1000 in PBS with 10% fetal bovine serum for 2 hours. The non-His-tagged protein blots were then incubated in secondary antibody (PIERCE™ goat anti-rabbit IgG(H+L) HRP conjugated) diluted 1:150 in PBS with 10% fetal bovine serum for 1 hour. The incubation was in color reagent substrate for HRP for up to 1 hour (1.0% O-dianisidine-saturated ETOH, 0.01% hydrogen peroxide in PBS).

For stable expression of mouse WISP-1 in mammalian cells, the starting vector employed was pRK5.CMV.puro-dhfR, the sequence of which is shown in FIGS. 16A–16D. This vector has two SAR sequences cloned into KpnI, SapI sites of the SVID5 splice-donor vector, and has the pSVI backbone with the pRK5 cloning linker (pSVI5) and the intron made from pSVI.WTSD.D by adding a linearization linker (LL) into the HpaI site. The sequence is edited to include changes in vector puc118 backbone derived from the sequence of pRK5 and includes a four-base insertion after MCS characteristic of the SVI vector.

The above inserts were ligated into pRK5.CMV.puro-dhfR at the BamHI/XbaI site using the BOEHRINGER MANNHEIM™ rapid ligation kit, producing pRK5.CMV.puro-dhfR.mu.WISP-1.6his or pRK5.CMV.puro-dhfR.mu.WISP-1.nohis. This construct allows for stable selection of expressing cells using either puromycin (2 µg/ml in 293 cells or 10 µg/ml in CHO-DP12 cells) or the DHFR deletion in the CHO-DP12 line, which allows for subsequent amplification in methotrexate. Isolated colonies representative of stably transfected cells were picked, cultured under selective pressure, and analyzed by antibody staining or Western blot as described above.

Example 9
Expression of WISP Polypeptide in Yeast

The following method describes recombinant expression of a WISP polypeptide in yeast.

First, yeast expression vectors are constructed for intracellular production or secretion of a WISP polypeptide from the ADH2/GAPDH promoter. DNA encoding a WISP polypeptide and the promoter is inserted into suitable restriction enzyme sites in the selected plasmid to direct intracellular expression. For secretion, DNA encoding a WISP polypeptide can be cloned into the selected plasmid, together with DNA encoding the ADH2/GAPDH promoter, a native WISP signal peptide or other mammalian signal peptide or yeast alpha-factor or invertase secretory signal/leader sequence, and linker sequences (if needed) for expression.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant WISP polypeptide can subsequently be isolated and purified by removing the yeast cells from the fermentation medium by centrifugation and then concentrating the medium using selected cartridge filters. The concentrate containing the WISP polypeptide may further be purified using selected column chromatography resins.

Example 10
Expression of WISP Polypeptide in Baculovirus-Infected Insect Cells and Purification Thereof The following method describes recombinant expression of a WISP polypeptide in baculovirus-infected insect cells, and purification thereof.

General

The sequence coding for WISP polypeptide is fused upstream of an epitope tag contained within a baculovirus expression vector. Such epitope tags include poly-His tags and immunoglobulin tags (like Fc regions of IgG). A variety of plasmids may be employed, including plasmids derived from commercially available plasmids such as pVL1393 (Novagen). Briefly, the sequence encoding WISP polypeptide or the desired portion of the coding sequence (such as the sequence encoding the mature protein if the protein is extracellular) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BACULOGOLD™ virus DNA (Pharmingen) into Spodoptera frugiperda ("Sf9") cells (ATCC CRL 1711) using lipofectin (commercially available from Gibco-BRL). After 4–5 days of incubation at 28° C., the released viruses are harvested and used for further amplifications. Viral infection and protein expression are performed as described by O'Reilley et al., *Baculovirus Expression Vectors: A Laboratory Manual* (Oxford: Oxford University Press, 1994).

Expressed poly-His-tagged WISP polypeptide can then be purified, for example, by $Ni^{2+}$-chelate affinity chromatography as follows. Extracts are prepared from recombinant virus-infected Sf9 cells as described by Rupert et al., *Nature*, 362:175–179 (1993). Briefly, Sf9 cells are washed, resuspended in sonication buffer (25 mL HEPES, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8), and filtered through a 0.45 µm filter. A $Ni^{2+}$-NTA agarose column (commercially available from Qiagen) is prepared with a bed volume of 5 mL, washed with 25 mL of water, and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes non-specifically bound protein. After reaching $A_{280}$ baseline again, the column is developed with a 0 to 500 mM imidazole gradient in the secondary wash buffer. One-mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged WISP polypeptide are pooled and dialyzed against loading buffer.

Alternatively, purification of the IgG-tagged (or Fc-tagged) WISP polypeptide can be performed using known chromatography techniques, including, for instance, Protein A or protein G column chromatography.

Specific

1. Expression

In particular, mouse WISP-1 polypeptide was expressed in a baculovirus expression system similar to that described above using as the baculovirus transfer vector pb.PH.mu.568.9.IgG.baculo or pbPH.mu.568.8his.baculo. FIGS. 17A–17D show the sequence (SEQ ID NO:54) of plasmid pb.PH.IgG, which was used to prepare pb.PH.mu.568.9.IgG.baculo. FIGS. 18A–18D show the sequence (SEQ ID NO:55) of plasmid pbPH.His.c, which was used to prepare pbPH.mu.568.8his.baculo.

Both of these baculovirus transfer vectors are based on pVL1393 (Pharmingen), which has neither the His nor Fc tags. The pb.PH.IgG vector (FIG. 17) allows the expression of foreign proteins under control of the AcNPV polyhedrin promoter, which is active in the very late phase of virus infection. The foreign protein can be expressed as a C-terminal human IgG fusion protein. The His(8)-tag will not be translated as a result of the IgG stop codon just 5' of the His(8)-tag. The sequence encoding the foreign protein should be inserted as a 3' blunt-ended fragment into the unique StuI site preceeding the His-tag. In that case an additional proline residue will be added. The 5' site can be either BamHI, EcoRI, NotI, NcoI, and NheI.

The IgG vector was constructed by NdeI digestion of the pVL1393.IgG plasmid followed by Klenow treatment to fill in the sticky end site. This is followed by a NcoI digest and insertion into the pbPH.His.c×NcoI/SmaI-digested vector.

The sequence of pbPH.His.c shown in FIGS. 18A–18D contains the backbone sequence of the vector pVL1392, which contains approximately the EcoRI/XmaIII fragment of AcMNPV C-6, from position 0.0 to 5.7 mu. Possee et al., *Virology*, 185: 229–241 (1991). It allows the expression of foreign proteins under control of the *Autographa californica* nuclear polyhedrosis virus (AcNPV) polyhedrin gene promoter, which is active in the very late phase of virus infection.

The foreign protein can be expressed as a C-terminally His- or a IgG (Fc region only)-tagged protein. The sequence encoding the foreign protein should be inserted as a 3'-blunt-ended fragment into the unique SmaI site preceding the His-tag or the StuI site for IgG. In that case an additional glycine residue will be added for His tags and a proline will be added for IgG tags. The 5' site can be either BamHI, NotI, EcoRI, or NcoI. Bam HI was used for both.

The vectors were constructed by inserting a PCR insert into BamHI/SmaI for the His vector and BamHI/StuI for the IgG vector. The PCR insert was made using 5'-phosphorylated primers as follows: m.568.pcr.top6 (5'-TTTCCCTTTGGATCCTAAACCAACAT-GAGGTGGCTCCTGCCC; SEQ ID NO:127) and m.568.pcr.bot3 (SEQ ID NO:125), 5' phosphorylated. A twenty-cycle PCR reaction with Pfu polymerase enzyme was performed using the following conditions: 1 min at 95° C., 30 sec at 60° C., 3.5 min at 72° C. The PCR product was purified with QIAQUICK™, and digested with BamHI at 37° C. for 1 hr. The digested PCR insert was ligated into the digested vector using a 1:3 ratio of insert to vector with 1 μl T4 DNA ligase (Bio Labs). ULTRA MAX™ DH5α FT competent cells, 100 μl, (Gibco BRL Cat #10643-013) were added to the ligation product, and the mixture was incubated on ice for 30 min, followed by a heat shock at 42° C. for 45 sec. Individual colonies were picked and miniscreen DNA was prepared using QIA PREP™ (Qiagen). Construct sequencing was performed using ABI Prism's dRHODAMINE DYE™ terminator cycle sequencing.

The plasmid pb.PH.IgG has a polylinker BamHI-NotI-EcoRI-NcoI-SrfI-StuI-(IgG Fc region only) -Stop-XbaI-SpeI-PstI-BglII. The location of particular regions in this plasmid is as follows: Insertion of polylinker/foreign gene: 4129-4912 (BamHI-BglII), polh coding: 4913-5479, ORF 1629: 7134-4820; ORF 588 (PK1) : 7133-7723; ColE1 origin of replication: 7973-8858, and ampicillin coding: 9779-8230. The plasmid pbPH.His.c has a polylinker BamHI-NotI-EcoRI-NcoI-SrfI-SmaI-(His8)-Stop-XbaI-SpeI-PstI-BglII. The NcoI site of pbPH.His.c resides within a Kozak sequence. The location of particular regions in this plasmid is as follows: ORF 504 (PTP): 76-582, ORF 984 (ORF2): 1600-614, ORF 453 (ORF3): 2323-1868, conotoxin: 1818-1657, ORF 327 (ORF4): 2352-2681, ORF 630 (lef-2) : 2662-3294, ORF 603: 3937-3332, ORF polh: 4093 (mutated codon ATG/ATT), insertion of polylinker/foreign gene: 4129-4218 (BamHI-BglII), polh coding: 4224-4790, ORF 1629: 6445-4820, ORF 588 (PK1): 6444-7034, ColEl origin of replication: 7284-8169, and ampicillin coding:9090-8230.

The mouse WISP-1 cDNA disclosed herein was inserted into the vectors pbPH.His.c and pb.PH.IgG to produce the respective expression plasmids by creating a 3' blunt-ended fragment for cloning into the unique SmaI site preceding the His-tag or IgG-tag. An additional glycine residue was added to the His protein produced. An additional proline was added to the IgG protein. The 5' site of the cDNA insert was BamHI.

2. Purification

For purification purposes, either a poly-His tag or the Fc portion of human IgG was added to the C-terminal coding region of the cDNA before expression. The conditioned media from the transfected cells (0.5 to 2 L) was harvested by centrifugation to remove the cells and filtered through 0.22 micron filters. For the poly-His-tagged constructs, the protein was purified using a $Ni^{+2}$-NTA column (Qiagen). Before purification, imidazole was added to the conditioned media to a concentration of 5 mM. The conditioned media was pumped onto a 6-ml $Ni^{+2}$-NTA column equilibrated in 20 mM HEPES, pH 7.4, buffer containing 0.3 M NaCl and 5 mM imidazole at a flow rate of 4–5 ml/min at 4° C. After loading, the column was washed with additional equilibration buffer and the protein was eluted with equilibration buffer containing 0.25 M imidazole. The highly purified protein was subsequently desalted into a storage buffer containing 10 mM HEPES, 0.14 M NaCl, and 4% mannitol, pH 6.8, with a 25 ml G25 SUPERFINE™ (Pharmacia) column and stored at −80° C.

Immunoadhesin (Fc-containing) constructs of WISP-1 protein were purified from the conditioned media as follows. The conditioned media was pumped onto a 5-ml Protein A column (Pharmacia) which had been equilibrated in a 20 mM Na phosphate buffer, pH 6.8. After loading, the column was washed extensively with equilibration buffer before elution with 100 mM citric acid, pH 3.5. The eluted protein was immediately neutralized by collecting 1-ml fractions into tubes containing 275 uL of 1 M Tris, pH 9, buffer. The highly purified protein was subsequently desalted into storage buffer as described above for the poly-His-tagged proteins. The homogeneity of the protein was assessed by SDS polyacrylamide gels and by N-terminal amino acid sequencing by Edman degradation.

Example 11

Axis Duplication Assay

Xenopus embryos were injected with human WISP-2 mRNA into either a presumptive ventral or presumptive dorsal vegetal blastomere at the 8- to 16-cell stage to overexpress locally the encoded protein and assay for its developmental effects. The methods used are described in Sokol et al., *Cell*, 67: 741–752 (1991).

More specifically, for synthesis of capped RNA, human WISP-2 and mouse Wnt-1 cDNAs were cloned into the pGEMHE vector (gift of Dr. Todd Evans, AECOM) to prepare pGEMHE.hu.WISP-2.8H and pGEMHE.mu.Wnt-1, respectively. The constructs were linearized at the 3' end using the SphI restriction enzyme. Capped RNAs were synthesized using AMBION's T7 MESSAGEMACHINE™ RNA synthesis kit.

For obtaining mature oocytes, an adult female *Xenopus laevis* was injected with 200 I.U pregnant mare serum 3 days before use. The night before the experiment, the female frog was injected with 800 I.U of human chorionic gonadotropin. Fresh oocytes were squeezed from female frogs the next morning. In vitro fertilization of oocytes was performed by mixing oocytes with minced testes from a sacrificed male frog. Fertilized eggs were dejellied with 2% cysteine (pH 7.8) for 10 minutes. Dejellied eggs were washed once with distilled water and transferred to 0.1×Modified Barth's Solution (MBS) (*Methods in Cell Biology*, Volume 36, *Xenopus laevis*: Practical uses in Cell and Molecular Biology, Kay and Peng, Eds (New York: Academic Press, 1991)) with 5% Ficoll. Eggs were lined on injection trays which contained 0.1×MBS with 5% Ficoll for injection. After injection, embryos were kept in 0.1×MBS in an 18° C. incubator. Embryos were staged according to Nieuwkoop and Faber, *Normal Table of Xenopus laevis*: (*Daudin*) (Amsterdam: North-Holland, 1967).

For animal cap assays, embryos were injected at the 2-cell stage with 1 ng of capped RNA, and animal caps were isolated at stage 8 and cultured in 1×MMR for another 24 hours for the RT-PCR assay. Total RNA was isolated from harvested animal caps using a RNEASY™ kit (Qiagen). RNA samples (approximately 1 μg) were reverse transcribed using random hexamer and GIBCO BRL SUPERSCRIPT II™ reverse transcriptase. The annealing temperature for the PCR reactions was 55° C. unless noted otherwise.

For axis duplication assays, embryos at the 8-cell stage were injected with 1 ng capped RNA at either the dorsal or ventral vegetal blastomere and incubated in 0.1×MBS for 72 hours.

The sequences of PCR primers used in this experiment were:

EF-1a.U: 5'-CAGATTGGTGCTGGATATGC (SEQ ID NO:128)

EF-1a.D: 5'-ACTGCCTTGATTACTCCTAC (SEQ ID NO:129)

noggin.U: 5'-AGTTGCAGATGTGGCTCT (SEQ ID NO:130)

noggin.D: 5'-AGTCCAAGAGTCTCAGCA (SEQ ID NO:131)

goosecoid.U: 5'-ACAACTGGAAGCACTGGA (SEQ ID NO:132)

goosecoid.D: 5'-TCTTATTCCAGAGGAACC (SEQ ID NO:133)

cardiac-actin.U: 5'-TCCCTGTACGCTTCTG GTCGTA (SEQ ID NO:134)

cardiac-actin.D: 5'-TCTCAAAGTCCAAAG CCACATA (SEQ ID NO:135)

NCAM.U: 5'-CACAGTTCCAGCAAATAC (SEQ ID NO:136)

NCAM.D: 5'-GGAATCAGGCGGTACAGT (SEQ ID NO:137)

It was found that human WISP-2 can partially induce axis duplication in this assay.

Example 12

Thymidine Incorporation Assay

In a ($^3$H)-thymidine incorporation assay, 19 different cell lines, including RAG (renal adenocarcinoma, mouse) and NRK-49F (normal kidney fibroblasts, rat) cells, identified in Table I below, were plated in 96-well plates at $3\times10^4$ in HGDMEM with 10% serum. Twenty four hours after plating, the medium was changed to HGDMEM with 0.2% serum before adding the test proteins. WISP proteins were added to a final concentration of approximately 3.6 ng/ul. Serial dilutions were made in a total volume of 70 μl/well of fresh media. After 18 hr incubation at 37° C., 5μ Ci/ml ($^3$H)thymidine was added for 5 hrs. Medium was aspirated and cells were removed with 1×trypsin onto a GF/C filter using Packard's™ 96-well FILTERMATE 196™. The filters were dried and 40 μl of scintillation fluid was added for counting on a top count, microplate scintillation counter (Packard).

The results are shown in Table I:

TABLE I $^3$H-Thymidine Incorporation Assay Results

| Cell line | Type | ATCC No. | mWISP-1 - IgG | hWISP-1 - IgG | hWISP-2 - IgG |
|---|---|---|---|---|---|
| HT-29 (human colon) | adenocarcinoma moderately well-differentiated | HTB-38 | No change | No change | |
| Wi-Dr (human colon) | adenocarcinoma | CCL-218 | No change | No change | |
| Calu-1 (human lung) | epidermoid carcinoma grade III, metastasis to pleura | HTB-54 | inhibits ~1.1X | inhibits ~1.2X | |
| Calu-6 (human lung) | anaplastic carcinoma, probably lung | HTB-56 | No change | stimulates ~1.4X | |
| SK-MES-1 (human lung) | squamous carcinoma, pleural effusion | HTB-58 | No change | No change | |
| A549 (human lung) | carcinoma | CCL-185 | inhibits ~1.5X | inhibits ~1.7X | |
| H460 (human lung) | large cell carcinoma | HTB-177 | inhibits ~1.4X | inhibits ~1.3X | |
| SW900 (human lung) | squamous cell carcinoma | HTB-59 | no change | no change | |

TABLE I-continued

³H-Thymidine Incorporation Assay Results

| Cell line | Type | ATCC No. | mWISP-1 - IgG | hWISP-1 - IgG | hWISP-2 - IgG |
|---|---|---|---|---|---|
| MRC5 (human lung) | normal diploid | CCL-171 | no change | no change | |
| IMR-90 (human lung) | normal diploid | CCL-186 | stimulates ~1.1X | stimulates ~1.5X | |
| Wnt-1 C57mg (mouse mammary gland) | myo-epithelial | | inhibits ~2X | | |
| MLg (mouse lung) | lung | | stimulates ~4X | | |
| LL/2 (mouse lung) | lung carcinoma | | | inhibits ~2X | |
| JC (mouse mammary gland) | carcinoma | | inhibits ~2X | inhibits ~3X | |
| N MuMG (mouse mammary gland) | normal | | stimulates ~2X | stimulates ~1.4X | |
| NRK-49F (rat kidney) | normal fibroblast | | stimulates ~3X | stimulates ~3.5X | |
| RAG (mouse kidney) | adenocarcinoma | | stimulates ~4.5X | stimulates ~3X | stimulates ~4X |
| NIH/3T3 (mouse embryo) | fibroblast | | stimulates ~3X | | |
| UCLA-P3 (human lung) | carcinoma | | inhibits ~1.5X | inhibits ~2X | |

It is seen that WISP-1 and WISP-2 exhibit both stimulatory and inhibitory effects on proliferation of normal and tumor cells, depending on the cell line employed.

Example 13
Preparation of Antibodies That Bind WISP Polypeptide
1. Polyclonal Antibodies Polyclonal antisera were generated in female New Zealand White rabbits against murine WISP-1 and human WISP-2. The antigens used were proteins fused with histidine for murine WISP-1 and proteins fused with the Fc portion of IgG for human WISP-2. The same protocol was used for both proteins. Each protein was homogenized with Freund's complete adjuvant for the primary injection and with Freund's incomplete adjuvant for all subsequent boosts. For the primary immunization and the first boost, 3.3 μg per kg body weight was injected directly into the popliteal lymph nodes as described in Bennett et al., *J. Biol. Chem.*, 266: 23060–23067 (1991) and "Production of Antibodies by Inoculation into Lymph Nodes" by Morton Sigel et al. in *Methods in Enzymology*, Vol. 93 (New York: Academic Press, 1983). For all subsequent boosts, 3.3 μg per kg body weight was injected into subcutaneous and intramuscular sites. Injections were done every 3 weeks with bleeds taken on the following two weeks.

2. Monoclonal Antibodies

Techniques for producing monoclonal antibodies that can specifically bind a WISP polypeptide are known in the art and are described, for instance, in Goding, supra. Immunogens that may be employed include purified WISP polypeptide, fusion proteins containing WISP polypeptide, and cells expressing recombinant WISP polypeptide on the cell surface. Selection of the immunogen can be made by the skilled artisan without undue experimentation.

Mice, such as Balb/c, are immunized with the WISP immunogen emulsified in complete Freund's adjuvant and injected subcutaneously or intraperitoneally in an amount from 1 to 100 micrograms. Alternatively, the immunogen is emulsified in MPL-TDM adjuvant (Ribi Immunochemical Research, Hamilton, Mo.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect antibodies to WISP polypeptide.

After a suitable antibody titer has been detected, the animals "positive" for antibodies can be injected with a final intravenous injection of a WISP polypeptide. Three to four days later, the mice are sacrificed and the spleen cells are harvested. The spleen cells are then fused (using 35% PEG) to a selected murine myeloma cell line such as P3X63AgU.1, available from ATCC, No. CRL 1597, or x63.Ag8.653 (Kearney et al., *J. Immunology*, 123: 1548 (1979)). The fusions generate hybridoma cells which can then be plated in 96-well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against a WISP polypeptide. Determination of "positive" hybridoma cells secreting the desired monoclonal antibodies against a WISP polypeptide is within the skill in the art.

The positive hybridoma cells can be injected intraperitoneally into syngeneic Balb/c mice to produce ascites containing the anti-WISP polypeptide monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel-exclusion chromatography. Alternatively, affinity chromatography based upon binding of antibody to protein A or protein G can be employed.

Specifically, for each of the human WISP-1 antibodies, five female Balb-c mice were pre-bled and then injected via their hind foot pads with purified human WISP-1, tagged with the Fc portion of IgG and emulsified prior to injection in MPL-TDM adjuvant (Ribi Immunochemical Research, Hamilton, Mont.) in a 1:1 ratio of WISP antigen to adjuvant. The dosing schedule for the WISP-1 immunogen was as follows:

| Injection Date | Dose/Site | Dose/Animal | Concentration |
|---|---|---|---|
| Day 16 of month 1 | 50 μl/site | 100 μl/animal | 6 μg/animal |
| Day 12 of month 2 | 50 μl/site | 100 μl/animal | 6 μg/animal |
| Day 21 of month 2 | 50 μl/site | 100 μl/animal | 6 μg/animal |
| Day 28 of month 2 | 50 μl/site | 100 μl/animal | 2 μg/animal |
| Day 4 of month 3 | 50 μl/site | 100 μl/animal | 2 μg/animal |
| Day 11 of month 3 | 50 μl/site | 100 μl/animal | 2 μg/animal |
| Day 18 of month 3 | 50 μl/site | 100 μl/animal | 2 μg/animal |
| Day 25 of month 3 | 50 μl/site | 100 μl/animal | 2 μg/animal |

For WISP-1, the mice were bled on Day 10 of month 4. After the mice were bled, the monoclonal antibodies were made by harvesting their spleens and by fusion as indicated above, using as the murine myeloma cell line X63.Ag8.653.

The five monoclonal antibodies generated to human WISP-1 are:

| | |
|---|---|
| 10F2.2A7 | gamma 2b/kappa |
| 10A9.2B1 | gamma 2a/kappa |
| 8F7.1B1 | gamma 1/kappa |
| 1H1.1D5 | gamma 1/kappa |
| 2G7.2H4 | gamma 1/kappa |

For WISP-2 monoclonal antibodies the same regimen is employed except that purified human WISP-2 is used as immunogen in the above protocol rather than purified human WISP-1 and the dosing schedule for the WISP-2 immunogen is as follows:

| Injection Date | Dose/Site | Dose/Animal | Concentration |
|---|---|---|---|
| Day 16 of month 1 | 50 μl/site | 100 μl/animal | 6 μg/animal |
| Day 21 of month 2 | 50 μl/site | 100 μl/animal | 1 μg/animal |
| Day 28 of month 2 | 50 μl/site | 100 μl/animal | 1 μg/animal |
| Day 4 of month 3 | 50 μl/site | 100 μl/animal | 1 μg/animal |
| Day 11 of month 3 | 50 μl/site | 100 μl/animal | 1 μg/animal |
| Day 18 of month 3 | 50 μl/site | 100 μl/animal | 1 μg/animal |
| Day 25 of month 3 | 50 μl/site | 100 μl/animal | 1 μg/animal |

Example 14

Uses of Antibodies That Bind WISP Polypeptide

1. Cell lines

The established human breast tumor cells BT474 and MDA-MB-231 (which are available from ATCC) are grown in minimum essential medium (Gibco, Grand Island, N.Y.) supplemented with 10% heat-inactivated fetal bovine serum (FBS) (HyClone, Logan, Utah), sodium pyruvate, L-glutamine (2 mM), non-essential amino acids, and 2×vitamin solution and maintained at 37° C. in 5% $CO_2$. Zhang et al., *Invas. & Metas.*, 11:204–215 (1991); Price et al., *Cancer Res.*, 50:717–721 (1990).

2. Antibodies

Anti-WISP-1 or anti-WISP-2 monoclonal antibodies that may be prepared as described above are harvested with PBS containing 25mM EDTA and used to immunize BALB/c mice. The mice are given injections i.p. of $10^7$ cells in 0.5 ml PBS on weeks 0, 2, 5 and 7. The mice with antisera that immunoprecipitated $^{32}$P-labeled Wnt-1 are given i.p. injections of a wheatgerm agglutinin-SEPHAROSE™ (WGA)-purified Wnt membrane extract on weeks 9 and 13. This is followed by an i.v. injection of 0.1 ml of the Wnt-1 preparation, and the splenocytes are fused with mouse myeloma line X63-Ag8.653. Hybridoma supernatants are screened for Wnt-1 binding by ELISA and radioimmunoprecipitation. MOPC-21 (IgG1) (Cappell, Durham, N.C.) is used as an isotype-matched control.

Additionally, the anti-ErbB2 IgG.K murine monoclonal antibodies 4D5 (ATCC CRL 10463 deposited May 24, 1990) and 7C2, specific for the extracellular domain of ErbB2, may be used with the above antibodies. They are produced as described in Fendly et al., *Cancer Research*, 50:1550–1558 (1990) and WO89/06692.

3. Analysis of Cell Cycle Status and Viability

Cells are simultaneously examined for viability and cell cycle status by flow cytometry on a FACSTAR PLUS™ (Becton Dickinson Immunocytometry Systems USA, San Jose, Calif.). Breast tumor cells are harvested by washing the monolayer with PBS, incubating cells in 0.05% trypsin and 0.53 mM EDTA (Gibco), and resuspending them in culture medium. The cells are washed twice with PBS containing 1% FBS and the pellet is incubated for 30 minutes on ice with 50 μl of 400 μM 7-aminoactinomycin D (7AAD) (Molecular Probes, Eugene, Oreg.), a vital dye which stains all permeable cells. Cells are then fixed with 1.0 ml of 0.5% paraformaldehyde in PBS and simultaneously permeabilized and stained for 16 hours at 4° C. with 220 μl of 10 μg/ml HOECHST 33342™ dye (also a DNA binding dye) containing 5% TWEEN 20™.

The data from $1 \times 10^4$ cells are collected and stored using LYSYS II™ software and analyzed using PAINT-A-GATE™ software (Becton Dickinson). Darzynkiewica et al., *Cytometry*, 13:795–808 (1992); Picker et al., *J. Immunol.*, 150:1105–1121 (1993). The viability and percentage of cells in each stage of the cell cycle are determined on gated single cells using 7AAD and Hoechst staining, respectively. (Cell doublets are excluded by pulse analysis of width vs. area of the Hoechst signal.) Cell numbers are determined using a hemocytometer.

4. DNA synthesis (($^3$H)-Thymidine Incorporation Assay)

The assay was performed exactly as described in Example 12, except that the WISP polypeptides used as test proteins were replaced by the polyclonal antibodies generated in New Zealand White rabbits against murine WISP-1 and human WISP-2 described in Example 13, and not all the cell lines in Example 12 were tested. The results are shown in Table II:

TABLE II $^3$H-Thymidine Incorporated Assay Results

| Cell line | Type | ATCC No. | pAB.mWISP-1 | pAB.hWISP-2 |
|---|---|---|---|---|
| HT-29 (human colon) | adenocarcinoma moderately well-differentiated | HTB-38 | No change | No change |
| Wi-Dr (human colon) | adenocarcinoma | CCL-218 | No change | No change |
| N MuMG (mouse mammary gland) | normal | | inhibits ~3x | |
| NRK-49F (rat kidney) | normal fibroblast | | stimulates ~2X | |
| RAG (mouse kidney) | adenocarcinoma | | stimulates ~4X | |
| NIH/3T3 (mouse embryo) | fibroblast | | inhibits ~2X | |

It is seen that the polyclonal antibodies to mouse WISP-1 and to human WISP-2 exhibited both stimulatory and inhibitory effects on proliferation of normal and tumor cells, depending on the cell line employed.

5. Affinity of Binding to Putative Receptor

Radioiodinated anti-WISP-1 and anti-WISP-2 antibodies are prepared by the IODOGEN™ method. Fracker et al., *Biochem. Biophys. Res. Comm.*, 80:849–857 (1978). Binding assays are performed using appropriate receptor-expressing cells (such as, for mouse anti-WISP antibodies, MLG, a mouse lung cell line available from the ATCC) cultured in 96-well tissue culture plates (Falcon, Becton Dickinson Labware, Lincoln Park, N.J.). The cells are trypsinized and seeded in wells of 96-well plates at a density of $10^4$ cells/well and allowed to adhere overnight. The monolayers are washed with cold culture medium supplemented with 0.1% sodium azide and then incubated in triplicate with 100 μl of serial dilutions of $^{125}$I-anti-WISP-1 or WISP-2 antibodies in cold culture medium containing 0.1% sodium azide for 4 hours on ice. Non-specific binding is estimated by the preincubation of each sample with a 100-fold molar excess of nonradioactive antibodies in a total volume of 100 μl. Unbound radioactivity is removed by two washes with cold medium containing 0.1% sodium azide. The cell-associated radioactivity is detected in a gamma counter after solubilization of the cells with 150 μl of 0.1 M NaOH/well. The WISP-1 and WISP-2 binding constants ($K_d$) and anti-WISP antibody binding affinities are determined by Scatchard analysis.

It is expected that the antibodies against WISP-1 and WISP-2 will affect the growth of these cells.

Example 15
Further Uses of Antibodies That Bind WISP Polypeptide

1. WISP-1 and WISP-2

This example shows that the WISP-1 and WISP-2 genes are amplified in the genome of certain human lung, colon, and/or breast malignant tumors and/or cell lines. Amplification is associated with overexpression of the gene product, indicating that the WISP-1 and WISP-2 proteins are useful targets for therapeutic intervention in certain cancers such as colon, lung, breast, and other cancers. A therapeutic agent may take the form of antagonists of WISP molecules, for example, murine-human, chimeric, humanized, or human antibodies against WISP-1 and WISP-2, such as the antibodies prepared as described above.

The starting material for the screen was genomic DNA isolated from a variety of cancers. The DNA is quantitated precisely, e.g., fluorometrically. As a negative control, DNA was isolated from the cells of ten normal healthy individuals, pooled, and used as an assay control for the gene copy in healthy individuals.

The 5' nuclease assay (for example, TAQMAN™) and real-time quantitative PCR (for example, ABI PRIZM 7700™ Sequence Detection System™ (Perkin Elmer, Applied Biosystems Division, Foster City, Calif.)), were used to find genes potentially amplified in certain cancers. The results were used to determine whether the DNAs encoding WISP-1 and WISP-2 are over-represented in any of the primary lung or colon cancers or cancer cell lines or breast cancer cell lines that were screened. The primary lung cancers were obtained from indiviuals with tumors of the type and stage as indicated in Table III. An explanation of the abbreviations used for the designation of the primary tumors listed in Table III and the primary tumors and cell lines referred to throughout this example is given below:

Human lung carcinoma cell lines include A549 (SRCC768), Calu-1 (SRCC769), Calu-6 (SRCC770), H157 (SRCC771), H441 (SRCC772), H460 (SRCC773), SKMES-1 (SRCC774) and SW900 (SRCC775), all available from ATCC. Primary human lung tumor cells usually derive from adenocarcinomas, squamous cell carcinomas, large cell carcinomas, non-small cell carcinomas, small cell carcinomas, and broncho alveolar carcinomas, and include, for example, SRCC724 (squamous cell carcinoma abbreviated as "SqCCa"), SRCC725 (non-small cell carcinoma, abbreviated as "NSCCa"), SRCC726 (adenocarcinoma, abbreviated as "AdenoCa"), SRCC727 (adenocarcinoma), SRCC728 (squamous cell carcinoma), SRCC729 (adenocarcinoma), SRCC730 (adeno/squamous cell carcinoma), SRCC731 (adenocarcinoma), SRCC732 (squamous cell carcinoma), SRCC733 (adenocarcinoma), SRCC734 (adenocarcinoma), SRCC735 (broncho alveolar carcinoma, abbreviated as "BAC"), SRCC736 (squamous cell carcinoma), SRCC738 (squamous cell carcinoma), SRCC739 (squamous cell carcinoma), SRCC740 (squamous cell carcinoma), and SRCC740 (lung cell carcinoma, abbreviated as "LCCa").

Colon cancer cell lines include, for example, ATCC cell lines SW480 (adenocarcinoma, SRCC776), SW620 (lymph node metastasis of colon adenocarcinoma, SRCC777), COLO320 (adenocarcinoma, SRCC778), HT29 (adenocarcinoma, SRCC779), HM7 (carcinoma, SRCC780), CaWiDr (adenocarcinoma, srcc781), HCT116 (carcinoma, SRCC782), SKCO1 (adenocarcinoma, SRCC783), SW403 (adenocarcinoma, SRCC784), LS174T (carcinoma, SRCC785), and HM7 (a high mucin producing variant of ATCC colon adenocarcinoma cell line LS 174T, obtained from Dr. Robert Warren, UCSF). Primary colon tumors include colon adenocarcinomas designated CT2 (SRCC742), CT3 (SRCC743), CT8 (SRCC744), CT10 (SRCC745), CT12 (SRCC746), CT14 (SRCC747), CT15 (SRCC748), CT17 (SRCC750), CT1 (SRCC751), CT4 (SRCC752), CT5 (SRCC753), CT6 (SRCC754), CT7 (SRCC755), CT9 (SRCC756), CT11 (SRCC757), CT18 (SRCC758), and DcR3, BACrev, BACfwd, T160, and T159.

Human breast carcinoma cell lines include, for example, HBL100 (SRCC759), MB435s (SRCC760), T47D (SRCC761), MB468(SRCC762), MB175 (SRCC763), MB361 (SRCC764), BT20 (SRCC765), MCF7 (SRCC766), and SKBR3 (SRCC767).

The results are reported in delta ($\Delta$) CT units. One unit corresponds to one PCR cycle or approximately a 2-fold amplification relative to normal, two units corresponds to 4-fold, 3 units to 8-fold amplification and so on. Quantitation was obtained using primers derived from the 3'-untranslated regions of the WISP-1 and WISP-2 cDNAs and a TAQMAN™ fluorescent probe corresponding to the respective intervening sequences. Using the 3' region tends to avoid crossing intron-exon boundaries in the genomic DNA, an essential requirement for accurate assessment of gene amplification using this method. The sequences for the primers and probes (forward, reverse, and probe) used for the WISP-1-encoding and WISP-2-encoding gene amplification were as follows: WISP-1 probe and primers:

enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI PRIZM $_{7700}$™ Sequence Detection System™. The system consists of a thermocyler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. This is defined as the cycle at which the reporter signal accumulates above the background level of fluorescence. The $\Delta$Ct values are used as quantitative measurement of the relative number of starting copies of a particular target sequence in a nucleic acid sample when comparing cancer DNA results to normal human DNA results.

The results of the first run performed are shown in FIGS. 19A–D and 20A–D for WISP-1 and WISP-2, respectively, and controls. Note the pattern shown in FIG. 19B (marked huWISP-1). The standard deviation for two samples of normal human DNA is shown in the column marked Nor Hu. This was used as a quality control tool. If the standard deviation was unacceptably large, the entire run was repeated. The nine additional columns corresponded to the human colon cancer cell lines noted above. The delta CT's for HT29 and WIDr were >3, corresponding to an about 8-fold over-representation of the WISP-1 gene in these samples compared to the normal samples. Similarly, FIG. 19B suggests an about 4-fold amplification of WISP-1 in the HCT116, SKCo-1, and SW403 cell lines.

As a comparison, see FIG. 20B (marked huFASr). The generally small delta CT values indicate that this gene was not significantly amplified in any of the cell lines (the value of 1 for SW620 corresponding to 2-fold amplification is within the noise level for the assay).

```
primers:
hu.WISP1.TMP (probe)            5'-AGCCTTTCCAAGTCACTAGAAGTCCTGCTGG  (SEQ ID NO:138)

hu.WISP1.TMP (forward primer)   5'-CTGGACTACACCCAAGCCTGA            (SEQ ID NO:139)

hu.WISP1.TMR (reverse primer)   5'-CATTTCTTGGGATTTAGGCAAGA          (SEQ ID NO:140)

WISP-2 probe and primers:
DNA33473.3utr-5 (forward primer) 5'-TCTAGCCCACTCCCTGCCT             (SEQ ID NO:141)

DNA33473.3utr-3 (reverse primer) 5'-GAAGTCGGAGAGAAAGCTCGC           (SEQ ID NO:142)

DNA33473.3utr-probe             5'-CACACACAGCCTATATCAAACATGCACACG   (SEQ ID NO:143)
```

The 5' nuclease assay reaction is a fluorescent PCR-based technique which makes use of the 5'exonuclease activity of Taq DNA polymerase enzyme to monitor amplification in real time. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase The WISP-1 result was confirmed in three replicate reactions. See FIGS. 21A–D, 22A–D, and 23A–C. The pattern and delta CT values obtained were very similar in FIGS. 21A–C (marked huWISP-1c, huWISP-1b, and huWISP-1a, respectively). The result was essentially identical to that obtained in the first run. HT29 and WIDr showed the highest levels of WISP-1 amplification, while HCT116, SKCo-1, and SW403 cell lines showed somewhat lower levels of WISP-1 gene amplification. Two additional reactions from a third run were confirmatory. See FIGS. 25A and 25B.

The WISP-1 gene is located on chromosome 8, in the general vicinity of the myc gene, which is known to be amplified in some colon cancer cell lines. The pattern obtained using primers and probe for the myc gene, namely, hu.c-myc.tm.p 5'-CTTGAGACTGAAAGATTTAGCCATAATGTAAACTGCCT (SEQ ID NO:144)

hu.c-myc.tm.f 5'-CAAATGCAACCTCACAACCTTG (SEQ ID NO:145), and hu.c-myc.tm.r 5'-TTCTTTTATGCCCAAAGTCCAATT (SEQ ID NO:146), is consistent with a published report (*Cancer Research,* 57: 1769–1775 (1997)), tending to validate the 5' nuclease assay method, but is clearly different from that obtained for WISP-1. These data prove that the myc gene is not the target of the amplification detected using the primers and probes for WISP-1.

The data using primers and probes based on the WISP-2 DNA sequence suggest that this gene may be the target of low-level gene amplification in most of the cell lines examined. See FIGS. 20C, 22A–D, and 25C and D. Hence, antibodies to both WISP-1 and WISP-2, particularly human-ized antibodies, are expected to be of benefit in combating certain types of cancer such as colon cancer, similar to the humanized anti-HER-2 antibody in clinical use.

2. WISP-2

Description of Tumors and Cell Lines

Amplification using several different tumor types was performed for human WISP-2 (PRO261), as described below. Table III describes the stage, T stage, and N stage of various primary tumors which were used to screen the WISP-2 compound of the invention.

TABLE III

Primary Lung and Colon Tumor Profiles

| Primary Tumor | Stage | Other Stage | Dukes Stage | T Stage | N Stage |
|---|---|---|---|---|---|
| Human lung tumor SqCCA (SRCC724) [LT1] | IB | — | — | T1 | N1 |
| Human lung tumor NSCCa (SRCC725) [LT1a] | IA | — | — | T3 | N0 |
| Human lung tumor AdenoCa (SRCC726) [LT2] | IB | — | — | T2 | N0 |
| Human lung tumor AdenoCa (SRCC727) [LT3] | IB | — | — | T1 | N2 |
| Human lung tumor SqCCq (SRCC728) [LT4] | IIB | — | — | T2 | N0 |
| Human lung tumor AdenoCa (SRCC729) [LT6] | IV | — | — | T1 | N0 |
| Human lung tumor Aden/SqCCa (SRCC730) [LT7] | IB | — | — | T1 | N0 |
| Human lung tumor AdenoCa (SRCC731) [LT9] | IIB | — | — | T2 | N0 |
| Human lung tumor SqCCa (SRCC732) [LT10] | IA | — | — | T2 | N1 |
| Human lung tumor AdenoCa (SRCC733) [LT11] | IB | — | — | T1 | N1 |
| Human lung tumor AdenoCa (SRCC734) [LT12] | IIA | — | — | T2 | N0 |
| Human lung tumor BAC (SRCC735) [LT13] | IB | — | — | T2 | N0 |
| Human lung tumor SqCCa (SRCC736) [LT15] | IB | — | — | T2 | N0 |
| Human lung tumor SqCCa (SRCC737) [LT16] | IB | — | — | T2 | N0 |
| Human lung tumor SqCCa (SRCC738) [LT17] | IIB | — | — | T2 | N1 |
| Human lung tumor SqCCa (SRCC739) [LT18] | IB | — | — | T2 | N0 |
| Human lung tumor SqCCa (SRCC740) [LT19] | IB | — | — | T2 | N0 |
| Human lung tumor LCCa (SRCC741) [LT21] | IIB | — | — | T3 | N1 |
| Human colon AdenoCa (SRCC742) [CT2] | — | M1 | D | pT4 | N0 |
| Human colon AdenoCa (SRCC743) [CT3] | | — | B | pT3 | N0 |
| Human colon AdenoCa (SRCC744) [CT8] | | | B | T3 | N0 |
| Human colon AdenoCa (SRCC745) [CT10] | | | A | pT2 | N0 |
| Human colon AdenoCa (SRCC746) [CT12] | | M0, R1 | B | T3 | N0 |
| Human colon AdenoCa (SRCC747) [CT14] | | pM0, R0 | B | pT3 | pN0 |
| Human colon AdenoCa (SRCC748) [CT15] | | M1, R2 | D | T4 | N2 |
| Human colon AdenoCa (SRCC749) [CT16] | | pM0 | B | pT3 | pN0 |
| Human colon AdenoCa (SRCC750) [CT17] | | | C1 | pT3 | pN1 |
| Human colon AdenoCa (SRCC751) [CT1] | | M0, R1 | B | pT3 | N0 |
| Human colon AdenoCa (SRCC752) [CT4] | | | B | pT3 | M0 |
| Human colon AdenoCa (SRCC753) [CT5] | | G2 | C1 | pT3 | pN0 |
| Human colon AdenoCa (SRCC754) [CT6] | | pM0, R0 | B | pT3 | pN0 |
| Human colon AdenoCa (SRCC755) [CT7] | | G1 | A | pT2 | pN0 |

TABLE III-continued

Primary Lung and Colon Tumor Profiles

| Primary Tumor | Stage | Other Stage | Dukes Stage | T Stage | N Stage |
|---|---|---|---|---|---|
| Human colon AdenoCa (SRCC756) [CT9] | | G3 | D | pT4 | pN2 |
| Human colon AdenoCa (SRCC757) [CT11] | | | B | T3 | N0 |
| Human colon AdenoCa (SRCC758) [CT18] | | M0, R0 | B | pT3 | pN0 |

DNA Preparation

DNA was prepared from cultured cell lines, primary tumors, and normal human blood (controls and framework and epicenter mapping). The isolation was performed using purification kit #13362 (which includes 10 purification tips with a capacity of 400 μg genomic DNA each), buffer set #1960 and protease #19155 and #19101, all from Quiagen, according to the manufacturer's instructions and the description below.

Cell Culture Lysis

Cells were washed and trypsinized at a concentration of $7.5 \times 10^8$ per tip and pelleted by centrifuging at 1000 rpm for 5 minutes at 4° C., followed by washing again with ½ volume of PBS recentrifugation. The pellets were washed a third time, and the suspended cells collected and washed 2× with PBS. The cells were then suspended into 10 mL PBS. Buffer C1 was equilibrated at 4° C. Protease #19155 (Quiagen) was diluted into 6.25 ml cold ddH$_2$O to a final concentration of 20 mg/ml and equilibrated at 4° C. 10 mL of G2 Buffer was prepared by diluting RNAse A stock (Quiagen) (100 mg/ml) to a final concentration of 200 μg/ml.

Buffer C1 (10 mL, 4° C.) and ddH2O (40 mL, 4° C.) were then added to the 10 mL of cell suspension, mixed by inverting and incubated on ice for 10 minutes. The cell nuclei were pelleted by centrifuging in a BECKMAN™ swinging bucket rotor at 2500 rpm at 4° C. for 15 minutes. The supernatant was discarded and the nuclei were suspended with a vortex into 2 mL Buffer C1 (at 4° C.) and 6 mL ddH$_2$O, followed by a second 4° C. centrifugation at 2500 rpm for 15 minutes. The nuclei were then resuspended into the residual buffer using 200 μl per tip. G2 buffer (10 ml) was added to the suspended nuclei while gentle vortexing was applied. Upon completion of buffer addition, vigorous vortexing was applied for 30 seconds. Quiagen protease (200 μl, prepared as indicated above) was added and incubated at 50° C. for 60 minutes. The incubation and centrifugation were repeated until the lysates were clear (e.g., incubating and additional 30–60 minutes, pelleting at 3000×g for 10 min., 4° C.).

Solid Human Tumor Sample Preparation and Lysis

Tumor samples were weighed and placed into 50-ml conical tubes and held on ice. Processing was limited to no more than 250 mg tissue per preparation (1 tip/preparation). The protease solution was freshly prepared by diluting into 6.25 ml cold ddH$_2$O to a final concentration of 20 mg/ml and stored at 4° C. G2 buffer (20 ml) was prepared by diluting DNAse A to a final concentration of 200 mg/ml (from 100 mg/ml stock). The tumor tissue was homogenated in 19 ml G2 buffer for 60 seconds using the large tip of the polytron in a laminar-flow TC hood to order to avoid inhalation of aerosols, and held at room temperature. Between samples, the polytron was cleaned by spinning at 2×30 seconds each in 2 L ddH$_2$O, followed by G2 buffer (50 ml). If tissue was still present on the generator tip, the apparatus was disassembled and cleaned.

Protease (Quiagen), prepared as indicated above, 1.0 ml, was added, followed by vortexing and incubation at 50° C. for 3 hours. The incubation and centrifugation were repeated until the lysates were clear (e.g., incubating additional 30–60 minutes, pelleting at 3000×g for 10 min., 4° C.).

Human Blood Preparation and Lysis

Blood was drawn from healthy volunteers using standard infectious agent protocols and citrated into 10 ml samples per tip. Protease (Quiagen) was freshly prepared by dilution into 6.25 ml cold ddH$_2$O to a final concentration of 20 mg/ml and stored at 4° C. G2 buffer was prepared by diluting RNAse A to a final concentration of 200 μg/ml from 100 mg/ml stock. The blood (10 ml) was placed into a 50-ml conical tube, and 10 ml Cl buffer and 30 ml ddH$_2$O (both previously equilibrated to 4° C.) were added, and the components mixed by inverting and held on ice for 10 minutes. The nuclei were pelleted with a BECKMAN™ swinging bucket rotor at 2500 rpm, 4° C. for 15 minutes and the supernatant was discarded. With a vortex, the nuclei were suspended into 2 ml C1 buffer (4° C.) and 6 ml ddH$_2$O (4° C.). Vortexing was repeated until the pellet was white. The nuclei were then suspended into the residual buffer using a 200-μl tip. G2 buffer (10 ml) was added to the suspended nuclei while gently vortexing, followed by vigorous vortexing for 30 seconds. Protease (Quiagen) was added (200 μl) and incubated at 50° C. for 60 minutes. The incubation and centrifugation were repeated until the lysates were clear (e.g., incubating an additional 30–60 minutes, pelleting at 3000×g for 10 min., 4° C.).

Purification of Cleared Lysates; Isolation of Genomic DNA

Genomic DNA was equilibrated (1 sample per maxi tip preparation) with 10 ml QBT buffer. QF elution buffer was equilibrated at 50° C. The samples were vortexed for 30 seconds, then loaded onto equilibrated tips and drained by gravity. The tips were washed with 2×15 ml QC buffer. The DNA was eluted into 30-ml silanized, autoclaved 30-ml COREX™ tubes with 15-ml QF buffer (50° C.). Isopropanol (10.5 ml) was added to each sample, and the tubes were covered with paraffin and mixed by repeated inversion until the DNA precipitated. Samples were pelleted by centrifugation in the SS-34 rotor at 15,000 rpm for 10 minutes at 4° C. The pellet location was marked, the supernatant discarded, and 10 ml 70% ethanol (4° C.) was added. Samples were pelleted again by centrifugation on the SS-34 rotor at 10,000 rpm for 10 minutes at 4° C. The pellet location was marked and the supernatant discarded. The tubes were then placed on their side in a drying rack and dried 10 minutes at 37° C., taking care not to overdry the samples.

After drying, the pellets were dissolved into 1.0 ml TE (pH 8.5) and placed at 50° C. for 1–2 hours. Samples were held overnight at 4° C. as dissolution continued. The DNA solution was then transferred to 1.5-ml tubes with a 26-gauge needle on a tuberculin syringe. The transfer was repeated 5× in order to shear the DNA. Samples were then placed at 50° C. for 1–2 hours.

Quantitation of Genomic DNA and Preparation For Gene Amplification Assay

The DNA levels in each tube were quantified by standard A260, A280 spectrophotometry on a 1:20 dilution (5 μl DNA+95 μl ddH$_2$O) using the 0.1-ml quartz cuvettes in the BECKMAN DU640™ spectrophotometer. A260/A280 ratios were in the range of 1.8–1.9. Each DNA sample was then diluted further to approximately 200 ng/ml in TE (pH 8.5). If the original material was highly concentrated (about 700 ng/μl), the material was placed at 50° C. for several hours until resuspended.

Fluorometric DNA quantitation was then performed on the diluted material (20–600 ng/ml) using the manufacturer's guidelines as modified below. This was accomplished by allowing a HOEFFER DYNA QUANT 200™ fluorometer to warm up for about 15 minutes. The HOECHST™ dye working solution (#H33258, 10 μl prepared within 12 hours of use) was diluted into 100 ml 1×TNE buffer. A 2-ml cuvette was filled with the fluorometer solution, placed into the machine, and the machine was zeroed. pGEM 3Zf(+) (2 μl, lot #360851026) was added to 2 ml of fluorometer solution and calibrated at 200 units. A second 2 μl of pGEM 3Zf(+) DNA was then tested and the reading confirmed at 400±10 units. Each sample was then read at least in triplicate. When 3 samples were found to be within 10% of each other, their average was taken and this value was used as the quantification value.

The fluorometrically-determined concentration was then used to dilute each sample to 10 ng/μl in ddH$_2$O. This was done simultaneously on all template samples for a single TAQMAN™ plate assay, and with enough material to run 500–1000 assays. The samples were tested in triplicate with both B-actin and GAPDH on a single plate with normal human DNA and no-template controls. The diluted samples were used, provided that the CT value of normal human DNA subtracted from test DNA was ±1 CT. The diluted, lot-qualified genomic DNA was stored in 1.0-ml aliquots at −80° C. Aliquots which were subsequently to be used in the gene amplification assay were stored at 4° C. Each 1-ml aliquot is enough for 8–9 plates or 64 tests.

Framework Mapping and Epicenter Marking

Human WISP-1 was reexamined with both framework and epicenter mapping. Selected tumors from the above initial screen were reexamined with both framework and epicenter mapping. Table IV indicates the chromosomal mapping of the framework markers that were used in the present example. The framework markers are located approximately every 20 megabases along Chromosome 8 and were used to control for aneuploidy.

TABLE IV

Framework Markers

| Map Position on Chromosome 8 | Stanford Human Genome Center Marker Name |
|---|---|
| H9 | EST-00040 |
| H59 | WI-961 |
| H121 | SHGC-11323 |
| H200 | SHGC-7433 |
| H256 | AFMa183zf1 |

Table V describes the epicenter markers that were employed in association with WISP-1. These markers are located in close proximity to the gene for WISP-1 and are used to assess the amplification status of the region of chromosome 8 in which the gene for WISP-1 is located. The distance between individual markers is measured in centirays (cR), which is a radiation breakage unit approximately equal to a 1% chance of a breakage between two markers. One cR is very roughly equivalent to 20 kilobases. The marker SHGC-32958 is the marker found to be the closest to the location on chromosome 8 to which the gene encoding WISP-1 most closely maps.

TABLE V

Epicenter Markers

| Map Position on Chromosome 8 | Stanford Human Genome Center Marker Name | Distance to next Marker (cR) |
|---|---|---|
| H257 | AFMa248tel | 103 (gap) |
| H259 | SHGC-36664 | 33 |
| H261 | AFM259xc5 | 63 |
| H266 | SHGC-32958 | 41 |
| H267 | AFMa175xcl | 19 |
| H268 | AFM337wg5 | 87 |
| H273 | SHGC-33759 | 71 |
| H274 | SHGC-32752 | 5 |
| H275 | WI-7711 | 21 |
| H277 | SHGC-34940 | — |

The framework markers for human WISP-2 are located approximately every 20 megabases along Chromosome 20, and are used to control for aneuploidy. The markers are shown in Table VI.

TABLE VI

Framework Markers

| Map Position on Chromosome 20 | Stanford Human Genome Center Marker Name |
|---|---|
| T10 | SHGC-2797 |
| T48 | UT759 |
| T73 | AFMa339xf5 |
| T115 | SHGC-33922 |
| T159 | SHGC-36268 |

The marker SHGC-33922 is the marker to which human WISP-2 DNA most closely maps. This marker is between the framework markers. Framework analysis showed that all markers were u7p in tumors; thus, chromosome 20 was aneuphoid in many tumors. Since the markers were up due to aneuploidy, epicenter analysis was not done for human WISP-2 gene.

The ΔCt values of the above described framework markers along Chromosome 8 relative for WISP-1 are indicated for selected tumors in Tables VII and VIII.

TABLE VII

Amplification of framework markers relative to Human WISP-1 DNA Framework Markers (Δct)

Probe/Delta CT

| Template | c-myc (SD) | WISP-1 (SD) | WISP-2 (SD) | H9 (SD) | H59 (SD) | H121 (SD) | H200 (SD) | H256 (SD) |
|---|---|---|---|---|---|---|---|---|
| Nor Hu | 0.00 (0.91) | 0.00 (0.01) | 0.00 (0.20) | 0.00 (0.13) | 0.00 (0.20) | 0.00 (0.14) | 0.00 (0.16) | 0.00 (0.04) |
| SW480 | 1.86 | 0.84 | 1.92 | −1.18 | 1.01 | 0.17 | 0.65 | 0.81 |
| SW620 | 1.45 | 0.98 | 1.60 | 0.45 | 0.75 | 1.00 | 0.81 | 0.52 |
| Colo320 | 3.73 | 0.65 | 1.88 | 0.69 | 0.70 | 0.89 | 0.60 | 0.40 |
| HT29 | 0.83 | 2.67 | 2.20 | −1.13 | −0.40 | −0.55 | 1.00 | 2.42 |
| HM7 | −2.03 | 0.07 | −0.28 | −0.28 | 0.24 | −0.48 | 0.12 | −0.26 |
| WiDr | −0.13 | 2.91 | 1.67 | −0.20 | 0.95 | 0.07 | 1.43 | 2.55 |
| HCT116 | −0.57 | 1.82 | 1.04 | 1.24 | 1.56 | 0.84 | 1.76 | 1.53 |
| SKCO-1 | 0.19 | 1.68 | 0.97 | −0.30 | 0.32 | 0.12 | 1.39 | 1.63 |
| SW403 | −0.72 | 1.34 | 1.77 | 0.23 | 0.53 | 0.26 | 1.48 | 1.48 |
| Nor Hu | — | 0.00 (0.18) | 0.00 (1.02) | 0.00 (0.08) | 0.00 (0.13) | 0.00 (0.01) | 0.00 (0.16) | 0.00 (0.37) |
| CT-2 | — | 0.65 | 0.44 | −0.25 | 0.11 | 0.07 | 0.13 | 0.95 |
| CT-3 | — | 0.90 | 0.95 | −0.27 | 0.05 | −0.10 | −0.11 | 0.32 |
| CT-8 | — | 0.47 | −0.34 | 0.07 | −0.20 | 0.00 | −0.04 | 0.07 |
| CT-10 | — | 0.76 | 0.50 | 0.23 | −0.36 | −0.08 | 0.17 | 0.70 |
| CT-12 | — | 1.30 | 2.14 | −0.70 | −0.45 | 0.24 | 0.47 | 1.75 |
| CT-14 | — | 1.17 | −0.48 | 0.05 | 0.18 | 0.31 | 0.23 | 1.51 |
| CT-15 | — | 0.22 | −0.13 | 0.13 | −0.48 | 0.29 | 0.11 | 0.59 |
| CT-16 | — | 0.26 | 0.10 | 0.00 | −0.15 | −0.23 | −0.09 | 0.95 |
| CT-17 | — | 0.57 | −0.33 | 0.73 | −0.11 | −0.05 | −0.11 | 0.25 |
| Nor Hu | — | 0.00 (0.45) | 0.00 (1.07) | 0.00 (0.04) | 0.00 (0.21) | 0.00 (0.18) | 0.00 (0.03) | 0.00 (0.18) |
| CT-1 | — | 0.84 | −0.37 | −0.36 | 0.19 | 0.68 | 0.01 | 0.66 |
| CT-4 | — | 0.15 | −0.23 | −1.00 | 0.24 | −0.11 | 0.30 | 0.14 |
| CT-5 | — | 0.86 | −1.23 | −0.60 | −0.25 | 0.22 | 0.51 | 0.62 |
| CT-6 | — | 0.03 | 0.39 | −0.24 | 0.61 | 0.70 | 0.01 | 0.19 |
| CT-7 | — | −0.20 | −1.36 | −0.76 | 0.00 | −0.09 | −0.13 | −0.18 |
| CT-9 | — | 0.30 | −0.54 | −0.50 | 0.29 | 0.54 | 0.11 | 0.18 |
| CT-11 | — | 0.48 | 0.14 | −0.89 | 0.34 | 0.82 | 0.17 | −0.06 |
| CT-18 | — | −0.20 | −1.37 | −0.52 | 0.32 | 0.66 | 0.08 | 0.12 |

TABLE VIII

Amplification of framework markers relative to Human WISP-1 DNA Framework Markers (Δct)

Probe/Delta CT

| Template | WISP-2 (SD) | T10 (SD) | T48 (SD) | T73 (SD) | T115 (SD) | T159 (SD) |
|---|---|---|---|---|---|---|
| Nor Hu | 0.00 (0.05) | 0.00 (0.16) | 0.00 (0.09) | 0.00 (0.21) | 0.00 (3.22) | 0.00 (0.09) |
| SW480 | 1.31 | 1.32 | 0.63 | 1.94 | −5.66 | 1.61 |
| SW620 | 1.32 | 2.02 | 1.42 | 1.06 | −10.95 | 1.48 |
| Colo320 | 0.43 | 1.35 | 1.37 | 0.61 | 0.30 | 1.37 |
| HT29 | 1.76 | 1.09 | −2.23 | 1.26 | −5.47 | 1.87 |
| HM7 | −0.32 | 0.32 | 0.38 | 0.41 | −6.3 | 0.48 |
| WiDr | 1.76 | 1.61 | −1.38 | 1.04 | −7.36 | 1.55 |
| HCT116 | 1.18 | 1.24 | 1.15 | 1.46 | −8.38 | 1.49 |
| SKCO-1 | 1.40 | 1.17 | 1.19 | 1.13 | −5.34 | 1.61 |
| SW403 | 1.92 | 2.24 | −17.23 | 1.38 | −3.66 | 2.12 |

Gene Amplification Assay Results

The human WISP-2 (PRO261) compound of the invention was screened in the following primary tumors and the resulting ΔCt values are reported in Table IX.

TABLE IX

ΔCt values in lung and colon primary tumor models

| Primary Tumor | PRO261 |
|---|---|
| LT1 | 0.41 |
| LT1a | 1.08 |
| LT2 | 0.27 |
| LT3 | 0.98 |
| LT4 | 0.32 |
| LT6 | 0.45 |
| LT7 | 0.03 |
| LT9 | 0.18 |
| LT10 | 1.16 |
| LT11 | 0.67, 1.59, 0.63, 0.19, |
| LT12 | 0.80, 1.73, 1.08, 2.23 |
| LT13 | 1.02, 1.13, 1.01, 0.29 |
| LT15 | 0.97, 2.64, 0.56, 2.38 |
| LT16 | 0.80, 0.75, 0.82, 2.05 |
| LT17 | 1.67, 2.01, 1.43, 0.93 |
| LT18 | 1.22, 0.46, 0.15, −0.17 |
| LT19 | 0.78, 1.38, 1.39, 2.33 |
| LT21 | 0.04, 1.14, 0.48, 3.40 |
| CT2 | 1.66 |
| CT3 | 2.14 |
| CT8 | 0.55 |
| CT10 | 1.00 |
| CT12 | 0.34 |
| CT14 | 1.03 |
| CT15 | 0.67 |
| CT16 | 0.87 |
| CT17 | −0.19 |
| CT1 | −0.06 |

TABLE IX-continued

ΔCt values in lung and colon primary tumor models

| Primary Tumor | PRO261 |
|---|---|
| CT4 | 1.00 |
| CT5 | 1.07 |
| CT6 | −0.08 |
| CT7 | 0.15 |
| CT9 | 0.68 |
| CT11 | 0.59 |
| CT18 | 0.73 |
| A549 | — |
| Calu-1 | — |
| Calu-6 | — |
| H157 | — |
| H441 | — |
| H460 | — |
| SKMES1 | — |
| SW900 | — |
| SW480 | 0.62, 1.90, 1.20, 1.57, 1.68, 1.36, 1.59, 1.86, 1.91, 2.36, 1.68, 1.53, 2.50 |
| SW620 | 0.66, 1.65, 1.85, 1.63, 1.61, 1.24, 1.52, 1.98, 1.57, 1.83, 1.41, 1.42, 1.59 |
| Colo320 | −0.33, 0.66, 0.48, 0.91, 0.72, 0.33, 2.49, 0.99, 1.06, 1.24, 1.04, 0.46, 0.27 |
| HT29 | 0.46, 1.95, 1.61, 2.58, 1.49, 1.38, 1.40, 2.00, 2.59, 2.59, 1.39, 1.32 |
| HM7 | −0.70, 0.74, −0.29, 0.66, 0.27, 0.08, 0.54, 0.67, 0.64, 0.34, 0.09, 0.29, 0.21 |
| WiDr | 0.19, 1.64, 1.00, 1.71, 1.44, 1.57, 0.93, 1.84, 1.58, 0.91, 0.87 |
| HCT116 | 0.25, 1.29, 1.04, 2.01, 1.29, 1.07, 1.08, 2.05, 1.81, 1.56, 1.05, 1.09, 0.96 |
| SKCO1 | 0.73, 1.99, 1.33, 1.00, 1.33, 1.26, 1.19, 2.10, 1.50, 2.13, 1.33, 1.29 |
| SW403 | 0.26, 1.98, 1.42, 2.20, 2.40, 1.50, 1.43, 2.15, 1.52, 1.67, 2.19, 1.40, 1.29 |
| LS174T | 1.48 |
| HBL100 | 1.40 |
| MB435s | 1.43 |
| T47D | 0.38 |
| MB468 | −0.08 |
| MB175 | 0.23 |
| MB361 | 0.37 |
| BT20 | 1.66 |
| MCF7 | 0.53 |
| SKBR3 | 1.73 |

The ΔCt values for DNA33473 (PRO261; human WISP-2) in a variety of primary lung and colon tumors as well as lung tumor cell lines are reported in Table IX. A ΔCt value of >1 was typically used as the threshold value for amplification scoring, as this represents a doubling of the gene copy. Table IX indicates that significant amplification of DNA33474 occurred in: (1) primary lung tumors LT1a, LT10, LT12, LT15, LT17 and LT19; (2) primary colon tumors CT2, CT3, CT14, and CT5; (3) colon tumor cell lines SW480, SW620, HT29, WiDr, HCT116, SKCO1, SW403, and LS174T and (4) breast tumor cell lines HBL100, MB435s, BT20 and SKBR3.

The ΔCt and average ΔCt values for the primary lung tumors were the following: 1.08, 1.16, 1.17, 1.64, 1.50 and 1.47, respectively; those for the primary colon tumors were 1.16, 2.14, 1.03 and 1.07, respectively; those for the colon tumor cell lines were 1.67, 1.54, 1.73, 1.24, 1.32, 1.35, 1.65, and 1.48, respectively; and those for the breast tumor cell lines were 1.40, 1.43, 1.66, and 1.73, respectively.

For the lung tumors, this represents approximately a 2.1-, 2.2-, 2.2-, 3.1-, 2.8-, and 2.8-, respectively, fold increase in gene copy relative to normal tissue. For the colon tumors, this represents a 2.2-, 4.4-, 2.0-, and 2.1-, respectively, fold increase in gene copy relative to normal tissue. For the colon tumor cell lines, this represents a 3.2-, 2.9-, 3.3-, 2.4-, 2.5-, 2.5-, 3.1-, and 2.8-, respectively, fold increase in gene copy relative to normal tissue. For the breast tumor cell lines, this represents a 2.6-, 2.7-, 3.2-, and 3.3-, respectively, fold increase in gene copy relative to normal tissue. Because amplification of DNA33473 (PRO261) occurs in various tumors, it is likely associated with tumor formation or growth. As a result, antagonists (e.g., antibodies) directed against the protein encoded by DNA33473 (PRO261) would be expected to be useful in cancer therapy.

Example 16

In Situ Hybridization

In situ hybridization is a powerful and versatile technique for the detection and localization of nucleic acid sequences within cell or tissue preparations. It may be useful, for example, in identifying sites of gene expression, analyzing the tissue distribution of transcription, identifying and localizing viral infection, following changes in specific mRNA synthesis, and aiding in chromosome mapping.

In situ hybridization was performed following an optimized version of the protocol by Lu and Gillett, *Cell Vision* 1: 169–176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A ($^{33}$-P)UTP-labeled antisense riboprobe was generated from a PCR product and hybridized at 55° C. overnight. The slides were dipped in KODAK NTB2™ nuclear track emulsion and exposed for 4 weeks.

$^{33}$P-Riboprobe Synthesis 6.0 μl (125 mCi) of $^{33}$P-UTP (Amersham BF 1002, SA<2000 Ci/mmol) were speed-vacuum dried. To each tube containing dried $^{33}$P-UTP, the following ingredients were added:

2.0 μl 5×transcription buffer
1.0 μl DTT (100 mM)
2.0 μl NTP mix (2.5 mM:10 μl each of 10 mM GTP, CTP & ATP+10 μl H$_2$O)
1.0 μl UTP (50 μM)
1.0 μl RNAsin
1.0 μl DNA template (1 μg)
1.0 μl H$_2$O
1.0 μl RNA polymerase (for PCR products T3=AS, T7=S, usually)

The tubes were incubated at 37° C. for one hour. A total of 1.0 μl RQ1 DNase was added, followed by incubation at 37° C. for 15 minutes. A total of 90 μl TE (10 mM Tris pH 7.6/1 mM EDTA, pH 8.0) was added, and the mixture was pipetted onto DE81 paper. The remaining solution was loaded in a MICROCON-50™ ultrafiltration unit, and spun using program 10 (6 minutes). The filtration unit was inverted over a second tube and spun using program 2 (3 minutes). After the final recovery spin, a total of 100 μl TE was added. Then 1 μl of the final product was pipetted on DE81 paper and counted in 6 ml of BIOFLUOR II™.

The probe was run on a TBE/urea gel. A total of 1–3 μl of the probe or 5 μl of RNA Mrk III was added to 3 μl of loading buffer. After heating on a 95° C. heat block for three minutes, the gel was immediately placed on ice. The wells of gel were flushed, and the sample was loaded and run at 180–250 volts for 45 minutes. The gel was wrapped in plastic wrap (SARAN™ brand) and exposed to XAR film with an intensifying screen in a −70° C. freezer one hour to overnight.

$^{33}$P-Hybridization

A. Pretreatment of Frozen Sections

The slides were removed from the freezer, placed on aluminum trays, and thawed at room temperature for 5 minutes. The trays were placed in a 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+975 ml s.c. H$_2$O). After deproteination in 0.5 µg/ml proteinase K for 10 minutes at 37° C. (12.5 µl of 10 mg/ml stock in 250 ml prewarmed RNAse-free RNAse buffer), the sections were washed in 0.5×SSC for 10 minutes at room temperature. The sections were dehydrated in 70%, 95%, and 100% ethanol, 2 minutes each.

B. Pretreatment of Paraffin-embedded Sections

The slides were deparaffinized, placed in s.c. H$_2$O, and rinsed twice in 2×SSC at room temperature, for 5 minutes each time. The sections were deproteinated in 20 µg/ml proteinase K (500 µl of 10 mg/ml in 250 ml RNAse-free RNAse buffer; 37° C., 15 minutes) for human embryo tissue, or 8×proteinase K (100 µl in 250 ml RNAse buffer, 37° C., 30 minutes) for formalin tissues. Subsequent rinsing in 0.5×SSC and dehydration were performed as described above.

C. Prehybridization

The slides were laid out in a plastic box lined with Box buffer (4×SSC, 50% formamide) The filter paper was saturated. The tissue was covered with 50 µl of hybridization buffer (3.75 g dextran sulfate+6 ml s.c. H$_2$O), vortexed, and heated in the microwave for 2 minutes with the cap loosened. After cooling on ice, 18.75 ml formamide, 3.75 ml 20×SSC, and 9 ml s.c. H$_2$O were added, and the tissue was vortexed well and incubated at 42° C. for 1–4 hours.

D. Hybridization $1.0 \times 10^6$ cpm probe and 1.0 µl tRNA (50 mg/ml stock) per slide were heated at 95° C. for 3 minutes. The slides were cooled on ice, and 48 µl hybridization buffer was added per slide. After vortexing, 50 µl $^{33}$P mix was added to 50 µl prehybridization on the slide. The slides were incubated overnight at 55° C.

E. Washes

Washing was done for 2×10 minutes with 2×SSC, EDTA at room temperature (400 ml 20×SSC+16 ml 0.25 M EDTA, V$_f$=4 L), followed by RNAseA treatment at 37° C. for 30 minutes (500 µl of 10 mg/ml in 250 ml RNAse buffer=20 µg/ml), The slides were washed 2×10 minutes with 2×SSC, EDTA at room temperature. The stringency wash conditions were as follows: 2 hours at 55° C., 0.1×SSC, EDTA (20 ml 20×SSC +16 ml EDTA, V$_f$=4 L).

F. Oligonucleotides

In situ analysis was performed on DNA sequences disclosed herein. The oligonucleotides employed for these analyses are as follows.

(1) Mouse WISP-1 (Clone 568)

Notrim-p1: 5'-GGA TTC TAA TAC GAC TCA CTA TAG GGC GTC CCT GGC CAG TGC TGT GAG-3' (SEQ ID NO:147)

Notrim-p2: 5'-CTA TGA AAT TAA CCC TCA CTA AAG GGA GGG CCA GGC TTT GCT TCC ATT-3' (SEQ ID NO:148)

(2) Human WISP-1 hmWISP-1 p1: 5'-GGA TTC TAA TAC GAC TCA CTA TAG GGC TGG AGG CAT GGC ACA GGA AC-3' (SEQ ID NO:149)

hmWISP-1 p2: 5'-CTA TGA AAT TAA CCC TCA CTA AAG GGA TCC GGA TCA GGC TTG GGT GTA-3' (SEQ ID NO:150)

(3) Mouse WISP-2 (Clone 1367.3)

1367.p1: 5'-GGA TTC TAA TAC GAC TCA CTA TAG GGC AGC TTG GGA TGG AGG TCT TTC-3' (SEQ ID NO:151)

1367.p2: 5'-CTA TGA AAT TAA CCC TCA CTA AAG GGA GGG CAC TGG GGT GGT GT-3' (SEQ ID NO:152)

(4) Human WISP-2 (DNA33473)

DNA33473-p1: 5'-GGA TTC TAA TAC GAC TCA CTA TAG GGC GCG AGG ACG GCG GCT TCA-3' (SEQ ID NO:153)

DNA33473-p2: 5'-CTA TGA AAT TAA CCC TCA CTA AAG GGA AGA GTC GCG GCC GCC CTT TTT-3' (SEQ ID NO:154)

(5) Human WISP-3

WISP3-p1 5'-GGA TTC TAA TAC GAC TCA CTA TAG GGC GGG GCT CCT CTT CTC CAC TCT-3' (SEQ ID NO:155)

WISP3-p2 5'-CTA TGA AAT TAA CCC TCA CTA AAG GGA GCT GTC GCA AGG CTG AAT GTA-3' (SEQ ID NO:156)

G. Results

In situ analysis was performed on the above DNA sequences disclosed herein. The results from these analyses are as follows.

(1) Mouse WISP-1

Expression in Mouse Tissues

Mouse Fetal Tissues

In situ hybridization of mouse WISP-1 showed strong expression in embryonic mesenchymal tissues. At E10.5 expression was observed in tissues that would develop into skeletal elements in the adult; this pattern was maintained at later stages of embryonic development. In later stages (E12.5 and E15.5), expression was highest in osteoblasts at the sites of bone formation. Expression was also observed in the embryonic heart, where the signal was particularly strong in the atria at E12.5 (atria were not included in sections at E15.5).

Mouse Adult Tissues

No expression was observed in any of the adult tissues examined, including heart, lung, kidney, adrenal, liver, pancreas, cerebrum, and cerebellum. These results do not correlate with the Northern data.

Additional sites of expression in the fetus were the walls of developing blood vessels and in fibroblast-like cells within the hepatic portal tract mesenchyme.

Expression in Normal and Wnt-1 Transgenic Tumors

Expression with the antisense probe was observed over fibroblast-like cells lying adjacent to the subcutaneous skeletal muscle in P10 (post-natal day 10 pups) and in pregnant females. Expression was not observed over breast epithelial cells at any of the time points examined in the study.

Expression of mouse WISP-1 was high in all three of the Wnt-1 transgenic tumors tested and appeared to be confined to the supporting fibroblast-like cells within the delicate connective tissue stroma. Some expression was seen over the tumor cells themselves; however, this likely represents overspill from tumor fibroblasts, rather than true expression by tumor cells.

In summary, mouse WISP-1 was expressed in embryonic skeletal mesenchyme and at sites of bone formation. It was additionally expressed in fibroblasts in the sub-cutus of growing pups and pregnant females. It is likely to play a role in osteogenesis, and may be involved in repair after injury. Expression was also observed in the embryonic heart.

(2) Human WISP-1

Expression in Human Tissues

Human Fetal Tissue

The fetal tissues examined (E12–E16 weeks) included: placenta, umbilical cord, liver, kidney, adrenals, thyroid, lungs, heart, great vessels, oesophagus, stomach, small intestine, spleen, thymus, pancreas, brain, eye, spinal cord, body wall, pelvis, and lower limb.

Human WISP-1 exhibited expression at sites of connective tissue interfaces in the fetus, for example, developing portal tracts, fascial planes in muscle, and connective tissue surrounding developing skeletal elements and tendons. Expression also was seen in the epithelium of the developing renal cortex and in spindle-shaped fibroblast-like cells in the fetal adrenal. Human WISP-1 was strongly expressed by osteoblasts at sites of bone formation in the fetal limb.

Human Adult Tissue

The adult tissues examined were: liver, kidney, adrenal, myocardium, aorta, spleen, lung, skin, chondrosarcoma, eye, stomach, gastric carcinoma, colon, colonic carcinoma, renal cell carcinoma, prostate, bladder mucosa, and gall bladder, as well as tissue with acetominophen-induced liver injury and hepatic cirrhosis.

No expression was seen in normal or diseased adult tissues in this study.

In summary, the overall pattern of expression of human WISP-1 was broadly similar to that observed for the mouse gene as noted above. The human WISP-1 probe did not cross react with the mouse embryo section.

Expression in Human Breast Carcinoma and Normal Breast Tissue

Human WISP-1 was negative on benign and malignant epithelial cells, but showed specific hybridization in mesenchmal cells, particularly in areas of tissue repair, including dystrophic ossification. Most positive cells had the morphology of fibroblasts; smooth muscle cells appeared to be negative.

In summary, this study shows expression of human WISP-1 RNA in mesenchymal cells involved in tissue repair and/or collagen deposition. The signal was particularly strong in benign fibroblast-like cells adjacent to either infiltrating breast carcinoma cells or tissue destruction due to benign, inflammatory conditions (duct rupture). Of note is the fact that deposition of benign osteoid seemed to correlate with strong expression of the RNA.

(3) Mouse WISP-2
Expression in Normal Mouse Tissues
Mouse Fetal Tissues

Expression of mouse WISP-2 was observed in osteoblasts in an E15.5 mouse embryo, within the developing mandible.

Mouse Adult Tissues

Expression of mouse WISP-2 was observed in stromal cells around the origin, and within the cusps of the mitral and tricuspid valves of the adult heart. Expression was also observed in the adventitial cells of the renal artery; expression was presumed to be present at this site in all arteries.

All other tissues were negative.

Expression in Wnt-1 Tumors

The results demonstrated specific expression of mouse WISP-2 in the stroma of all Wnt-1 tumors examined. There was a signal over mononuclear cells with open vesicular nuclei, possibly macrophages. No expression was observed in either the benign or the malignant epithelium.

(4) Human WISP-2
Expression in Human Tissues

Strong expression of the WISP-2-encoding gene was observed in dermal fibroblasts in normal adult skin. Additionally, strong expression was seen in two cirrhotic livers, at sites of active hepatic fibrosis. Moderate expression was found over fasiculata cells of adrenal cortex. This localization supports a role for human WISP-2 in extracellular matrix formation or turnover.

Expression in Human Breast Carcinoma and Normal Breast Tissue, and in Lung Carcinoma Human WISP-2 showed a similar hybridization pattern to human WISP-1 (described above) in the two breast tumors examined. It was negative on benign and malignant epithelial cells, but showed specific hybridization in mesenchmal cells, particularly in areas of tissue repair, including dystrophic ossification. The signal appeared to localize to the same cell population for both probes WISP-1 and WISP-2; however, in some areas (breast tumor 02), the signal for WISP-2 was significantly stronger than that for human WISP-1. Most positive cells had the morphology of fibroblasts; smooth muscle cells appeared to be negative. The signal for human WISP-2 was less intense in the lung tumor tissue; however, this section also showed less tissue repair compared with the breast tumor slides. Normal lung and kidney tissue were essentially negative for human WISP-2, as for human WISP-1.

In summary, this study shows expression of human WISP-2 RNA in mesenchymal cells involved in tissue repair and/or collagen deposition. The signal was particularly strong in benign fibroblast-like cells adjacent to either infiltrating breast carcinoma cells or tissue destruction due to benign, inflammatory conditions (duct rupture). Of note is the fact that deposition of benign osteoid seemed to correlate with strong expression of the RNA.

(5) Human WISP-3
Expression in Normal Adult and Fetal Tissues and in Human Breast Carcinoma and Normal Breast Tissue and in Colon Carcinoma The analysis shows strong expression of human WISP-3 in dermal fibroblasts in normal adult skin and in cirrhotic livers at sites of active hepatic fibrosis. This localization pattern supports a role for this growth factor in extracellular matrix formation and turnover.

The probe for human WISP-3 was negative on most tissues examined. It showed a weak, diffuse positivity on sections of an osteosarcoma; some of the positive cells do represent malignant cells. WISP-3 was negative on all normal and fetal tissues examined.

Example 17
Ability of WISP Polypeptides to Inhibit VEGF-Stimulated Proliferation of Endothelial Cell Growth The ability of mouse and human WISP-1 and human WISP-2 polypeptides to inhibit VEGF-stimulated proliferation of endothelial cells was tested. Specifically, bovine adrenal cortical capillary endothelial (ACE) cells (from primary culture, maximum 12–14 passages) were plated on 96-well microtiter plates (Amersham Life Science) at a density of 500 cells/well per 100 $\mu$L in low-glucose DMEM, 10% calf serum, 2 mM glutamine, 1×pen/strept, and fungizone, supplemented with 3 ng/mL VEGF. Controls were plated the same way but some did not include VEGF. A test sample of either mouse WISP-1, human WISP-1 conjugated to IgG, or human WISP-2 (PRO261) conjugated to poly-His was added in a 100-$\mu$l volume for a 200-$\mu$L final volume. Cells were incubated for 5–7 days at 37° C. The media were aspirated and the cells washed 1× with PBS. An acid phosphatase reaction mixture (100 $\mu$L, 0.1 M sodium acetate, pH 5.5, 0.1% TRITON-100™, 10 mM p-nitrophenyl phosphate) was added. After incubation for 2 hours at 37° C., the reaction was stopped by addition of 10 $\mu$L 1 N NaOH. OD was measured on a microtiter plate reader at 405 nm. Controls were: no cells, cells alone, cells+FGF (5 ng/mL), cells+VEGF (3 ng/mL), cells+VEGF (3 ng/ml)+TGF-$\beta$ (1 ng/ml), and cells+VEGF (3 ng/mL)+ LIF (5 ng/mL). (TGF-$\beta$ at a 1 ng/ml concentration is known to block 70–90% of VEGF-stimulated cell proliferation.)

The results were asse(ssed by calculating the percentage inhibition of VEGF(3 ng/ml)-stimulated cell proliferation, determined by measuring acid phosphatase activity at OD405 nm (1) relative to cells without stimulation, and (2) relative to the reference TGF-β inhibition of VEGF-stimulated activity. The results, as shown in Table X below, are indicative of the utility of the WISP polypeptides in cancer therapy and specifically in inhibiting tumor angiogenesis. The numerical values (relative inhibition) shown in Table X are determined by calculating the percent inhibition of VEGF-stimulated proliferation by the mouse WISP-1, human WISP-1-IgG, and human WISP-2-poly-His polypeptides relative to cells without stimulation and then dividing that percentage into the percent inhibition obtained by TGF-β at 1 ng/ml, which is known to block 70–90% of VEGF-stimulated cell proliferation. Human WISP-1 and human WISP-2 appear to be particularly useful as angiostatic agents.

TABLE X

| Polypeptide | Concentration (nM) | Relative Inhibition |
|---|---|---|
| Mouse WISP-1 | 0.1 | 113 |
| " | 1.0 | 108 |
| " | 10.0 | 109 |
| Human WISP-1-IgG | 1.1 | 1 |
| " | 11.0 | 0.95 |
| " | 110.0 | 0.9 |
| Human WISP-2-poly-His | 0.01% | 0.95 |
| " | 0.01% | 1.1 |
| " | 0.1 | 0.62 |
| " | 1.0 | 1.03 |
| " | 1.0 | 0.5 |
| " | 1.0 | 0.6 |

\* \* \* \*

Deposit of Material

The following materials have been deposited with the American Type Culture Collection, 10801 University Blvd., Manassas, Va., USA (ATCC):

| Material | ATCC Dep. No. | Deposit Date |
|---|---|---|
| pRK5E.h.WIG-1.568.38 | 209533 | December 10, 1997 |
| pRK5E.m.WIG-1.568.6his | 209537 | December 10, 1997 |
| Plasmid (encoding human WISP-2) | 209391 | October 17, 1997 |
| pRKE.m.WIG-2.1367.3 | 209538 | December 10, 1997 |
| DNA56350-1176-2 | 209706 | March 26, 1998 |
| DNA58800-1176-2 | 209707 | March 26, 1998 |

These deposits were made under the provisions of the Budapest Treaty on the International Recognition of the Deposit of Microorganisms for the Purpose of Patent Procedure and the Regulations thereunder (Budapest Treaty). This assures maintenance of viable cultures of the deposits for 30 years from the date of deposit. The deposits will be made available by ATCC under the terms of the Budapest Treaty, and subject to an agreement between Genentech, Inc. and ATCC, which assures permanent and unrestricted availability of the progeny of the cultures of the deposits to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited materials is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the constructs deposited, since the deposited embodiment is intended as a single illustration of certain aspects of the invention and any constructs that are functionally equivalent are within the scope of this invention. The deposits of materials herein do not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. Isolated nucleic acid comprising DNA encoding a human WISP-1 polypeptide having amino acid residues 23 to 367 of FIGS. 3A and 3B (SEQ ID NO:3), or DNA encoding a human WISP-1 polypeptide having amino acid residues 1 to 367 of FIGS. 3A and 3B (SEQ ID NO:4), or a complement of either of the encoding DNAs.

2. A vector comprising the nucleic acid of claim 1.

3. The vector of claim 2 comprising the vector deposited in ATCC Deposit No. 209533.

4. A host cell comprising the vector of claim 2.

5. A process for producing a WISP-1 polypeptide comprising culturing the host cell of claim 4 under conditions suitable for expression of the WISP-1 polypeptide and recovering the WISP-1 polypeptide from the cell culture.

6. The host cell of claim 4 wherein said host cell is a CHO cell.

7. The host cell of claim 4 wherein said host cell is a yeast cell.

8. The host cell of claim 4 wherein said host cell is an E. coli.

9. The nucleic acid of claim 1 comprising the coding sequence in ATCC Deposit No. 209533 which encodes human WISP-1 polypeptide.

10. The nucleic acid of claim 1 wherein said DNA encodes a human WISP-1 polypeptide having amino acid residues 23 to 367 of FIGS. 3A and 3B (SEQ ID NO:3).

11. The nucleic acid of claim 1 wherein said DNA encodes a human WISP-1 polypeptide consisting of amino acid residues 23 to 367 of FIGS. 3A and 3B (SEQ ID NO:3).

12. The nucleic acid of claim 1 wherein said DNA encodes a human WISP-1 polypeptide having amino acid residues 1 to 367 of FIGS. 3A and 3B (SEQ ID NO:4).

13. The nucleic acid of claim 1 wherein said DNA encodes a human WISP-1 pulypeptide consisting of amino acid residues 1 to 367 of FIGS. 3A and 3B (SEQ ID NO: 4).

14. Isolated nucleic acid comprising DNA encoding a human WISP-1 polypeptide having amino acid residues 23 to 367 or 1 to 367 of FIGS. 3A and 3B except for an isoleucine residue at position 184 rather than a valine residue (SEQ ID NOS: 5 and 6, respectively).

15. Isolated nucleic acid comprising DNA encoding a human WISP-1 polypeptide having amino acid residues 23 to 367 or 1 to 367 of FIGS. 3A and 3B except for a serine residue at position 202 rather than an alanine residue (SEQ ID NOS: 7 and 8, respectively).

16. Isolated nucleic acid comprising DNA encoding a human WISP-1 polypeptide having amino acid residues 23 to 367 or 1 to 367 of FIGS. 3A and 3B except for an isoleucine residue at position 184 rather than a valine residue and except for a serine residue at position 202 rather than an alanine residue (SEQ ID NOS: 21 and 22, respectively).

17. Isolated nucleic acid comprising the nucleotide sequence of SEQ ID NO: 23, 24, 25, 26, 27, 28, or 29.

18. Isolated nucleic acid comprising DNA encoding a mouse WISP-1 polypeptide having amino acid residues 23 to 367 of FIG. 1 (SEQ ID NO:11), or DNA oncoding a mouse WISP-1 polypeptide having amino acid residues 1 to 367 of FIG. 1 (SEQ ID NO:12), or a complement of either of the encoding DNAs.

19. A vector comprising the nucleic acid of claim 14, 15, 16, or 18.

20. A host cell comprising the vector of claim 19.

21. The host cell of claim 20 wherein said host cell is a CHO cell.

22. The host cell of claim 20 wherein said host cell is a yeast cell.

23. The host cell of claim 20 wherein said host cell is an *E. coli*.

24. A process for producing a WISP-1 polypeptide comprising culturing the host cell of claim 20 under conditions suitable for expression of the WISP-1 polypeptide and recovering the WISP-1 polypeptide from the cell culture.

* * * * *

UNITED STATES PATENT AND TRADEMARK OFFICE
CERTIFICATE OF CORRECTION

PATENT NO.   : 6,387,657 B1
DATED        : May 14, 2002
INVENTOR(S)  : Levine et al.

It is certified that error appears in the above-identified patent and that said Letters Patent is hereby corrected as shown below:

Title page,
Items [12] and [75],
Delete "Botstein et al" and insert therefor -- Levine et al. --
Delete "David A. Botstein, Belmont; Robert L. Cohen, San Mateo; Audrey D. Goddard, San Francisco; Austin L. Gurney, Belmont; Kenneth J. Hillan; David A. Lawrence, both of San Francisco, all of CA (US); Margaret Ann Roy, San Francisco, CA (US); William I. Wood, Hillsborough, CA (US)"

Column 284,
Line 37, delete "pulypeptpide" and insert therefor -- polypeptide --.

Signed and Sealed this

Eleventh Day of March, 2003

JAMES E. ROGAN
*Director of the United States Patent and Trademark Office*